US006518268B1

(12) United States Patent
Chin et al.

(10) Patent No.: US 6,518,268 B1
(45) Date of Patent: Feb. 11, 2003

(54) TELOMERASE INHIBITORS AND METHODS OF THEIR USE

(75) Inventors: Allison C. Chin, Stanford, CA (US); Ryan Holcomb, San Carlos, CA (US); Mieczyslaw A. Piatyszek, Morgan Hill, CA (US); Upinder Singh, Fremont, CA (US); Richard L. Tolman, Los Altos, CA (US); Tsutomu Akama, Redwood City, CA (US); Yutaka Kanda, Tokyo (JP); Akira Asai, Sagamihara (JP); Yoshinori Yamashita, Tokyo (JP); Kaori Endo, Kamakura (JP); Hiroyuki Yamaguchi, Tokyo (JP)

(73) Assignees: Geron Corporation, Menlo Park, CA (US); Kyowa Hakko Kogyo Co., Ltd., Tokyo (JP)

( * ) Notice: Subject to any disclaimer, the term of this patent is extended or adjusted under 35 U.S.C. 154(b) by 0 days.

(21) Appl. No.: 09/608,636

(22) Filed: Jun. 30, 2000

Related U.S. Application Data

(60) Provisional application No. 60/142,173, filed on Jul. 1, 1999.

(30) Foreign Application Priority Data

Jul. 1, 1999 (JP) .......................................... 11-187616
Oct. 28, 1999 (JP) .......................................... 11-307576

(51) Int. Cl.[7] ...................... A61K 31/535; A01N 43/58; A01N 43/78; A01N 43/50; C07D 415/00

(52) U.S. Cl. ............................. 514/236.8; 514/254.02; 514/369; 514/386; 544/133; 544/367; 548/183

(58) Field of Search ......................... 514/236.8, 254.02, 514/369, 386; 544/133, 367; 549/183

(56) References Cited

U.S. PATENT DOCUMENTS

| | | | | |
|---|---|---|---|---|
| 4,287,200 A | | 9/1981 | Kawamatsu et al. | 424/270 |
| 4,340,605 A | | 7/1982 | Kawamatsu et al. | 424/263 |
| 4,376,777 A | | 3/1983 | Kawamatsu et al. | 424/270 |
| 4,438,141 A | | 3/1984 | Kawamatsu et al. | 424/248.51 |
| 4,444,779 A | | 4/1984 | Kawamatsu et al. | 424/263 |
| 4,461,902 A | | 7/1984 | Kawamatsu et al. | 548/183 |
| 4,486,594 A | | 12/1984 | Kawamatsu et al. | 548/183 |
| 4,572,912 A | | 2/1986 | Yoshioka et al. | 514/369 |
| 4,582,839 A | | 4/1986 | Meguro et al. | 514/342 |
| 4,687,777 A | | 8/1987 | Meguro et al. | 514/342 |
| 4,703,052 A | | 10/1987 | Eggler et al. | 514/337 |
| 4,725,610 A | | 2/1988 | Meguro et al. | 514/369 |
| 4,738,972 A | | 4/1988 | Eggler et al. | 514/314 |
| 4,775,687 A | | 10/1988 | Meguro et al. | 514/389 |
| 4,791,125 A | | 12/1988 | Clark | 514/369 |
| 4,812,570 A | | 3/1989 | Meguro et al. | 546/280 |
| 4,873,255 A | | 10/1989 | Yoshioka et al. | 514/369 |
| 4,879,393 A | | 1/1990 | Iijima et al. | 514/233.8 |
| 4,897,405 A | | 1/1990 | Alessi et al. | 514/360 |
| 4,918,091 A | | 4/1990 | Cantello et al. | 514/369 |
| 4,948,900 A | | 8/1990 | Iijima et al. | 548/183 |
| 5,002,953 A | | 3/1991 | Hindley et al. | 514/275 |
| 5,023,085 A | | 6/1991 | Francoeur et al. | 424/449 |
| 5,053,420 A | | 10/1991 | Pershadsingh et al. | 514/369 |
| 5,061,717 A | | 10/1991 | Clark et al. | 514/342 |
| 5,120,754 A | | 6/1992 | Clark et al. | 514/369 |
| 5,132,317 A | | 7/1992 | Cantello et al. | 514/369 |
| 5,143,928 A | | 9/1992 | Cetenko et al. | 514/369 |
| 5,143,929 A | | 9/1992 | Belliotti | 514/364 |
| 5,194,443 A | | 3/1993 | Hindley et al. | 514/367 |
| 5,223,522 A | | 6/1993 | Clark et al. | 514/369 |
| 5,232,925 A | | 8/1993 | Hindley | 514/272 |
| 5,252,735 A | | 10/1993 | Morris | 544/121 |
| 5,260,445 A | | 11/1993 | Hindley | 548/183 |
| 5,554,767 A | * | 9/1996 | Wang et al. | 548/496 |
| 5,814,647 A | | 9/1998 | Urban et al. | 514/369 |
| 5,824,694 A | | 10/1998 | Kurtz et al. | 514/369 |
| 5,874,454 A | | 2/1999 | Antonucci et al. | 514/369 |

FOREIGN PATENT DOCUMENTS

| | | |
|---|---|---|
| EP | 0155 845 A1 | 9/1985 |
| EP | 0155 848 A2 | 9/1985 |
| EP | 0155 848 B1 | 9/1985 |
| EP | 0193 256 A1 | 9/1986 |
| EP | 0193 256 B1 | 9/1986 |
| EP | 0295 828 A1 | 12/1988 |
| EP | 0332 332 A1 | 9/1989 |
| EP | 0343643 B1 | 11/1989 |
| EP | 0343 643 A2 | 11/1989 |
| EP | 0677 517 A1 | 10/1995 |
| WO | WO 89/08651 | 9/1989 |
| WO | WO 91/07107 | 5/1991 |
| WO | WO 92/02520 | 2/1992 |
| WO | WO 94/01433 | 1/1994 |

* cited by examiner

*Primary Examiner*—Jezia Riley
(74) *Attorney, Agent, or Firm*—David J. Earp; Narinder S. Banait

(57) ABSTRACT

Thiazolidinedione compounds, compositions, and methods of inhibiting telomerase activity in vitro and treatment of telomerase mediated conditions or diseases ex vivo and in vivo are provided. The methods, compounds and compositions of the invention may be employed alone, or in combination with other pharmacologically active agents in the treatment of conditions or diseases mediated by telomerase activity, such as in the treatment of cancer. Also disclosed are novel methods for assaying or screening for inhibitors of telomerase activity.

33 Claims, No Drawings

TELOMERASE INHIBITORS AND METHODS OF THEIR USE

CROSS-REFERENCE TO RELATED APPLICATION

The application claims priority from U.S. Application No. 60/142,173, filed Jul. 1, 1999, and Japanese Application Nos. 11-187616, filed Jul. 1, 1999, and 11-307576, filed Oct. 28, 1999, which are herein incorporated by reference in their entirety.

FIELD OF THE INVENTION

The present invention relates to thiazolidinone compounds that inhibit telomerase activity, to pharmaceutical compositions containing the compounds and to the use of the compounds and compositions, alone or in combination with other pharmaceutically active agents, in the treatment of telomerase-mediated conditions or diseases, such as cancer.

BACKGROUND OF THE INVENTION

Telomerase catalyzes the synthesis of telomeres. Telomeres are characteristic tandem repeats (TTAGGG in mammals) found at the ends of most eukaryotic chromosomes, that may be 15–25 kilobases long in human germline cells. With each cell division, about 60–100 bases are lost from the ends of the chromosomes, and as the telomeres shorten, cells eventually reach crisis and apotosis is triggered. See Harley et al., (1991) Mutation Res. 256: 271–282). Telomerase acts to maintain the telomere length just above the crisis level, and are thus responsible for chromosome stability and are involved in the regulation of the cell cycle.

Telomerase is a ribonucleoprotein reverse transcriptase that contains its own RNA template for the synthesis of telomeric DNA. See Blackburn, 1992, Annu. Rev. Biochem., 61:113–129. Telomerase is present in stem and germline cells of normal tissues, and at much higher levels in over 85% of tumors (Kim et al., 1994, Science, 266:2011–2014). Thus, drugs targeted towards telomerase potentially will have a high selectivity for tumor over healthy tissues. Consequently, telomerase inhibition has been proposed as a new approach to cancer therapy.

The inhibition of telomerase activity by antisense strategies directed towards the telomerase RNA component, for example peptide nucleic acids (Norton et al., (1996) Nature Biotech. 14: 615–619) and phosphorothioate oligonucleotides has been reported. Since telomerase is a reverse transcriptase, the use of inhibitors of reverse transcriptases, such as AZT, and other nucleosides has also been reported. Telomerase inhibition by cisplatin, possibly due to crosslinking of the telomeric repeat sequences, is also known (Burger et al., (1997) Eur. J. Cancer 33: 638–644).

Thiazolidinediones comprise a group of structurally related antidiabetic compounds that increases the insulin sensitivity of target tissues (skeletal muscle, liver, adipose) in insulin resistant animals. In addition to these effects on hyperglycemia, thiazolidinediones also reduce lipid and insulin levels in animal models of NIDDM. Recently, the thiazolidinedione troglitazone was shown to have these same beneficial effects in human patients suffering from impaired glucose tolerance, a metabolic condition that precedes the development of NIDDM, as in patients suffering from NIDDM (Nolan et al., (1994) N. Eng. J. Med. 331, 1188–1193). While their mechanism of action remains unclear, it is known that the thiazolidinediones do not cause increases in insulin secretion or in the number or affinity of insulin receptor binding sites, suggesting that thiazolidinediones amplify post-receptor events in the insulin signaling (Colca, J. R., and Morton, D. R. (1990) in New Antidiabetic Drugs (C. J. Bailey and P. R. Flatt, eds.). Smith-Gordon, New York, 255–261; Chang et al. (1983) Diabetes 32, 839–845).

Thiazolidinediones have been found to be efficacious inducers of differentiation in cultured pre-adipocyte cell lines (Hiragun et al. (1988) J. Cell Physiol. 134, 124–130; Sparks et al. (1991) J. Cell. Physiol. 146, 101–109; Kleitzien et al. (1992) Mol. Pharmacol. 41, 393–398). Additionally, thiazolidinediones have been implicated in appetite regulation disorders (see WO 94/25026 A1), and in increase of bone marrow fat content. In addition, thiazolidinedione compounds have been suggested for use in the treatment of psoriasis (U.S. Pat. No. 5,824,694) and climacteric symptoms and mesenchymal tumors (U.S. Pat. No. 5,814,647).

Some of the compounds useful for practicing the method of the present invention, and methods of making some of these compounds are known. For example, some of these compounds are disclosed in WO 91/07107; WO 92/02520; WO 94/01433; WO 89/08651; JP Kokai 69383/92; EP 0 155845; EP 0 155848; EP 0 193256; EP 0 295828; and U.S. Pat. Nos. 4,287,200; 4,340,605; 4,376,777; 4,438,141; 4,444,779; 4,461,902; 4,486,594; 4,572,912; 4,582,839; 4,687,777; 4,703,052; 4,725,610; 4,738,972; 4,775,687; 4,791,125; 4,812,570; 4,873,255; 4,897,393; 4,897,405; 4,918,091; 4,948,900; 5,002,953; 5,023,085; 5,053,420; 5,061,717; 5,120,754; 5,132,317; 5,143,928; 5,194,443; 5,223,522; 5,232,925; 5,252,735; 5,260,445; 5,814,647; 5,824,694; and 5,874,454.

The identification of compounds that inhibit telomerase activity provides important benefits to efforts at treating human disease. Compounds that inhibit telomerase activity can be used to treat telomerase-mediated disorders, such as cancer, since cancer cells express telomerase activity and normal human somatic cells do not possess telomerase activity at biologically relevant levels (i.e., at levels sufficient to maintain telomere length over many cell divisions). Unfortunately, few such compounds, especially compounds with high potency or activity and compounds that are orally bioavailable, have been identified and characterized. Hence, there remains a need for compounds that act as telomerase inhibitors that have relatively high potency or activity and that are orally bioavailable, and for compositions and methods for treating cancer and other diseases in which telomerase activity is present abnormally. The present invention meets these and other needs.

SUMMARY OF THE INVENTION

The present invention provides methods, compounds and compositions that are specific and effective for treating telomerase-mediated disorders, such as malignant conditions by targeting cells having telomerase activity. The methods, compounds, and compositions of the invention can be applied to a wide variety of malignant cell types and avoid the problems inherent in current cancer treatment modalities which are non-specific and excessively toxic.

In a first aspect, the present invention is based on the finding that certain known thiazolidinone compounds, as well as new thiazolidinone derivatives disclosed herein, are effective in the inhibition of telomerase enzyme activity, in vitro, ex vivo and in vivo. Thus, in certain aspects, the present invention provides methods of inhibiting telomerase by contacting telomerase with the compounds described herein. In particular embodiments, the telomerase to be inhibited is a mammalian telomerase, such as a human telomerase. A related aspect of the present invention is the discovery that thiazolidinone compounds inhibit the proliferation of cells that have telomerase activity, such as many cancer cells. Thus, this aspect of the present invention provides methods of inhibiting telomerase activity in a patient, preferably a mammal, suffering from a telomerase-mediated condition or disease, comprising administering to the patient a therapeutically effective amount of a telomerase inhibiting thiazolidinone compound, or a pharmaceutically acceptable salt thereof.

In another aspect, the present invention provides methods, compounds and compositions for inhibiting a telomerase enzyme, comprising contacting the telomerase enzyme with a composition or a compound of formula (I):

(I)

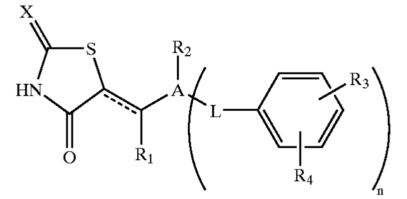

Or its pharmaceutically acceptable salts, wherein X is oxygen or sulfur,  is a single or double bond; A is aryl or heteroaryl; $R_1$ is hydrogen or lower alkyl; $R_2$, $R_3$ and $R_4$ are independently selected from the group consisting of hydrogen, halo, alkyl, aryl, hydroxyl, alkoxyl, aryloxyl, aralkoxyl, cyano, nitro, alkylcarbamido, arylcarbamido, dialkylcarbamido, diarylcarbamido, alkylarylcarbamido, alkylthiocarbamido, arylthiocarbamido, dialkylthiocarbamido, diarylthiocarbamido, alkylarylthiocarbamido, amino, alkylamino, arylamino, dialkylamino, diarylamino, arylalkylamino, aminocarbonyl, alkylaminocarbonyl, arylaminocarbonyl, dialkylaminocarbonyl, diarylaminocarbonyl, arylalkylaminocarbonyl, alkylcarbonyloxy, arylcarbonyloxy, carboxyl, alkoxycarbonyl, aryloxycarbonyl, sulfo, alkylsulfonylamido, arylsulfonamido, alkylsulfonyl, arylsulfonyl, alkylsulfinyl, arylsulfinyl and heteroaryl; L is a direct bond or a linking group having from 1 to 3 atoms independently selected from unsubstituted or substituted carbon, N, O or S; and n is 1 or 2.

In another aspect, the present invention provides methods, compounds and compositions for inhibiting a telomerase enzyme, comprising contacting the telomerase enzyme with a compound, or its pharmaceutically acceptable salt, having the formula (IV):

(IV)

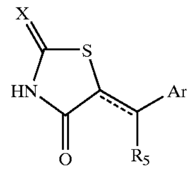

where X is O or S;  is a single or double bond; $R_5$ is H or lower alkyl; and Ar is a substituted or unsubstituted aryl, heteroaryl, aralkyl, heteroarylalkyl, arylalkeryl, heteroarylalkeryl, arylalkynyl or heteroarylalkynyl.

In another aspect, the present invention provides methods, compounds and compositions for inhibiting a telomerase enzyme, comprising contacting the telomerase enzyme with a composition or a compound of formula (V):

(V)

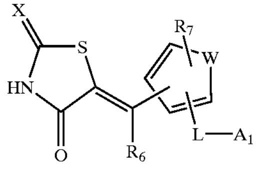

or its pharmaceutically acceptable salt, wherein X is O or S; $R_6$ is H or lower alkyl; W is CH=CH, S, or —N=C—; $R_7$ is OH, halogen, mercapto, nitro, cyano, lower alkylthio, lower alkyl, lower alkoxy, lower alkanoyloxy, $NR_{11}R_{12}$ (wherein $R_{11}$ and $R_{12}$ are independently selected from the group consisting of hydrogen, lower alkyl, lower alkanoyl, aryl, heteroaryl, heteroarylalkyl, or $R_{11}$ and $R_{12}$ form a substituted or unsubstituted heterocyclic ring), $CO_2R_{13}$ (wherein $R_{13}$ is selected from the group consisting of hydrogen, lower alkyl, aralkyl, and heteroarylalkyl), $CONR_{11}R_{12}$, substituted or unsubstituted aryl, substituted or unsubstituted heteroaryl, aryloxy, heteroaryloxy, aralkyloxy, heteroarylalkyloxy, lower alkanoyl, aroyl, lower alkenyl, arylthio, or lower alkynyl; and when W represents S, $R^7$ may also be H; L is O, S, SO, $SO_2$, $OCH_2$, $SCH_2$, $SOCH_2$, $SO_2CH_2$, or $N(R_{10})(CH_2)_m$ (wherein $R_{10}$ is substituted or unsubstituted aryl, heteroaryl, aralkyl, or heteroarylalkyl, and m is 0 or 1), $(CH_2)N(R_{10})(CH_2)_m$, or $CR_{13}R_{14}$ (wherein $R_{13}$ and $R_{14}$ are independently selected from the group consisting of hydrogen, hydroxy, aryl, and heteroaryl); and $A_1$ is cycloalkyl of formula (A1):

(A1)

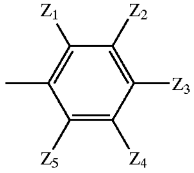

wherein $Z_1$ to $Z_5$ are independently selected from the group consisting of hydrogen, lower alkyl, lower alkenyl, lower alkanoyloxy, mercapto, alkylthio, $NR_{11}R_{12}$; nitro, cyano, $CO_2R_{13}$, $CONR_{11}R_{12}$, aryl, heteroaryl, aryloxy, heteroaryloxy, aralkyloxy, heteroarylalkyloxy, halogen, and lower alkanoyl provided that when W is CH=CH, A may also by pyridyl.

The new compounds of the invention have many valuable uses as inhibitors of deleterious telomerase activity, such as, for example, in the treatment of cancer in mammals, such as humans. The pharmaceutical compositions of this invention can be employed in treatment regimens in which cancer cells are killed, in vivo, or can be used to kill cancer cells ex vivo. Thus, this invention provides therapeutic compounds and compositions for treating cancer, and methods for treating cancer and other telomerase-mediated conditions or diseases in humans and other mammals (e.g., cows, horses, sheep, steer, pigs and animals of veterinary interest such as cats and dogs).

DETAILED DESCRIPTION

I. Definitions

Unless otherwise defined below, the terms used herein have their normally accepted scientific meanings. Definition of standard chemistry terms may be found in reference works, including Carey and Sundberg (1992) "Advanced Organic Chemistry 3rd Ed." Vols. A and B, Plenum Press, New York.

The term "thiazolidinone" or "thiazolidinone derivative" as used herein refers to compounds of the general formula:

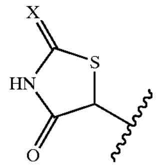

wherein X is O or S. When X is O, the derivatives are thiazolidinedione derivatives. When X is S, the derivatives are the thiazolidinonethione derivatives also known as rhodanines (see Examples 25–28, below).

The term "alkyl" as used herein refers to a straight, branched, or cyclic hydrocarbon chain fragment or radical containing between about one and about twenty carbon atoms, more preferably between about one and about ten carbon atoms (e.g., methyl, ethyl, n-propyl, iso-propyl, cyclopropyl, n-butyl, iso-butyl, tert-butyl, cyclobutyl, adamantyl, noradamantyl and the like). Straight, branched, or cyclic hydrocarbon chains having eight or fewer carbon atoms will also be referred to herein as "lower alkyl". The hydrocarbon chains may further include one or more degrees of unsaturation, i.e., one or more double or triple bonds (e.g., vinyl, propargyl, allyl, 2-buten-1-yl, 2-cyclopenten-1-yl, 1,3-cyclohexadien-1-yl, 3-cyclohexen-1-yl and the like Alkyl groups containing double bonds such as just described will also be referred to herein as "alkenes". Similarly, alkyl groups having triple bonds will also be referred to herein as "alkynes". However, as used in context with respect to cyclic alkyl groups, the combinations of double and/or triple bonds do not include those bonding arrangements that render the cyclic hydrocarbon chain aromatic.

In addition, the term "alkyl" as used herein further includes one or more substitutions at one or more carbon atoms of the hydrocarbon fragment or radical. Such substitutions include, but are not limited to: aryl; heterocycle; halogen (to form, e.g., trifluoromethyl, —$CF_3$); nitro (—$NO_2$); cyano (—CN); hydroxyl (also referred to herein as "hydroxy"), alkoxyl (also referred herein as alkoxy) or aryloxyl (also referred to herein as "aryloxy")(—OR); thio or mercapto, alkyl- or arylthio (—SR); amino, alkylamino, arylamino, dialkyl- or diarylamino, or arylalkylamino (—NRR'); aminocarbonyl, alkylaminocarbonyl, arylaminocarbonyl, dialkylaminocarbonyl, diarylaminocarbonyl or arylalkylaminocarbonyl (—C(O)NRR'); carboxyl, or alkyl- or aryloxycarbonyl (—C(O)OR); carboxaldehyde, or aryl- or alkylcarbonyl (—C(O)R); iminyl, aryl- or alkyliminyl (—C(=NR)R'); sulfo (—$SO_2$OR); alkyl- or arylsulfonyl (—$SO_2$R); ureido (—HNC(=O)NRR'); or thioureido (—HNC(=S)NRR'); where R and R' independently are hydrogen, aryl or alkyl as defined herein. Substituents including heterocyclic groups (i.e., heterocycle, heteroaryl, and heteroaralkyl) are defined by analogy to the above-described terms. For example, the term "heterocycleoxy" refers to the group —OR, where R is heterocycle as defined below.

The alkyl moiety of "lower alkanoyl", "lower alkoxy", "lower alkanoyloxy", "lower alkylthio", is the same as "alkyl" defined above.

The term "methylene" refers to the group —$CH_2$—.

The term "methine" refers to a methylene group for which one hydrogen atom has been replaced by a substituent as described above. The term "methine" can also refer to a methylene group for which one hydrogen atom is replaced by bond to form an $sp^2$-hybridized carbon center (i.e., >C=O).

The term "halo" or "halogen" as used herein refers to the substituents fluoro, bromo, chloro, and iodo.

The term "carbonyl" as used herein refers to the functional group —C(O)—. However, it will be appreciated that this group may be replaced with well-known groups that have similar electronic and/or steric character, such as thiocarbonyl (—C(S)—); sulfinyl (—S(O)—); sulfonyl (—$SO_2$—), phosphonyl (—$PO_2$—), and methylidene (—C(=$CH_2$)—). Other carbonyl equivalents will be familiar to those having skill in the medicinal and organic chemical arts.

The term "aryl" as used herein refers to cyclic aromatic, hydrocarbon chains having twenty or fewer carbon atoms, e.g., phenyl, naphthyl, biphenyl and anthracenyl. One or more carbon atoms of the aryl group may also be substituted with, e.g.: alkyl; aryl; heterocycle; formyl; halogen; nitro; cyano; hydroxyl, alkoxyl or aryloxyl; thio or mercapto, alkyl-, or arylthio; amino, alkylamino, arylamino, dialkyl-, diaryl-, or arylalkylamino; aminocarbonyl, alkylaminocarbonyl, arylaminocarbonyl, dialkylaminocarbonyl, diarylaminocarbonyl or arylalkylaminocarbonyl; carboxyl, or alkyl- or aryloxycarbonyl; carboxaldehyde, or aryl- or alkylcarbonyl; iminyl, or aryl- or alkyliminyl; sulfo; alkyl- or arylsulfonyl; hydroximinyl, or aryl- or alkoximinyl; ureido; or thioureido. In addition, two or more alkyl or heteroalkyl substituents of an aryl group may be combined to form fused aryl-alkyl or aryl-heteroalkyl ring systems (e.g., tetrahydronaphthyl). Substituents including heterocyclic groups (e.g., heterocycleoxy, heteroaryloxy, and heteroaralkylthio) are defined by analogy to the above-described terms.

The term "aralkyl" as used herein refers to an aryl group that is joined to a parent structure by an alkyl group as described above, e.g., benzyl, α-methylbenzyl, phenethyl, and the like. The aralkyl moiety of "aralkylsulfonyl" aralkyloxy is the same as "aralkyl" defined above.

The aryl moiety of "aroyl", "arylalkenyl", "arylalkenyl", "arylsulfonyl", "arylthio", "aryloxy", "arylalkenylsulfonyl", "arylalkynylsulfonyl" is the same as "aryl" defined above.

The term "heterocycle" as used herein refers to a cyclic alkyl group or aryl group as defined above in which one or more carbon atoms have been replaced by a non-carbon atom, especially nitrogen, oxygen, or sulfur. Non-aromatic heterocycles will also be referred to herein as "cyclic heteroalkyl". Aromatic heterocycles are also referred to herein as "heteroaryl". For example, such groups include furyl, tetrahydrofuryl, pyrrolyl, pyrrolidinyl, thienyl, tetrahydrothienyl, oxazolyl, isoxazolyl, triazolyl, thiazolyl, isothiazolyl, pyrazolyl, pyrazolidinyl, oxadiazolyl, thiadiazolyl, imidazolyl, imidazolinyl, pyridyl, pyridazinyl, triazinyl, piperidinyl, morpholinyl, thiomorpholinyl, pyrazinyl, piperazinyl, pyrimidinyl, naphthyridinyl, benzofuranyl, benzothienyl, indolyl, indolinyl, indolizinyl, indazolyl, quinolizinyl, quinolinyl, isoquinolinyl, cinnolinyl, phthalazinyl, quinazolinyl, quinoxalinyl, pteridinyl, quinuclidinyl, carbazolyl, acridiniyl, phenazinyl, phenothiazinyl, phenoxazinyl, purinyl, benzimidazolyl, benzthiazolyl, and benzoxazolyl.

The heteroaryl moiety of "heteroarylalkyl", "heteroarylalkenyl", "heteroarylalkynyl", "heteroarylsulfonyl", "heteroarylalkylsulfonyl", "heteroarylalkenylsulfonyl", "heteroarylalkynylsulfonyl", "heteroaryloxy", "heteroarylalkyloxy" is the same as "heteroaryl" defined above.

The above heterocyclic groups may further include one or more substituents at one or more carbon and/or non-carbon atoms of the heteroaryl group, e.g.: alkyl; aryl; heterocycle; halogen; nitro; cyano; hydroxyl, alkoxyl or aryloxyl; thio or mercapto, alkyl- or arylthio; amino, alkyl-, aryl-, dialkyl-diaryl-, or arylalkylamino; aminocarbonyl, alkylaminocarbonyl, arylaminocarbonyl, dialkylaminocarbonyl, diarylaminocarbonyl or arylalkylaminocarbonyl; carboxyl, or alkyl- or aryloxycarbonyl; carboxaldehyde, or aryl- or alkylcarbonyl; iminyl, or aryl- or alkyliminyl; sulfo; alkyl- or arylsulfonyl; hydroximinyl, or aryl- or alkoximinyl; ureido; or thioureido. In addition, two or more alkyl substituents may be combined to form fused heterocycle-alkyl or heterocycle-aryl ring systems. Substituents including heterocyclic groups (e.g., heterocycleoxy, heteroaryloxy, and heteroaralkylthio) are defined by analogy to the above-described terms.

The term "heterocyclealkyl" refers to a heterocycle group that is joined to a parent structure by one or more alkyl groups as described above, e.g., 2-piperidylmethyl, and the like. The term "heteroaralkyl" as used herein refers to a heteroaryl group that is joined to a parent structure by one or more alkyl groups as described above, e.g., 2-thienylmethyl, and the like.

The compounds of the present invention may be used to inhibit or reduce telomerase enzyme activity and/or proliferation of cells having telomerase activity. In these contexts, inhibition and reduction of the enzyme or cell proliferation refers to a lower level of the measured activity relative to a control experiment in which the enzyme or cells are not treated with the test compound. In particular embodiments, the inhibition or reduction in the measured activity is at least a 10% reduction or inhibition. One of skill in the art will appreciate that reduction or inhibition of the measured activity of at least 20%, 50%, 75%, 90% or 100% may be preferred for particular applications.

II. Telomerase Inhibitors

As noted above, the immortalization of cells involves inter alia the activation of telomerase. More specifically, the connection between telomerase activity and the ability of many tumor cell lines, including skin, connective tissue, adipose, breast, lung, stomach, pancreas, ovary, cervix, uterus, kidney, bladder, colon, prostate, central nervous system (CNS), retina and blood tumor cell lines, to remain immortal has been demonstrated by analysis of telomerase activity (Kim et al.). This analysis, supplemented by data that indicates that the shortening of telomere length can provide the signal for replicative senescence in normal cells (see WO 93/23572), demonstrates that inhibition of telomerase activity can be an effective anti-cancer therapy. By "inhibition" is simply meant a reagent, drug or chemical which is able to decrease the activity of the telomerase enzyme in vitro or in vivo. Such inhibitors can be readily identified using standard screening protocols in which a cellular extract or other preparation having telomerase activity is placed in contact with a potential inhibitor, and the level of telomerase activity measured in the presence or absence of the inhibitor, or in the presence of varying amounts of inhibitor. In this way, not only can useful inhibitors be identified, but the optimum level of such an inhibitor can be determined in vitro for further testing in vivo.

In a related aspect, the invention proves a method for inhibiting the ability of a cell to proliferate or replicate. In this method, one or more of the thiazolidinone compounds of the invention, that are capable of inhibiting telomerase enzyme activity, are provided during cell replication. As explained above, telomeres play a critical role in allowing the end of the linear chromosomal DNA to be replicated completely without the loss of terminal bases at the 5'-end of each strand. Immortal cells and rapidly proliferating cells use telomerase to add telomeric DNA repeats to chromosomal ends. Inhibition of telomerase will result in the proliferating cells not being able to add telomeres and they will eventually stop dividing. As will be evident to those of ordinary skill in the art, this method for inhibiting the ability of a cell to proliferate is useful for the treatment of a condition associated with an increased rate of proliferation of a cell, such as in cancer (telomerase-activity in malignant cells), and hematopoiesis (telomerase activity in hematopoietic stem cells), for example.

Thus, in one aspect, the present invention provides compositions and compounds for the prevention or treatment of many types of malignancies. In particular, the compounds of the present invention can provide a highly general method of treating many, if not most, malignancies, as demonstrated by the highly varied human tumor cell lines and tumors having telomerase activity. More importantly, the thiazolidinone compounds of the present invention can be effective in providing treatments that discriminate between malignant and normal cells to a high degree, avoiding many of the deleterious side-effects present with most current chemotherapeutic regimes which rely on agents that kill dividing cells indiscriminately. Representative known thiazolidinedione compounds include the glitazones, such as, for example, troglitazone (also known as CS-045 (Sankyo) and CI-991 (Park-Davis)), pioglitazone (also known as AD-4833 and U-72107E), rosiglitazone (also known as BRL49653), englitazone (also known as CP-68,722), and ciglitazone.

In another aspect, the present invention provides new compounds, pharmaceutical compositions and methods relating to the new compounds, or their pharmaceutically acceptable salts, for inhibiting a telomerase enzyme, comprising contacting the telomerase enzyme with a compound, or its pharmaceutically acceptable salt, having the formula (I):

(IV)

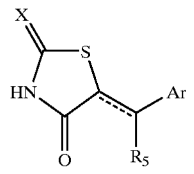

wherein X is oxygen or sulfur,  is a single or double bond; A is aryl or heteroaryl; $R_1$ is hydrogen or lower alkyl; $R_2$, $R_3$ and $R_4$ are independently selected from the group consisting of hydrogen, halo, alkyl, aryl, hydroxyl, alkoxyl, aryloxyl, aralkoxyl, cyano, nitro, alkylcarbamido, arylcarbamido, dialkylcarbamido, diarylcarbamido, alkylarylcarbamido, alkylthiocarbamido, arylthiocarbamido, dialkylthiocarbamido, diarylthiocarbamido, alkylarylthiocarbamido, amino, alkylamino, arylamino, dialkylamino, diarylamino, arylalkylamino, aminocarbonyl, alkylaminocarbonyl, arylaminocarbonyl, dialkylaminocarbonyl, diarylaminocarbonyl, arylalkylaminocarbonyl, alkylcarbonyloxy, arylcarbonyloxy, carboxyl, alkoxycarbonyl, aryloxycarbonyl, sulfo, alkylsulfonylamido, arylsulfonamido, alkylsulfonyl, arylsulfonyl, alkylsulfinyl, arylsulfinyl and heteroaryl; L is a direct bond or a linking group having from 1 to 3 atoms independently selected from unsubstituted or substituted carbon, N, O or S; and n is 1 or 2.

In certain embodiments, the new compounds of the present invention have the general structure shown as formula II below:

(II)

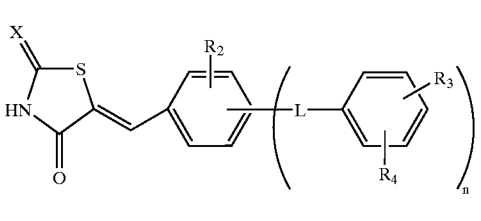

and their pharmaceutically acceptable salts, wherein X is O or S, and $R_2$, $R_3$, $R_4$, L, and n are as defined above.

In the compounds of formula I, A may be aryl to form, for example, a phenyl moiety. Alternatively, A may be heteroaryl, such as, for example, pyridine, quinoline, isoquinoline, thiophene, furan, imidazole, benzimidazole, pyrazole, and the like. In presently preferred embodiments, A is phenyl, as in formula (II). In other presently preferred embodiments, when n is 1, $R_1$ can not be hydrogen. In yet other presently preferred embodiments, at least one of $R_2$ and $R_3$ is other than hydrogen. In presently particularly preferred embodiments, at least one of $R_2$ and $R_3$ is halo, and most preferably both $R_2$ and $R_3$ are halo to form a dihalo-substituted phenyl moiety.

As noted above, L may be a direct bond, or may be a 1 to 3 atom linking group wherein the atoms of the linking group independently selected from unsubstituted or substituted carbon, N, O or S. Representative linking groups useful in the compounds of the invention include, for example —O—, —S—, —NH—, —$CH_2$, —$OCH_2$—, —OC(O)—, —$C0_2$—, —NHC(O)—, —C(O)NH—, —OC(O)$CH_2$—, —OC(O)NH—, and —NHC(O)NH—.

For purposes of illustration, representative compounds include, without limitation, 5-(2-(3,4-Dichlorophenyl) benzylidene)thiazolidine-2,4-dione, 5-(3-(3,4-Dichlorophenyl)benzylidene)thiazolidine-2,4-dione, 5-(4-(3,4-Dichlorobenzyloxy)benzylidene)thiazolidine-2,4-dione, 5-(2-(3,4-Dichlorobenzyloxy)benzylidene) thiazolidine-2,4-dione, 5-(4-(3,4-Dichlorobenzamido) benzylidene)thiazolidine-2,4-dione, 5-(4-(N-3,4-Dichlorophenyureido)-benzylidene)thiazolidine-2,4-dione, 5-(2-(N-3,4-Dichlorophenyureido)benzylidene)-thiazolidine-2,4-dione, 5-(2-(N-3,4-Dichlorophenylcarbamido)benzylidene)thiazolidine-2,4-dione, 5-(3-(N-3,4-Dichlorophenylcarbarmido)benzylidene)thiazolidine-2,4-dione, 5-(4-(N-3,4-Dichlorophenylcarbamido)benzylidene) thiazolidine-2,4-dione, 5-(4-(N-3,4-Dichlorophenylcarbamoyloxy)benzylidene)thiazolidine-2,4-dione, 5-(4-(3,4-Dichlorophenoxycarbonyl)benzylidene)thiazolidine-2,4-dione, 5-(2-(3,4-Dichlorophenoxycarbonyl)benzylidene) thiazolidine-2,4-dione, 5-(2-(3,4-Dichlorophenylacetoxy) benzylidene)thiazolidine-2,4-dione, 5-(3-(3,4-Dichlorophenylacetoxy)-benzylidene)thiazolidine-2,4-dione, 5-(4-(3,4-Dichlorophenylacetoxy)benzylidene) thiazolidine-2,4-dione, 5-(2-(3,4-Dichlorobenzoyloxy) benzylidene)thiazolidine-2,4-dione, 5-(3-(3,4-Dichlorobenezoyloxy)-benzylidene)thiazolidine-2,4-dione, 5-(4-(3,4-Dichlorobenzoyloxy)-benzylidene)thiazolidine-2, 4-dione, 5-(3,4-Bis-(3,4-dichlorobenzyloxy)benzylidine) thiazolidine-2,4-dione, 5-(2-(3,4-Dichlorophenoxy) benzylidine)thiazolidine-2,4-dione, 5-(4-(3,4-Dichlorophenoxy)benzylidine)thiazolidine-2,4-dione, 5-(2, 5-Bis-(3,4-dichlorobenzyloxy)-benzylidine)thiazolidine-2, 4-dione, 5-(2,4-Bis-(3,4-dichlorobenzyloxy)benzylidine)-thiazolidine-2,4-dione, 5-(2-(3,4-Dichlorobenylthio)-3H-pyrimidin-4-on-6-ylmethylidene)-rhodanine, 5-(2-(3,4-Dichlorobenzylthio)pyrimidin-4-ylmethylidene)rhodanine, 5-(2-(3,4-Dichlorobenzylthio)pyrimidin-4-ylmethylidene) rhodanine, 5-(3-Cyano-2-(3,4-dichlorobenzylthio)pyridin-6-ylmethylidene)thiazolidine-2,4-dione and 5-(3-(3,4-Dichlorobenzyloxy)benzylidene)thiazolidine-2,4-dione.

In certain embodiments, the new compounds of the present invention have the general structure shown as formula III below:

(III)

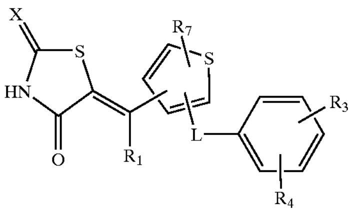

and their pharmaceutically acceptable salts, wherein X is O or S, and $R_1$, $R_2$, $R_3$, $R_4$, and L are as defined above.

In another embodiment, the present invention provides methods, compounds and compositions for inhibiting a telomerase enzyme, comprising contacting the telomerase enzyme with a compound, or its pharmaceutically acceptable salt, having the formula (IV):

(IV)

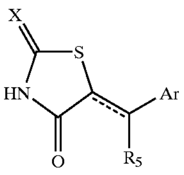

where X is O or S;  is a single or double bond; $R_5$ is H or lower alkyl; and Ar is a substituted or unsubstituted aryl, heteroaryl, aralkyl, heteroarylalky, arylalkenyl, heteroarylalkenyl, arylalkynyl or heteroarylalkynyl.

Compounds of formula (IV) having the double bond can be obtained by reacting a thiazolidine derivative with an aromatic carbonyl compound. The reaction can be carried out optionally in the presence of a base catalyst and optionally in a solvent. The base catalyst, usually present in about 0.1 to about 1 equivalent, may be piperidine, piperidinium acetate, diethylamine, pyridine, sodium acetate, potassium carbonate, sodium carbonate, and the like. The solvent may be an alcohol, such as methanol, ethanol, propanol, or the like, an ether, such as diethyl ether, tetrahydrofuran, dioxane, or the like, or a hydrocarbon, such as benzene, roluene, xylene, or the like, and mixtures thereof. The reaction is carried out at a temperature of about room temperature to about 200° C., preferably about 50–100° C., and completes in about one hour to about 50 hours. Compounds of formula (IV) wherein  is a single bond can be synthesized by reducing the double bond of the compound made above. Typically, hydrogenation is carried out using a noble metal catalyst, such as palladium, platinum, rhodium, or the like, as is well known in the art.

In another aspect, the present invention provides methods, compounds and compositions for inhibiting a telomerase enzyme, comprising contacting the telomerase enzyme with a compound, or its pharmaceutically acceptable salt, having the formula (V):

(V)

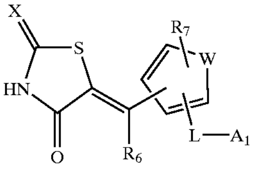

wherein X is O or S; $R_6$ is H or lower alkyl; W is CH═CH, S, or —N═C—; $R_7$ is H, OH, halogen, mercapto, nitro, cyano, lower alkylthio, lower alkyl, lower alkoxy, lower alkanoyloxy, $NR_{11}R_{12}$ (wherein $R_{11}$ and $R_{12}$ are independently selected from the group consisting of hydrogen, lower alkyl, lower alkanoyl, aryl, heteroaryl, heteroarylalkyl, or $R_{11}$ and $R_{12}$ form a substituted or unsubstituted heterocyclic ring), $CO_2R_{13}$ (wherein $R_{13}$ is selected from the group consisting of hydrogen, lower alkyl, aralkyl, and heteroarylalkyl), $CONR_{11}R_{12}$, substituted or unsubstituted aryl, substituted or unsubstituted heteroaryl, aryloxy, heteroaryloxy, aralkyloxy, heteroarylalkyloxy, lower alkanoyl, aroyl, lower alkenyl, arylthio, or lower alkynyl; L is O, S, SO, $SO_2$, $OCH_2$, $SCH_2$, $SOCH_2$, $SO_2CH_2$, or $N(R_{10})(CH_2)_m$ (wherein $R_{10}$ is substituted or unsubstituted aryl, heteroaryl, aralkyl, or heteroarylalkyl, and m is 0 or 1), $(CH_2)N(R_{10})(CH_2)_m$, or $CR_{13}R_{14}$ (wherein $R_{13}$ and $R_{14}$ are independently selected from the group consisting of hydrogen, hydroxy, aryl, and heteroaryl); and $A_1$ is cycloarlkyl of formula (A1):

(A1)

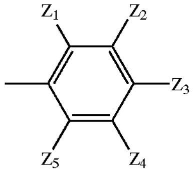

wherein $Z_1$ to $Z_5$ are independently selected from the group consisting of hydrogen, lower alkyl, lower alkenyl, lower alkanoyloxy, mercapto, alkylthio, $NR_{11}R_{12}$, nitro, cyano, $CO_2R_{13}$, $CONR_{11}R_{12}$, aryl, heteroaryl, aryloxy, heteroaryloxy, aralkyloxy, heteroarylalkyloxy, halogen, and lower alkanoyl provided that when W is CH═CH, $A_1$ may also by pyridyl.

Examples of the compound of the present invention represented by formulae I to V are shown in Tables 1 to 6 below, though compounds of the present invention are not restricted thereby.

TABLE 1

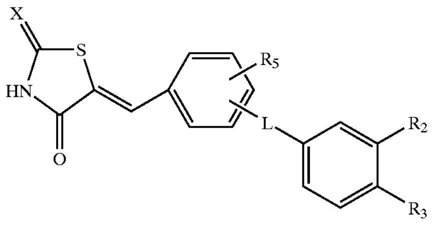

| Compound No. | X | $R_5$ | L | $R_2$ | $R_3$ |
|---|---|---|---|---|---|
| 1 | O | 5-$NO_2$ | 2-S | H | $CH_3$ |
| 2 | O | 5-$NH_2$ | 2-S | H | $CH_3$ |
| 3 | O | 5-$NHCOCH_3$ | 2-S | H | $CH_3$ |
| 4 | O | 5-$NO_2$ | 2-SO | H | $CH_3$ |
| 5 | O | 5-$NO_2$ | 2-$SO_2$ | H | $CH_3$ |
| 6 | O | H | 2-S | H | Cl |
| 7 | O | H | 2-SO | H | Cl |
| 8 | O | H | 2-$SO_2$ | H | Cl |
| 9 | O | 3-$NO_2$ | 4-S | H | $CH_3$ |
| 10 | O | H | 2-O | H | H |
| 11 | O | H | 3-O | H | H |
| 12 | O | H | 3-O | H | $CH_3$ |
| 13 | O | H | 3-O | Cl | Cl |
| 14 | O | H | 4-O | H | H |
| 15 | O | H | 4-O | H | $CH_3$ |
| 16 | O | 5-$NO_2$ | 2-$OCH_2$ | H | H |
| 17 | O | 5-$NO_2$ | 2-$OCH_2$ | Cl | Cl |
| 18 | O | 5-$NO_2$ | 2-$OCH_2$ | H | $CH_3$ |
| 19 | O | 4-$NO_2$ | 3-$OCH_2$ | H | $CH_3$ |
| 20 | O | 3-$NO_2$ | 4-$OCH_2$ | H | $CH_3$ |
| 21 | O | 2-$NO_2$ | 5-$OCH_2$ | H | $CH_3$ |
| 46 | O | H | 4-N-(4-bromophenyl) | H | Br |
| 47 | O | 5-Ph | 2-$OCH_2$— | H | $CH_3$ |
| 48 | O | 5-(2-thienyl) | 2-$OCH_2$— | H | $CH_3$ |
| 49 | O | H | 4-N-(4-hydroxy methylphenyl) | H | $CH_2OH$ |
| 50 | O | H | 2-$NCH_2$(4-bromophenyl) | H | H |

TABLE 2

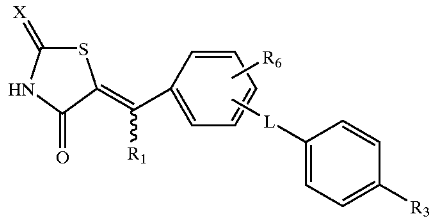

| Compound No. | X | $R_1$ | $R_6$ | L | $R_3$ |
|---|---|---|---|---|---|
| 22 | O | H | H | $2-OCH_2$ | $CH_3$ |
| 23 | O | H | $5-OCH_3$ | $2-OCH_2$ | $CH_3$ |
| 24 | O | H | 5-Cl | $2-OCH_2$ | $CH_3$ |
| 25 | O | H | 5-Br | $2-OCH_2$ | $CH_3$ |
| 26 | O | H | H | $4-NC_6H_5$ | H |
| 27 | O | H | H | 2- | H |
| 28 | O | H | H | 3- | H |
| 29 | O | H | H | 4- | H |
| 30 | O | H | H | 4-CHOH | H |
| 31 | O | H | H | 4-CO | H |
| 32 | O | H | H | $4-CH_2$ | H |
| 33 | O | H | H | $4-C(OH)C_6H_5$ | H |
| 34 | O | H | H | $4-CHC_6H_5$ | H |
| 35 | O | H | H | $4-CH_2NC_6H_5$ | H |
| 36 | O | H | H | $4-N(CH_2C_6H_5)CH_2$ | H |
| 37 | S | H | $5-NO_2$ | 2-S | Cl |
| 38 | S | H | $5-NO_2$ | 2-S | $CH_3$ |
| 39 | O | H | $5-NO_2$ | 2-O | $CF_3$ |
| 40 | O | H | 2-Br | $5-OCH_2$ | $CH_3$ |
| 41 | O | H | $2-OCH_2$(p-Tol)* | $5-OCH_2$ | $CH_3$ |
| 42 | O | $CH_3$ | 5-Br | $2-OCH_2$ | $CH_3$ |

*p-Tol = 4-methylphenyl

TABLE 3

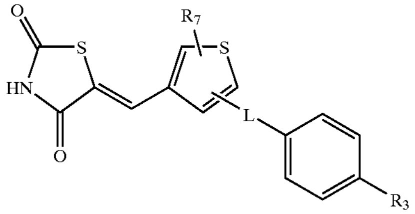

| Compound No. | $R_7$ | L | $R_3$ |
|---|---|---|---|
| 43 | 5-Br | 2-S | Cl |
| 44 | $5-C_6H_5$ | 2-S | Cl |
| 45 | H | 2-S | Cl |
| 51 | 5-Br | 2-SO | Cl |
| 52 | 5-Br | $2-SO_2$ | Cl |

TABLE 3-continued

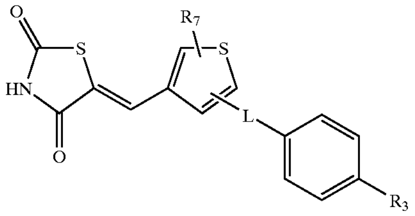

| Compound No. | $R_7$ | L | $R_3$ |
|---|---|---|---|
| 53 | $5-CO_2H$ | 2-S | Cl |
| 54 | $5-CONEt_2$ | 2-S | Cl |
| 55 | 5-CONHPh | 2-S | Cl |
| 56 | 5-CO(N-methyl piperazine) | 2-S | Cl |
| 57 | 5-CO-morpholine | 2-S | Cl |
| 58 | $5-CO_2CH_3$ | 2-S | Cl |

TABLE 4

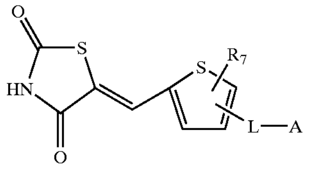

| Compound No. | $R_7$ | L-A |
|---|---|---|
| 59 | H | 3-OPh |
| 60 | H | 4-S-(4-chlorophenyl) |
| 61 | 4-S-(4-chlorophenyl) | 5-S-(4-chlorophenyl) |
| 62 | H | 5-S-(4-chlorophenyl) |
| 63 | 4-Br | 5-S-(4-chlorophenyl) |
| 64 | 4-Br | 5-SO-(4-chlorophenyl) |
| 65 | 4-CO-(4-chlorophenyl) | 5-S-(4-chlorophenyl) |
| 66 | 4-CO-(4-chlorophenyl) | $5-SO_2$-(4-chlorophenyl) |

TABLE 5

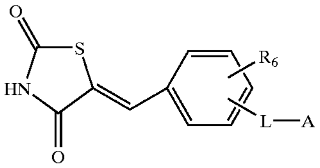

| Compound No. | $R_6$ | L-A |
|---|---|---|
| 67 | $5-NO_2$ | 2-S(4-chlorophenyl) |
| 68 | $5-NO_2$ | 2-SO(4-chlorophenyl) |

TABLE 5-continued

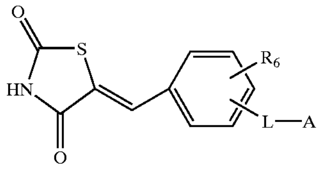

| Compound No. | $R_6$ | L-A |
|---|---|---|
| 69 | 5-$NO_2$ | 2-$SO_2$(4-chlorophenyl) |
| 70 | 5-$NO_2$ | 2-S(3-chlorophenyl) |
| 71 | 5-$NO_2$ | 2-S(2-chlorophenyl) |
| 72 | 5-$NO_2$ | 2-S(3,4-dichlorophenyl) |
| 73 | 5-$NO_2$ | 2-S(4-bromophenyl) |
| 74 | 5-$NO_2$ | 2-S(4-methoxyphenyl) |
| 75 | 5-$NO_2$ | 2-S(4-ethylphenyl) |
| 76 | 5-$NO_2$ | 2-$SCH_2C_6H_5$ |
| 77 | 5-$NO_2$ | 2-$SOCH_2C_6H_5$ |
| 78 | 5-$NO_2$ | 2-$SO_2CH_2C_6H_5$ |
| 79 | 5-$NO_2$ | 2-$SCH_2$(4-chlorophenyl) |
| 80 | 3-$NO_2$ | 4-S(4-bromophenyl) |
| 81 | 3-$NO_2$ | 4-S(4-chlorophenyl) |
| 82 | 3-$NO_2$ | 4-SO(4-methylphenyl) |
| 83 | 3-$NO_2$ | 4-$SO_2$(4-methylphenyl) |
| 84 | 5-$NO_2$ | 2-S-cyclohexyl |
| 85 | 5-$NO_2$ | 2-SO-cyclohexyl |
| 86 | 5-$NO_2$ | 2-$SO_2$-cyclohexyl |
| 87 | 5-Br | 2-S(4-methylphenyl) |
| 88 | 3-Br | 4-S(4-methylphenyl) |
| 89 | 5-(2-pyridyl) | 2-S(4-methylphenyl) |
| 90 | 5-(2-furyl) | 2-S(4-methylphenyl) |
| 91 | 5-(2-furyl) | 2-SO(4-methylphenyl) |
| 92 | 5-(2-thienyl) | 2-S(4-methylphenyl) |
| 93 | 5-(2-thienyl) | 2-SO(4-methylphenyl) |
| 94 | 5-CN | 2-S(4-methylphenyl) |
| 95 | 3-CN | 4-S(4-methylphenyl) |
| 96 | 5-$CH_2OH$ | 2-S(4-methylphenyl) |
| 97 | 5-$COCH_3$ | 2-S(4-methylphenyl) |
| 98 | 5-$COCH_3$ | 2-SO(4-methylphenyl) |
| 99 | 6-$CF_3$ | 2-S(4-methylphenyl) |
| 100 | 5-$CF_3$ | 2-S(4-methylphenyl) |
| 101 | 4-$CF_3$ | 2-S(4-methylphenyl) |
| 102 | 3-$CF_3$ | 2-S(4-methylphenyl) |
| 103 | 3-$CF_3$ | 2-SO(4-methylphenyl) |
| 104 | 5-$OCH_3$ | 2-S(4-methylphenyl) |
| 105 | 4-$OCH_3$ | 2-S(4-methylphenyl) |
| 106 | 5-Cl | 2-S(4-methylphenyl) |
| 107 | 5-Cl | 2-SO(4-methylphenyl) |
| 108 | 4-Cl | 2-S(4-methylphenyl) |
| 109 | 3-Cl | 4-S(4-methylphenyl) |
| 110 | 5-$NO_2$ | 2-$OC_6H_5$ |
| 111 | 5-$NO_2$ | 2-O(4-methylphenyl) |
| 112 | 5-$NO_2$ | 2-O[4-(2',2'-dimethyl-ethyl)phenyl] |
| 113 | 5-$CF_3$ | 2-SO(4-methylphenyl) |
| 114 | 5-CN | 2-SO(4-methylphenyl) |
| 115 | 5-$NO_2$ | 2-S[4-(trifluoromethyl)phenyl] |
| 116 | 5-$NO_2$ | 2-SO(4-methoxyphenyl) |
| 117 | 5-$NO_2$ | 2-SO(2-chlorophenyl) |
| 118 | 5-$CO_2H$ | 2-S(4-methylphenyl) |
| 119 | 5-$NO_2$ | 2-S(2-pyridyl) |
| 120 | 5-$NO_2$ | 2-SO(4-pyridyl) |
| 121 | H | 4-$N(C_6H_5)CH_2C_6H_5$ |
| 122 | 5-$NO_2$ | 2-S(2-hydroxyethyl) |
| 123 | 5-$NO_2$ | 2-N(propyl)$_2$ |
| 124 | 5-$NO_2$ | a |
| 125 | 5-$NO_2$ | b |
| 126 | 2-$OCH_3$ | 4-OH |
| 127 | H | 2-$OCF_3$ |
| 129 | 5-$NO_2$ | 2-S(4-carboxylphenyl) |
| 130 | 5-$NO_2$ | c |
| 131 | 5-$NO_2$ | d |
| 132 | 5-$NO_2$ | 2-S(4-methylthiophenyl) |
| 133 | 5-$NO_2$ | 2-SO(4-ethylphenyl) |
| 134 | 5-$NO_2$ | 2-SO(3-chlorophenyl) |
| 135 | 5-$NO_2$ | 2-SO(3,4-dichlorophenyl) |
| 136 | 3-$NO_2$ | 4-S(4-bromophenyl) |
| 137 | 3-$OC_6H_5$ | 4-S(4-methylphenyl) |

TABLE 5-continued

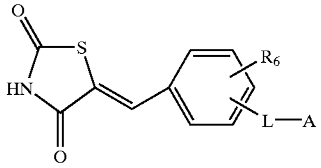

| Compound No. | $R_6$ | L-A |
|---|---|---|
| 138 | 3-$OCH_3$ | 4-S(4-methylphenyl) |
| 139 | 5-$CO_2CH_2C_6H_5$ | 2-S(4-methylphenyl) |
| 140 | 3-CN | 4-SO(4-methylphenyl) |
| 141 | 3-Cl | 4-SO(4-methylphenyl) |
| 142 | 5-$CH(OCH_3)_2$ | 2-S(4-methylphenyl) |
| 143 | 3-Br | 4-SO(4-methylphenyl) |
| 144 | 5-CHO | 2-S(4-methylphenyl) |
| 145 | 5-$CH{=}CHCO_2C(CH_3)_3$ | 2-S(4-methylphenyl) |
| 146 | 5-$CH{=}CHCO_2H$ | 2-S(4-methylphenyl) |
| 147 | 3-$CF_3$ | 4-S(4-methylphenyl) |
| 148 | 3-$CF_3$ | 4-SO(4-methylphenyl) |
| 149 | 5-$CON(C_2H_5)_2$ | 2-S(4-methylphenyl) |
| 150 | 5-$CON(C_2H_5)_2$ | 2-SO(4-methylphenyl) |
| 151 | e | 2-S(4-methylphenyl) |
| 152 | 3-$COCH_3$ | 2-S(3,4-dichlorophenyl) |
| 153 | 3-$COCH_3$ | 2-SO(3,4-dichlorophenyl) |
| 154 | 5-$NO_2$ | 2-S(2,3 -dichlorophenyl) |
| 155 | 5-$NO_2$ | 2-S(2,4-dichlorophenyl) |
| 156 | 5-$NO_2$ | 2-SO(2,3-dichlorophenyl) |
| 157 | 5-$NO_2$ | 2-SO(2,4-dichlorophenyl) |
| 158 | 5-$NO_2$ | 2-$SO_2$(2,3-dichlorophenyl) |
| 159 | 5-$NO_2$ | 2-$SO_2$(2,4-dichlorophenyl) |
| 160 | 5-$NO_2$ | 2-S(4-hydroxyphenyl) |
| 161 | 5-$NO_2$ | 2-S(3,4-dimethylphenyl) |
| 162 | 5-$NO_2$ | 2-$SO_2$(3,4-dichlorophenyl) |
| 163 | 3-$NO_2$ | 4-SO(4-chlorophenyl) |
| 164 | 3-$NO_2$ | 4-S(4-ethylphenyl) |
| 165 | 3-$NO_2$ | 4-SO(4-ethylphenyl) |
| 166 | 3-$NO_2$ | 2-$SO_2$(4-ethylphenyl) |
| 167 | 3-$NO_2$ | 4-S(3,4-dichlorophenyl) |
| 168 | 3-$NO_2$ | 4-SO(3,4-dichlorophenyl) |
| 169 | 5-$NO_2$ | 2-SO(2,3-dimethylphenyl) |
| 170 | 5-$NO_2$ | 2-$SO_2$(2,3-dimethylphenyl) |
| 171 | 5-$NO_2$ | f |

a =

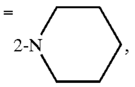

b =

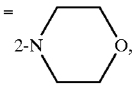

c =

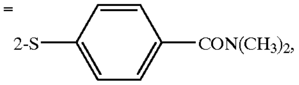

d =

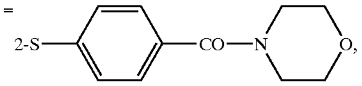

e =

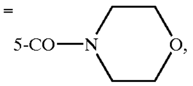

f =

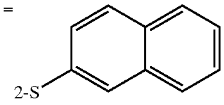

TABLE 6

| Compound No. | |
|---|---|
| 128 | 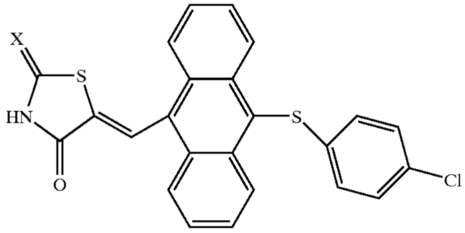 |

III. Synthesis of Telomerase Inhibitors

The compounds of the present invention can be synthesized using techniques and materials known to those of skill in the art, such as described, for example, in March, ADVANCED ORGANIC CHEMISTRY $4^{th}$ Ed., (Wiley 1992); Carey and Sundberg, ADVANCED ORGANIC CHEMISTRY $3^{rd}$ Ed., Vols. A and B (Plenum 1992), and Green and Wuts, PROTECTIVE GROUPS IN ORGANIC SYNTHESIS $2^{nd}$ Ed. (Wiley 1991). Starting materials for the compounds of the invention may be obtained using standard techniques and commercially available precursor materials, such as those available from Aldrich Chemical Co. (Milwaukee, Wis.), Sigma Chemical Co. (St. Louis, Miss.), Lancaster Synthesis (Windham, N.H.), Apin Chemicals, Ltd. (New Brunswick, N.J.), Ryan Scientific (Columbia, S.C.), Maybridge (Cornwall, England), Arcos (Pittsburgh, Pa.), and Trans World Chemicals (Rockville, Md.).

The procedures described herein for synthesizing the compounds of the invention may include one or more steps of protection and deprotection (e.g., the formation and removal of acetal groups). In addition, the synthetic procedures disclosed below can include various purifications, such as column chromatography, flash chromatography, thin-layer chromatography (TLC), recrystallization, distillation, high-pressure liquid chromatography (HPLC) and the like. Also, various techniques well known in the chemical arts for the identification and quantification of chemical reaction products, such as proton and carbon-13 nuclear magnetic resonance ($^1H$ and $^{13}C$ NMR), infrared and ultraviolet spectroscopy (IR and UV), X-ray crystallography, elemental analysis (EA), HPLC and mass spectroscopy (MS) can be used as well. Methods of protection and deprotection, purification, identification and quantification are well known in the chemical arts.

Compounds of the class represented by formulas I, II and III can be synthesized using General Procedure 1 and General Procedure 2 described in detail in the Examples below. Detailed protocols from which the individual compounds described above can be synthesized are also provided in the Examples. The compounds of formula IV, where L is SO or $SO_2$ can be synthesised by oxidizing the corresponsing S compound in an inert solvent. The inert solvent may be dichloromethane, methanol, tetrahydrofuran, ether, hexane, toluene, cyclohexane, or the like, and mixtures thereof. The oxidizing agent may be m-chloroperbenzoic acid, hydrogen peroxide, or the like. The reaction is carried out at a temperature in the range of about −78° C. to the boiling point of the solvent, preferably from about 0° C. to about 30° C. for about 0.5 to about 12 hours.

IV. Anti-Tumor Activity of the Telomerase Inhibitors of the Invention

The compounds of the present invention demonstrate inhibitory activity against telomerase activity in vivo, as has been and can be demonstrated as described below. The in vitro activities of the compounds of the invention can also be demonstrated using the methods described herein. As used herein, the term “ex vivo” refers to tests performed using living cells in tissue culture.

One method used to identify compounds of the invention that inhibit telomerase activity involves placing cells, tissues, or preferably a cellular extract or other preparation containing telomerase in contact with several known concentrations of a test compound in a buffer compatible with telomerase activity. The level of telomerase activity for each concentration of test compound is measured and the $IC_{50}$ (the concentration of the test compound at which the observed activity for a sample preparation was observed to fall one-half of its original or a control value) for the compound is determined using standard techniques. Other methods for determining the inhibitory concentration of a compound of the invention against telomerase can be employed as will be apparent to those of skill in the art based on the disclosure herein.

With the above-described methods, $IC_{50}$ values for several of the compounds of the present invention were determined, and found to be below 100 $\mu$M.

With respect to the treatment of malignant diseases using the compounds described herein, compounds of the present invention are expected to induce crisis in telomerase-positive cell lines. Treatment of telomerase-positive cell lines, such as HEK-293 and HeLa cells, with a compound of the invention is also expected to induce a reduction of telomere length in the treated cells.

Compounds of the invention are also expected to induce telomere reduction during cell division in human tumor cell lines, such as the ovarian tumor cell lines OVCAR-5 and SK-OV-3. Importantly, however, in normal human cells used as a control, such as BJ cells of fibroblast origin, the observed reduction in telomere length is expected to be no different from cells treated with a control substance, e.g., dimethyl sulfoxide (DMSO). The compounds of the invention also are expected to demonstrate no significant cytotoxic effects at concentrations below about 5 $\mu$M in the normal cells.

In addition, the specificity of the compounds of the present invention for telomerase can be determined by comparing their activity ($IC_{50}$) with respect to telomerase to other enzymes having similar nucleic acid binding or modifying activity similar to telomerase in vitro. Such enzymes include DNA Polymerase I, HeLa RNA Polymerase II, T3 RNA Polymerase, MMLV Reverse Transcriptase, Topoisomerase I, Topoisomerase II, Terminal Transferase and Single-Stranded DNA Binding Protein (SSB). Compounds having lower $IC_{50}$ values for telomerase as compared to the $IC_{50}$ values toward the other enzymes being screened are said to possess specificity for telomerase.

In vivo testing can also be performed using a mouse xenograft model, for example, in which OVCAR-5 tumor cells are grafted onto nude mice, in which mice treated with a compound of the invention are expected to have tumor masses that, on average, may increase for a period following the initial dosing, but will begin to shrink in mass with continuing treatment. In contrast, mice treated with a control (e.g., DMSO) are expected to have tumor masses that continue to increase.

From the foregoing those skilled in the art will appreciate that the present invention also provides methods for selecting treatment regimens involving administration of a compound of the invention. For such purposes, it may be helpful to perform a terminal restriction fragment (TRF) analysis in which DNA from tumor cells is analyzed by digestion with restriction enzymes specific for sequences other than the telomeric $(T_2\ AG_3)_N$ sequence. Following digestion of the DNA, gel electrophoresis is performed to separate the restriction fragments according to size. The separated fragments are then probed with nucleic acid probes specific for telomeric sequences to determine the lengths of the terminal fragments containing the telomere DNA of the cells in the sample. By measuring the length of telomeric DNA, one can estimate how long a telomerase inhibitor should be administered and whether other methods of therapy (e.g., surgery, chemotherapy and/or radiation) should also be employed. In addition, during treatment, one can test cells to determine whether a decrease in telomere length over progressive cell divisions is occurring to demonstrate treatment efficacy.

V. Telomerase Inhibiting Compositions and Methods for Treating Diseases

The present invention also provides pharmaceutical compositions for inhibiting cell proliferation of telomerase positive cells, and treating cancer and other conditions in which inhibition of telomerase is an effective therapy. These compositions include a therapeutically effective amount of a telomerase inhibiting compound of the invention in a pharmaceutically acceptable carrier or salt.

In one embodiment, the present invention provides methods, compounds and compositions for inhibiting a telomerase enzyme, inhibiting proliferation of telomerase positive cells, and for treating cancer in a mammal. The compositions of the invention include a therapeutically effective amount of a compound of formulas I to V (or a pharmaceutically acceptable salt thereof) in a pharmaceutically acceptable carrier. The compounds and compositions of the present invention may also be used for the treatment of other telomerase mediated conditions or diseases, such as, for example, other hyperproliferative or autoimmune disorders such as psoriasis, rheumatoid arthritis, immune system disorders requiring immune system suppression, immune system reactions to poison ivy or poison oak, and the like.

In addition, it will be appreciated that therapeutic benefits for treatment of cancer can be realized by combining a telomerase inhibitor of the invention with other anti-cancer agents, including other inhibitors of telomerase such as described in U.S. Pat. Nos. 5,656,638, 5,760,062, 5,767,278, 5,770,613 and 5,863,936. The choice of such combinations will depend on various factors including, but not limited to, the type of disease, the age and general health of the patient, the aggressiveness of disease progression, the TRF length and telomerase activity of the diseased cells to be treated and the ability of the patient to tolerate the agents that comprise the combination. For example, in cases where tumor progression has reached an advanced state, it may be advisable to combine a telomerase inhibiting compound of the invention with other agents and therapeutic regimens that are effective at reducing tumor size (e.g. radiation, surgery, chemotherapy and/or hormonal treatments). In addition, in some cases it may be advisable to combine a telomerase inhibiting agent of the invention with one or more agents that treat the side effects of a disease, e.g., an analgesic, or agents effective to stimulate the patient's own immune response (e.g., colony stimulating factor).

In one such method, a pharmaceutical formulation comprises a telomerase inhibitor of the invention with an anti-angiogenesis agent, such as fumagillin, fumagillin derivatives, or AGM-1470. The latter compound is available from Takeda Chemical Industries, Ltd., while the former compounds are described in Ingber, et al., Dec. 6, 1990, "Synthetic analogues of fumagillin that inhibit angiogenesis and suppress tumor growth", Nature 348:555–557. Other combinations may include, but are not limited to, a telomerase inhibitor of the invention in addition to one or more antineoplastic agents or adjuncts (e.g., folinic acid or mesna).

Antineoplastic agents suitable for combination with the compounds of the present invention include, but are not limited to, alkylating agents including alkyl sulfonates such as busulfan, improsulfan and piposulfan; aziridines, such as a benzodizepa, carboquone, meturedepa and uredepa; ethylenimines and methylmelamines such as altretamine, triethylenemelamine, triethylenephosphoramide, triethylenethiophosphoramide and trimethylolmelamine; nitrogen mustards such as chlorambucil, chlornaphazine, cyclophosphamide, estramustine, iphosphamide, mechlorethamine, mechlorethamine oxide hydrochloride, melphalan, novembichine, phenesterine, prednimustine, trofosfamide, and uracil mustard; nitroso ureas, such as carmustine, chlorozotocin, fotemustine, lomustine, nimustine and ranimustine. Additional agents include dacarbazine, mannomustine, mitobronitol, mitolactol and pipobroman. Still other classes of relevant agents include antibiotics, hormonal antineoplastics and antimetabolites. Yet other combinations will be apparent to those of skill in the art.

Additional agents suitable for combination with the compounds of the present invention include protein synthesis inhibitors such as abrin, aurintricarboxylic acid, chloramphenicol, colicin E3, cycloheximide, diphtheria toxin, edeine A, emetine, erythromycin, ethionine, fluoride, 5-fluorotryptophan, fusidic acid, guanylyl methylene diphosphonate and guanylyl imidodiphosphate, kanamycin, kasugamycin, kirromycin, and O-methyl threonine. Additional protein synthesis inhibitors include modeccin, neomycin, norvaline, pactamycin, paromomycine, puromycin, ricin, __-sarcin, shiga toxin, showdomycin, sparsomycin, spectinomycin, streptomycin, tetracycline, thiostrepton and trimethoprim. Inhibitors of DNA synthesis, including alkylating agents such as dimethyl sulfate, mitomycin C, nitrogen and sulfur mustards, MNNG and NMS; intercalating agents such as acridine dyes, actinomycins, adriamycin, anthracenes, benzopyrene, ethidium bromide, propidium diiodide-intertwining, and agents such as distamycin and netropsin, can also be combined with compounds of the present invention in pharmaceutical compositions. DNA base analogs such as acyclovir, adenine $\beta$-1-D-arabinoside, amethopterin, aminopterin, 2-aminopurine, aphidicolin, 8-azaguanine, azaserine, 6-azauracil, 2'-azido-2'-deoxynucleosides, 5-bromodeoxycytidine, cytosine $\beta$-1-D-arabinoside, diazooxynorleucine, dideoxynucleosides, 5-fluorodeoxycytidine, 5-fluorodeoxyuridine, 5-fluorouracil, hydroxyurea and 6-mercaptopurine also can be used in combination therapies with the compounds of the invention. Topoisomerase inhibitors, such as coumermycin, nalidixic acid, novobiocin and oxolinic acid, inhibitors of cell division, including colcemide, colchicine, vinblastine and vincristine; and RNA synthesis inhibitors including actinomycin D, $\alpha$-amanitine and other fungal amatoxins, cordycepin (3'-deoxyadenosine), dichlororibofuranosyl benzimidazole, rifampicine, streptovaricin and streptolydigin also can be combined with the compounds of the invention to provide pharmaceutical compositions.

In another embodiment, the present invention includes compounds and compositions in which a telomerase inhibitor is either combined with or covalently bound to a cytotoxic agent bound to a targeting agent, such as a monoclonal antibody (e.g., a murine or humanized monoclonal antibody). It will be appreciated that the latter combination may allow the introduction of cytotoxic agents into cancer cells with greater specificity. Thus, the active form of the cytotoxic agent (i.e., the free form) will be present only in cells targeted by the antibody. Of course, the telomerase inhibitors of the invention may also be combined with monoclonal antibodies that have therapeutic activity against cancer.

In addition to the application of the telomerase inhibitors of the present invention to the treatment of mammalian diseases characterized by telomerase activity, telomerase inhibitors such as those disclosed herein, can be applied to agricultural phytopathogenic organisms that are characterized by telomerase activity. These organisms include nematodes such as *Ceanorhabditis elegans,* in which telomerase activity has been found, and in fungi which are expected to have telomerase activity based on the determination that the DNA of the fungus *Ustilago maydis* exhibits telomeres having the tandem TTAGGG (SEQ ID NO:1) repeats that are maintained by telomerase. Also, protozoans have TTAGGG (SEQ ID NO:1) telomeres and cause human disease. The telomerase-inhibiting compounds of the invention can be administered to plants and soil infected with phytopathogenic organisms having telomerase activity alone, or in combination with other telomerase-inhibiting agents and/or other agents used to control plant diseases. The determination of the compositions used to control such phytopathogenic organisms and the appropriate modes of delivering such compositions will be known to those having skill in the agricultural arts.

The determination that nematodes, protozoans and possibly fungi have telomerase activity also indicates that the telomerase inhibitors provided by the present invention can be used to treat nematode infections in humans and animals of veterinary interest such as dogs and cats. Nematode infection in humans and animals often is in the form of hookworm or roundworm infection and leads to a host of deadly secondary illnesses such as meningitis, myocarditis, and various neurological diseases. Thus, it will be appreciated that administration of the telomerase-inhibiting compounds such as those of the invention, alone, or in combination with other telomerase-inhibiting agents and/or other therapeutic agents, can be used to control nematode, protozoan and fungal infections in humans and animals.

In general, a suitable effective dose of a compound of the invention will be in the range of 0.001 to 1000 milligram (mg) per kilogram (kg) of body weight of the recipient per day, preferably in the range of 0.001 to 100 mg per kg of body weight per day, more preferably between about 0.1 and 100 mg per kg of body weight per day and still more preferably in the range of between 0.1 to 10 mg per kg of body weight per day. The desired dosage is preferably presented in one, two, three, four, or more subdoses administered at appropriate intervals throughout the day, or by the action of a continuous pump. These subdoses can be administered as unit dosage form, for example, containing 5 to 10,000 mg, preferably 10 to 1000 mg of active ingredient per unit dosage from. Preferably, the dosage is presented once per day at a dosing at least equal to TID, or is administered using a continuous pump delivery system.

The composition used in these therapies can be in a variety of forms. These include, for example, solid, semi-solid, and liquid dosage forms, such as tablets, pills, powders, liquid solutions or suspensions, liposomes, and injectable and infusible solutions. The preferred form depends on the intended mode of administration and therapeutic application. The compositions also preferably include conventional pharmaceutically acceptable carriers and adjuvants, as is well known to those of skill in the art. See, e.g., REMINGTON'S PHARMACEUTICAL SCIENCES, Mack Publishing Co.: Easton, Pa., 17th Ed. (1985). Preferably, administration will be by oral or parenteral (including subcutaneous, intramuscular, intravenous, and intradernal) routes. More preferably, the route of administration will be oral. The therapeutic methods and agents of this invention can of course be used concomitantly or in combination with other methods and agents for treating a particular disease or disease condition.

While it is possible to administer the active ingredient of this invention alone, it is preferable to present a therapeutic agent as part of a pharmaceutical formulation or composition. The formulations of the present invention comprise at least one telomerase activity-inhibiting compound of this invention in a therapeutically or pharmaceutically effective dose together with one or more pharmaceutically or therapeutically acceptable carriers and optionally other therapeutic ingredients. Various considerations for preparing such formulations are described, e.g., in Gilman et al. (eds.) GOODMAN AND GILMAN'S: THE PHARMACOLOGICAL BASES OF THERAPEUTICS, 8th Ed., Pergamon Press (1990); and REMINGTON'S supra. Methods for administration are discussed therein, e.g., for oral, intravenous, intraperitoneal, intramuscular, and other forms of administration. Typically, methods for administering pharmaceutical compositions will be either topical, parenteral, or oral administration methods for prophylactic and/or therapeutic treatment. Oral administration is preferred. The pharmaceutical compositions can be administered in a variety of unit dosage forms depending upon the method of administration. As noted above, unit dosage forms suitable for oral administration include powders, tablets, pills, and capsules.

One can use topical administration to deliver a compound of the invention by percutaneous passage of the drug into the systemic circulation of the patient. The skin sites include anatomic regions for transdermally administering the drug, such as the forearm, abdomen, chest, back, buttock, and mastoidal area. The compound is administered to the skin by placing on the skin either a topical formulation comprising the compound or a transdermal drug delivery device that administers the compound. In either embodiment, the delivery vehicle is designed, shaped, sized, and adapted for easy placement and comfortable retention on the skin.

A variety of transdermal drug delivery devices can be employed with the compounds of this invention. For example, a simple adhesive patch comprising a backing material and an acrylate adhesive can be prepared. The drug and any penetration enhancer can be formulated into the adhesive casting solution. The adhesive casting solution can be cast directly onto the backing material or can be applied to the skin to form an adherent coating. See, e.g., U.S. Pat. Nos. 4,310,509; 4,560,555; and 4,542,012.

In other embodiments, the compound of the invention will be delivered using a liquid reservoir system drug delivery device. These systems typically comprise a backing material, a membrane, an acrylate based adhesive, and a release liner. The membrane is sealed to the backing to form a reservoir. The drug or compound and any vehicles, enhancers, stabilizers, gelling agents, and the like are then incorporated into the reservoir. See, e.g., U.S. Pat. Nos. 4,597,961; 4,485,097; 4,608,249; 4,505,891; 3,843,480; 3,948,254; 3,948,262; 3,053,255; and 3,993,073.

Matrix patches comprising a backing, a drug/penetration enhancer matrix, a membrane, and an adhesive can also be employed to deliver a compound of the invention transdermally. The matrix material typically will comprise a polyurethane foam. The drug, any enhancers, vehicles, stabilizers, and the like are combined with the foam precursors. The foam is allowed to cure to produce a tacky, elastomeric matrix which can be directly affixed to the backing material. See, e.g., U.S. Pat. Nos. 4,542,013; 4,460,562; 4,466,953; 4,482,534; and 4,533,540.

Also included within the invention are preparations for topical application to the skin comprising a compound of the invention, typically in concentrations in the range from about 0.001% to 10%, together with a non-toxic, pharmaceutically acceptable topical carrier. These topical preparations can be prepared by combining an active ingredient according to this invention with conventional pharmaceutical diluents and carriers commonly used in topical dry, liquid, and cream formulations. Ointment and creams may, for example, be formulated with an aqueous or oily base with the addition of suitable thickening and/or gelling agents. Such bases may include water and/or an oil, such as liquid paraffin or a vegetable oil, such as peanut oil or castor oil. Thickening agents that may be used according to the nature of the base include soft paraffin, aluminum stearate, cetostearyl alcohol, propylene glycol, polyethylene glycols, woolfat, hydrogenated lanolin, beeswax, and the like.

Lotions may be formulated with an aqueous or oily base and will, in general, also include one or more of the following: stabilizing agents, emulsifying agents, dispersing agents, suspending agents, thickening agents, coloring agents, perfumes, and the like. Powders may be formed with the aid of any suitable powder base, e.g., talc, lactose, starch, and the like. Drops may be formulated with an aqueous base or non-aqueous base also comprising one or more dispersing agents, suspending agents, solubilizing agents, and the like. Topical administration of compounds of the invention may also be preferred for treating diseases such as skin cancer and fungal infections of the skin (pathogenic fungi typically express telomerase activity).

The topical pharmaceutical compositions according to this invention may also include one or more preservatives or bacteriostatic agents, e.g., methyl hydroxybenzoate, propyl hydroxybenzoate, chlorocreosol, benzalkonium chlorides, and the like. The topical pharmaceutical compositions also can contain other active ingredients such as antimicrobial agents, particularly antibiotics, anesthetics, analgesics, and antipruritic agents.

The compounds of the present invention can also be delivered through mucosal membranes. Transmucosal (i.e., sublingual, buccal, and vaginal) drug delivery provides for an efficient entry of active substances to systemic circulation and reduces immediate metabolism by the liver and intestinal wall flora. Transmucosal drug dosage forms (e.g., tablet, suppository, ointment, pessary, membrane, and powder) are typically held in contact with the mucosal membrane and disintegrate and/or dissolve rapidly to allow immediate systemic absorption. Note that certain such routes may be used even where the patient is unable to ingest a treatment composition orally. Note also that where delivery of a telomerase inhibitor of the invention would be enhanced, one can select a composition for delivery to a mucosal membrane, e.g., in cases of colon cancer one can use a suppository to deliver the telomerase inhibitor.

For delivery to the buccal or sublingual membranes, typically an oral formulation, such as a lozenge, tablet, or capsule, will be used. The method of manufacture of these formulations is known in the art, including, but not limited to, the addition of the pharmacological agent to a pre-manufactured tablet; cold compression of an inert filler, a binder, and either a pharmacological agent or a substance containing the agent (as described in U.S. Pat. No. 4,806,356); and encapsulation. Another oral formulation is one that can be applied with an adhesive, such as the cellulose derivative hydroxypropyl cellulose, to the oral mucosa, for example as described in U.S. Pat. No. 4,940,587. This buccal adhesive formulation, when applied to the buccal mucosa, allows for controlled release of the pharmacological agent into the mouth and through the buccal mucosa.

Parenteral administration is generally characterized by injection, either subcutaneously, intramuscularly, or intravenously. Thus, this invention provides compositions for intravenous administration that comprise a solution of a compound of the invention dissolved or suspended in an acceptable carrier. Injectables can be prepared in conventional forms, either as liquid solutions or suspensions, solid forms suitable for solution or suspension in liquid prior to injection, or as emulsions. Suitable excipients are, for example, water, buffered water, saline, dextrose, glycerol, ethanol, or the like. These compositions will be sterilized by conventional, well known sterilization techniques, such as sterile filtration. The resulting solutions can be packaged for use as is or lyophilized, the lyophilized preparation being combined with a sterile solution prior to administration. In addition, if desired, the pharmaceutical compositions to be administered may also contain minor amounts of non-toxic auxiliary substances, such as wetting or emulsifying agents, pH buffering agents and the like, such as for example, sodium acetate, sorbitan monolaurate, triethanolamine oleate, etc. Such formulations will be useful in treating ovarian cancers.

Another method of parenteral administration employs the implantation of a slow-release or sustained-release system, such that a constant level of dosage is maintained. See, e.g., U.S. Pat. No. 3,710,795.

Liquid pharmaceutically administrable compositions can, for example, be prepared by dissolving, dispersing, etc., an active compound as defined above and optional pharmaceutical adjuvants in an excipient, such as, for example, water, saline, aqueous dextrose, glycerol, ethanol, olive oil, and other lipophilic solvents, and the like, to form a solution or suspension. If desired, the pharmaceutical composition to be administered may also contain minor amounts of nontoxic auxiliary substances, such as wetting or emulsifying agents, pH buffering agents, and the like, for example, sodium acetate, sorbitan monolaurate, triethanolamine sodium acetate, triethanolamine oleate, etc. Actual methods of preparing such dosage forms are known and will be apparent to those skilled in this art; for example, see REMINGTON'S PHARMACEUTICAL SCIENCES, supra. The composition or formulation to be administered will contain an effective amount of an active compound of the invention.

For solid compositions, conventional nontoxic solid carriers can be used and include, for example, pharmaceutical grades of mannitol, lactose, starch, magnesium stearate, sodium saccharin, talcum, cellulose, glucose, sucrose, magnesium carbonate, and the like. For oral administration, a pharmaceutically acceptable nontoxic composition is formed by incorporating any of the normally employed excipients, such as those carriers previously listed, and generally 0.1–95% of active ingredient, preferably about 20%.

The compositions containing the compounds of the invention can be administered for prophylactic and/or therapeutic treatments. In therapeutic applications, compositions are administered to a patient already suffering from a disease, as described above, in an amount sufficient to cure or at least partially arrest the symptoms of the disease and its complications. An amount adequate to accomplish this is defined as a "therapeutically effective amount or dose." Amounts effective for this use will depend on the severity of the disease and the weight and general state of the patient.

In addition to internal (in vivo) administration, the compounds and compositions of the invention may be applied ex vivo to achieve therapeutic effects, as for example, in the case of a patient suffering from leukemia. In such an application, cells to be treated, e.g., blood or bone marrow cells, are removed from a patient and treated with a pharmaceutically effective amount of a compound of the invention. The cells are returned to the patient following treatment. Such a procedure can allow for exposure of cells to concentrations of therapeutic agent for longer periods or at higher concentrations than otherwise available.

Once improvement of the patient's conditions has occurred, as, for example, by the occurrence of remission in the case of a cancer patient, a maintenance dose is administered if necessary. Subsequently, the dosage or the frequency of administration, or both, can be reduced, as a function of the systems, to a level at which the improved condition is retained. When the symptoms have been alleviated to the desired level, treatment can cease. Patients can, however, require additional treatment upon any recurrence of the disease symptoms.

In prophylactic applications (e.g. chemoprevention), compositions containing the compounds of the invention are administered to a patient susceptible to or otherwise at risk of a particular disease. Such an amount is defined to be a "prophylactically effective amount or dose." In this use, the precise amounts again depend on the patient's state of health and weight.

As will be apparent to those of skill in the art upon reading of this disclosure, the present invention provides valuable reagents relating to human and mammalian telomerase. The above description of necessity provides a limited and merely illustrative sampling of specific compounds, and should not be construed as limiting the scope of the invention. Other features and advantages of the invention will be apparent from the following examples and claims.

EXAMPLES

The following examples describe specific aspects of the invention to illustrate the invention and also provide a description of methods that can be used to identify and test compounds that inhibit the activity of telomerase to aid those of skill in the art in understanding and practicing the invention. The examples should not be construed as limiting the invention in any manner.

In the following Examples 1–24 the following general procedure was employed:

General Procedure 1: Coupling 2,4-thiazolidinedione (TZD) to Aldehyde

A solution of appropriately substituted aldehyde (1 eq.), 2,4-thiazolidinedione (1.5 eq.) and piperidine (1.5 eq.) in EtOH was heated to 90° C. for 2–16 h. The resulting solution was acidified with aqueous 1N HCl. The resulting solid was either filtered and washed with water and/or ether to afford pure product. Alternatively, the acidified solution was extracted with chloroform or ethyl acetate, organic phase washed with water, dried over $Na_2SO_4$ and concentrated under reduced pressure to yield crude product as a solid that was purified either by column chromatography or recrystallization from appropriate solvent system.

Reactions were generally run on a 0.5 molar scale.

Example 1

Preparation of 5-(2-(3,4-Dichlorophenyl)benzylidene)thiazolidine-2,4-dione

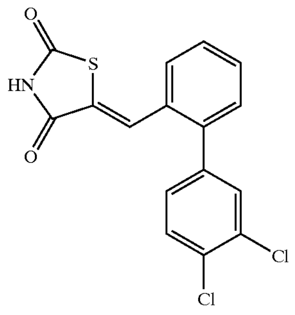

Step A: Preparation of Aldehyde

To a solution of 2-bromobenzaldehyde (1 eq.) and 3,4-dichlorophenylboronic acid (1.2 eq.) in acetonitrile was added $K_2CO_3$ (1.5 eq.) followed by addition of $Pd(PPh_3)_4$ (cat.). The reaction was heated to 75° C. with stirring for 16 h at which time the reaction was diluted with EtOAc, washed with water, dried over $Na_2SO_4$ and concentrated under reduced pressure to yield crude aldehyde that was purified by column chromatography.

Step B. General Procedure 1

General Procedure 1 was then followed to obtain 5-(2-(3,4-Dichlorophenyl)benzylidene)thiazolidine-2,4-dione.

NMR (DMSO-$d_6$, δ): 7.70 (d, 1H), 7.76 (d, 1H), 7.59–7.42 (m, 5H), 7.28 (dd, 1H)

MS(ESI) Calcd. 349. Found 348 $(M-H)^-$.

Example 2

Preparation of 5-(3-(3,4-Dichlorophenyl)benzylidene)thiazolidine-2,4-dione

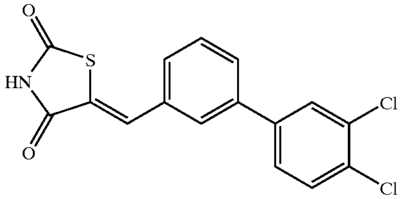

Step A: Preparation of Aldehyde

The requisite aldehyde was prepared from 3-bromobenzaldehyde using the procedure of Example 1, Step A.

Step B. General Procedure 1

General Procedure 1 was then followed to obtain 5-(3-(3,4-Dichlorophenyl)benzylidene)-thiazolidine-2,4-dione.

NMR (DMSO-$d_6$, δ): 7.98 (s, 1H), 7.94 (s, 1H), 7.84 (s, 1H), 7.79 (d, 1H), 7.74–7.66 (m, 2H), 7.63–7.53 (m, 2H)

MS(ESI) Cadcd. 349, found 348 $(M-H)^-$.

Example 3

Preparation of 5-(4-(3,4-Dichlorobenzyloxy)benzylidene)thiazolidine-2,4-dione

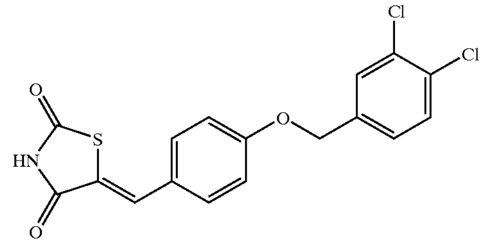

Step A: Preparation of Aldehyde

To a solution of 4-hydroxybenzaldehyde in acetonitrile was added $K_2CO_3$ (1.5 eq.) followed by addition of 3,4-dichlorobenzylchloride (3 eq.). The resulting reaction mixture was heated to 90° C. for 2–16 h at which time the precipitate was filtered off. The filtrate was diluted with EtOAc, washed with water, dried over $Na_2SO_4$ and concentrated under reduced pressure to provide crude product. This product was purified by recrystallization from $CH_2Cl_2$/hexane solvent system to yield pure aldehyde.

Step B. General Procedure 1

General Procedure 1 was then followed to obtain 5-(4-(3,4-Dichlorobenzyloxy)benzylidene)thiazolidine-2,4-dione.

NMR (DMSO-$d_6$, δ): 7.69 (d, 2H), 7.62(d, 1H), 7.52 (d, 2H), 7.41 (d, 1H), 7.12 (d, 2H), 5.20 (s, 2H).

MS (ESI) Calcd. 379. Found 378 $(M-H)^-$.

Example 4

Preparation of 5-(2-(3,4-Dichlorobenzyloxy)benzylidene)thiazolidine-2,4-dione

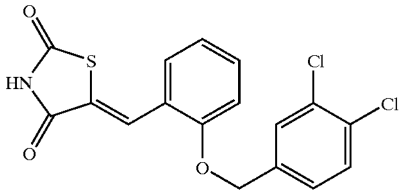

Step A: Preparation of Aldehyde

The requisite aldehyde was prepared from 2-hydroxybenzaldehyde using the procedure of Example 3, Step A.

Step B. General Procedure 1

General Procedure 1 was then followed to obt a in 5-(2-(3,4-Dichlorobenzyloxy)benzylidene)thiazolidine-2,4-dione.

Example 5

Preparation of 5-(4-(3,4-Dichlorobenzamido)benzylidene)thiazolidine-2,4-dione

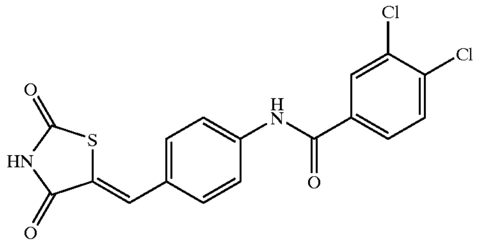

Step A: Preparation of aldehyde

To a solution of 4-nitrobenzaldehyde (1 eq.) in trimethylorthoformate was added PTSA (cat.) and the resulting mixture was heated to reflux for 3–5 h at which time the reaction mixture was concentrated under reduced pressure. The residue was dissolved in ether, washed with $NaHCO_3$ followed by water, dried over $Na_2SO_4$ and concentrated under reduced pressure to yield dimethyl acetal.

The crude dimethylacetal was dissolved in EtOH followed by addition of Raney Ni (cat). To this mixture at 0° C. was added hydrazine hydrate (5 eq) drop wise over 15 min to keep the effervescence under control. The reaction was warmed to room temp, stirred for additional 3 h followed by filtration of catalyst. The filtrate was concentrated under reduced pressure. The residue was redissolved in EtOAc, washed with water, dried over $Na_2SO_4$ and concentrated under reduced pressure to yield crude 4-aminobenzaldehydedimethylacetal.

To a solution of 4-aminobenzaldehydedimethylacetal in $CH_2Cl_2$ at 0° C. was added TEA (2 eq.) followed by addition of 3,4-dichlorobenzoylchloride (1.5 eq). The resulting mixture was stirred for 2–16 h at room temperature at which time it was diluted with water and EtOAc. The organic layer was separated, washed with water followed by concentration under reduced pressure. The residue was dissolved in $CHCl_3$ followed by addition of 2N aq. HCl. This mixture was stirred for 1 h at which time the organic phase was separated, washed with sat. $NaHCO_3$, water, dried over $Na_2SO_4$ followed by concentration under reduced pressure to yield crude aldehyde that was purified by either column chromatography or recrystallization from appropriate solvent system to yield pure 4-(3,4-Dichlorobenzamido)benzaldehyde.

Step B. General Procedure 1

General Procedure 1 was then followed to obtain 5-(2-(3,4-Dichlorobenzyloxy)benzylidene)thiazolidine-2,4-dione.

NMR (DMSO-$d_6$, δ): 12.50 (br s, 1H), 10.60 (s, 1H), 8.18 (d, 1H), 7.90–7.86 (m, 3H), 7.78 (d, 1H), 7.70 (s, 1H), 7.56 (d, 1H).

MS(ESI) Calcd. 392. Found 391 $(M-H)^-$.

Example 6

Preparation of 5-(4-(N-3,4-Dichlorophenyureido) benzylidene)thiazolidine-2,4-dione

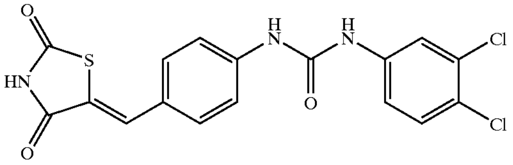

Step A: Preparation of Aldehyde

To a solution of 4-nitrobenzaldehyde (1 eq.) in trimethylorthoformate was added PTSA (cat.) and the resulting mixture was heated to reflux for 3–5 h at which time the reaction mixture was concentrated under reduced pressure. The residue was dissolved in ether, washed with $NaHCO_3$ followed by water, dried over $Na_2SO_4$ and concentrated under reduced pressure to yield dimethyl acetal.

The crude dimethyl acetal was dissolved in EtOH followed by addition of Raney Ni (cat). To this mixture at 0° C. was added hydrazine hydrate (5 eq) drop wise over 15 min to keep the effervescence under control. The reaction was warmed to room temp, stirred for additional 3 h followed by filtration of catalyst. The filtrate was concentrated under reduced pressure. The residue was redissolved in EtOAc, washed with water, dried over $Na_2SO_4$ and concentrated under reduced pressure to yield crude aminobenzaldehydedimethylacetal.

To a solution of aminobenzaldehydedimethylacetal.(1 eq.) in acetonitrile was added solid 3,4-dichlorphenylisocynate (2 eq.). The resulting mixture was stirred for 6–16 h at which time the reaction was diluted with EtOAc, washed with water, dried over $Na_2SO_4$ followed by concentration under reduced pressure to yield crude urea. This urea was dissolved in $CH_2Cl_2$ followed by addition of 50% aq. TFA. The resulting mixture was stirred for 2 h at which time the organic phase was separated, washed with sat aq. $NaHCO_3$ and water, and dried over $Na_2SO_4$ followed by concentration under reduced pressure to yield crude product.

Step B. General Procedure

General Procedure 1 was then followed to obtain 5-(4-(N-3,4-Dichlorophenyureido)benzylidene)thiazolidine-2,4-dione.

NMR (DMSO-$d_6$, δ): 9.40 (d, 2H), 8.58 (s, 1H), 7.84 (d, 1H), 7.76 (d, 2H), 7.54 (d, 2H), 7.48 (d, 1H), 7.30 (dd, 1H).

MS(ESI) Calcd. 407. Found 406 $(M-H)^-$.

Example 7

Preparation of 5-(2-(N-3,4-Dichlorophenyureido) benzylidene)thiazolidine-2,4-dione

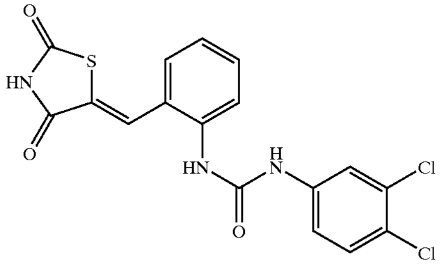

Step A: Preparation of Aldehyde

The requisite aldehyde was prepared from 2-nitrobenzaldehyde using the procedure of Example 6, Step A.

Step B. General Procedure 1

General Procedure 1 was then followed to obtain 5-(2-(N-3,4-Dichlorophenyureido)benzylidene)thiazolidine-2,4-dione.

NMR (DMSO-$d_6$, δ): 10.10 (Br s, 1H), 7.70 (d, 1H), 7.62 (d, 1H), 7.42 (dd, 1H), 7.26–7.22 (m, 2H), 6.94 (t, 1H), 6.90 (d, 1H), 6.70 (d, 1H), 5.86 (d, 1H).

Example 8

Preparation of 5-(2-(N-3,4-Dichlorophenylcarbamido)benzylidene)thiazolidine-2,4-dione

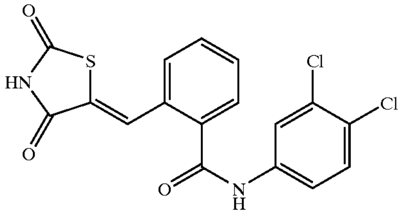

Step A: Preparation of 5-(2-carboxybenzylidene) thiazolidine-2,4-dione 5-(2-carboxybenzylidene)thiazolidine-2,4-dione was prepared by the method of General Procedure 1 from 2-carboxybenzaldehyde.

Step B. Elaboration of Carboxy Group

The 5-(2-carboxybenzylidene)thiazolidine-2,4-dione was dissolved in $SO_2Cl_2$ followed by addition of 1–2 drops of DMF. This resulting mixture was heated to ~80° C. for 15–30 min at which time the reaction was concentrated under reduced pressure. The residue was dissolved in THF and added drop wise to a solution of 3,4-dichloroaniline (1.5 eq) and TEA (2 eq). This mixture was stirred for additional 1–2 h at which time the solid in the reaction mixture was filtered. The filtrate was concentrated under reduced pressure to yield solid that was washed with water and ether to afford pure product.

NMR (DMSO-$d_6$, δ): 10.80 (Br s, 1H), 8.06 (d, 1H), 7.93 (s, 1H), 7.73–7.54 (m, 6H).

MS(ESI) Calcd. 392. Found 391 $(M-H)^-$

Example 9

Preparation of 5-(3-(N-3,4-Dichlorophenylcarbamido)benzylidene)thiazolidine-2,4-dione

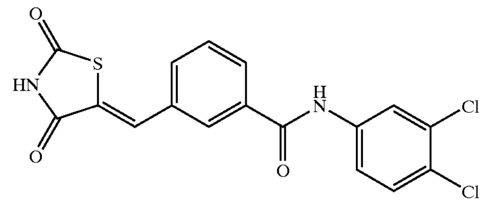

5-(3-(N-3,4-Dichlorophenylcarbamido)benzylidene)thiazolidine-2,4-dione was prepared in two steps by the method of Example 8 from 3-carboxybenzaldehyde.

NMR (DMSO-$d_6$, δ): 8.12 (d, 1H), 8.08 (s, 1H), 7.97 (d, 1H), 7.82 (s, 1H), 7.77 (d, 1H), 7.72–7.64 (m, 2H), 7.60 (d, 2H).

MS(ESI) Calcd. 392. Found 391 $(M-H)^-$.

Example 10

Preparation of 5-(4-(N-3,4-Dichlorophenylcarbamido)benzylidene)thiazolidine-2,4-dione

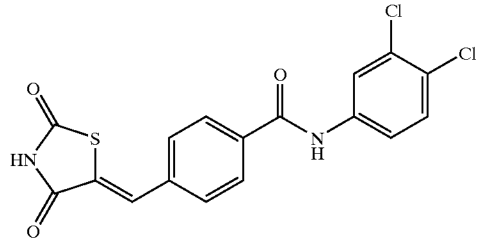

5-(4-(N-3,4-Dichlorophenylcarbamido)benzylidene)-thiazolidine-2,4-dione was prepared by the method of Example 8 from 4-carboxybenzaldehyde.

NMR (DMSO-$d_6$, δ): 10.60 (Br s, 1H), 8.12 (s, 1H), 8.02 (d, 2H), 7.82 (s, 1H), 7.71 (d, 3H), 7.58 (d, 1H).

MS(ESI) Calcd. 392. Found 391 $(M-H)^-$.

Example 11

Preparation of 5-(4-(N-3,4-Dichlorophenylcarbamoyloxy)benzylidene)thiazolidine-2,4-dione

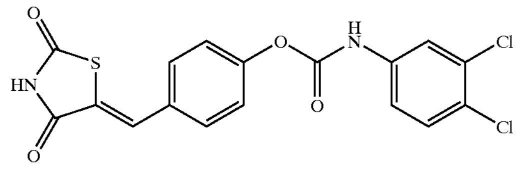

Step A: Preparation of 5-(4-hydroxybenzylidene)thiazolidine-2,4-dione 5-(4-hydroxybenzylidene)thiazolidine-2,4-dione was prepared by the method of General Procedure 1 from 4-hydroxybenzaldehyde.

Step B. Elaboration of Hydroxy Group

To a solution of 5-(4-hydroxybenzylidene)thiazolidine-2,4-dione (1 eq.) in acetonitrile was added $K_2CO_3$ (xs) followed by addition of solid 3,4-dichlorphenylisocyanate (2 eq.). The resulting mixture was stirred for 6–16 h at which time the solid was filtered, washed with water to yield pure product.

NMR (DMSO-$d_6$, δ): 12.60 (Br s, 1H), 10.60 (br s, 1H), 7.76 (d, 2H), 7.62 (d, 2H), 7.56 dd, 1H), 7.41 (dd, 1H), 7.37 (dd, 1H).

MS(ESI) Calcd. 408. Found 407 $(M-H)^-$.

Example 12

Preparation of 5-(4-(3,4-Dichlorophenoxycarbonyl)benzylidene)thiazolidine-2,4-dione

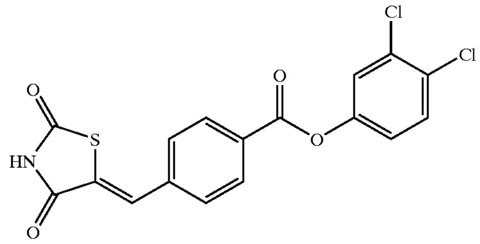

5-(4-Carboxybenzylidene)thiazolidine-2,4-dione (from Example 8, Step A) was dissolved in $SO_2Cl_2$ followed by addition of 1–2 drops of DMF. This resulting mixture was heated to ~80° C. for 15–30 min at which time the reaction was concentrated under reduced pressure. The residue was dissolved in THF and added drop wise to a solution of 3,4-dichlorophenol (1.5 eq) and TEA (2 eq). This resulting mixture was stirred for additional 1–2 h at which time the solid in the reaction mixture was filtered off. The filtrate was concentrated under reduced pressure to yield solid that was washed with water and ether to afford pure ester. Alternatively, to a solution of 5-(4-carboxybenzylidene)thiazolidine-2,4-dione (1 eq) and 3,4-dichlorophenol (1 eq) in $CH_2Cl_2$ was added DCC (1 eq). The resulting reaction mixture was stirred for 16 h at which time the reaction was filtered, the filtrate was washed with water and concentrated under reduced pressure to provide crude product that was purified by recystallization.

NMR (DMSO-$d_6$, δ): 8.18 (d, 2H), 7.80 (d, 2H), 7.77–7.68 (m, 3H), 7.38–7.33 (m, 1H).

MS(ESI) Calcd. 393. Found 392 $(M-H)^-$

Example 13

Preparation of 5-(2-(3,4-Dichlorophenoxycarbonyl)benzylidene)thiazolidine-2,4-dione

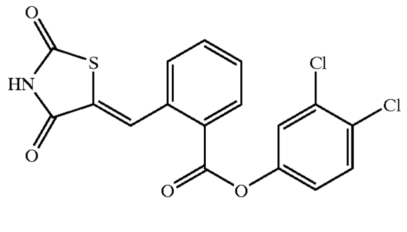

5-(2-(3,4-Dichlorophenoxycarbonyl)benzylidene)thiazolidine-2,4-dione was prepared by the method of Example 12.

NMR (DMSO-$d_6$, δ): 8.28 (s, 1H), 8.22 (d, 1H), 7.80 (t, 1H), 7.76 (d, 1H), 7.73 (d, 1H), 7.64 (d, 1H), 7.38 (dd, 1H).

MS(ESI) Calcd. 393. Found 392 $(M-H)^-$.

Example 14

Preparation of 5-(2-(3,4-Dichlorophenylacetoxy) benzylidene)thiazolidine-2,4-dione

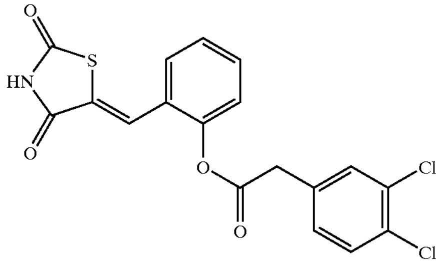

Step A: Preparation of 5-(2-hydroxybenzylidene) thiazolidine-2,4-dione 5-(2-Hydroxybenzylidene)thiazolidine-2,4-dione was prepared by General Procedure 1 from 2-hydroxybenzaldehyde.

Step B. Elaboration of Hydroxy Group 3,4-Dichlorophenylacetic acid was dissolved in $SO_2Cl_2$ followed by addition of a few drops of DMF. This resulting mixture was heated to 80 ° C for 15–30 min. followed by concentration of the reaction mixture under reduced pressure. The residue was dissolved in THF and slowly added to a solution of 5-(hydroxybenzylidene)thiazolidine-2,4-dione (1.5 eq.) and TEA (1.5 eq.) in THF. The resulting reaction was stirred for 1–2 h at which time the solid was filtered off and filtrate was concentrated under reduced pressure to yield light yellow solid. The solid was dissolved in EtOAc followed by washing with sat. aq. $K_2CO_3$. The organic phase was separated, and dried over $Na_2SO_4$ followed by concentration under reduced pressure to yield pure compound.

NMR (DMSO-$d_6$, δ): 12.65 (Br s, 1H), 7.65 (d, 1H), 7.57 (d, 1H), 7.55 (s, 1H), 7.54–7.6 (m, 2H), 7.41 (d, 1H), 7.37 (dd, 1H), 7.30 (d, 1H), 4.00 (s, 2H).

MS(ESI) Calcd. 407. Found 406 $(M-H)^-$.

Example 15

Preparation of 5-(3-(3,4-Dichlorophenylacetoxy) benzylidene)thiazolidine-2,4-dione

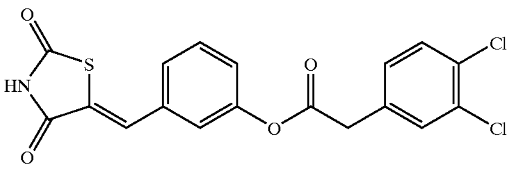

5-(3-(3,4-Dichlorophenylacetoxy)benzylidene) thiazolidine-2,4-dione was prepared by the method of Example 14 from 3-hydroxybenzaldehyde.

NMR (DMSO-$d_6$, δ): 12.60 (Br s, 1H), 7.74 (s, 1H), 7.66 (d, 1H), 7.59 (d, 1H), 7.53 (t, 1H), 7.45 (d, 1H), 7.38–7.33 (m, 2H), 7.24 (d, 1H), 4.00 (s, 2H).

MS(ESI) Calcd. 407. Found 406 $(M-H)^-$

Example 16

Preparation of 5-(4-(3,4-Dichlorophenylacetoxy) benzylidene)thiazolidine-2,4-dione

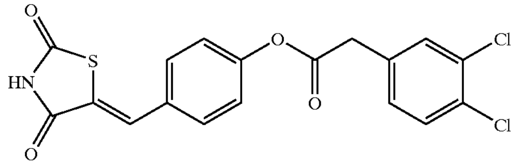

5-(4-(3,4-Dichlorophenylacetoxy)benzylidene) thiazolidine-2,4-dione was prepared by the method of Example 14 from 4-hydroxybenzaldehyde.

NMR (DMSO-$d_6$, δ): 7.76 (s, 1H), 7.66 (d, 1H), 7.60 (m, 3H), 7.36 (dd, 1H), 7.28 (d, 2H), 4.00 (s, 2H).

MS(ESI): Calcd. 407. Found 406 $(M-H)^-$

Example 17

Preparation of 5-(2-(3,4-Dichlorobenzoyloxy) benzylidene)thiazolidine-2,4-dione

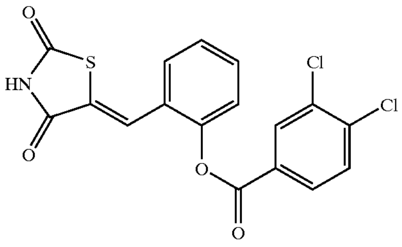

Step A: Preparation of 5-(2-hydroxybenzylidene) thiazolidine-2,4-dione 5-(2-Hydroxybenzylidene)thiazolidine-2,4-dione was prepared by General Procedure 1 from 2-hydroxybenzaldehyde.

Step B. Acylation of the Hydroxy Group

A solution of 3,4-dichlorobenzoylchloride in THF was slowly added to a solution of 5-(hydroxybenzylidene) thiazolidine-2,4-dione (1.5 eq.) and TEA (1.5 eq.) in THF. The resulting reaction was stirred for 1–2 h at which time the solid was filtered and filtrate was concentrated under reduced pressure to yield light yellow solid. The solid was dissolved in EtOAc followed by washing with sat. aq. $K_2CO_3$. The organic phase was separated, and dried over $Na_2SO_4$ followed by concentration under reduced pressure to yield pure compound.

NMR (DMSO-$d_6$, δ): 8.30 (s, 1H), 8.09 (dd, 1H), 7.90 (d, 1H), 7.68–7.62 (m, 1H), 7.42–7.28 (m, 3H), 7.18 (s, 1H).

MS (ESI): Calcd. 393. Found 392 $(M-H)^-$

Example 18

Preparation of 5-(3-(3,4-Dichlorobenezoyloxy) benzylidene)thiazolidine-2,4-dione

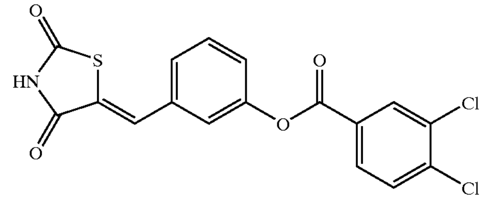

5-(3-(3,4-Dichlorobenezoyloxy)benzylidene) thiazolidine-2,4-dione was prepared by the method of Example 17 from 3-hydroxybenzaldehyde.

NMR (DMSO-$d_6$, δ): 8.27 (s, 1H), 8.06 (d, 1H), 7.86 (d, 1H), 7.52–7.38 (m, 3H), 7.24 (s, 1H), 7.20 (d, 1H).

MS(ESI): Calcd. 393. Found 392 $(M-H)^-$.

Example 19

Preparation of 5-(4-(3,4-Dichlorobenzoyloxy) benzylidene)thiazolidine-2,4-dione

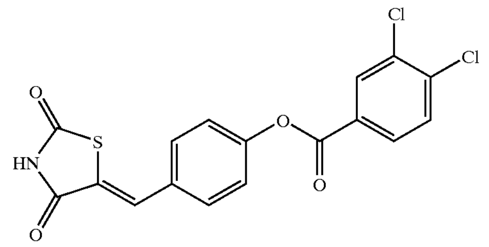

5-(4-(3,4-Dichlorobenzoyloxy)benzylidene)thiazolidine-2,4-dione was prepared by the method of Example 17 from 4-hydroxybenzaldehyde.

NMR (DMSO-$D_6$, δ): 8.26 (d, 1H), 8.04 (dd, 1H), 7.85 (d, 1H), 7.58 (d, 2H), 7.36 (d, 2H), 7.39–7.34 (m, 3H).

MS(ESI): Calcd. 393. Found 392 $(M-H)^-$.

Example 20

Preparation of 5-(3,4-Bis-(3,4-dichlorobenzyloxy) benzylidine)thiazolidine-2,4-dione

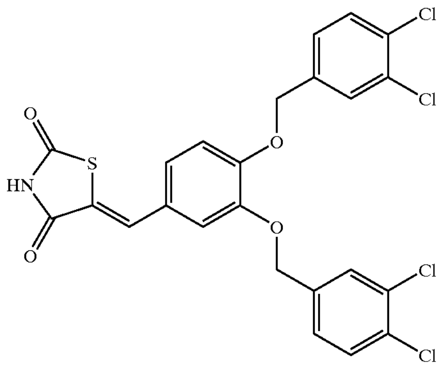

Step A: Preparation of Aldehyde 3,4-Dichlorobenzyl chloride (415 μl, 3 mmol) was added to a mixture of 138 mg (1 mmol) of 3,4-dihydroxy benzaldehyde and 690 mg of potassium carbonate in DMF. The resulting mixture was warmed to 70° C. and stirred overnight. The reaction was then diluted with 20 mL of water and the mixture was filtered. The resulting white precipitate was collected by filtration and air dried to give 426 mg (93%) of the desired product.

1H NMR (partial) (400 MHz, DMSO-$d_6$) δ 9.9 (s, 1H), 5.24 (s, 2H), 5.19 (s, 2H).

Step B. General Procedure 1

NMR (400 MHz, DMSO-$d_6$, δ): 7.68–7.66 (m, 2H), 7.65 (s, 1H), 7.63–7.59 (m, 2H), 7.41–7.37 (m, 2H), 7.21–7.20 (m, 1H), 7.18–7.15 (m, 2H).

MS(ESI): Calcd. 553 Found 552 $(M-H)^-$.

Example 21

Preparation of 5-(2-(3,4-Dichlorophenoxy) benzylidine)thiazolidine-2,4-dione

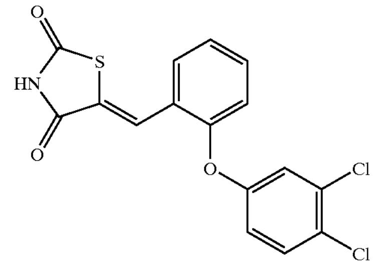

Step A: Preparation of Aldehyde

A mixture of 2-fluorobenzaldehyde (248.23 mg 210 μL, 2 mmol) and 3,4-dichlorophenol was stirred with potassium carbonate in 5 mL of dimethylacetamide at 90° C. for 12 hours. The reaction was diluted with 20 mL of water and extracted with 25 mL of ethyl acetate. The organic layer was washed with saturated aqueous sodium bicarbonate and saturated sodium chloride solutions then dried over sodium sulfate and concentrated in vacuo to give a brown oil that was taken on without further purification.

Step B. General Procedure 1

NMR (DMSO-$d_6$, δ): 7.73 (s, 1H), 7.59 (m, 2H), 7.46 (t, 1H), 7.34 (m, 2H), 7.02 (m, 2H).

MS(ESI): Calcd. 365. Found 364$(M-H)^-$

Example 22

Preparation of 5-(4-(3,4-Dichlorophenoxy) benzylidine)thiazolidine-2,4-dione

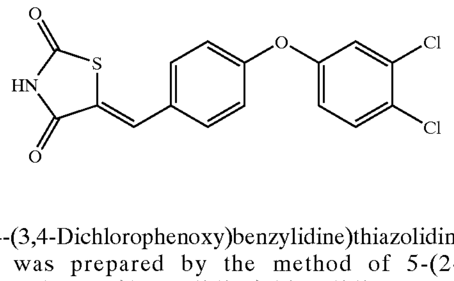

5-(4-(3,4-Dichlorophenoxy)benzylidine)thiazolidine-2,4-dione was prepared by the method of 5-(2-(3,4-dichlorophenoxy)benzylidine)thiazolidine-2,4-dione, (Example 21).

MS(ESI): Calcd. 365. Found 364 $(M-H)^-$.

Example 23

Preparation of 5-(2,5-Bis-(3,4-dichlorobenzyloxy)benzylidine)thiazolidine-2,4-dione

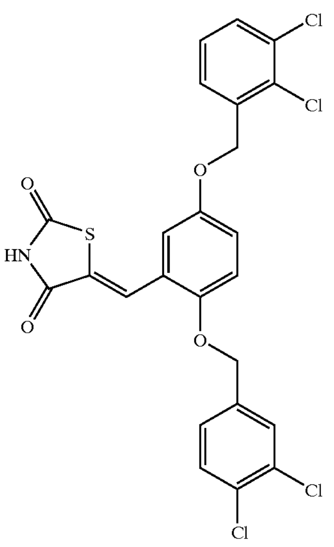

5-(2,5-Bis-(3,4-dichlorobenzyloxy)benzylidine)thiazolidine-2,4-dione was prepared by the method of 5-(3,4-Bis-(3,4-dichlorobenzyloxy)benzylidine)thiazolidine-2,4-dione, (Example 20).

NMR (DMSO-$d_6$, δ): 7.88 (s, 1H), 7.70–7.66 (m, 2H), 7.64–7.60 (m, 2H), 7.42–7.34 (m, 2H), 7.12–7.10 (m, 2H), 6.90 (brs, 1H).

MS(ESI): Calcd. 553. Found 552 $(M-H)^-$.

Example 24

Preparation of 5-(2,4-Bis-(3,4-dichlorobenzyloxy)benzylidine)thiazolidine-2,4-dione

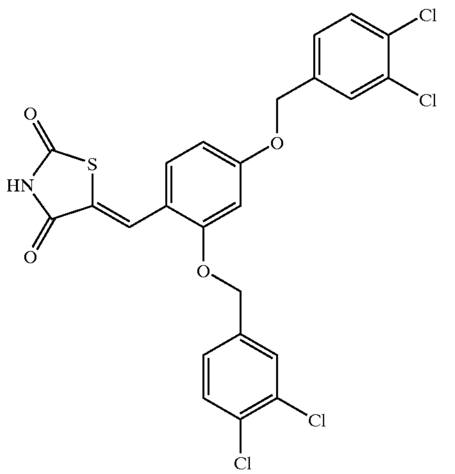

5-(2,4-Bis-(3,4-dichlorobenzyloxy)benzylidine)thiazolidine-2,4-dione was prepared by the method of 5-(3,4-Bis-(3,4-dichlorobenzyloxy)benzylidine)thiazolidine-2,4-dione, (Example 20).

MS(ESI): Calcd. 553. Found 552 $(M-H)^-$

In the following Examples 25–28, the following General Procedure 2 was employed:

General Procedure 2: Coupling Rhodanine to Aldehyde

A solution of appropriately substituted aldehyde (1 eq.), rhodanine (1 eq.) and ethylenediamine diacetate (1 eq.) in methanol was heated to reflux for 1–3 h. The resulting precipitate was isolated and washed with methanol, water, 10% aqueous sodium bisulfate, saturated aqueous sodium bicarbonate and water and then air dried.

Reactions were generally run on a 0.1 mmolar scale.

Example 25

Preparation of 5-(2-(3,4-Dichlorobenzylthio)-3H-pyrimidin-4-on-6-ylmethylidene)rhodanine

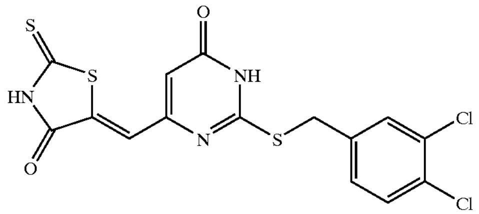

Step A: Preparation of Aldehyde

To a suspension of 0.75 g (3.7 mmol) of 6-dimethoxymethyl-2-mercapto-3H-pyrimidin-4-one in DMF with 0.66 g of potassium carbonate was added 0.512 mL (3.7 mmol) of 3,4-dichlorobenzyl chloride. The suspension was allowed to stand for 2 days. The mixture was diluted with 40 mL of ethyl acetate and 40 mL of 10% aqueous sodium bisulfate. The precipitate was isolated by filtration and washed with water to give 1.0 g of pure acetal.

A solution of 0.8 g of 6-dimethoxymethyl-2-(3,4-dichlorobenzylthio)-3H-pyrimidin-4-one in 70% trifluoroacetic acid in water was allowed to stir for 12 hours. The solution was neutralized with solid sodium bicarbonate and extracted with ethyl acetate. The organic layer was dried over magnesium sulfate and concentrated. Trituration of the residue with 1:1 ether:hexane provided 600 mg of a pure product.

Step B. General Procedure 2

General Procedure 2 was followed to obtain 5-(2-(3,4-dichlorobenzylthio)pyrimidin-4-on-6-ylmethylidene)rhodanine.

Example 26

Preparation of 5-(2-(3,4-Dichlorobenzylthio)pyrimidin-4-ylmethylidene)rhodanine

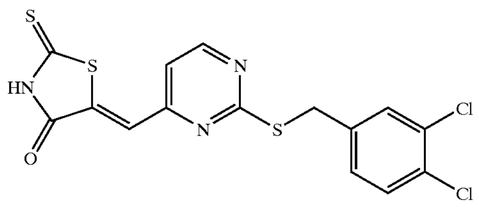

Step A: Preparation of Aldehyde

A suspension of 1.66 g (7.98 mmol) of 4-dimethoxymethylpyrimidine-2-thione sodium salt, 2.7 g of potassium carbonate and α,3,4-trichlorotoluene was stirred for 2 days. The mixture was poured into water and extracted with ethyl acetate. The organic layer was washed with saturated aqueous sodium chloride solution then dried ($MgSO_4$) and concentrated to give 1.65 g of product mercapto acetal.

A suspension of 0.8 g of the acetal in 5 mL of concentrated hydrochloric acid was refluxed for approximately 5 minutes until the solution became clear. The solution was allowed to cool then diluted with water, neutralized with saturated aqueous sodium bicarbonate solution and extracted with ethyl acetate. The organic layer was dried (anhydrous sodium sulfate) and concentrated to afford 100 mg of the desired aldehyde.

Step B. General Procedure 2

General Procedure 2 was followed to obtain 5-(2-(3,4-Dichlorobenzylthio)pyrimidin-4-ylmethylidene)rhodanine.

Example 27

Preparation of 5-(2-(3,4-Dichlorobenzylthio) pyrimidin-4-ylmethylidene)rhodanine

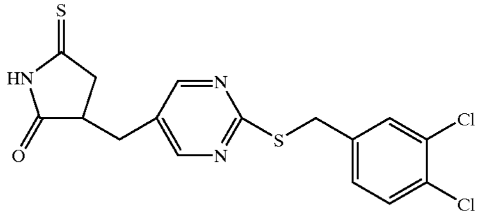

To a stirred suspension of 5-(2-(3,4-dichlorobenzylthio) pyrimidin-4-ylmethylidene)rhodanine (Example 25, 0.3 mmol) in toluene (5 mL) was added diethyl 2,6-dimethyl-1,4-dihydro-3,5-pyridine dicarboxylate (109 mg, 0.39 mmol) and 0.3 g of activated silica gel. The mixture was heated to 80° C. for 20 h then filtered while warm. The filter cake was rinsed with ethyl acetate and the combined filtrates were evaporated to dryness. The residue was redissolved in ethyl acetate and extracted with 1 N aqueous hydrochloric acid. The organic layer was dried (sodium sulfate) and concentrated to give 11 mg of pure product.

Example 28

Preparation of 5-(3-Cyano-2-(3,4-dichlorobenzylthio)pyridin-6-ylmethylidene) thiazolidine-2,4-dione

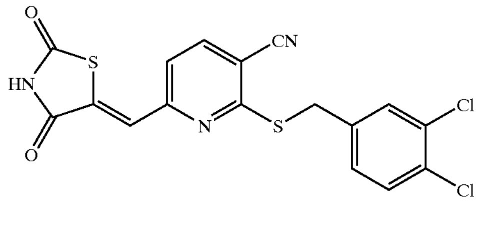

Step A: Preparation of Aldehyde

A suspension of 0.2 g (1 mmol) of 3-cyano-6-dimethoxymethyl-pyridine-2-thiol, excess potassium carbonate and α,3,4-trichlorotoluene (3mmol) in acetonitrile was heated at 75° for 10 minutes. Tlc indicated the reaction to be complete. The mixture was poured into water and extracted with ethyl acetate. The organic layer was dried ($Na_2SO_4$) and concentrated to give the product mercapto acetal as a solid, which was washed with hexane.

The acetal was dissolved in chloroform (2 ml) and 2 mL of 50% aqueous trifluoroacetic acid was added. After 16 h, TLC indicated the reaction to be nearly complete. The mixture was evaporated to dryness and used immediately in the Step B (the NMR spectrum was consistent with proposed structure).

Step B. General Procedure 1

General Procedure 1 was followed to obtain 5-(3-Cyano-2-(3,4-dichlorobenzylthio)pyridin-6-ylmethylidene) thiazolidine-2,4-dione.

NMR (DMSO-$d_6$, δ): 8.12(d, 1H), 7.68(d, 1H), 7.53(d, 1H) 7.48(d, 1H) 7.38–7.34(m, 1H) 7.31 (s, 1H) 4.80(s, 1H).

Example 29

Preparation of 5-(3-(3,4-Dichlorobenzyloxy) benzylidene)thiazolidine-2,4-dione

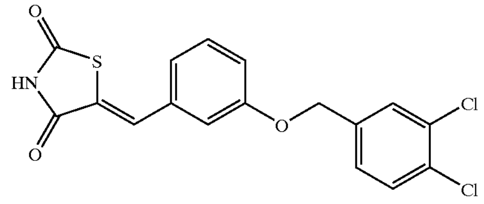

Step A: Preparation of Aldehyde

To a solution of 3-hydroxybenzaldehyde in acetonitrile was added $K_2CO_3$ (1.5 eq.) followed by addition of 3,4-dichlorobenzylchloride (3 eq.). The resulting reaction mixture was heated to 90° C. for 2–16 h at which time the precipitate was filtered off. The filtrate was diluted with EtOAc, washed with water, dried over $Na_2SO_4$ and concentrated under reduced pressure to provide crude product. This product was purified by recystallization from $CH_2Cl_2$/hexane solvent system to yield pure aldehyde.

Step B. General Procedure 1

General Procedure 1 was followed to obtain 5-(3-(3,4-Dichlorobenzyloxy)benzylidene)thiazolidine-2,4-dione.

NMR (DMSO-$d_6$, δ): 7.69 (d, 2H), 7.61 (d, 1H), 7.43–7.31 (m, 3H), 7.12–7.08 (m, 2H), 6.96 (d, 1H), 5.11 (s, 2H).

MS (ESI): Calcd. 378.98. Found 378 $(M-H)^-$.

Example 30

Preparation of Compound 1

2-(4-Methylphenylthio)-5-nitrobenzaldehyde (1.00 g, 3.66 mmol), 2,4-thiazolidinedione (1.72 g, 14.7 mmol) and piperidine (0.14 mL, 1. 5 mmol) were heated under reflux for 26 hours in ethanol (40 mL). The reaction solution was cooled down to room temperature, and the thus precipitated crystals were collected by filtration to give Compound 1 (577 mg, 42%).

$^1$H NMR (300 MHz, DMSO-$d_6$) δ 2.38 (s, 3H), 7.07 (d, J=8.8 Hz, 1H), 7.37 (d, J=8.1 Hz, 2H), 7.49 (d, J=7.9 Hz, 2H), 7.89 (s, 1H), 8.14 (dd, J=8.8, 2.2 Hz, 1H), 8.22 (d, J=2.2 Hz, 1H), 12.8 (br s, 1H)

FABMS m/z 373 $(M+H)^+$ $C_{17}H_{12}N_2O_4S_2$=372

Example 31

Preparation of Compound 2

Compound 1 (200 mg, 0.538 mmol) was dissolved in acetone (30 mL), and the solution was mixed with titanium trichloride (20% aqueous solution, 4 mL), followed by stirring at room temperature for 30 minutes. To the reaction solution was added an aqueous saturated sodium bicarbonate solution, and the mixture was extracted twice with ethyl acetate. The organic layer was washed with water and brine, and then dried over anhydrous sodium sulfate. The solvent was evaporated under reduced pressure, and the residue was recrystallized from ethyl acetate/hexane to give Compound 2 (69 mg, 38%).

$^1$H NMR (300 MHz, $CDCl_3$) δ 2.21 (s, 3H), 5.86 (br s, 2H), 6.70 (dd, J=8.4, 2.6 Hz, 1H), 6.82 (d, J=2.4 Hz, 1H), 6.89 (d, J=8.3 Hz, 2H), 7.06 (d, J=8.1 Hz, 2H), 7.33 (d, J=8.4 Hz, 1H), 8.06 (s, 1H), 12.5 (br s, 1H)

FABMS m/z 342 ($M^+$) $C_{17}H_{24}N_2O_2S_2$=342.

Example 32

Preparation of Compound 3

Compound 2 (20 mg, 0.058 mmol) was dissolved in dimethylformamide (1 mL), and to the solution were added acetic anhydride (1 mL) and triethylamine (0.016 mL, 0.12 mmol), followed by stirring at room temperature for 50 minutes. To the reaction solution was added water, and the mixture was extracted with ethyl acetate. The organic layer was washed with water and brine, and then dried over anhydrous sodium sulfate. The solvent was evaporated under reduced pressure, and the residue was purified by preparative thin layer chromatography (9/1 chloroform/ methanol) to give Compound 3 (7.0 mg, 31%).

$^1$H NMR (300 MHz, DMSO-$d_6$) δ 2.08 (s, 3H), 2.25 (s, 3H), 7.07 (d, J=8.3 Hz, 2H), 7.14 (d, J=8.3 Hz, 2H), 7.45 (d, J=8.6 Hz, 1H), 7.58 (dd, J=8.4, 2.2 Hz, 1H), 8.08 (s, 1H), 8.09 (d, J=2.4 Hz, 1H), 10.3 (s, 1H), 12.6 (br s, 1H)

FABMS m/z 385 $(M+H)^+$ $C_{19}H_{16}N_2O_3S_2$=384.

Example 33

Preparation of Compound 4

Under ice-cooling, Compound 1 (100 mg, 0.269 mmol) was dissolved in a mixed solvent of dichloromethane (20 mL) and methanol (4 mL), and the solution was mixed with m-chloroperbenzoic acid (50% purity, 100 mg, 0.289 mmol), followed by stirring at room temperature for 3 hours. The reaction solution was mixed with a 10% aqueous sodium hydrogen sulfite solution and extracted with chloroform. The organic layer was washed with an aqueous saturated sodium bicarbonate solution and brine, and then dried over anhydrous sodium sulfate. The solvent was evaporated under reduced pressure, and the residue was triturated with ethyl acetate to give Compound 4 (86 mg, 82%).

$^1$H NMR (300 MHz, DMSO-$d_6$) δ 2.30 (s, 3H), 7.32 (d, J=8.1 Hz, 2H), 7.48 (d, J=8.3 Hz, 2H), 7.88 (s, 1H), 8.20 (d, J=2.2 Hz, 1H), 8.32 (d, J=8.6 Hz, 1H), 8.50 (dd, J=8.6, 2.2 Hz, 1H), 12.6 (br s, 1H)

FABMS m/z 387 $(M-H)^-$ $C_{17}H_{12}N_2O_5S_2$=388

Example 34

Preparation of Compound 5

Compound 1 (20 mg, 0.054 mmol) was dissolved in a mixed solvent of dichloromethane (5 mL) and methanol (1 mL), and the solution was mixed with m-chloroperbenzoic acid (50% purity, 187 mg, 0.540 mmol), followed by stirring at room temperature for 1.5 hours. The reaction solution was mixed with a 10% aqueous sodium hydrogen sulfite solution and extracted four times with chloroform-methanol (9:1). The organic layer was washed with an aqueous saturated sodium bicarbonate solution and brine, and then dried over anhydrous sodium sulfate. The solvent was evaporated under reduced pressure, and the residue was purified by preparative thin layer chromatography (6:1 chloroform/ acetonitrile) to give Compound (10 mg, 46%).

$^1$H NMR (300 MHz, DMSO-$d_6$) δ 2.36 (s, 3H), 7.43 (d, J=8.3 Hz, 2H), 7.74(d, J=8.4 Hz, 2H), 8.06 (s, 1H), 8.28 (br s, 1H), 8.49 (s, 2H), 12.9 (br s, 1H)

FABMS m/z 403 $(M-H)^-$ $C_{17}H_{12}N_2O_6S_2$=404

Example 35

Preparation of Compound 6

2-(4-Chlorophenylthio)benzaldehyde (249 mg, 1.00 mmol), 2,4-thiazolidinedione (176 mg, 1.50 mmol) and piperidine (0.10 mL, 1.0 mmol) were heated under reflux for 3 hours in ethanol (8 mL). The reaction solution was cooled down to room temperature, and water and 1 N HCl (1 mL) were added and the mixture was extracted with ethyl acetate. The organic layer was washed with brine, and then dried over anhydrous sodium sulfate. The solvent was evaporated under reduced pressure, and the residue was triturated with ethyl acetate to give Compound 6 (274 mg, 70%).

$^1$H NMR (300 MHz, DMSO-$d_6$) δ 7.24 (d, J=8.4 Hz, 2H), 7.42 (d, J=8.6 Hz, 2H), 7.5–7.6 (m, 4H), 8.03 (s, 1H), 12.7 (br s, 1H)

FABMS m/z 348 $(M+H)^+$ $C_{16}H_{10}{}^{35}ClNO_2S_2$=347

Example 36

Preparation of Compound 7

Under ice-cooling, Compound 6 (20 mg, 0.057 mmol) was suspended in dichloromethane (5 mL), and the suspension was mixed with m-chloroperbenzoic acid (50% purity, 22 mg, 0.063 mmol), followed by stirring for 20 minutes. To the reaction solution was added a 10% aqueous sodium hydrogen sulfite solution, and the mixture was extracted with chloroformmethanol (9:1). The organic layer was washed with an aqueous sodium bicarbonate solution, water and brine, and then dried over anhydrous sodium sulfate. The solvent was evaporated under reduced pressure, and the residue was triturated with diisopropyl ether to give Compound 7 (15 mg, 72%).

$^1$H NMR (300 MHz, DMSO-$d_6$) δ 7.55 (d, J=9.0 Hz, 2H), 7.59 (d, J=9.0 Hz, 2H), 7.6–7.8 (m, 2H), 7.9–8.0 (m, 2H), 8.02 (s, 1H), 12.7 (br s, 1H)

FABMS m/z 364 $(M+H)^+$ $C_{16}H_{10}{}^{35}ClNO_3S_2$=363

Example 37

Preparation of Compound 8

Under ice-cooling, Compound 6 (20 mg, 0.057 mmol) was suspended in dichloromethane (5 mL), and the suspension was mixed with m-chloroperbenzoic acid (50% purity, 200 mg, 0.57 mmol), followed by stirring for 3 hours. To the reaction solution was added a 10% aqueous sodium hydrogen sulfite solution, and the mixture was extracted with chloroformmethanol (9:1). The organic layer was washed with an aqueous saturated sodium bicarbonate solution, water and brine, and then dried over anhydrous sodium sulfate. The solvent was evaporated under reduced pressure, and the residue was triturated with diisopropyl ether to give Compound 8 (16 mg, 74%).

$^1H$ NMR (300 MHz, DMSO-$d_6$) δ 7.60 (d, J=7.5 Hz, 1H), 7.68 (d, J=8.8 Hz, 2H), 7.7–7.8 (m, 1H), 7.81 (d, J=8.8 Hz, 2H), 7.87 (td, J=7.7, 1.3 Hz, 1H), 8.11 (s, 1H), 8.27 (dd, J=7.9, 1.3 Hz, 1H), 12.8 (br s, 1H)

FABMS m/z 380 $(M+H)^+$ $C_{16}H_{10}{}^{35}ClNO_4S_2$=379

Example 38

Preparation of Compound 9

4-(4-Methylphenylthio)-3-nitrobenzaldehyde (273mg, 1.00 mmol), 2,4-thiazolidinedione (176 mg, 1.50 mmol) and piperidine (0.40 mL, 0.40 mmol) were heated under reflux for 19 hours in ethanol (8 mL). The reaction solution was cooled down to room temperature, and the thus precipitated crystals were collected by filtration to give Compound 9 (175 mg, 47%).

$^1H$ NMR (300 MHz, DMSO-$d_6$) δ 2.41 (s, 3H), 6.92 (d, J=8.6 Hz, 1H), 7.40 (d, J=7.9 Hz, 2H), 7.54 (d, J=8. 3 Hz, 2H), 7.72 (dd, J=8.6, 2.2 Hz, 1H), 7.73 (s, 1H), 8.46 (d, J=1.8 Hz, 1H), 12.7 (br s, 1H)

FABMS m/z 373 $(M+H)^+$ $C_{17}H_{12}N_2O_4S_2$=372

Example 39

Preparation of Compound 10

2-Phenoxybenzaldehyde (Synthesis, 28 (1995)) (198 mg, 1.00 mmol), 2,4-thiazolidinedione (176 mg, 1.50 mmol) and piperidine (0.10 mL, 1.0 mmol) were heated under reflux for 4 hours in ethanol (5 mL). The reaction solution was cooled down to room temperature, water and 1 N HCl (1 mL) were added, and then the mixture was extracted with ethyl acetate. The organic layer was washed with water and brine, and then dried over anhydrous sodium sulfate. The solvent was evaporated under reduced pressure, and the residue was triturated with diisopropyl ether to give Compound 10 (199 mg, 67%).

$^1H$ NMR (300 MHz, DMSO-$d_6$) δ 6.95 (d, J=8.1 Hz, 1H), 7.05 (d, J=7.5 Hz, 2H), 7.20 (t, J=7.3 Hz, 1H), 7.32 (t, J=7.7 Hz, 1H), 7.4–7.5 (m, 3H), 7.58 (dd, J=7.7, 1.3 Hz, 1H), 7.95 (s, 1H), 12.6 (br s, 1H)

FABMS m/z 298 $(M+H)^+$ $C_{16}H_{11}NO_3S$=297

Example 40

Preparation of Compound 11

3-Phenoxybenzaldehyde (0.172 mL, 1.00 mmol), 2,4-thiazolidinedione (176 mg, 1.50 mmol) and piperidine (0.10 mL, 1.0 mmol) were heated under reflux for 10 hours in ethanol (5 mL). The reaction solution was cooled down to room temperature, water and 1 N HCl (1 mL) were added, and then the mixture was extracted with ethyl acetate. The organic layer was washed with water and brine, and then dried over anhydrous sodium sulfate. The solvent was evaporated under reduced pressure, and the residue was triturated with diisopropyl ether to give Compound 11 (141 mg, 47%).

$^1H$ NMR (300 MHz, DMSO-$d_6$) δ 7.0–7.3 (m, 5H), 7.35 (d, J=7.9 Hz, 1H), 7.44 (dd, J=8.4, 7.5 Hz, 2H), 7.54 (t, J=7.9 Hz, 1H), 7.82 (s, 1H), 12.6 (br s, 1H)

FABMS m/z 298 $(M+H)^+$ $C_{16}H_{11}NO_3S$=297

Example 41

Preparation of Compound 12

3-(4-Methylphenoxy)benzaldehyde (0.193 mL, 1.00 mmol), 2,4-thiazolidinedione (176 mg, 1.50 mmol) and piperidine (0.10 mL, 1.0 mmol) were heated under reflux for 7 hours in ethanol (5 mL). The reaction solution was cooled down to room temperature, and water and 1 N HCl (1 mL) were added, and then the mixture was extracted with ethyl acetate. The organic layer was washed with water and brine, and then dried over anhydrous sodium sulfate. The solvent was evaporated under reduced pressure, and the residue was recrystallized from ethanol/ethyl acetate to give Compound 12 (98 mg, 32%).

$^1H$ NMR (300 MHz, DMSO-$d_6$) δ 2.3 1 (s, 3H), 6.9–7.0 (m, 3H), 7.12 (t, J=2.0 Hz, 1H), 7.23 (d, J=8.4 Hz, 2H), 7.29 (br d, J=7.9 Hz, 1H), 7.45 (t, J=7.9 Hz, 1H), 7.49 (s, 1H)

FABMS m/z 312 $(M+H)^+$ $C_{17}H_{13}NO_3S$=311

Example 42

Preparation of Compound 13

3-(3,4-Dichlorophenoxy)benzaldehyde (0.198 mL, 1.00 mmol), 2,4-thiazolidinedione (176 mg, 1.50 mmol) and piperidine (0.10 mL, 1.0 mmol) were heated under reflux for 7 hours in ethanol (5 mL). The reaction solution was cooled down to room temperature, water and 1 N HCl (1 mL) were added, and then the mixture was extracted with ethyl acetate. The organic layer was washed with water and brine, and then dried over anhydrous sodium sulfate. The solvent was evaporated under reduced pressure, and the residue was triturated with ethyl acetate to give Compound 13 (252 mg, 69%).

$^1H$ NMR (300 MHz, DMSO-$d_6$) δ 7.0–7.2 (m, 2H), 7.25 (t, J=2.0 Hz, 1H), 7.38 (d, J=7.7 Hz, 1H), 7.38 (d, J=2.8 Hz, 1H), 7.52 (t, J=8.0 Hz, 1H), 7.53 (s, 1H), 7.66 (d, J=8.8 Hz, 1H)

FABMS m/z 366 $(M+H)^+$ $C_{16}H9ClNO_3S$=365

Example 43

Preparation of Compound 14

4-Phenoxybenzaldehyde (0.175 mL, 1.00 mmol), 2,4-thiazolidinedione (176 mg, 1.50 mmol) and piperidine (0.10 mL, 1.0 mmol) were heated under reflux for 6 hours in ethanol (5 mL). The reaction solution was cooled down to room temperature, and water and 1 N HCl (1 mL) were added, and then the mixture was extracted with ethyl acetate. The organic layer was washed with water and brine, and then dried over anhydrous sodium sulfate. The solvent was evaporated under reduced pressure, and the residue was triturated with hexane/diisopropyl ether to give Compound 14 (252 mg, 85%).

$^1H$ NMR (300 MHz, DMSO-$d_6$) δ 7.0–7.2 (m, 4H), 7.23 (t, J=7.3 Hz, 1H), 7.4–7.5 (m, 2H), 7.62 (d, J=8.8 Hz, 2H), 7.78 (s, 1H), 12.6 (br s, 1H)

FABMS m/z 298 $(M+H)^+$ $C_{16}H_{11}NO_3S$=297

Example 44

Preparation of Compound 15

In an argon atmosphere, 4-fluorobenzaldehyde (0.53 mL, 5.0 mmol) and p-cresol (648 mg, 6.0 mmol) were dissolved in dimethylacetamide (8 mL), and to the solution were added potassium carbonate (828 mg, 6.0 mmol) and cupric oxide (95 mg, 0.50 mmol) and the mixture was heated under reflux for 1.5 hours. The reaction solution was cooled down to room temperature, and water was added, and then the mixture was extracted with ethyl acetate. The organic layer was washed with a 0.5 N aqueous sodium hydroxide solution, water and brine, and then dried over anhydrous sodium sulfate. The solvent was evaporated under reduced pressure, and the residue was purified by silica gel column chromatography (6:1 hexane/ethyl acetate) to obtain 4-(4methylphenoxy)benzaldehyde (697 mg, 66%).

$^1$H NMR (300 MHz, $CDCl_3$) δ 2.37 (s, 3H), 6.98 (d, J=8.4 Hz, 2H), 7.03 (d, J=8.6 Hz, 2H), 7.21 (d, J=8.6 Hz, 2H), 7.82 (d, J=9.0 Hz, 2H), 9. 91 (s, 1H)

FABMS m/z 213 ($M+H^+$) $C_{14}H_{12}O_2$=212

The thus obtained 4-(4-methylphenoxy)benzaldehyde (212 mg, 1.00 mmol), 2,4-thiazolidinedione (176 mg, 1.50 mmol) and piperidine (0.10 mL, 1.0 mmol) were heated under reflux for 4 hours in ethanol (5 mL). The reaction solution was cooled down to room temperature, and water and 1 N H1 (1 mL) were added, and then the mixture was extracted with ethyl acetate. The organic layer was washed with water and brine, and then dried over anhydrous sodium sulfate. The solvent was evaporated under reduced pressure, and the residue was triturated with diisopropyl ether to give Compound 15 (252 mg, 81%).

$^1$H NMR (300 MHz, DMSO-$d_6$) δ 2.31 (s, 3H), 7.01 (d, J=8.4 Hz, 2H), 7.06 (d, J=8.8 Hz, 2H), 7.25 (d, J=8.6 Hz, 2H), 7.60 (d, J=8.8 Hz, 2H), 7.76 (s, 1H), 12.6 (br s, 1H)

FABMS m/z 312 ($M+H^+$) $C_{17}H_{13}NO_3S$=311.

Example 45

Preparation of Compound 16

(1) In an argon atmosphere, 5-nitrosalicylaldehyde (334 mg, 2.00 mmol) was dissolved in dimethyformamide (5 mL), and the solution was mixed with benzyl bromide (0.238 mL, 2.00 mmol) and sodium hydride (88 mg, 2.4 mmol), followed by stirring at 70° C. for 13 hours. The reaction solution was cooled with ice, and water was added, and then the mixture was extracted with ethyl acetate. The organic layer was washed with water and brine, and then dried over anhydrous sodium sulfate. The solvent was evaporated under reduced pressure, and the residue was triturated with diisopropyl ether to obtain 2-benzyloxy-5-nitrobenzaldehyde (337 mg, 66%).

$^1$H NMR (300 MHz, $CDC_{13}$) δ 5.33 (s, 2H), 7.18 (d, J=9.2 Hz, 1H), 7.4–7.5 (m, 5H), 8.42 (dd, J=9.2, 2.9 Hz, 1H), 8.73 (d, J=2.9 Hz, 1H), 10.5 (s, 1H)

FABMS m/z 258 $(M+H)^+$ $C_{14}H_{11}NO_4$=257

(2) The obtained 2-benzyloxy-5-nitrobenzaldehyde (257 mg, 1.00 mmol), 2,4-thiazolidinedione (176 mg, 1.50 mmol) and piperidine (0.10 mL, 1.0 mmol) were heated under reflux for 11 hours in ethanol (5 mL). The reaction solution was cooled down to room temperature, and water and 1 N HCl (1 mL) were added, and then the mixture was extracted with ethyl acetate. The organic layer was washed with water and brine, and then dried over anhydrous sodium sulfate. The solvent was evaporated under reduced pressure, and the residue was triturated with diisopropyl ether to give Compound 16 (211 mg, 59%).

$^1$H NMR (300 MHz, DMSO-$d_6$) δ 5.42 (s, 2H), 7.3–7.6 (m, 6H), 7.91 (s, 1H), 8.25 (d, J=2.6 Hz, 1H), 8.35 (dd, J=9.2, 2.8 Hz, 1H), 12.7 (br s, 1H)

FABMS m/z 357 $(M+H)^+$ $C_{17}H_{12}N_2O_5S$=356

Example 46

Preparation of Compound 17

(1) In the same manner as described in Example 45 (1), 2-(3,4-dichlorobenzyloxy)-5-nitrobenzaldehyde (482 mg, 74%) was obtained from 5-nitrosalicylaldehyde (334 mg, 2.00 mmol) and 3,4-dichlorobenzyl chloride (0.305 mL, 2.20,mmol).

$^1$H NMR (300 MHz, $CDCl_3$) δ 5.27 (s, 2H), 7.14 (d, J=9.2 Hz, 1H), 7.30 (dd, J=8.3, 2.2 Hz, 1H), 7.53 (d, J=8.3 Hz, 1H), 7.56 (d, J=2.2 Hz, 1H), 8.43 (dd, J=9.2, 2.9 Hz, 1H), 8.74 (d, J=2.9 Hz, 1H), 10.5 (s, 1H)

(2) The thus obtained 2-(3,4-dichlorobenzyloxy)-5-nitrobenzaldehyde (326 mg, 1.00 mmol) was treated in the same manner as described in Example 45 (2) to give Compound 17 (142mg,33%).

$^1$H NMR (300 MHz, DMSO-$d_6$) δ 5.42 (s, 2H), 7.44 (d, J=9.4 Hz, 1H), 7.49 (dd, J=8.3, 2.0 Hz, 1H), 7.72 (d, J=8.3 Hz, 1H), 7.80 (d, J=1.8 Hz, 1H), 7.90 (s, 1H), 8.26 (d, J=2.6 Hz 1H) 8.36 (dd, J=9.4, 2.8 Hz, 1H), 12.8 (br s, 1H)

FABMS m/z 425 $(M+H)^+$ $C_{17}H_{10}{}^{35}C_{12}N_2O_5S$=424

Example 47

Preparation of Compound 18

(1) In the same manner as described in Example 45 (1), 2-(4-methylbenzyloxy)-5-nitrobenzaldehyde (413 mg, 76%) was obtained from 5-nitrosalicylaldehyde (334 mg, 2.00 mmol) and 4-methylbenzyl bromide (370 mg, 2.00 mmol).

$^1$H NMR (300 MHz, $CDCl_3$) 67 2.18 (s, 3H), 5.28 (s, 2H), 7.18 (d, J=9.4Hz, 1H), 7.24 (d, J=8.1 Hz, 2H), 7.33 (d, J=8.1 Hz, 2H), 8.40 (dd, J=9.2, 2.9 Hz, 1H), 8.72 (d, J=2.9 Hz, 1H), 10.5 (s, 1H) FABMS m/z 272 $(M+H)^+$ $C_{15}H_{13}NO_4$=271

(2) The thus obtained 2-(4-methylbenzyloxy)-5-nitrobenzaldehyde (271 mg, 1.00 mmol) was treated in the same manner as described in Example 45 (2) to give Compound 18 (200 mg, 54%).

$^1$H NMR (300 MHz, DMSO-$d_6$) δ 2.32 (s, 3H), 5.35 (s, 2H), 7.24 (d, J=7.9 Hz, 2H), 7.38 (d, J=7.9 Hz, 2H), 7.47 (d, J=9.3 Hz, 1H), 7.88 (s, 1H), 8.24 (d, J=2.8 Hz, 1H), 8.34 (dd, J=9.2, 2.8 Hz, 1H), 12.7 (br s, 1H)

FABMS m/z 371 $(M+H)^+$ $C_{18}H_{14}N_2O_5S$=370

Example 48

Preparation of Compound 19

(1) In the same manner as described in Example 45 (1), 3-(4-methylbenzyloxy)-4-nitrobenzaldehyde (315 mg, 58%) was obtained from 3-hydroxy-4-nitrobenzaldehyde (334 mg, 2.00 mmol) and 4-methylbenzyl bromide (370 mg, 2.00 mmol).

$^1$H NMR (300 MHz, $CDCl_3$) 67 2.36 (s, 3H), 5.27 (s, 2H), 7.20 (d, J=7.9 Hz, 2H),7.34 (d, J=8.1 Hz, 2H), 7.53 (dd, J=8.1, 1.5 Hz, 1H), 7.64 (d, J=1.5 Hz, 1H), 7.92 (d, J=8.1 Hz, 1H), 10.0 (s, 1H)

FABMS m/z 272 $(M+H)^+$ $C_{15}H_{13}NO_4$=271

(2) The obtained 3-(4-methylbenzyloxy)-4-nitrobenzaldehyde (271 mg, 1.00 mmol) was treated in the same manner as described in Example 45 (2) and recrystallized from ethyl acetate/hexane to obtain Compound 19 (95 mg, 26%).

$^1$H NMR (300 MHz, DMSO-$d_6$) 67 2.31 (s, 3H), 5.32 (s, 2H), 7.22 (d, J=7.9 Hz, 2H), 7.29 (dd, J=8.4, 1.5 Hz, 1H), 7.36 (d, J=8.1 Hz, 2H), 7.64 (d, J=1.7Hz, 1H), 7.81 (s, 1H), 8.02 (d, J=8.4 Hz, 1H), 12.8 (br s, 1H)

FABMS m/z 371 $(M+H)^+$ $C_{18}H_{14}N_2O_5S$=370

Example 49

Preparation of Compound 20

(1) In the same manner as described in Example 45 (1), 4-(4-methylbenzyloxy)-3-nitrobenzaldehyde (365 mg, 67%)

was obtained from 4-hydroxy-3-nitrobenzaldehyde (334 mg, 2.00 mmol) and 4-methylbenzyl bromide (370 mg, 2.00 mmol).

$^1$H NMR (300 MHz, $CDCl_3$) δ 2.36 (s, 3H), 5.31 (s, 2H), 7.21 (d, J=8.1 Hz, 2H), 7.26 (d, J=8.8 Hz, 1H), 7.33 (d, J=8.1 Hz, 2H), 8.02 (dd, J=8.6, 2.0 Hz, 1H), 8.34 (d, J=2.0 Hz, 1H), 9.92 (s, 1H)

FABMS m/z 272 $(M+H)^+$ $C_{15}H_{13}NO_4$=271

(2) The thus obtained 4-(4-methylbenzyloxy)-3-nitrobenzaldehyde (271 mg, 1.00 mmol) was treated in the same manner as described in Example 45 (2) and recrystallized from ethyl acetate/hexane to obtain Compound 20 (123 mg, 33%).

$^1$H NMR (300 MHz, DMSO-$d_6$) δ 2.31 (s, 3H), 5.34 (s, 2H), 7.22 (d, J=7.9 Hz, 2H), 7.35 (d, J=8.1 Hz, 2H), 7.60 (d, J=9.0Hz, 1H), 7.81 (s, 1H),7.84 (dd, J=9.0, 2.2 Hz, 1H), 8.15 (d, J=2.2 Hz, 1H), 12.7 (br s, 1H)

FABMS m/z 371 $(M+H)^+$ $C_{18}H_{14}N_2O_5S$=370

Example 50

Preparation of Compound 21

(1) In the same manner as described in Example 45 (1), 5-(4-methylbenzyloxy)-2-nitrobenzaldehyde (413 mg, 76%) was obtained from 5-hydroxy-2-nitrobenzaldehyde (334 mg, 2.00 mmol) and 4-methylbenzyl bromide (370 mg, 2.00 mmol).

$^1$H NMR (300 MHz, $CDCl_3$) δ 2.37 (s, 3H), 5.16 (s, 2H), 7.19 (dd, J=9.0, 2.9 Hz, 1H), 7.21 (d, J=7.5 Hz, 2H), 7.31 (d, J=8.1 Hz, 2H), 7.41 (d, J=2.9Hz, 1H), 8.15 (d, J=9.2 Hz, 1H), 10.5 (s, 1H)

FABMS m/z 272 $(M+H)^+$ $C_{15}H_{13}NO_4$=271

(2) The thus obtained 5-(4-methylbenzyloxy)-2-nitrobenzaldehyde (271 mg, 1.00 mmol), 2,4-thiazolidinedione (176 mg, 1.50 mmol) and piperidine (0.10 mL, 1.0 mmol) were heated under reflux for 1.5 hours in ethanol (8 mL). The reaction solution was cooled down to room temperature, and water and 1 N HCl (1 mL) were added, and then the mixture was extracted with ethyl acetate. The organic layer was washed with water and brine, and then dried over anhydrous sodium sulfate. The solvent was evaporated under reduced pressure, and the residue was purified silica gel column chromatography (19:1 chloroform/acetonitrile) and preparative thin layer chromatography (10:1 chloroform/methanol) to give Compound 21 (30 mg, 8.1%).

$^1$H NMR (300 MHz, $CDCl_3$) δ 2.38 (s, 3H), 5.16 (s, 2H), 7.04 (d, J=2.4 Hz, 1H), 7.09 (dd, J=9.2, 2.6 Hz, 1H), 7.22 (d, J=7.9 Hz, 1H), 7.30 (d, J=7.8 Hz, 2H), 8.22 (d, J=9.2 Hz, 1H), 8.24 (s, 1H), 9.00 (br SR1H)

FABMS m/z 371 $(M+H)^+$ $C_{18}H_{14}N_2O_5S$=370

Example 51

Preparation of Compound 22

In an argon atmosphere, salicylaldehyde (0.213 mL, 2.00 mmol) was dissolved in dimethyl formamide (5 mL), and to the solution were added 4-methylbenzyl bromide (370 mg, 2.00 mmol) and sodium hydride (88 mg, 2.4 mmol), followed by stirring at 70° C. for 1.5 hours. The reaction solution was cooled with ice, and water was added thereto, and then the mixture was extracted with ethyl acetate. The organic layer was washed with water and brine, and then dried over anhydrous sodium sulfate. The solvent was evaporated under reduced pressure. 2,4-Thiazolidinedione (176 mg, 1.50 mmol), piperidine (0.10 mL, 1.0 mmol) and ethanol (5 mL) were added thereto, followed by heating under reflux for 1.5 hours. The reaction solution was cooled down to room temperature, and water and 1 N HCl (1 mL) were added, and then the mixture was extracted with ethyl acetate. The organic layer was washed with water and brine, and then dried over anhydrous sodium sulfate. The solvent was evaporated under reduced pressure, and the residue was triturated with hexane/diisopropyl ether to give Compound 22 (542 mg, 83% by two steps).

$^1$H NMR (300 MHz, DMSO-$d_6$) δ 2.31 (s, 3H), 5.19 (s, 2H), 7.10 (t, J=7.5 Hz, 1H), 7.22 (d, J=7.7 Hz, 2H), 7.24 (d, J=7.5 Hz, 1H), 7.35 (d, J=8.1 Hz, 2H), 7.4–7.5 (m, 2H), 8.01 (s, 1H), 12.6 (br s, 1H)

FABMS m/z 326 $(M+H)^+$ $C_{18}H_{15}NO_3S$=325

Example 52

Preparation of Compound 23

In an argon atmosphere, 5-methoxysalicylaldehyde (0.249 ML, 2.00 mmol) was dissolved in dimethyl formamide (5 mL), and to the solution were added 4-methylbenzyl bromide (370 mg, 2.00 mmol) and sodium hydride (88 mg, 2.4 mmol), followed by stirring at 70° C. for 1.5 hours. The reaction solution was cooled with ice, and water was added, and then the mixture was extracted with ethyl acetate. The organic layer was washed with water and brine, and then dried over anhydrous sodium sulfate. The solvent was evaporated under reduced pressure. 2,4-Thiazolidinedione (176 mg, 1.50 mmol), piperidine (0.10 mL, 1.0 mmol) and ethanol (5 mL) were added thereto, followed by heating under reflux for 1.5 hours. The reaction solution was cooled down to room temperature, and the thus precipitated crystals were collected by filtration to give Compound 23 (419 mg, 59% by two steps).

$^1$H NMR (300 MHz, DMSO-$d_6$) δ 2.31 (s, 3H), 3.75 (s, 3H), 5.12 (s, 2H), 6.90 (d, J=2.9Hz, 1H), 7.05 (dd, J=9.0, 2.9 Hz, 1H), 7.18 (d, J=9.0 Hz, 1H), 7.20 (d, J=7.7 Hz, 2H), 7.32 (d, J=8.1 Hz, 2H), 7.95 (s, 1H), 12.6 (brs, 1H)

FABMS m/z 356 $(M+H)^+$ $C_{19}H_{17}NO_4S$=355

Example 53

Preparation of Compound 24

In an argon atmosphere, 5-chlorosalicylaldehyde (313 mg, 2.00 mmol) was dissolved in dimethyl formamide (5 mL), and to the solution were added 4-methylbenzyl bromide (370 mg, 2.00 mmol) and sodium hydride (88 mg, 2.4 mmol), followed by stirring at 70° C. for 0.5 hour. The reaction solution was cooled with ice, and water was added, and then the mixture was extracted with ethyl acetate. The organic layer was washed with water and brine, and then dried over anhydrous sodium sulfate. The solvent was evaporated under reduced pressure. 2,4-Thiazolidinedione (176 mg, 1.50 mmol), piperidine (0.10 mL, 1.0 mmol) and ethanol (15 mL) were added thereto, followed by heating under reflux for 4 hours. The reaction solution was cooled down to room temperature, and water and 1 N HCl (1 mL) were added, and then the mixture was extracted with ethyl acetate. The organic layer was washed with water and brine, and then dried over anhydrous sodium sulfate. The solvent was evaporated under reduced pressure, and the residue was triturated with hexane/diisopropyl ether to give Compound 24 (428 mg, 60% by two steps).

$^1$H NMR (300 MHz, DMSO-$d_6$) δ 2.31 (s, 3H), 5.19 (s, 2H), 7.21 (d, J=8.3 Hz, 2H), 7.27 (d, J=9.0 Hz, 1H), 7.34 (d,

J=8.4 Hz, 2H), 7.36 (d, J=2.9 Hz, 1H), 7.51 (dd, J=9.0, 2.8 Hz, 1H), 7.87 (s, 1H), 12.6 (br s, 1H)

FABMS m/z 360 $(M+H)^+$ $C_{18}H_{14}{}^{35}ClNO_3S$=359

Example 54

Preparation of Compound 25

In an argon atmosphere, 5-bromosalicylaldehyde (1.00 g, 5.00 mmol) was dissolved in dimethylformamide (10 mL), and to the solution were added 4-methylbenzyl bromide (925 mg, 5.00 mmol) and sodium hydride (220 mg, 5.50 mmol), followed by stirring at 70° C. for 0.5 hour. The reaction solution was cooled with ice, and water was added, and then the mixture was extracted with ethyl acetate. The organic layer was washed with water and brine, and then dried over anhydrous sodium sulfate. The solvent was evaporated under reduced pressure. 2,4-Thiazolidinedione (702 mg, 6.00 mmol), piperidine (0.50 mL, 5.0 mmol) and ethanol (40 mL) were added thereto, followed by heating under reflux for 4 hours. The reaction solution was cooled down to room temperature, and water and 1 N HCl (5 mL) were added, and then the mixture was extracted with ethyl acetate. The organic layer was washed with water and brine, and then dried over anhydrous sodium sulfate. The solvent was evaporated under reduced pressure, and the residue was triturated with hexane/diisopropyl ether to give Compound 25 (1.27 mg, 63% by two steps).

$^1H$ NMR (300 MHz, DMSO-$d_6$) δ 2.31 (s, 3H), 5.19 (s, 2H), 7.21 (d, J=8.8 Hz, 3H), 7.34 (d, J=8.0 Hz, 2H), 7.48 (d, J=2.4 Hz, 1H), 7.62 (dd, J=8.8, 2.4 Hz, 1H), 7.86 (s, 1H), 12.6 (brs, 1H)

FABMS m/z 406, 404 $(M+H)^+$ $C_{18}H_{14}{}^{79}BrNO_3S$=403

Example 55

Preparation of Compound 26

4-Diphenylaminobenzaldehyde (273 mg, 1.00 mmol), 2,4-thiazolidinedione (176 mg, 1.50 mmol) and piperidine (0.10 mL, 1.0 mmol) were heated under reflux for 4 hours in ethanol (8 mL). The reaction solution was cooled down to room temperature, and water and 1 N HCl (1 mL) were added, and then the mixture was extracted with ethyl acetate. The organic layer was washed with water and brine, and then dried over anhydrous sodium sulfate. The solvent was evaporated under reduced pressure, and the residue was triturated with ethyl acetate to give Compound 26 (293 mg, 79%).

$^1H$ NMR (300 MHz, DMSO-$d_6$) δ 6.93 (d, J=7.2 Hz, 2H), 7.1–7.2 (m, 6H), 7.3–7.5 (m, 6H), 7.67 (s, 1H), 12.5 (br s, 1H)

FABMS m/z 373 $(M+H)^+$ $C_{22}H^{16}N_2O_2S$=372

Example 56

Preparation of Compound 27

2-Phenylbenzaldehyde (*Tetrahedron Lett.,* 38(32):5575 (1997)) (273mg, 1.50 mmol), 2,4-thiazolidinedione (263 mg, 2.25 mmol) and piperidine (0.15 mL, 1.5 mmol) were heated under reflux for 3 hours in ethanol (8 mL). The reaction solution was cooled down to room temperature, and water and 1 N HCl (2 mL) were added, and then the mixture was extracted with ethyl acetate. The organic layer was washed with water and brine, and then dried over anhydrous sodium sulfate. The solvent was evaporated under reduced pressure, and the residue was triturated with diisopropyl ether to give Compound 27 (344 mg, 82%).

$^1H$ NMR (300 MHz, DMSO-$d_6$) δ 7.3–7.4 (m, 2H), 7.4–7.7 (m, 8H), 12.6 (br s, 1H)

FABMS m/z 282 $(M+H)^+$ $C_{16}H_{11}NO_2S$=281

Example 57

Preparation of Compound 28

3-Phenylbenzaldehyde (*Tetrahedron Lett.,* 38(32):5575 (1997)) (269 mg, 1.48 mmol), 2,4-thiazolidinedione (259 mg, 2.22 mmol) and piperidine (0.15 mL, 1.5 mmol) were heated under reflux for 3 hours in ethanol (8 mL). The reaction solution was cooled down to room temperature, and water and 1N HCl (2 mL) were added, and then the mixture was extracted with ethyl acetate. The organic layer was washed with water and brine, and then dried over anhydrous sodium sulfate. The solvent was evaporated under reduced pressure, and the residue was triturated with diisopropyl ether to give Compound 28 (355 mg, 85%).

$^1H$ NMR (300 MHz, DMSO-$d_6$) δ 7.3–7.8 (m, 8H), 7.89 (s, 2H), 12.6 (br s, 1H)

FABMS m/z 282 $(M+H)^+$ $C_{16}H_{11}NO_2S$=281

Example 58

Preparation of Compound 29

4-Phenylbenzaldehyde (182 mg, 1.00 mmol), 2,4-thiazolidinedione (176 mg, 1.5 mmol) and piperidine (0.10 mL, 1.0 mmol) were heated under reflux for 3 hours in ethanol (6 mL). The reaction solution was cooled down to room temperature, and water and 1 N HCl (1 mL) were added, and then the mixture was extracted with ethyl acetate. The organic layer was washed with water and brine, and then dried over anhydrous sodium sulfate. The solvent was evaporated under reduced pressure, and the residue was triturated with diisopropyl ether to give Compound 29 (187 mg, 67%).

$^1H$ NMR (300 MHz, DMSO-$d_6$) δ 7.4–7.6 (m, 3H), 7.70 (d, J=8.4 Hz, 2H), 7.75 (d, J=7.2 Hz, 2H), 7.85 (s, 1H), 7.86 (d, J=8.1 Hz, 2H), 12.6 (br s, 1H)

FABMS m/z 282 $(M+H)^+$ $C_{16}H_{11}NO_2S$=281

Example 59

Preparation of Compound 30

4-(α-Hydroxybenzyl)benzaldehyde (*J. Org. Chem.,* 62: 4643 (1997)) (1.35 g, 6.37 mmol), 2,4-thiazolidinedione (894 mg, 7.64 mmol) and piperidine (0.64 mL, 6.4 mmol) were heated under reflux for 10 hours in ethanol (6 mL). The reaction solution was cooled down to room temperature, and water and 1 N HCl (7 mL) were added, and then the mixture was extracted with ethyl acetate. The organic layer was washed with water and brine, and then dried over anhydrous sodium sulfate. The-solvent was evaporated under reduced pressure, and the residue was triturated with diisopropyl ether to give Compound 30 (1.73 g, 87%).

$^1H$ NMR (300 MHz, DMSO-$d_6$) δ 5.75 (d, J 2.7 Hz, 1H), 6.03 (d, J=2.7 Hz, 1H), 7.21 (tt, J=7.2, 1.5 Hz, 1H), 7.31 (t, J=7.2 Hz, 2H), 7.38 (d, J=7.3 Hz, 2H), 7.53 (s, 4H), 7.75 (s, 1H), 12.6 (br s, 1H)

FABMS m/z 312 $(M+H)^+$ $C_{17}H_{13}NO_3S$=311

Example 60

Preparation of Compound 31

Compound 30 (622 mg, 2.00 mmol) was dissolved in acetonitrile (80 mL), and to the solution was added manganese dioxide (2.61 g) and the mixture was heated under reflux for 4.5 hours. The reaction solution was cooled down to room temperature and filtered through celite, and then the solvent was evaporated under reduced pressure. The residue was purified by silica gel column chromatography (9:1 chloroform/acetonitrile) and triturated with diisopropyl ether to give Compound 31 (73 mg, 12%).

$^1$H NMR (300 MHz, DMSO-$d_6$) δ 7.58 (t, J=7.5 Hz, 2H), 7.6–7.8 (m, 5H),7.86 (d, J=7.9 Hz, 2H), 7.87 (s, 1H), 12.7 (br s, 1H)

FABMS m/z 310 $(M+H)^+$ $C_{17}H_{11}NO_3S$=309.

Example 61

Preparation of Compound 32

Compound 30 (115 mg, 0.39 mmol) was dissolved in dichloromethane (15 mL), and to the solution were added trifluoroacetic acid (0.30 mL, 3.9 mmol) and triethylsilane (0.81 mL, 5.1 mmol) and the mixture was heated under reflux for 12 hours. The solvent was evaporated under reduced pressure, and the residue was recrystallized from acetone/hexane to give Compound 32 (70 mg, 61 %).

$^1$H NMR (300 MHz, DMSO-$d_6$) δ 4.00 (s, 2H), 7.1–7.3 (m, 5H),7.39 (d, J=8.1 Hz, 2H), 7.52(d, J=8.1 Hz, 2H), 7.75 (s, 1H), 12.6 (br s, 1H)

FABMS m/z 296 $(M+H)^+$ $C_{17}H_{13}NO_2S$=295

Example 62

Preparation of Compound 33

4-Formyltrityl alcohol (*J. Org. Chem.,* 63:9924 (1998)) (576 mg, 2.00 mmol), 2,4-thiazolidinedione (281 mg, 2.40 mmol) and piperidine (0.20 mL, 2.0 mmol) were heated under reflux for 9 hours in ethanol (15 mL). The reaction solution was cooled down to room temperature, and water and 1 N HCl (2 mL) were added, and then the mixture was extracted with ethyl acetate. The organic layer was washed with water and brine, and then dried over anhydrous sodium sulfate. The solvent was evaporated under reduced pressure, and the residue was triturated with ethyl acetate/diisopropyl ether to give Compound 33 (684 mg, 78%).

$^1$H NMR (300 MHz, DMSO-$d_6$) δ 6.61 (s, 1H), 7.2–7.4 (m, 10H),7.37 (d, J=8.4 Hz, 2H),7.55 (d, J=8.4 Hz, 2H), 7.76 (s, 1H), 12.6 (br s, 1H)

FABMS m/z 388 $(M+H)^+$ $C_{23}H_{17}NO_3S$=387

Example 63

Preparation of Compound 34

Compound 33 (219 mg, 0.566 mmol) was dissolved in dichloromethane (15 mL), and to the solution were added trifluoroacetic acid (0.385 mL, 0.50 mmol) and triethylsilane (0.80 mL, 0.50 mmol), followed by stirring at room temperature for 10 minutes. The solvent was evaporated under reduced pressure, and the residue was triturated with hexane to give Compound 34 (198 mg, 94%).

$^1$H NMR (300 MHz, DMSO-$d_6$) δ 5.70 (s, 1H), 7.1–7.4 (m, 12H), 7.55 (d, J=8.3 Hz, 2H), 7.75 (s, 1H), 12.6 (br s, 1H)

FABMS m/z 372 $(M+H)^+$ $C_{23}H_{17}NO_2S$=371

Example 64

Preparation of Compound 35

In an argon atmosphere, diphenylamine (338 mg, 2.00 mmol) and 4-bromobenzyl bromide (500 mg, 2.00 mmol) were dissolved in dimethylformamide (8 mL), and to the solution was added sodium hydride (88 mg, 2.2 mmol) under ice -cooling, followed by stirring at room temperature for 4 hours. To the reaction solution was added water, and the mixture was extracted with ethyl acetate. The organic layer was washed with water and brine, and then dried over anhydrous sodium sulfate. The solvent was evaporated under reduced pressure, and the residue was purified by silica gel column chromatography (14:1 hexane/acetone) to obtain N-(4-bromobenzyl)diphenylamine (478 mg, 71%).

$^1$H NMR (300 MHz, $CDCl_3$) δ 4.93 (s, 2H), 6.94 (tt, J=7.3, 1.1 Hz, 2H), 7.03 (dd, J=8.8, 1.1 Hz, 4H), 7.2–7.3 (m, 6H), 7.42 (d, J=8.6 Hz, 2H)

FABMS m/z 339, 337 $(M^+)$ $C_{19}H_{16}{}^{79}BrN$=337

In an argon atmosphere, the thus obtained N-(4-bromobenzyl)diphenylamine (440 mg, 1.30 mmol) was dissolved in tetrahydrofuran (6 mL) and cooled to −78° C. A 1.6 M n-butyl lithium hexane solution (1.3 mL, 2.0 mmol) was added thereto, and, 5 minutes thereafter, dimethylformamide (0.20 mL, 2.6 mmol) was further added thereto, followed by stirring for 5 minutes. To the reaction solution was added water, and the mixture was extracted with ethyl acetate. The organic layer was washed with brine, and then dried over anhydrous sodium sulfate. The solvent was evaporated under reduced pressure, and the residue was purified by silica gel column chromatography (9:1 hexane/ethyl acetate) to obtain 4-(N,N-diphenylaminomethyl)benzaldehyde (213 mg, 57%).

$^1$H NMR (300 MHz, $CDCl_3$) δ 5.06 (s, 2H), 6.96 (t, J=7.3 Hz, 2H), 7.03 (d, J=8.6 Hz, 4H), 7.25 (dd, J=8.6, 7.3 Hz, 4H), 7.52 (d, J=8.4 Hz, 2H), 7.83 (d, J=8.3 Hz, 2H), 9.97 (s, 1H)

FABMS m/z 287 $(M^+)$ $C_{20}H_{17}NO$=287

The obtained 4-(N,N-diphenylaminomethyl)benzaldehyde (198 mg, 0.690 mmol), 2,4-thiazolidinedione (117 mg, 1.10 mmol) and piperidine (0.068 mL, 0.69 mmol) were heated under reflux for 5 hours in ethanol (6 mL). The reaction solution was cooled down to room temperature, and the precipitated crystals were collected by filtration to give Compound 35 (240 mg, 90%).

$^1$H NMR (300 MHz, DMSO-$d_6$) δ 5.06 (s, 2H), 6.92 (t, J=7.2 Hz, 2H), 7.05 (d, J=8.4 Hz, 4H), 7.25 (t, J=7.7 Hz, 4H), 7.48 (d, J=8.3 Hz, 2H), 7.55 (d, J=8.4 Hz, 2H), 7.75 (s, 1H), 12.6 (br s, 1H)

FABMS m/z 386 $(M^+)$ $C_{23}H_{18}N_2O_2S$=386

Example 65

Preparation of Compound 36

In an argon atmosphere, 4-bromoaniline (344 mg, 2.00 mmol) was dissolved in dimethylformamide (5 mL), and to the solution were added sodium hydride (200 mg, 5.00 mmol) and benzyl bromide (0.52 mL, 4.4 mmol) under ice-cooling, followed by stirring at room temperature for 11 hours. To the reaction solution was added water, and the mixture was extracted with ethyl acetate. The organic layer was washed with water and brine, and then dried over anhydrous sodium sulfate. The solvent was evaporated under reduced pressure, and the residue was recrystallized from ethyl acetate/hexane to obtain 4-bromo-N,N-dibenzylaniline (442 mg, 63%).

$^1$H NMR (300 MHz, $CDCl_3$) δ 4.63 (s, 4H), 6.59 (d, J=9.0, 2H), 7.2–7.4 (m, 12H)

FABMS m/z 353, 351 $(M^+)$ $C_{20}H_{18}{}^{79}BrN$=351

In an argon atmosphere, the obtained 4-bromo-N,N-dibenzylaniline (425 mg, 1.21 mmol) was dissolved in tetrahydrofuran (5 mL) and cooled to −78° C. A 1.6 M n-butyl lithium hexane solution (1.1 mL, 1.8 mmol) was added thereto, and, 5 minutes thereafter, dimethylformamide (0.186 mL, 2.4 mmol) was further added thereto, followed by stirring for 5 minutes. To the reaction solution was added water, and the mixture was extracted with ethyl acetate. The organic layer was washed with a saturated brine, and then dried over anhydrous sodium sulfate. The solvent was evaporated under reduced pressure, and the residue was purified by silica gel column chromatography (9:1 hexane/ethyl acetate) to obtain 4-(dibenzylamino)benzaldehyde (192 mg, 53%).

$^1$H NMR (300 MHz, $CDCl_3$) δ 4.75 (s, 4H), 6.79 (d, J=9.0 Hz, 2H), 7.2–7.4 (m, 1OH), 7.69 (d, J=9.0, 2H), 9.73 (s, 1H) FABMS m/z302 $(M+H)^+$ $C_{21}H_{19}NO$=301

The obtained 4-(dibenzylamino)benzaldehyde (181 mg, 0.601 mmol), 2,4-thiazolidinedione (105 mg, 0.900 mmol) and piperidine (0.059 mL, 0.60 mmol) were heated under reflux for 5 hours in ethanol (7 mL). The reaction solution was cooled down to room temperature, and water and 1 N HCl (0.6 mL) were added, and then the mixture was extracted with ethyl acetate. The organic layer was washed with water and brine, and then dried over anhydrous sodium sulfate. The solvent was evaporated under reduced pressure, and the residue was triturated with diisopropyl ether to give Compound 36 (207 mg, 86%).

$^1$H NMR (300 MHz, DMSO-$d_6$) δ 4.81 (s, 4H), 6.81 (d, J=8.8 Hz, 2H), 7.2–7.4 (m, 12H), 7.61 (s, 1H), 12.3 (br s, 1H)

FABMS m/z 400 $(M^+)$ $C_{24}H_{20}N_2O_2S$=400.

Example 66

Preparation of Compound 39

5-Nitro-2-[(4-trifluoromethyl)phenoxy]benzaldehyde (311 mg, 1.00 mmol), 2,4-thiazolidinedione (234 mg, 2.00 mmol) and piperidine (0.10 mL, 1.0 mmol) were heated under reflux for 13 hours in ethanol (8 mL). The reaction solution was cooled down to room temperature, and water and 1 N HCl (1mL) were added, and then the mixture was extracted with ethyl acetate. The organic layer was washed with water and brine, and then dried over anhydrous sodium sulfate. The solvent was evaporated under reduced pressure, and the residue was purified by silica gel column chromatography (15:1 chloroform/acetonitrile), and then triturated with diisopropyl ether to give Compound 39 (146 mg, 36%).

$^1$H NMR (300 MHz, DMSO-$d_6$) δ 7.16 (d, J=9.2 Hz, 1H), 7.45 (d, J=8.4Hz, 2H), 7.89 (d, J=8.4Hz, 2H), 7.93 (s, 1H), 8.30 (dd, J=9.2, 2.8 Hz, 1H), 8.39 (d, J=2.2 Hz, 1H), 12.8 (br s, 1H)

FABMS m/z 41 1 $(M+H)^+$ $C_{17}H_9F_3N_2O_5S$=410.

Example 67

Preparation of Compound 40

In an argon atmosphere, 2-bromo-5-hydroxybenzaldehyde (201 mg, 1.00 mmol) was dissolved in dimethyl formamide (3 mL), and to the solution were added 4-methylbenzyl bromide (185 mg, 1.00 mmol) and sodium hydride (48 mg, 1.2 mmol), followed by stirring at 70° C. for 3 hours. The reaction solution was cooled with ice, and water was added, and then the mixture was extracted with ethyl acetate. The organic layer was washed with water and brine, and then dried over anhydrous sodium sulfate. The solvent was evaporated under reduced pressure. 2,4-Thiazolidinedione (176 mg, 1.5 mmol), piperidine (0.10 mL, 1.0 mmol) and ethanol (6 mL) were added thereto, followed by heating under reflux for 13 hours. The reaction solution was cooled down to room temperature, and water and 1 N HCl (5 mL) were added, and then the mixture was extracted with ethyl acetate. The organic layer was washed with water and brine, and then dried over anhydrous sodium sulfate. The solvent was evaporated under reduced pressure, and the residue was purified by silica gel column chromatography (20:1 chloroform/acetonitrile) and triturated with diisopropyl ether to give Compound 40 (142 mg, 35% by two steps).

$^1$H NMR (300 MHz, DMSO-$d_6$) δ 2.31 (s, 3H), 5.13 (s, 2H), 7.0–7.1 (m, 2H), 7.21 (d, J=7.7 Hz, 2H), 7.34 (d, J=7.7 Hz, 1H), 7.69 (d, J=8.6 Hz, 1H), 7.79 (s, 1H), 12.7 (br s, 1H)

FABMS m/z 406, 404 $(M+H)^+$ $C_{18}H_{14}{}^{79}BrNO_3S$=403.

Example 68

Preparation of Compound 41

In an argon atmosphere, 2,5-dihydroxybenzaldehyde (138 mg, 1.00 mmol) was dissolved in dimethylformamide (5 mL), and to the solution were added 4-methylbenzyl bromide (370 mg, 2.00 mmol) and sodium hydride (88 mg, 2.2 mmol), followed by stirring at 70° C. for 2 hours. The reaction solution was cooled with ice, and water Was added, and then the mixture was extracted with ethyl acetate. The organic layer was washed with water and brine, and then dried over anhydrous sodium sulfate. The solvent was evaporated under reduced pressure. 2,4-Thiazolidinedione (176 mg, 1.5 mmol), piperidine (0. 10 mL, 1.0 mmol) and ethanol (8 mL) were added thereto, followed by heating under reflux for 2 hour. The reaction solution was cooled down to room temperature, and water and 1 N HCl (5 mL) were added, and then the mixture was extracted with ethyl acetate. The organic layer was washed with water and brine, and then dried over anhydrous sodium sulfate. The solvent was evaporated under reduced pressure, and the residue was triturated with hexane/diisopropyl ether to give Compound 41 (340 mg, 76% by two steps).

$^1$H NMR (300 MHz, DMSO-$d_6$) δ 2.30 (s, 6H), 5.05 (s, 2H), 5.11 (s, 2H), 6.93 (br s, 1H), 7.1–7.2 (m, 2H), 7.20 (d, J=7.7 Hz, 4H), 7.32 (d, J=7.9 Hz, 4H), 7.93 (s, 1H), 12.6 Hz, 1H)

FABMS m/z 446 $(M+H)^+$ $C_{26}H_{23}NO_4S$=445

Example 69

Preparation of Compound 42

In an argon atmosphere, 5'-bromo-2'-hydroxyacetophenone (215 mg, 1.00 mmol) was dissolved in dimethylformamide (5 mL), and to the solution were mixed with 4-methylbenzyl bromide (185 mg, 1.00 mmol) and potassium carbonate (152 mg, 1.1 mmol), followed by stirring at 70° C. for 5 hours. The reaction solution was cooled with ice, and water was added, and then the mixture was extracted with ethyl acetate. The organic layer was washed with a 0.1 N aqueous sodium hydroxide solution, water and brine, and then dried over anhydrous sodium sulfate. The solvent was evaporated under reduced pressure. 2,4-Thiazolidinedione (176 mg, 1.5 mmol) and sodium acetate (123 mg, 1.0 mmol) were added thereto, followed by heating at 190° C. for 3–5 hours. The reaction solution was cooled down to room temperature, and water and 1 N HCl (1 mL) were added, and then the mixture was extracted with ethyl acetate. The organic layer was washed with water and a saturated brine, and then dried over anhydrous sodium sulfate. The solvent was evaporated under reduced pressure, and the residue was purified by silica gel column chromatography (30:1 chloroform/acetonitrile) to give Compound 42 (102 mg, 24% by two steps).

$^1H$ NMR (300 MHz, DMSO-$d_6$) δ 2.35 (s, 3H), 2.61 (s, 3H), 6.88 (d, J=9.0 Hz, 1H), 7.1–7.3 (m, 5H), 7.41 (dd, J=8.8, 2.6 Hz, 1H), 8.14 (br s, 1H)

FABMS m/z 419, 418 $(M+H)^+$ $C_{19}H_{16}{}^{79}BrNO_3S$=417.

Example 70

Preparation of Compound 43

5-Bromo-2-(4-chlorophenylthio)thiophene-3-carboxyaldehyde (167 mg, 0.500 mmol), 2,4-thiazolidinedione (88 mg, 0.75 mmol) and piperidine (0.049 mL, 0.5 mmol) were heated under reflux for 6 hours in ethanol (5 mL). The reaction solution was cooled down to room temperature, water and 1 N HCl (0.5 mL) were added, and then the mixture was extracted with chloroform. The organic layer was washed with water and brine, and then dried over anhydrous sodium sulfate. The solvent was evaporated under reduced pressure, and the residue was triturated with diisopropyl ether/ethyl acetate to give Compound 43 (138 mg, 64%).

$^1H$ NMR (300 MHz, DMSO-$d_6$) δ 7.32 (d, J=8.6 Hz, 2H), 7.47 (d, J=8.6 Hz, 2H), 7.82 (s, 1H), 7.98 (s, 1H), 12.7 (br s, 1H).

FABMS m/z 433, 431 $(M^+)$ $C_{14}H_7{}^{79}Br^{35}ClNO_2S_3$=431.

Example 71

Preparation of Compound 44

In an argon atmosphere, Compound 43 (22 mg, 0.051 mmol) was dissolved in dimethoxyethane (2 mL), and to the solution were added tetrakistriphenylphosphine palladium (6 mg, 10 mol %), sodium carbonate aqueous solution (0.5 M, 0.6 mL) and phenyl boronic acid (31 mg, 0.25 mmol) and heated under reflux for 12 hours. The reaction solution was cooled down to room temperature, and water was added, and then the mixture was extracted with ethyl acetate. The organic layer was washed with brine, and then dried over anhydrous sodium sulfate. The solvent was evaporated under reduced pressure, and the residue was purified by preparative thin layer chromatography (10:1 chloroform/acetone) to give Compound 44 (8.3 mg, 38%).

$^1H$ NMR (300 MHz, DMSO-$d_6$) δ 7.17 (d, J=8.4 Hz, 2H), 7.2–7.5 (m, 8H), 7.91 (s, 1H), 8.16 (br s, 1H)

FABMS m/z 429 $(M^+)$ $C_{20}H_{12}{}^{35}ClNO_2S_3$=429.

Example 72

Preparation of Compound 45

In an argon atmosphere, Compound 43 (32 mg, 0.075 mmol) was dissolved in tetrahydrofuran (5 mL) and cooled down to −78° C. n-Butyl lithium (a 1.6 mol/L hexane solution, 0.3 mL) was added thereto, followed by stirring for 15 minutes. The reaction solution was mixed with water and extracted with ethyl acetate. The organic layer was washed with brine, and then dried over anhydrous sodium sulfate. The solvent was evaporated under reduced pressure, and the residue was purified by preparative thin layer chromatography (10:1 chloroform/acetone) to give Compound 45 (3.8 mg, 14%).

$^1H$ NMR (300 MHz, DMSO-$d_6$) δ 7.24.(d, J=4.2 Hz, 1H), 7.27 (d, J=9.0 Hz, 2H), 7.30 (d, J=3.9 Hz, 1H), 7.31 (d, J=9.2 Hz, 2H), 7.91 (s, 1H), 8.42 (br s, 1H)

FABMS m/z 353 $(M^+)$ $C_{14}H_8{}^{35}ClNO_2S_3$=353.

Example 73

Preparation of Compound 46

In an argon atmosphere, tris(4-bromophenyl)amine (964 mg, 2.00 mmol) was dissolved in tetrahydrofuran (10 mL) and cooled to −78° C. n-Butyl lithium (a 1.6 mol/L hexane solution, 1.5 mL, 2.4 mmol) and dimethylformamide (0.19 mL, 2.4 mmol) was dripped thereto at a system temperature of −60° C. or less, followed by stirring for 10 minutes. To the reaction liquid was added water and the product was extracted with ethyl acetate. The organic layer was washed with water and brine, and then dried over anhydrous sodium sulfate. The solvent was evaporated under reduced pressure, and the residue was purified by silica gel column chromatography (elution solvent: hexane/ethyl acetate=8/1) to give 4-[bis(4-bromophenyl)amino]benzaldehyde (377 mg, 44%).

$^1H$ NMR (300 MHz, $CDCl_3$) δ (ppm) 7.02 (d, J=8.8 Hz, 4H), 7.04 (d, J=8.6 Hz, 2H), 7.45 (d, J=8.8 Hz, 4H), 7.71 (d, J=8.8 Hz, 2H), 9.84 (s, 1H)

FABMS m/z 433, 431, 429 $(M^+)$ $C_{19}H_{13}{}^{79}BR_2NO$=429

The 4-[bis(4-bromophenyl)amino]benzaldehyde (356 mg, 0.826 mmol), 2,4-thiazolidinedione (145 mg, 1,24 mmol), and piperidine (0.083 mL, 0.83 mmol) were heated under reflux for four hours in ethanol (8 mL). The reaction liquid was cooled to room temperature, mixed with water and 1 mol/L HCl (1 mL), and was extracted with chloroform. The organic layer was washed with water and brine, and then dried over anhydrous sodium sulfate. The solvent was evaporated under reduced pressure, the residue was purified by silica gel column chromatography (elution solvents chloroform/acetonitrile=15/1) and was triturated with hexane to give Compound 46 (388 mg, 89%).

$^1H$ NMR (300 MHz, DMSO-$d_6$) δ (ppm) 7.03 (d, J=8.8 Hz, 2H), 7.06 (d, J=8.8 Hz, 4H), 7.51 (d, J=8.8 Hz, 2H), 7.54 (d, J=8.8 Hz, 4H), 7.70 (s, 1H), 12.5 (br s, 1H)

FABMS m/z 532, 530, 528 $(M^+)$ $C_{22}H_{14}{}^{79}BR_2N_2O_2S$=528

Example 74

Preparation of Compound 47

In an argon atmosphere, Compound 25 (40 mg, 0.10 mmol) was dissolved in 1,2-dimethoxyethane, (4 mL). Phenyl boric acid (24 mg, 0.20 mmol), a 2 mol/L sodium carbonate aqueous solution (0.15 mL), water (0.5 mL), and tetrakis(triphenylphosphine) palladium (6 mg, 5 mol %) were added and the product was heated under reflux for 8 hours. The reaction liquid was cooled to room temperature, mixed with water and 1 mol/L HCl, and was extracted with ethyl acetate. The organic layer was washed with water and brine, and then dried over anhydrous sodium sulfate. The solvent was evaporated under reduced pressure, and the residue was purified by preparative thin layer chromatography (development solvent: chloroform/acetonitrile=12/1) and was triturated with isopropyl ether to give Compound 47 (27 mg, 67%).

$^1H$ NMR (300 MHz, DMSO-$d_6$) δ (ppm) 2.32 (s, 3H), 5.25 2H), 7.23 (d, J=8.1 Hz, 2H), 7.3–7.4 (m, 4H), 7.49 (t, J=7.6 Hz, 2H), 7.63 (d, J=8.6 Hz, 2H), 7.64 (d, J=1.7 Hz, 1H), 7.76 (dd, J=8.6, 2.2 Hz, 1H), 8.03 (s, 1H), 12.6 (br s, 1H)

FABMS m/z 401 $(M^+)$ $C_{24}H_{19}NO_3S$=401

Example 75

Preparation of Compound 48

2-Thienyl boric acid (26 mg, 0.20 mmol) was used instead of phenyl boric acid to obtain Compound 48 (7.5 mg, 18%)

from Compound 25 (40 mg, 0.10 mmol), using the same method as Example 74.

$^1$H NMR (300 MHz, DMSO-$_6$) δ (ppm) 2.32 (s, 3H), 5.23 (s, 2H), 7.14 (dd, J=5.0, 3.7 Hz, 1H), 7.22 (d, J=7.9 Hz, 2H), 7.30 (d, J=8.8 Hz, 1H), 7.36 (d, J=8.1 Hz, 2H), 7.44 (d, J=3.5 Hz, 1H), 7.53 (d, J=4.8 Hz, 1H), 7.62 (d, J 2.0 Hz, 1H), 7.75 (dd, J=8.8, 2.0 Hz, 1H), 7.98 (s, 1H), 12.6 (br s, 1H)

FABMS m/z 407 ($M^+$) $C_{22}H_{17}NO_3S_2$=407.

Example 76

Preparation of Compound 49

In an argon atmosphere, tris(4-bromophenyl)amine (7.23 g, 15.0 mmol) was dissolved in tetrahydrofuran (100 mL) and cooled to −78° C. n-Butyl lithium (a 1.6 mol/L hexane solution, 34 mL, 54 mmol) and dimethylformamide (4.6 mL, 60 mmol) was dripped thereto at a system temperature of −60° C. or less, followed by stirring for 10 minutes at the same temperature. Water was added to the reaction liquid and the product was extracted with ethyl acetate. The organic layer was washed with water and brine, and then dried over anhydrous sodium sulfate. The solvent was evaporated under reduced pressure, and the residue was purified by silica gel column chromatography (elution solvent: hexane/ethyl acetate=4/1 followed by chloroform/acetonitrile=30/1) to give tris(4-formylphenyl)amine (2.97 g, 60%).

$^1$H NMR (300 MHz, $CDCl_3$) δ (ppm) 7.25 (d, J=8.8 Hz, 6H), 7.85 (d, J=8.8 Hz, 6H), 9.95 (s, 3H).

FABMS m/z 330 $(M+H)^+$ $C_{21}H_{15}NO_3$=329.

The tris(4-formylphenyl)amine (165 mg, 0.502mmol) was dissolved in methyl alcohol (8 mL) and chloroform (5 mL). To the solution sodium borohydride (9.5 mg, 0.25 mmol) was added under ice-cooling, followed by stirring at room temperature for 15 minutes. Water was added to the reaction liquid and the product was extracted with chloroform. The organic layer was washed with brine, and then dried over anhydrous sodium sulfate. The solvent was evaporated under reduced pressure, and the residue was purified by silica gel column chromatography (elution solvent: chloroform/acetonitrile=20/1–10/1) to give 4-[[bis(4-hydroxymethyl)phenyl]amino]benzaldehyde (107 mg, 64%).

$^1$H NMR (300 MHz, $CDCl_3$) δ (ppm) 2.46 (br s, 2H), 4.66 (s, 4H), 6.99 (d, J=8.8 Hz, 2H), 7.13 (d, J=8.4 Hz, 4H), 7.32 (d, J=8.4 Hz, 4H), 7.64 (d, J=8.8 Hz, 2H), 9.75 (s, 1H)

FABMS m/z 333 ($M^+$) $C_{21}H^{19}NO_3$=333.

The 4-[[bis(4-hydroxymethyl)phenyl]amino]benzaldehyde (100 mg, 0.300 mmol)$^0$, 2,4-thiazolidinedione (53 mg, 0.45 mmol), and piperidine (0.030 mL, 0.30 mmol) were heated under reflux for three hours in ethanol (5 mL). The reaction liquid was cooled to room temperature, mixed with water and 1 mol/L HCl (1 mL), and the product was extracted with ethyl acetate. The organic layer was washed with water and brine, and then dried over anhydrous sodium sulfate. The solvent was evaporated under reduced pressure, and triturated with hexane to give Compound 49 (113 mg, 87%).

$^1$H NMR (300 MHz, DMSO-$d_6$) δ (ppm) 4.48 (d, J=4.4 Hz, 4H), 5.16 (br t, J=5.1 Hz 2H), 6.89 (d, J=8.8 Hz, 2H), 7.09 (d, J=8.3 Hz, 4H), 7.32 (d, J=8.5 Hz, 4H), 7.44 (d, J=9.0 Hz, 2H), 7.66 (s, 1H), 12.4 (br s, 1H)

FABMS m/z 432 ($M^+$) $C_{24}H_{20}N_2O_4S$=432.

Example 77

Preparation of Compound 50

In an argon atmosphere, N-(4-bromobenzyl)diphenylamine (169 mg, 0.500 mmol) obtained in Example 64 was dissolved in dimethylformamide (1.5 mL), and phosphorus oxychloride (0.116 mL, 1.25 mmol) was added thereto, followed by stirring at 100° C. for 30 minutes. The reaction liquid was cooled to room temperature, poured into saturated sodium acetate aqueous solution, and was extracted with ethyl acetate. The organic layer was washed with brine, and then dried over anhydrous sodium sulfate. The solvent was evaporated under reduced pressure, and the residue was purified by silica gel column chromatography (elution solvent:hexane/ethyl acetate=4/1) to give 4-[N-(4-bromobenzyl)-N-phenylamino]-benzaldehyde (159 mg, 87%).

$^1$H NMR (300 MHz, $CDCl_3$) δ (ppm) 4.98 (s, 2H), 6.78 (d, J=8.8 Hz, 2H), 7.18 (d, J=8.3 Hz, 2H), 7.26 (m, 1H), 7.27 (d, J=8.4 Hz, 2H), 7.42 (m, 2H), 7.45 (d, J=8.4 Hz, 2H), 7.65 (d, J=8.8 Hz, 2H), 9.75 (s, 1H)

FABMS m/z 368, 366 $(M+H)^+$ $C_{20}H_{16}{}^{79}BrNO$=365.

The 4-[N-(4-bromobenzyl)-N-phenylamino]benzaldehyde (153 mg, 0.418 mmol), 2,4-thiazolidinedione (73 mg, 0.63. mmol), and piperidine (0.042 mL, 0.42 mmol) were heated under reflux for three hours in ethanol (5 mL). The reaction liquid was cooled to room temperature, mixed with water and 1 mol/L HCl (1 mL), and was extracted with ethyl acetate. The organic layer was washed with water and brine, and then dried over anhydrous sodium sulfate. The solvent was evaporated under reduced pressure, and triturated with hexane/isopropyl ether to give Compound 50 (150 mg, 87%).

hu 1H NMR (300 MHz, DMSO-$d_6$) δ (ppm) 5.06 (s, 2H), 6.88 (d, J=8.8 Hz, 2H), 7.21 (t, J=7.3Hz, 1H), 7.27(d, J=8.3Hz,2H),7.32(d, J=7.5Hz,2H),7.40(d, J=8.8 Hz, 2H), 7.42 (t, J=7.3 Hz, 2H), 7.51 (d, J=8.3 Hz, 2H), 7.64 (s, 1H), 12.4 (br s, 1H)

FABMS m/z 466, 464 ($M^+$) $C_{23}H_{17}{}^{79}BrN_2O_2S$=464.

Example 78

Preparation of Compound 51

Under ice-cooling, Compound 43 (50 mg, 0.12 mmol) was dissolved in a mixed solvent of dichloromethane (8 mL) and methanol (2 mL). m-Chloroperbenzoic acid (50% purity, 65 mg, 0.19 mmol) was added thereto, followed by stirring at room temperature for 18 hours. To the reaction liquid a 5% sodium hydrogen sulfite aqueous solution was added and the product was extracted with chloroform. The organic layer was washed, with sodium bi-carbonate aqueous solution and brine, and then dried over anhydrous sodium sulfate. The solvent was evaporated under reduced pressure, and the residue was triturated with methanol to give Compound 51 (30 mg, 56%).

$^1$H NMR (300 MHz, DMSO-$d_6$) δ (ppm) 7.73 (d, J=8.4 Hz, 2H), 7.75 (s, 1H), 7.84 (d, J=8.6 Hz, 2H), 7.98 (s, 1H), 12.8 (br s, 1H)

FABMS mn/z 450, 448 $(M-H)^-$ $C_{14}H_7{}^{79}Br^{35}Cl_1NO_3S_3$=449.

Example 79

Preparation of Compound 52

Under ice-cooling, Compound 43 (50 mg, 0.12. mmol) was dissolved in a mixed solvent of dichloromethane (8 mL) and methanol (2 mL). m-Chloroperbanzoic acid (50% purity, 398 mg, 1.2 mmol) was added thereto, followed by stirring at room temperature for 17 hours. To the reaction liquid a 5% sodium hydrogen sulfite aqueous solution was added and the product was extracted with chloroform. The organic layer was washed with sodium hydrogencarbonate aqueous solution and brine, and then dried over anhydrous sodium sulfate. The solvent was evaporated under reduced pressure, and triturated with methanol to give Compound 52 (23 mg, 41%).

$^1$H NMR (300 MHz, DMSO-$d_6$) δ (ppm) 7.71 (d, J 8.6 Hz, 2H), 7.78 (s, 1H), 8.00 (s, 1H), 8.05 (d, J=8.6 Hz, 2H), 12.9 (br s, 1H)

FABMS m/z 466, 464 (M−H)$^-$ $C_{14}H_7{}^{79}Br_{35}C_1NO_4S_3$=465.

Example 80

Preparation of Compound 53

Commercially available 5-bromo-2-(4-chlorophenyl-thio) thiophene-3-carboxaldehyde (1.00 g, 2.99 mmol) (MAYBRIDGE, Catalog Number: KM05476) was dissolved in methanol (75 mL). p-Toluenesulfonic acid (52 mg, 0.30 mol) was added thereto, and the mixture was heated under reflux for 1.5 hours. The solvent was evaporated under reduced pressure until the total volume becomes about 30 mL. Water and saturated sodium bicarbonate aqueous solution were added thereto, and the product was extracted with ethyl acetate. The organic layer was washed with water and brine, and then dried over anhydrous sodium sulfate. The solvent was evaporated under reduced pressure to give 5-bromo-2-(4-chlorophenylthio)-3-(dimethoxymethyl)-thiophene (1.12 g, 100%).

$^1$H NMR (300 MHz, $CDCl_3$) δ (ppm) 3.36 (s, 6H), 5.55 (s, 1H), 7.07 (s, 1H), 7.15 (d, =J=8.6 Hz, 2H), 7.24 (d, J=8.8 Hz, 2H)

FABMS m/z 380, 378 (M$^+$) $C_{13}H_{12}{}^{79}Br_{35}ClO_2S_2$=378.

In an argon atmosphere, 5-bromo-2-(4-chlorophenylthio)-3-(dimethoxymethyl)thiophene (1.04 g, 2.75 mmol) was dissolved in tetrahydrofuran (15 mL) and the mixture was cooled to −78° C. n-Butyl lithium (1.6 mol/L hexane solution; 2.5 mL, 4.1 mmol) was added thereto, followed by stirring for 5 minutes. Dry ice (about 1 g) was added thereto, followed by stirring for 10 minutes. Water and 1 mol/L sodium hydroxide aqueous solution was added to the reaction liquid so that pH becomes 10, and the mixture was washed with ether. 1 mol/L Hydrochloric acid was added to the aqueous layer so that pH becomes 3, and the aqueous layer was extracted with ethyl acetate. The organic layer was washed with water and brine and then dried over anhydrous sodium sulfate, and the solvent was evaporated under reduced pressure. The residue was dissolved in tetrahydrofuran (10 mL). 1 mol/L hydrochloric acid (2 mL) was added thereto, followed by stirring at room temperature for 2 hours. Water was added to the reaction liquid and the product was extracted with ethyl acetate. The organic layer was washed with water and brine, and then dried over anhydrous sodium sulfate. The solvent was evaporated under reduced pressure, and the residue was triturated with isopropyl ether to give 2-(4-chlorophenylthio)-3-formyl-5-thiophenecarboxylic acid (439 mg, 54%).

$^1$H NMR (300 MHz, $CDCl_3$) δ (ppm) 7.50 (d, J=8.6 Hz, 2H), 7.62 (d, J=8.6 Hz, 2H), 8.06 (s, 1H), 9.68 (s, 1H)

FABMS m/z 299 (M+H)$^+$ $C_{12}H_7{}^{35}ClO_3S^2$=298.

2-(4-Chlorophenylthio)-3-formyl-5-thiophensecarboxylic acid (400 mg, 1.34 mmol), 2,4-thiazolidinedione (188 mg, 1.01 mmol), and piperidine (0.133 mL, 1.34 mmol) were heated under reflux for 3.5 hours in ethanol (12 mL). The reaction mixture was cooled to room temperature. 1 mol/L hydrochloric acid (1.5 mL) was added thereto, and the thus precipitated crystals were collected by filtration to give Compound 53 (411 mg, 77%).

$^1$H NMR (300 MHz, DMSO-$d_6$) δ (ppm) 7.66 (d, J=8.4 Hz, 2H), 7.77 (d, J=8.4 Hz, 2H), 7.83 (s, 1H), 7.90 (s, 1H), 12.6 (br s, 1H), 13.4 (br s, 1H)

FABMS m/z 396 (M−H)$^-$ $C_{15}H_8{}^{35}ClNO_4S_3$=397.

Example 81

Preparation of Compound 54

Compound 53 (80 mg, 0.20 mmol) was dissolved in dimethylformamide (3 mL). 1-(3-Dimethylaminopropyl)-3-ethylcarbodiimide hydrochloride (77 mg, 0.40 mmol) and diethylamine (0.041 mL, 0.40 mmol) were added thereto, followed by stirring at room temperature for 3 hours. Water was added to the reaction liquid and the product was extracted with ethyl acetate. The organic layer was washed with water and brine, and then dried over anhydrous sodium sulfate. The solvent was evaporated under reduced pressure, and the residue was purified by preparative thin layer chromatography (9:1 chloroform/methanol) and was triturated with hexane to give Compound 54 (22 mg, 24%).

$^1$H NMR (300 MHz, DMSO-$d_6$) δ (ppm) 1.06 (br s, 6H), 3.13 (br s, 2H), 3.41 (br s, 2H), 7.41 (d, J=8.6 Hz, 2H), 7.47 (d, J=8.6 Hz, 2H), 7.69 (s, 1H), 8.00 (s, 1H), 12.7 (br s, 1H)

FABMS m/z 451 (M−H)$^-$ $C_{19}H_{17}{}^{35}ClN_2O_3S_3$=452.

Example 82

Preparation of Compound 55

Aniline (0.037 mL, 0.40 mmol) was used instead of diethylamine to obtain Compound 55 (37 mg, 39%), using the same method as Example 81.

$^1$H NMR (300 MHz, DMSO-$d_6$) δ (ppm) 7.13 (t, J=7.3 Hz, 1H), 7.37 (t, J=7.7 Hz, 2H), 7.60 (d, J=8.4 Hz, 2H), 7.68 (d, J=8.6 Hz, 2H), 7.71 (d, J=7.7 Hz, 2H), 7.84(s, 1H), 8.04 (s, 1H), 10.3 (s, 1H), 12.6 (br s, 1H)

FABMS m/z 471 (M−H)$^-$ $C_{21}H_{13}ClN_2O_3S_3$=472.

Example 83

Preparation of Compound 56

1-Methylpiperazine (0.044 mL, 0.40 mmol) was used instead of diethylamine to obtain Compound 56 (11 mg, 12%), using the same method as Example 81. Compound 56 was obtained in the form of hydrochloride.

$^1$H NMR (300 MHz, DMSO-$d_6$, hydrochloride) δ (ppm) 2.80 (s, 3H), 3.25 (m, 8H), 7.46 (d, J=8.8 Hz, 2H), 7.49 (d, J=8.8 Hz, 2H), 7.69 (s, 1H), 7.98 (s, 1H)

FABMS m/z 478 (M−H)$^-$ $C_{20}H_{18}ClN_3O_3S_3$=479.

Example 84

Preparation of Compound 57

Morpholine (0.035 mL, 0.40 mmol) was used instead of diethylamine to obtain Compound 57 (22 mg, 24%), using the same method as Example 81.

$^1$H NMR (300 MHz, DMSO-$d_6$) δ (ppm) 3.32 (m, 4H), 3.55 (m, 4H), 7.43 (d, J=8.6 Hz, 2H), 7.47 (d, J=8.6 Hz, 2H), 7.69 (s, 1H), 7.98 (s, 1H), 12.7 (br s, 1H)

FABMS m/z 465 (M−H)$^-$ $C_{19}H_{15}ClN_2O_4S_3$=466.

Example 85

Preparation of Compound 58

Compound 53 (36 mg, 0.090 mmol) was dissolved in dichloromethane (2 mL) and tetrahydrofuran (2 mL). Thionyl chloride (0.032 mL, 0.36 mmol) was added to the solution and the mixture was heated under reflux for 2 hours. The reaction liquid was cooled with ice. Methanol (1 mL) and triethylamine (0.038 mL, 0.27 mmol) were added thereto, followed by stirring for 10 minutes. Water was added to the reaction liquid and the product was extracted with ethyl acetate. The organic layer was washed with water and brine, and then dried over anhydrous sodium sulfate. The solvent was evaporated under reduced pressure, and the residue was purified by preparative thin layer chromatography (9:1 chloroform/methanol) and was triturated with isopropyl ether to give Compound 58 (15 mg, 40%).

$^1$H NMR (300 MHz, DMSO-d$_6$) δ (ppm) 3.85 (s, 3H), 7.67 (d, J=8.6 Hz, 2H), 7.77 (d, J=8.4 Hz, 2H), 7.88 (s, 1H), 7.92 (s, 1H), 12.6 (br s, 1H)

FABMS m/z 410 (M−H)$^-$ $C_{16}H_{10}{}^{35}ClNO_4S_3$=411.

Example 86

Preparation of Compound 59

Compound 59 (260 mg, 86%) was obtained from commercially available 3-phenoxythiophene-2-carboxaldehyde (204 mg, 1.00 mmol) (MAYBRIDGE, Catalog Number: KM05428), 2,4-thiazolidinedione (176 mg, 1.5 mmol), and piperidine (0.099 mL, 1.0 mmol), using the same method as Example 70.

$^1$H NMR (300 MHz, DMSO-d$_6$) δ (ppm) 6.93 (d, J=5.5 Hz, 1H), 7.02 (dd, J=8.6, 1.1 Hz, 2H), 7.15 (t, J=7.5 Hz, 1H), 7.39 (dd, J=8.6, 7.5 Hz, 2H), 7.61 (s, 1H), 7.91 (d, J=5.5 Hz, 1H)

FABMS m/z 302 (M−H)$^-$ $C_{14}H_9NO_3S_2$=303.

Example 87

Preparation of Compound 60

4-Bromothiophene-2-carboxaldehyde (2.00 g, 10.5 mmol) was dissolved in methanol (80 mL). p-Toluenesulfonic acid (181 mg, 1.05 mmol) was added thereto, followed by stirring for 3 hours. The solvent was evaporated under reduced pressure until the total volume becomes about 20 mL. Sodium hydrogencarbonate aqueous solution was added thereto, and the product was extracted with ether. The organic layer was washed with water and brine, and then dried over anhydrous sodium sulfate. The solvent was evaporated under reduced pressure to give 4-bromo-2-dimethoxymethylthiophene (2.36g, 100%).

$^1$H NMR (300 MHz, CDCl$_3$) δ (ppm) 3.36 (s, 6H), 5.58 (s, 1H), 7.00 (t, J=1.0 Hz, 1H), 7.20 (d, J=1.3 Hz, 1H)

In an argon atmosphere, 4-bromo-2-dimethoxymethylthiophene (236 mg, 1.00 mmol) was dissolved in tetrahydrofuran (4 mL) and cooled to −78° C. n-Butyl lithium (1.6 mol/L hexane solution, 0.81 mL, 1.3 mmol), and tetrahydrofuran (1.5 mL) solution of 4,4'-dichlorodiphenyl disulfide (287 mg, 1.0 mmol) was added thereto, followed by stirring for 15 minutes. Water was added to the reaction liquid and the product was extracted with ether. The organic layer was washed with water and brine and then dried over anhydrous sodium sulfate, and the solvent was evaporated under reduced pressure. The residue was dissolved in tetrahydrofuran (6 mL) and 1 mol/L hydrochloric acid was added thereto, followed by stirring at room temperature for 1 hour. Sodium hydrogencarbonate aqueous solution was added to the reaction liquid and the product was extracted with ethyl acetate. The organic layer was washed with water and brine, and then dried over anhydrous sodium sulfate. The solvent was evaporated under reduced pressure, and the residue was purified by preparative thin layer chromatography (9:1 hexane/ethyl acetate) to give 4-(4-chlorophenylthio)thiophene-2-carboxaldehyde (71 mg, 28%), 2,3-bis(4-chlorophenylthio)thiophene-5-carboxaldehyde (29 mg, 7.3%), and 5-(4-chlorophenylthio)thiophene-2-carboxaldehyde (53 mg, 21%).

4-(4-chlorophenylthio)thiophene-2-carboxaldshyde:

$^1$H NMR (300 MHz, CDCl$_3$) δ (ppm) 7.21 (d, J=8.8 Hz, 2H), 7.28 (d, J=9.0 Hz, 2H), 7.65 (d, J=1.5 Hz, 1H), 7.69 (t, J=1.4 Hz, 1H), 9.87 (d, J=1.3 Hz, 1H)

FABMS m/z 254 (M$^+$) $C_{11}H_7{}^{35}ClOS_2$=254.

2,3-bis(4-chlorophenylthio)thiophene-5-carboxaldehyde:

$^1$H NMR (300 MHz, CDCl$_3$) δ (ppm) 7.19 (d, J=8.4 Hz, 2H), 7.29 (d, J=8.4 Hz, 2H), 7.37 (d, J=8.6 Hz, 2H), 7.43 (d, J=8.6 Hz, 2H), 7.53 (s, 1H), 9.67 (s, 1H)

FABMS m/z 397 (M+H)$^+$ $C_{17}H_{10}{}^{35}Cl_2OS_3$=396.

5-(4-chlorophenylthio)thiophenes-2-carboxaldehyde:

$^1$H NMR (300 MHz, CDCl$_3$) δ (ppm) 7.13 (d, J=3.9 Hz, 1H), 7.33 (d, J=8.8 Hz, 2H), 7.37 (d, J=9.0 Hz, 2H), 7.63 (d, J=3.9 Hz, 1H), 9.78 (s, 1H)

FABMS m/z 255 (M+H)$^+$ $C_{11}H_7{}^{35}ClOS_2$=254.

4-(4-chlorophenylthio)thiophene-2-carboxyaldehyde (70 mg, 0.28 mmol), 2,4-thiazolidinedione (39 mg, 0.33 mmol), and piperidine (0.028 mL, 0.28 mmol) were heated under reflux for 4 hours in ethanol (4 mL). The reaction liquid was cooled to room temperature, mixed with water and 1 mol/L hydrochloric acid (1 mL), and the product was extracted with ethyl acetate. The organic layer was washed with water and brine, and then dried over anhydrous sodium sulfate. The solvent was evaporated under reduced pressure and the residue was recrystallized from ethyl acetate to give Compound 60 (57 mg, 58%).

$^1$H NMR (300 MHz, DMSO-d$_6$) δ (ppm) 7.25 (d, J=8.6 Hz, 2H), 7.41 (d, J=8.6 Hz, 2H), 7.65 (m, 1H), 8.02 (s, 1H), 8.12 (m, 1H), 12.6 (br s, 1H)

FABMS m/z 352 (M−H)$^-$ $C_{13}H_8{}^{35}ClNO_2S^2$=353.

Example 88

Preparation of Compound 61

Compound 61 (19 mg, 54%) was obtained from 2,3-bis(4-chlorophenylthio)thiophene-5-carboxyaldehyde (28 mg, 0.071 mmol) obtained in Example 87, 2,4-thiazolidinedione (10 mg, 0.085 mmol), and piperidine (0.007 mL, 0.07 mmol), using the same method as Example 87.

$^1$NMR (300 MHz, DMSO-d$_6$) δ (ppm) 7.30 (d, J=8.6 Hz, 2H), 7.35 (d, J=8.6,Hz, 2H), 7.42 (d, J=8.6 Hz, 2H), 7.46 (d, J=8.6 Hz, 2H), 7.56 (s, 1H), 7.96 (s, 1H), 12.7 (br s, 1H)

FABMS m/z 494 (M−H)$^-$ $C_{19}H_{11}{}^{35}Cl_2NO_2S_4$=495.

Example 89

Preparation of Compound 62

Compound 62 (113 mg, 62%) was obtained from 5-(4-chlorophenylthio)thiophene-2-carboxyaldehyde (132 mg, 0.520 mmol) obtained in Example 87, 2,4-thiazolidinedione (73 mg, 0.62 mmol), and piperidine (0.052 mL, 0.52 mmol), using the same method as Example 87.

$^1$H NMR (300 MHz, DMSO-d$_6$) δ (ppm) 7.33 (d, J=8.6 Hz, 2H), 7.44 (d, J=8.6 Hz, 2H), 7.54 (d, J=3.9 Hz, 1H), 7.68 (d, J=3.9 Hz, 1H), 8.01 (s, 1H), 12.6 (br s, 1H)

FABMS m/z 352 (M−H)$^-$ $C_{13}H_8{}^{35}ClNO_2S_2$=353.

Example 90

Preparation of Compound 63

In an argon atmosphere, a tetrahydrofuran (3 mL) solution of diisopropylamine (0.21 mL, 1.5 mol) was cooled with ice, n-butyl lithium (1.6 mol/L hexane solution, 0.81 ml, 1.3 mmol) was added thereto, and the mixture was cooled to −78° C. A tetrahydrofuran (1 mL) solution of 4-bromo-2-dimethoxymethylthiophene (236 mg. 1.00 mmol) obtained in Example 87 was added thereto, followed by stirring for 30 minutes. Then, a tetrahydrofuran (1 mL) solution of 4,4'-dichlorodiphenyl disulfide (287 mg, 1.0 mmol) was added thereto, followed by stirring for 10 minutes. To the reaction liquid water was added, and the product was extracted with ether. The organic layer was washed with water and brine, dried over anhydrous sodium sulfate and then the solvent was evaporated under reduced pressure to give 3-bromo-2-(4-chlorophenylthio)-5-dimethoxymethylthiophen (355 mg, 94%).

$^1$H NMR (300 MHz, $CDCl_3$) δ (ppm.) 3.36 (s, 6H), 5.55 (d, J=0.7 Hz, 1H), 7.07 (d, J=0.9 Hz, 1H), 7.16 (d, J=8.4 Hz, 2H), 7.24 (d, J=8.6 Hz, 2H)

FABMS m/z 380, 378 ($M^+$) $C_{13}H_{12}{}^{79}Br^{35}ClO_2S_2$=378.

3-Bromo-2-(4-chlorophenylthio)-5-dimethoxymethylthiophen (170 mg, 0.449 mmol) was dissolved in tetrahydrofuran (4 mL) and 1 mol/L hydrochloric acid (0.5 mL) was added thereto, followed by stirring at room temperature for 4.5 hours. To the reaction liquid was added a sodium hydrogencarbonate aqueous solution and the product was extracted with ethyl acetate. The organic layer was washed with water and brine, and then dried over anhydrous sodium sulfate. The solvent was evaporated under reduced pressure, and the residue was purified by silica gel column chromatography (9:1 hexane/ethyl acetate) to give 3-bromo-2-(4-chlorophenylthio)thiophan-5-carboxaldehyde (126 mg, 85%).

$^1$H NMR (300 MHz, $CDCl_3$) δ (ppm) 7.38 (d, J=8.4 Hz, 2H), 7.43 (d, J=8.6 Hz, 2H), 7.63 (s, 1H), 9.71 (s, 1H)

FABMS m/z 335, 333 $(M+H)^+$ $C_{11}H_6{}^{79}Br^{35}ClOS_2$=332.

Compound 63 (73 mg, 49%) was obtained from 3-bromo-2-(4-chlorophenylthio)thiophen-5-carboxaldehyde (114 mg, 0.342 mmol), 2,4-thiazolidinedione (48 mg, 0.41 mmol), and piperidine (0.034 mL, 0.34 mmol) using the same method as Example 87.

$^1$H NMR (300 MHz, DMSO-$d_6$) δ (ppm) 7.31 (d, J=8.8 Hz, 2H), 7.47 (d, J=8.6 Hz, 2H), 7.81 (s, 1H), 7.96 (s, 1H), 12.7 (br s, 1H)

FABMS m/z 432, 430 $(M-H)^-$ $C_{14}H_7{}^{79}Br^{35}ClNO_2S_3$=431.

Example 91

Preparation of Compound 64

Compound 64 (14 mg, 714) was obtained from Compound 63 (19 mg, 0.044 mmol) and m-chloroperbenzoic acid (50% purity, 23 mg, 0.066 mmol), using the same method as Example 78.

$^1$H NMR (300 MHz, DMSO-$d_6$) δ (ppm) 7.73 (d, J=9.0 Hz, 2H), 7.75 (s, 1H), 7.84 (d, J=8.6 Hz, 2H), 7.98 (s, 1H), 12.8 (br s, 1H)

FABMS m/z 448, 446 $(M-H)^-$ $C_{14}H_7{}^{79}Br^{35}ClNO_3S_3$=447.

Example 92

Preparation of Compound 65

In an argon atmosphere, 3-bromo-2-(4-chlorophenylthio)-5-dimethoxymethylthiophene (500 mg, 1.32 mmol) obtained in Example 90 was dissolved in tetrahydrofuran (6 mL) and cooled to −78° C. n-Butyl lithium (a 1.6 mol/L hexane solution, 0.81 mL, 1.3 mmol) and tetrahydrofuran (1 mL) solution of 4-chloro-N-methoxy-N-methylbenzamide (528 mg, 2.64 mmol) were added thereto, followed by stirring for 10 minutes. Water was added to the reaction liquid and the product was extracted with ethyl acetate. The organic layer was washed with water and brine, and then dried over anhydrous sodium sulfate. The solvent was evaporated under reduced pressure, and the residue was purified by silica gel column chromatography (15:1 hexane/ethyl acetate) to give 3-(4-chlorobenzoyl)-2-(4-chlorophenylthio)-5-dimethoxymethylthiophene (345 mg, 60%).

$^1$H NMR (300 MHz, $CDCl_3$) δ (ppm) 3.31 (s, 6H), 5.45 1H), 7.15 (d, J=1.1 Hz, 114), 7.39 (d, J=8.8 Hz, 2H), 7.46 (d, J=8.6 Hz, 2H), 7.53 (d, J=8.8 Hz, 2H), 7.73 (d, J=8.6 Hz, 2H)

FABMS m/z 439 $(M+H)^+$ $C_{20}H_{16}{}^{35}Cl_2O_3S_2$=438.

3-(4-Chlorobenzoyl)-2-(4-chlorophenylthio)-5-dimethoxymethylthiopene (335 mg, 0.736 mmol) was dissolved in tetrahydrofuran (6 mL). 1 mol/L Hydrochloric acid (1 mL) was added thereto, followed by stirring at room temperature for 1.5 hours. Sodium hydrogencarbonate aqueous solution was added to the reaction liquid and the product was extracted with ethyl acetate. The organic layer was washed with water and brine, and then dried over anhydrous sodium sulfate. The solvent was evaporated under reduced pressure, and the residue was purified by silica gel column chromatography (5:1 hexane/ethyl acetate) and recrystallized from ethyl acetate/hexane to give 3-(4-chlorobenzoyl)-2-(4-chlorophenylthio)thiophen-5-carboxyaldehyde (203 mg, 68%).

$^1$H NMR (300 MHz, $CDCl_3$) δ (ppm) 7.50 (d, J=8.4 Hz, 2H), 7.52 (d, J=8.4 Hz, 2H), 7.62 (d, J=8.8 Hz, 2H), 7.74 (d, J=8.8 Hz, 2H), 7.83 (s, 1H), 9.65 (s, 1H)

FABMS m/z 393 $(M+H)^+$ $C_{16}H_{10}{}^{35}Cl_2O_2S_2$=392.

Compound 65 (211 mg, 88%) was obtained from 3-(4-chlorobenzoyl)-2-(4-chlorophenylthio)thiophen-5-carboxyaldehyde (193 mg, 0.490 mmol), 2,4-thiazolidinedione (69 mg, 0.59 mmol), and piperidine (0.049 mL, 0.49 mmol), using the same method as Example 70.

$^1$H NMR (300 MHz, DMSO-$d_6$) δ (ppm) 7.64 (d, J=8.6 Hz, 2H), 7.65 (d,J=8.6 Hz, 2H), 7.73 (d, J=8.4 Hz, 2H), 7.81 (d, J=8.4 Hz, 2H), 7.87 (s, 1H), 7.94 (s, 1H), 12.6 (br s, 1H)

FABMS m/z 490 $(M-H)^-$ $C_{21}H_{11}{}^{35}Cl_2NO_3S_3$=491.

Example 93

Preparation of Compound 66

Compound 66 (14 mg, 28%) was obtained from Compound 65 (50 mg, 0.10 mmol) and m-chloroperbenzoic acid (50% purity, 53 mg, 0.15 mol), using the same method as Example 78.

$^1$H NMR (300 MHz, DMSO-$d_6$) δ (ppm) 7.60 (d, J=8.4 Hz, 2H), 7.71 (d, J=8.4 Hz, 2H), 7.72 (d, J=8.8 Hz, 2H), 7.82 (s, 1H), 7.89 (d, J=8.8 Hz, 2H), 8.04 (s, 1H), 12.8 (br s, 1H)

FABMS m/z 506 $(M-H)^-$ $C_{21}H_{11}{}^{35}Cl_2NO_4S_3$=507.

Example 94

Preparation of Compound 67

Commercially available 2-[(4-chlorophenyl)thio]-5-nitrobenzaldehyde (0.3 g, 1.0 mmol) (MAYBRIDGE, Catalog Number: XAX00154) was dissolved in ethanol (8 mL), and thiazolidinedione (0.36 g, 3.0 mmol) and piperidine (0.1 mL, 1.0 mmol) were added thereto, and the mixture was heated under reflux for 5.5 hours in a flask equipped with a reflux condenser and drying tube ($CaCl_2$), the temperature was reduced to room temperature, and a 1 M HCl aqueous solution was added thereto. After a conventional treatment, the residue was purified by silica gel column chromatography (chloroform-chloroform:methanol=99:1), and purified by recrystallization from ethyl acetate and hexane, to obtain Compound 67 (0.109 g, 27.9%).

$^1$H NMR(300 MHz, DMSO-$d_6$) δ (ppm) 7.24 (d, J=8.8 Hz, 1H), 7.59(s, 4H), 7.88 (s, 1H), 8.17 (dd, J=2.6, 8.8 Hz, 1H), 8.24(d, J=2.6Hz, 1H), 12.84 (br s, 1H)

FABMS m/z 393 $(M+H)^+$ $C_{16}H_9{}^{35}ClN_2O_4S_2$=392.

Example 95

Preparation of Compound 68

Compound 68 (0.0137 g, 65.7%) was obtained by using Compound 67 (0.02 g, 0.051 mmol), using the same method as Example 78.

$^1$H-NMR(300 MHz, DMSO-$d_6$) δ (ppm) 7.61(d, J=2.6Hz, 4H), 7.67(s, 1H), 8.25(d, J=8.8 Hz, 1H), 8.35(d, J=2.3Hz, 1H), 8.40 (dd, J=2.3, 8.8 Hz, 1H), NH is not found EIMS m/z 409 $(M+H)^+$ $C_{16}H_9{}^{35}ClN_2O_5S_2$=408.

Example 96

Preparation of Compound 69

Compound 67 (0.03 g, 0.077 mmol) was dissolved in dichloromethane (5 mL) and methanol (1 mL), and m-chloroperbenzoic acid (0.03 g, 0.0092 mmol) was added thereto, followed by stirring at room temperature for 1 hour. A 10% aqueous sodium hydrogen sulfite solution was added, and a conventional treatment was performed, after which the residue was purified by thin layer column chromatography (chloroform:methanol=12:1), followed by another purification by thin layer chromatography (chloroform:acetonitryl=6:1), to obtain Compound 69 (0.014 g, 15.9%).

$^1$H-NMR(300 MHz, DMSO-d6) δ (ppm) 7.71 (dt, J=2.0, 8.8 Hz, 2H), 7.87 (dt, J=2.0, 8.8 Hz, 2H), 7.98 (s, 1H), 8.31 (s, 1H), 8.49 (d, J=2.0 Hz, 2H), NH is not found EIMS m/z 423(M–H)– C16H935ClN2O6S2=424.

Example 97

Preparation of Compound 70

A 2.5 mol/L sodium hydroxide aqueous solution (1.2 mL, 3.1 mmol) and tetrabutylammonium bromide (0.012 g, 0.031 mmol) were added to 3-chlorobenzenethiol (0.11 g, 0.73 mmol), followed by stirring at 25° C. for 10 minutes. A toluene (1.2 mL) solution of 2-fluoro-5-nitrobenzaldehyde (0.12 g, 0.73 mmol) was added to the reaction liquid, followed by stirring at 110° C. for 1.5 hours. After the conventional post-reaction treatment, the residue was purified by silica gel chromatography (eluted by chloroform) to give 2-[(3-chlorophenyl)thio]-5-nitrobenzaldehyde (72 mg, 34%).

$^1$H NMR (300 MHz, CDCl3) δ (ppm) 7.01 (d, J=8.8 Hz, 1H), 7.44–7.54 (m, 3H), 7.58 (br s, 1H), 8.17 (dd, J=2.4, 8.8 Hz, 1H), 8.69 (d, J=2.6 Hz, 1H), 10.29 (s, 1H).

FABMS m/z 294 $(M+H)^+$ $C_{13}H_8{}^{35}ClNO_3S$=293.

2-[(3-Chlorophenyl)thiol-5-nitrobenzaldehyde (70 mg, 0.24 mmol) was dissolved in toluene (3.5 mL). 2,4-Thiazolidinedione (0.11 g, 0.95 mmol), piperidine (0.0094 mL, 0.095 mmol), acetic acid (0.0054 mL, 0.095 mmol) and molecular sieves 4A (0.35 g) were added thereto, followed by stirring at 110° C. for 3 hours. After the conventional post-reaction treatment, the residue was purified by thin-layer chromatography (developed with chloroform/acetonitrile=10/1) to give Compound 70 (41 mg, 440).

$^1$H NMR (300 MHz, DMSO-$d_6$) δ (ppm) 7.34 (d, J=8.8 Hz, 1H), 7.60–7.47 (m, 3H), 7.63 (br s, 1H), 7.88 (s, 1H), 8.20 (dd, J=8.8, 2.6 Hz, 1H), 8.26 (d, J=2.6 Hz, 1H), 12.83 (m, 1H)

FABMS m/z 391 $(M-H)^-$ $C_{16}H_9{}^{35}ClN_2O_4S_2$=392.

Example 98

Preparation of Compound 71

A 2.5 mol/L sodium hydroxide aqueous solution (1.7 mL, 4.4 mmol) and tetrabutylammonium bromide (0.017 g, 0.051 mmol) were added to 2-chlorobenzenethiol (0.17 g, 1.0 mmol), followed by stirring at 25° C. for 10 minutes. To the reaction liquid was added a toluene (1.7 mL) solution of 2-fluoro-5-nitrobenzaldehyde (0.18 g, 1.0 mmol), followed by stirring at 110° C. for 2 hours. After the conventional post-reaction treatment, the residue was purified by silica gel chromatography (eluted by chloroform) to give 2-[(2-chlorophenyl)thio]-5-nitrobenzaldehyde (0.25 g, 83%).

$^1$H NMR (300 MHz, $CDCl_3$) δ (ppm) 6.88 (d, J=8.8 Hz, 1H), 7.42 (ddd, J=7.5, 7.5, 1.4 Hz, 1H), 7.51 (ddd, J=7.3, 7.3, 1.6 Hz, 1H), 7.62 (dd, J=8.1, 1.5 Hz, 1H), 7.69 (dd, J=7.5, 1.7 Hz, 1H), 8.16 (dd, J=8.8, 2.6 Hz, 1H), 8.70 (d, J=2.5 Hz, 1H), 10.32 (s, 1H)

FABMS m/z 293 $(M^+)$ $C_{13}H_8{}^{35}ClNO_3S$=293

2-[(2-Chlorophenyl)thio]-5-nitrobenzaldehyde (0.14 g, 0.49 mmol) was dissolved in ethanol (5.8 mL). 2,4-Thiazolidinedione (0.23 g, 2.0 mmol) and piperidine (0.039 mL, 0.39 mmol) were added thereto, followed by stirring at 80° C. for 3 hours. After the conventional post-reaction treatment, the residue was purified by thin-layer chromatography (developed with chloroform/acetonitrile=10/1) to give Compound 71 (24 mg, 13%).

$^1$H NMR (300 MHz, DMSO-$d_6$) δ (ppm) 7.20 (d, J=8.8 Hz, 1H), 7.43–7.62 (m, 3H), 7.71 (m, 1H), 7.89 (s, 1H), 8.20 (dd, J=8.8, 2.6 Hz, 1H), 8.28 (m, 1H), 12.82 (m, 1H)

FABMS m/z 391 $(M-H)^-$ $C_{16}H_9{}^{35}ClN_2O_4S_2$=392.

Example 99

Preparation of Compound 72

2-[(3,4-Dichlorophenyl)thio]-5-nitrobenzaldehyde (0.16 g, 79%) was obtained from 3,4-dichlorobenzenethiol (0.12 g, 0.68 mmol), a 2.5 mol/L sodium hydroxide aqueous solution (1.2 mL, 2.9 mmol), tetrabutylammonium bromide (0.011 g, 0.034 mmol) and a toluene (1.2 mL) solution of 2-fluoro-5-nitrobenzaldehyde (0.12 g, 0.68 mmol) using the same method as Example 97. $^1$H NMR (300 MHz, $CDCl_3$) δ (ppm) 7.02 (d, J=8.8 Hz, 1H), 7.41 (dd, J=8.2, 2.0 Hz, 1H), 7.60 (d, J=8.2 Hz, 1H), 7.69 (d, J=2.0 Hz, 1H), 8.18 (dd, J=8.8, 2.5 Hz, 1H), 8.69 (d, J=2.6 Hz, 1H), 10.28 (s, 1H)

FABMS m/z 328 $(M+H)^+$ $C_{13}H_7{}^{35}Cl_2NO_3S$=327.

Compound 72 (74 mg, 49%) was obtained from 2-[(3,4-dichlorophenyl)thio]-5-nitrobenzaldehyde (0.12 g, 0.35 mmol), toluene (5.8 mL), 2,4-thiazolidinedione (0.16 g, 1.4 mmol), piperidine (0.014 mL, 0.14 mmol), acetic acid (0.0080 mL, 0.14 mmol) and molecular sieves 4A (0.58 g) using the same method as Example 97.

$^1H$ NMR (300 MHz, DMSO-$d_6$) δ (ppm) 7.39 (d, J=8.8 Hz, 1H), 7.50 (dd, J=8.4, 1.8 Hz, 1H), 7.75 (d, J=8.5 Hz, 1H), 7.88–7.83 (m, 2H), 8.18 (d, J=8.6, 2.2 Hz, 1H), 8.25 (m, 1H), 12.82 (m, 1H)

FABMS m/z 425 $(M-H)^-$ $C_{16}H_8{}^{35}Cl_2N_2O_4S_2$=426.

Example 100

Preparation of Compound 73

2-[(4-Bromophenyl)thio]-5-nitrobenzaldehyde (0.28 g, 82%) was obtained from 4-bromobenzenethiol (0.19 g, 1.0 mmol), a 2.5 mol/L sodium hydroxide aqueous solution (1.7 mL, 4.3 mmol), tetrabutylammonium bromide (0.016 g, 0.051 mmol) and a toluene(1.7 mL) solution of 2-fluoro-5-nitrobenzaldehyde (0.17 g, 1.0 mmol) using the same method as Example 97.

$^1H$ NMR (300 MHz, $CDCl_3$) δ (ppm) 6.98 (d, J=8.9 Hz, 1H), 7.41–7.46 (m, 2H), 7.63–7.69 (m, 2H), 8.13 (dd, J=8.8, 2.4 Hz, 1H), 8.68 (d, J=2.6 Hz, 1H), 10.29 (s, 1H)

FABMS m/z 338 $(M+H)^+$ $C_{13}H_8{}^{79}BrNO_3S$=337.

Compound 73 (26 mg, 66%) was obtained from 2-[(4-bromophenyl)thio]-5-nitrobenzaldehyde (0.031 g, 0.091 mmol), toluene (1.5 mL), 2.4-thiazolidinedlone (0.043 g, 0.36 mmol), piperidine (0.0036 mL, 0.036 mmol), acetic acid (0.0025 mL, 0.036 mmol) and molecular sieves 4A (0–092 g) using the same method an Example 97.

Compound 73: $^1H$ NMR (300 MHz, DMSO-$d_6$) δ (ppm) 7.25 (d, J=8.8 Hz, 1H), 7.48–7.52 (m, 2H), 7.20–7.25 (m, 2H), 7.88 (s, 1H), 8.18 (dd, J=8.8, 2.6 Hz, 1H), 8.25 (d, J=2.4 Hz, 1H), 12.85 (br s, 1H)

FABMS m/z 435 $(M-H)^-$ $C_{16}H_9{}^{79}BrN_2O_4S_2$=436.

Example 101

Preparation of Compound 74

2-[(4-Methoxyphenyl)thio]-5-nitrobenzaldehyde (0.22 g, 76%) was obtained from 4-methoxybenzenethiol (0.14 g, 0.99 mmol), a 2.5 mol/L sodium hydroxide aqueous solution (1.8 mL, 4.4 mmol), tetrabutylammonium bromide (0.016 g, 0.050 mmol) and a toluene (1.8 mL) solution of 2-fluoro-5-nitrobenzaldehyde (0.17 g. 0.99 mmol) using the same method as Example 98.

$^1H$ NMR (300 MHz, $CDCl_3$) δ (ppm) 3.89 (s, 3H), 6.92 (d, J=8.9 Hz, 1H), 7.03 (d, J=8.6 Hz, 2H), 7.49 (d, J=8.6 Hz, 2H), 8.08 (dd, J=9.0, 2.4 Hz, 1H), 8.63 (d, J=2.2 Hz, 1H), 10.29 (s, 1H)

FABMS m/z 289 $(M^+)$ $C_{14}H_{11}N_2O_4$=289.

Compound 74 (26 mg, 18%) was obtained from 2-[(4-methoxyphenyl)thio]-5-nitrobenzaldehyde (0.11 g, 0.39 mmol) ethanol (4.4 mL), 2,4-thiazolidinedione (0.18 g, 1.5 mmol), and piperidine (0.015 mL, 0.15 mmol) using the same method as Example 98.

$^1H$ NMR (300 MHz, DMSO-$d_6$) δ (ppm) 3.34 (s, 3H), 6.98 (d, J=8.8 Hz, 1H), 7.13 (d, J=9.0 Hz, 2H), 7.57 (d, J=8.6 Hz, 2H), 7.89 (s, 1H), 8.14 (dd, J=8.6, 2.4 Hz, 1H), 8.21 (d, J=2.4 Hz, 1H)

FABMS m/z 387 $(M-H)^-$ $C_{17}H_{12}N_2O_5S_2$=388.

Example 102

Preparation of Compound 75

2-[(4-Ethylphenyl)thio]-5-nitrobenzaldehyde (0.22 g, 82%) was obtained from 4-ethylbenzenethiol (0.13 g, 0.95 mmol), a 2.5 mol/L sodium hydroxide aqueous solution (1.6 mL, 4.0 mmol), tetrabutylammonium bromide (0.015 g, 0.047 mmol) and a toluene (1.6 mL) solution of 2-fluoro-5-nitrobenzaldehyde (0.16 g, 0.95 mmol) using the same method as Example 97.

$^1H$ NMR (300 MHz, $CDCl_3$) δ (ppm) 1.30 (t, J=7.6 Hz, 3H), 2.74 (q, J=7.5 Hz, 2H), 6.96 (d, J=9.0 Hz, 1H), 7.36 (d, J=7.5 Hz, 2H), 7.48 (d, J=8.1 Hz, 2H), 8.10 (dd, J=9.0. 2.2 Hz, 1H), 8.66 (d, J=2.6 Hz, 1H), 10.31 (s, 1H)

FABMS m/z 288 $(M+H)^+$ $C_{15}H_{13}NO_3S$=287.

Compound 75 (0.14 g, 51%) was obtained from 2-[(4-ethylphenyl)thio]-5-nitrobenzaldehyde (0.20 g, 0.69 mmol), toluene (9.9 mL), 2,4-thiazolidinedione (0.32 g, 2.7 mmol), piperidine (0.027 mL, 0.27 mmol), acetic acid (0.016 mL, 0.27 mmol) and a molecular sieve 4A (0.99 g) using the same method as Example 97.

Compound 75: $^1H$ NMR (300 MHz, DMSO-$d_6$) δ (ppm) 1.21 (t, J=7.7 Hz, 3H), 2.68 (q, J=7.7 Hz, 2H), 7.09 (d, J=8.8 Hz, 1H), 7.39 (d, J=8.1 Hz, 2H), 7.51 (d, J=8.1 Hz, 2H), 7.39 (s, 1H), 8.16 (dd, J=8.8, 2.3 Hz, 1H), 8.22 (d, J=2.0 Hz, 1H), 12.82 (m, 1H)

FABMS m/z 385 $(M-H)^-$ $C_{18}H_{14}N_2O_4S_2$=386.

Example 103

Preparation of Compound 76

Compound 76 (0.134 g, 35.9%) was obtained by using commercially available (MAYBRIDGE, Catalog Number: XAX00131) 2-benzylthio-5-nitrobenzaldehyde (0.27 g, 1.0 mmol) using the same method as Example 94.

$^1H$-NMR(300 MHz, DMSO-$d_6$) δ (ppm) 4.51 (s, 2H), 7.31 (m, 3H), 7.46 (dt, J=1.7, 6.6 Hz, 2H), 7.78 (s, 1H), 7.81 (d, J=8.9 Hz, 1H), 8.17 (d, J=2.6 Hz, 1H), 8.22 (dd, J=2.6, 8.9 Hz, 1H), 12.82 (br s, 1H)

EIMS m/z 371$(M-H)^-$ $C_{17}H_{12}N_2O_4S_2$=372.

Example 104

Preparation of Compound 77

Compound 77 (0.0055 g, 17.6%) was obtained by using Compound 76 (0.03 g, 0.081 mmol) using the same method as Example 96.

$^1H$-NMR, (300 MHz, DMSO-$d_6$) δ (ppm) 4.24 (d, J=6.8 Hz, 2H), 6.94 (dd, J=2.2, 5.0 Hz, 2H), 7.20 (dd, J=2.2, 5.0 Hz, 3H), 7.4 (s, 1H), 7.89 (d, J=8.7 Hz, 1H), 8.21 d, J=2.2 Hz, 1H), 8.38 (dd, J=2.2, 8.7 Hz, 1H), NH is not found EIMS m/z 369$(M+H)^-$ $C_{17}H_{12}N_2O_5S_2$=388.

Example 105

Preparation of Compound 78

Compound 78 (0.0192 g, 59.0%) was obtained by using Compound 76 (0.03 g, 0.081 mmol) using the same method as Example 96.

$^1H$-NMR (300 MHz, DMSO-$d_6$) δ (ppm) 4.78 (s, 2H), 7.10 (dd, J=1.8, 4.5 Hz, 2H), 7.27 (dd, J=1.8, 4.5 Hz, 3H), 8.06 (d, J=8.8 Hz, 1H), 8.08 (s, 1H), 8.36 (dd, J=2.5, 8.8 Hz, 1H), 8.39 (d, J=2.5 Hz, 1H), NH is not found EIMS m/z 403$(M-H)^-$ $C_{17}H_{12}N_2O_6S_2$=404.

Example 106

Preparation of Compound 79

2-[(4-Chlorobenzyl)thio]-5-nitrobenzaldehyde (0.17 g, 67%) was obtained from 4-chlorobenzylthiol (0.11 g, 0.83 mmol), a 2.5 mol/L sodium hydroxide aqueous solution (1.4 mL, 3.5 mmol), tetrabutylammonium bromide (0.013 g, 0.041 mmol) and a toluene (1.4 mL) solution of 2-fluoro-5-nitrobenzaldehyde (0.14 g, 0.83 mmol) using the same method as Example 97. Compound 79 (0.11 g, 70%) was obtained from 2-[(4-chlorobenzyl)thio]-5-nitroberzaldehyde (0.12 g, 0.39 mmol), toluene (6.1 mL), 2,4-thiazolidinedione (0.18 g, 1.6 mmol), piperidine (0.016 mL, 0.16 mmol), acetic acid (0.0090 mL, 0.16 mmol) and molecular sieves 4A (0.61 g) using the same method as Example 97.

2-[(4-chlorobenzyl)thio]-5-nitrobenzaldehyde:

$^1H$ NMR (300 MHz, $CDCl_3$) δ (ppm) 4.26 (s, 2H), 7.34 (s, 4H), 7.49 (d, J=8.8 Hz, 1H), 8.29 (dd, J=8.8, 2.6 Hz, 1H), 8.65 (d, J=2.5 Hz, 1H), 10.23 (s, 1H)

FABMS m/z 307 ($M^+$) $C_{14}H_{10}{}^{35}ClNO_3S$=307.

Compound 79:

$^1H$ NMR (300 MHz, DMSO-$d_6$) δ (ppm) 4.50 (s, 2H), 7.39 (d, J=8.5 Hz, 2H), 7.46 (d, J=8.4 Hz, 2H), 7.77 (s, 1H), 7.80 (d, J=8.8 Hz, 1H), 8.17 (d, J=2.4 Hz, 1H), 8.31 (dd, J=9.0, 2.6 Hz, 1H), 12.81 (m, 1H)

FABMS m/z 405 $(M-H)^-$ $C_{17}H_{11}{}^{35}ClN_2O_4S_2$=406.

Example 107

Preparation of Compound 80

Commercially available (MAYBRIDGE, Catalog Number: XAX00146) 4-[(4-bromophenyl)thio]-3-nitrobenzaldehyde (0.12 g, 0.35 mmol) was dissolved in toluene (5.9 mL). 2,4-Thiazolidinedione (0.16 g, 1.4 mmol), piperidine (0.014 mL, 0.14 mmol), acetic acid (0.0080 mL, 0.14 mmol) and molecular sieves 4A (0.59 g) were added thereto, followed by stirring at 110° C. for 3 hours. After the conventional post-reaction treatment, the residue was triturated by using ethanol to give Compound 80 (21 mg, 14%).

$^1H$ NMR (300 MHz, DMSO-$d_6$) δ (ppm) 7.01 (d, J=8.6 Hz, 1H), 7.58–7.62 (m, 2H), 7.73–7.82 (m, 4H), 8.50 (d, J=2.0 Hz, 1H), 12.71 (m, 1H)

FABMS m/z 435 $(M-H)^-$ $C_{16}H_9{}^{79}BrN_2O_4S_2$=436.

Example 108

Preparation of Compound 81

Commercially available (MAYBRIDGE, Catalog Number: NRBOO117) 4-[(4-chlorophenyl)thio]-3-nitrobenzaldehyde (0.31 g, 1.0 mmol) was dissolved in ethanol (12 mL). 2,4-Thiazolidinedione (0.16 g, 1.4 mmol) and piperidine (0.014 mL, 0.14 mmol) were added thereto, followed by stirring at 80° C. for 3 hours. The reaction liquid was cooled to 25° C., and the precipitated crystals were collected by filtration to give Compound 81 (0.15 g, 36%).

$^1H$ NMR (300 MHz, DMSO-$d_6$) δ (ppm) 6.98 (d, J=8.5 Hz, 1H), 7.08 (br s, 1H), 7.70–7.59 (m, 5H), 7.73 (dd, J=8.6, 2.0 Hz, 1H), 8.45 (d, J=2.0 Hz, 1H)

FABMS m/z 391 $(M-H)^-$ $C_{16}H_9{}^{35}ClN_2O_4S_2$=392.

Example 109

Preparation of Compound 82

Compound 82 (0.0195 g, 62.0%) was obtained by using Compound 9 (0.03 g, 0.081 mmol) using the same method as Example 96.

$^1H$-NMR(300 MHz, DMSO-$d_6$) δ (ppm) 2.49 (s, 3H), 7.31 (d, J=8.2 Hz, 2H), 7.56 (d, J=8.2 Hz, 2H), 7.84 (s, 1H), 8.28 (dd, J=1.8, 8.4 Hz, 1H), 8.46 (s, 1H), 8.49 (t, J=1.8 Hz, 1H), NH is not found EIMS m/z 389 $(M+H)^+$ $C_{17}H_{12}N_2O_5S_2$=388.

Example 110

Preparation of Compound 83

Compound 9 (0.07 g, 0.19 mmol) was dissolved in dichloromethane (12 mL), methanol (2.3 mL) and m-chloroperbenzoic acid (0.13 g, 0.38 mmol) was added thereto, followed by stirring at room temperature for 1 hour. A 10% sodium hydrogen sulfite aqueous solution was added thereto. After the conventional treatment, the residue was purified by thin-layer chromatography (chloroform: methanol=12:1) followed by trituration with chloroform to give Compound 83 (0.019 g, 25.4%) by triturating with chloroform.

$^1H$-NMR (300 MHz, DMSO-$d_6$) δ (ppm) 2.41(s, 3H), 7.50 (d, J=8.3 Hz, 2H), 7.84 (s, 1H), 7.86 (d, J=8.1 Hz, 2H), 8.03 (d, J=8.3 Hz, 1H), 8.23 (d, J=1.7 Hz, 1H), 8.44 (d, J=8.3 Hz, 1H), NH is not found EIMS m/z 405$(M+H)^+$ $C_{17}H_{12}N_2O_6S_2$=404.

Example 111

Preparation of Compound 84

Compound 84 (0.152 g, 41.8%) was obtained by using commercially available (MAYBRIDGE, Catalog Number: XAX00135) 2-(cyclohexylthio)-5-nitrobenzaldehyde (0.26 g, 1.0 mmol) using the same method as Example 94.

$^1H$-NMR (300 MHz, DMSO-$d_6$) δ (ppm) 1.30 (m, 1H), 1.46 (m, 4H), 1.61 (m, 1H), 1.73 (m, 2H), 2.00 (m, 2H), 3.67 (m, 1H), 7.79 (d, J=8.5 Hz, 1H), 7.83 (s, 1H), 8.19 (d, J=2.4 Hz, 1H), 8.22 (dd, J=2.4, 8.5 Hz, 1H), 12.82 (br s, 1H)

FABMS m/z 363$(M-H)^-$ $C_{16}H_{16}N_2O_4S_2$=364.

Example 112

Preparation of Compound 85

Compound 85 (0.0149 g, 71.3%) was obtained by using Compound 84 (0.02 g, 0.055 mmol) using the same method as Example 96.

$^1H$-NMR (300 MHz, DMSO-$d_6$) δ (ppm) 1.30 (m, 8H), 1.77 (m, 2H), 2.73(m, 1H), 7.60 (s, 1H), 8.24 (s, 1H), 8.05 (d, J=8.6 Hz, 1H), 8.36 (d, J=2.2 Hz, 1H), 8.43 (dd, J=2.2, 8.6 Hz, 1H), NH is not found FABMS m/z 381$(M+H)^-$ $C_{16}H_{16}N_2O_5S_2$=380.

Example 113

Preparation of Compound 86

Compound 86 (0.0034 g, 10.9%) was obtained by using Compound 84 (0.03 g, 0.082 mmol) using the same method as Example 96.

$^1H$-NMR (300 MHz, DMSO-$d_6$) δ (ppm) 1.27 (m, 6H), 1.59 (m, 1H), 1.69 (m, 4H), 8.23 (d, J=8.4 Hz, 1H), 8.24 (s, 1H), 8.44 (s, 1H), 8.46 (d, J=8.4 Hz, 1H), NH is not found EIMS m/z 395 $(M-H)^-$ $C_{16}H_{16}N_2O_6S_2$=396.

Example 114

Preparation of Compound 87 p-Toluenethiol (0.12 g, 1.0 mmol) was dissolved in a 10% sodium hydroxide aqueous solution (1.7 mL), and tetrabutylammonium bromide (0.016 g, 0.05 mmol) was added thereto, followed by stirring at room temperature for 5 minutes. 5-Bromo-2-fluorobenzaldehyde (0.2 g, 1.0 mmol) dissolved in toluene (1.7 mL) was added thereto by dropping, followed by stirring at room temperature for 4 hours. After the conventional treatment, and was recrystallized and purified with ethanol and hexane, to give 5-bromo-2-[(4-methylphenyl)thio]benzaldehyde (0.23 g, 74.1%).

$^1$HNMR (300 MHz, $CDCl_3$) δ (ppm) 2.39 (s, 3H), 6.90 (d, J=8.4 Hz, 1H), 7.22 (d, J=7.9 Hz, 2H), 7.35 (dd, J=1.7, 8.1 Hz, 2H), 7.46 (dd, J=2.4, 8.4 Hz, 1H), 7.96 (d, J=2.2 Hz, 1H), 10.32 (s, 1H).

FABMS m/z 308(M+H)$^+$ $C_{14}H_{11}{}^{79}BrOS$=307.

Compound 87 (0.021 g, 52%) was obtained by using 5-bromo-2-[(4-methylphenyl)-thio]benzaldehyde (0.03 g, 0.1 mmol) using the same method as Example 94.

$^1$H-NMR (300 MHz, DMSO-$d_6$) δ (ppm) 2.31 (m, 3H), 7.14 (d, J=8.8 Hz, 1H), 8.23 (d, J=8.3 Hz, 2H), 8.28 (d, J=8.3 Hz, 2H), 7.60 (s, 1H), 7.62 (dd, J=2.2, 8.8 Hz, 1H), 7.90 (s, 1H), 12.82 (br s, 1H)

EIMS m/z 407(M+H)$^+$ $C_{17}H_{12}{}^{79}BrNO_2S_2$=406.

Example 115

Preparation of Compound 88

3-Bromo-4-[(4-methylphenyl)thio]benzaldehyde (0.19 g, 63.6%) was obtained by using 3-bromo-4-fluorobenzaldehyde (0.2 g, 0.99 mmol) using the same method as Example 114 (synthesis of 5-bromo-2-[(4-methylphenyl)thio]benzaldehyde).

$^1$H-NMR (300 MHz, $CDCl_3$) δ (ppm) 2.44 (s, 3H), 6.73 (d, J=8.3 Hz, 1H), 7.30 (d, J=8.4 Hz, 2H), 7.47 (d, J=8.1 Hz, 2H), 7.54 (dd, J=1.7, 8.4 Hz, 1H), 8.00 (d, J=1.7 Hz, 1H), 9.84 (s, 1H)

FABMS m/z 307(M$^+$) $C_{14}H_{11}BrOS$=307.

Compound 88 (0.087 g, 43.9%) was obtained by using 3-bromo-4-[(4-methylphenyl)thio]benzaldehyde (0.15 g, 0.49 mmol) using the same method as Example 94.

$^1$H-NMR (300 MHz, DMSO-$d_6$) δ (ppm) 2.49 (s, 3H), 6.74 (d, J=8.3 Hz, 1H), 7.37 (d, J=8.1 Hz, 2H), 7.44 (dd, J=2.0, 8.5 Hz, 1H), 7.48 (d, J=8.1 Hz, 2H), 7.70 (s, 1H), 7.89 (d, J=2.0 Hz, 1H), 12.64 (br s, 1H)

EIMS m/z 407(M+H)$^+$ $C_{17}H_{12}{}^{79}BrNO_2S_2$=406.

Example 116

Preparation of Compound 89

The reaction was performed in accordance with a document (Tetrahedron Lett. Vol. 36, No. 50, pp. 9085–9088, 1995) and the product was treated by using 5-bromo-2-[(4-methyphenyl)thio]-benzaldehyde (0.06 g, 0.2 mmol) and 2-pyridyl trifluoromethanesulfonate (0.03 g, 0.2 mmol). The residue was purified by thin-layer chromatography (hexane: ethyl acetate=8:1)) to obtain 2-[(4-methylphenyl)thio]-5-(2-pyridyl)benzaldehyde (0.024 g, 38.5%).

$^1$H-NMR (300 MHz,$CDCl_3$) δ (ppm) 2.41 (s, 3H), 7.09 (d, J=8.4 Hz, 1H), 7.24 (m, 3H), 7.42 (d, J=8.4 Hz, 2H), 7.76 (dd, J=1.7, 6.6 Hz, 2H), 8.01 (dd, J=2.2, 8.5 Hz, 1H), 8.50 (d, J=2.2 Hz, 1H), 8.69 (d, J=4.6 Hz, 1H), 10.43 (s, 1H)

EIMS m/z 306(M+H)$^+$ $C_{19}H_{15}NOS$=305.

Compound 89 (0.026 g, 84.4%) was obtained by using 2-[(4-methylphenyl)thio]-5-(2-pyridyl)benzaldehyde (0.024 g, 0.08 mmol) using the same method as Example 94.

$^1$H-NMR (300 MHz, DMSO-$d_6$) δ (ppm) 2.32 (s, 3H), 7.26 (d, J=8.4 Hz, 2H), 7.30 (d, J=8.4 Hz, 2H),7.33 (d, J=8.3 Hz, 2H), 7.41 (m, 1H), 7.92 (m, 1H), 7.97 (d, J=7.7 Hz, 1H), 8.08 (s, 1H), 8.07 (dd, J=2.0, 7.7 Hz, 1H), 8.32 (d, J=1.7 Hz, 1H), 8.7 (d, J=4.8 Hz, 1H), 12.70 (br s, 1H)

EIMS m/z 405 (M−H)$^-$ $C_{22}H_{16}N_2O_2S_2$=406.

Example 117

Preparation of Compound 90

Tri(dibenzylideneacetone)-dipalladium (0.18 g, 0.2 mmol), and triphenylphosphine (0.21 g, 0.8 mmol) were dissolved in tetrahydrofuran (60 mL), followed by stirring at room temperature for 30 minutes. Then, 5-bromo-2-fluorobenzaldehyde (0.4 g, 2.0 mmol) and 2-(tributylstannyl)-furan (1.25 mL, 4. 0 mmol) were added thereto, followed by heating under reflux for 10 hours. The mixture was cooled to room temperature, and after the conventional treatment, the residue was purified by silica gel column chromatography (hexane: ethyl acetate=8:1), to give 2-fluoro-5-(2-furyl)benzaldehyde (0.38 g, 100%).

$^1$H-NMR (300 MHz, $CDCl_3$) δ (ppm) 6.49 (dd, J=1.8, 3.5 Hz, 1H), 6.69 (d, J=3.3 Hz, 1H), 7.21 (t, J=9.9 Hz, 1H), 6.49 (d, J=1.8 Hz, 1H), 7.90 (m, 1H), 8.14 (dd, J=2.4, 6.6 Hz, 1H), 10.39 (s, 1H)

FABMS m/z 190(M$^+$) $C_{11}H_7{}^{19}FO_2$=190

2-[(4-Methylphenyl)thio]-5-(2-furyl)benzaldehyde (0.14 g, 87.8%) was obtained by using 2-fluoro-5-(2-furyl) benzaldehyde (0.1 g, 0.53 mmol) using the same method as Example 114 (synthesis of 5-bromo-2-[(4-methylphenyl) thio]benzaldehyde).

$^1$H-NMR (300 MHz, $CDCl_3$) δ (ppm) 2.39 (s, 3H), 6.59 (d, J=1.8 Hz, 1H), 6.69 d, J=3.3 Hz, 1H), 7.07 (d, J=8.4 Hz, 1H), 7.21 (d, J=8.3 Hz, 2H), 7.36 (d, J=8.1 Hz, 2H) 7.48 (s, 1H), 7.66 (dd, J=2.0, 8.3 Hz, 1H), 8.14 (d, J=2.0 Hz, 1H),10.41 (s, 1H)

FABMS m/z 294(M$^+$) $C_{18}H_{14}O_2S$=294

Compound 90 (0.17 g, 92.8%) was obtained by using 2-[(4-methylphenyl)thio]-5-(2-furyl)benzaldehyde (0.14 g, 0.47 mmol) using the same method as Example 94.

$^1$H-NMR (300 MHz, DMSO-$d_6$) δ (ppm) 2.50 (s, 3H), 6.65 (m, 1H), 7.04 (d, J=3.5 Hz, 1H), 7.22 (d, J=8.4 Hz, 2H), 7.26 (d, J=8.4 Hz, 2H), 7.32 (d, J=8.4 Hz, 1H),7.74 (d, J=8.2 Hz, 1H), 7.81 (d, J=7.7 Hz, 1H), 8.03 (s, 1H), 12.71 (br s, 1H)

EIMS m/z 392 (M−H)$^-$ $C_{21}H_{15}NO_3S_2$=393.

Example 118

Preparation of Compound 91

Compound 91 (0.069 g, 66.5%) was obtained by using compound 74 (0.1 g, 0.25 mmol) using the same method as Example 96.

$^1$H-NMR (300 MHz, DMSO-$d_6$) δ (ppm) 2.30 (s, 3H), 6.67 (dd, J=1.8, 3.5 Hz, 1H), 7.17 (d, J=8.6 Hz, 2H), 7.31 (d, J=8.6 Hz, 2H), 7.45 (d, J=8.3 Hz, 2H), 7.76 (s, 1H), 7.87 (d, J=1.8 Hz, 1H), 8.01 (d, J=5.9 Hz, 2H), 8.02 (s, 1H), 12.77 (br s, 1H)

EIMS m/z 410 (M+H)$^+$, $C_{21}H_{15}NO_4S_2$=409.

Example 119

Preparation of Compound 92

2-Fluoro-5-(2-thienyl)benzaldehyde (0.2 g, 100%) was obtained by using 2-(triutylstannyl)thiophene (0.63 mL, 2.0 mmol) using the same method as Example 117 (synthesis of 2-fluoro-5-(2-furyl)benzaldehyde).

$^1$H-NMR (300 MHz, $CDCl_3$) δ (ppm) 7.10 (t, J=4.4 Hz, 1H), 7.21 (dd, J=8.8, 9.9 Hz, 1H), 7.33 (d, J=4.4 Hz, 2H), 7.83 (m, 1H), 8.08 (dd, J=2.6, 6.5 Hz, 1H), 10.40 (s, 1H)

FABMS m/z 206 ($M^+$) $C_{11}$ $H_7{}^{19}FOS$=206.

2-[(4-Methylphenyl)thio]-5-(2-thienyl)benzaldehyde (0.12 g, 77.4%) was obtained by using 2-fluoro-5-(2-thienyl)benzaldehyde (0.1 g, 0.49 mmol) using the same method as Example 114 (synthesis of 5-bromo-2-[(4-methylphenyl)thio]benzaldehyde).

$^1$H-NMR (300 MHz, $CDCl_3$) δ (ppm) 2.39 (s, 3H), 7.06 (d, J=8.3 Hz, 1H), 7.10 (m, 1H), 7.24 (d, J=8.3 Hz, 2H), 7.33 (m, 4H), 7.37 (d, J=8.1 Hz, 2H), 7.60 (dd, J=2.4, 8.3 Hz, 1H), 8.07 (d, J=2.4 Hz, 1H),10.42 (s, 1H)

FABMS m/z 310 ($M^+$) $C_{18}H_{14}OS_2$=310.

Compound 92 (0.14 g, 91.3%) was obtained by using 2-[(4-methylphenyl)thiol-5-(2-thienyl)benzaldehyde (0.12 g, 0.38 mmol) using the same method as Example 94.

$^1$H-NMR (300 MHz, DMSO-$d_6$) δ (ppm) 2.30 (s, 3H), 7.18 (t, J=3.8 Hz, 1H), 7.24 (d, J=4.8 Hz, 4H), 7.56 (d, J=7.7 Hz, 1H), 7.63 (d, J=5.1 Hz, 1H), 7.72 (s, 1H), 7.73 (d, J=7.5 Hz, 1H), 8.03 (s, 1H), 12.71 (br s, 1H)

EIMS m/z 408 $(M-H)^-$ $C_{21}H_{15}NO_2S_3$=409.

Example 120

Preparation of Compound 93

Compound 93 (0.051 g, 49.4%) was obtained by using Compound 92 (0.1 g, 0.24 mmol) using the same method as Example 96.

$^1$H-NMR (300 MHz, DMSO-$d_6$) δ (ppm) 2.30 (s, 3H), 7.20 (dd, J=3.7, 5.0 Hz, 1H), 7.32 (d, J=8.1 Hz, 2H), 7.46 (d, J=8.3 Hz, 2H), 7.66 (d, J=3.7 Hz, 1H), 7.69 (d, J=3.7 Hz, 2H), 8.01 (m, 3H), 12.78 (br s, 1H)

EIMS m/z 426 $(M+H)^+$ $C_{21}Hl_5NO_3S_3$=425.

Example 121

Preparation of Compound 94

Diisopropylamine (0.35 mL, 2.5 mmol) was dissolved in tetrahydrofuran (3.5 mL) and the temperature was adjusted to 0° C. Then, n-butyllithium (hexane solution) (1.24 mL, 2.0 mmol) was dropped thereto, followed by stirring for 10 minutes. Thereafter the reaction temperature was brought to −78° C. 4-Fluorobenzonitile (0.2 g, 1.65 mmol) was added thereto, stirring for 1 hour. Then, dimethylformamide (0.19 mL, 2.5 mmol) was dropped thereto, followed by stirring for 20 minutes and then the conventional treatment was performed. The residue was purified by thin-layer chromatography (hexane: ethyl acetate=8:1), to give 2-fluoro-5-cyanobenzaldehyde (0.11 g, 43.4%).

$^1$H-NMR (300 MHz, $CDCl_3$) δ (ppm) 7.46 (t, J=8.8 Hz, 1H), 7.90 (m, 1H), 7.71 (dd, J=2.2, 6.2 Hz, 1H), 10.36 (s, 1H)

EIMS m/z 148(M−H) $C_8H_4{}^{19}FNO$=149

5-Cyano-2-[(4-methylphenyl)thio]benzaldehyde (0.15 g, 86.9%) was obtained by using 2-fluoro-5-cyanobenzaldehyde (0.1 g, 0.67 mmol) using the same method as Example 114 (synthesis of 5-bromo-2-[(4-methylphenyl)thio]benzaldehyde).

$^1$H-NMR (300 MHz, $CDCl_3$) δ (ppm) 2.44 (s, 3H), 6.92 (d, J=8.6 Hz, 1H), 7.31 (d, J=7.9 Hz, 2H), 7.44 (d, J=8.3 Hz, 2H), 7.49 (dd, J=1.8, 8.4 Hz, 1H), 8.07 (d, J=2.0 Hz, 1H), 10.27 (s, 1H)

EIMS m/z 253($M^+$) $C_{15}H_{11}NOS$=253.

Compound 94 (0.09 g, 64.5%) was obtained by using 5-cyano-2-[(4-methylphenyl)-thio]benzaldehyde (0.1 g, 0.4 mmol) using the same method as Example 94.

$^1$H-NMR (300 MHz, DMSO-$d_6$) δ (ppm) 2.37 (s, 3H), 7.00 (d, J=8.3 Hz, 1H), 7.34 (d, J=8.3 Hz, 2H), 7.46 (d, J=8.3 Hz, 2H), 7.76 (dd, J=1.7, 8.4 Hz, 1H), 7.80 (s, 1H), 7.84 (s, 1H), 12.01 (br s, 1H)

EIMS m/z 353 $(M+H)^+$ $C_{18}H_{12}N_2O_2S_2$=352.

Example 122

Preparation of Compound 95

3-Cyano-4-[(4-methylphenyl)thio]benzaldehyde (0.3 g, 89.9%) was obtained by using 2-fluoro-5-formylbenzonnitrile (0.2 g, 1.34 mmol) using the same method as Example 114 (synthesis of 5-bromo-2-[(4-methylphenyl)thio]benzaldehyde).

$^1$H-NMR (300 MHz, $CDCl_3$) δ (ppm) 2.44 (s, 3H), 6.94 (d, J=8.4 Hz, 1H), 7.31 (d, J=7.9 Hz, 2H), 7.47 (dd, J=1.8, 8.1 Hz, 2H), 7.78 (dd, J=1.8, 8.4 Hz, 1H), 8.07 (d, J=5 Hz, 1H), 9.90 (s, 1H)

FABMS m/z 254 $(M+H)^+$ $C_{15}H_{11}NOS$=253.

Compound 95 (0.126 g, 45.3%) was obtained by using 3-cyano-4-[(4-methylphanyl)thio]benzaldehyde (0.2 g, 0.79 mmol) using the same method as Example 94.

$^1$H-NMR (300 MHz, DMSO-$d_6$) δ (ppm) 2.50 (s, 3H), 7.06 (d, J=8.6 Hz, 1H), 7.36 (d, J=8.4 Hz, 2H), 7.49 (d, J=8.3 Hz, 2H), 7.66 (s, 1H), 7.71 (dd, J=2.0, 8.5 Hz 1H), 8.08 (d, J=2.0 Hz, 1H), NH is not found EIMS m/z 352 ($M^+$) $C_{18}H_{12}N_2O_2S_2$=352.

Example 123

Preparation of Compound 96

3-Bromo-4-[(4-methylphenyl)thio]benzaldehyde (0.18 g, 59.0%) was obtained by using 3-bromo-4-fuluorobenzaldehyde (0.12 g, 1.0 mmol) using the same method an Example 114 (synthesis of 5-bromo-2-[(4-methylphenyl)thio]benzaldehyde).

$^1$H-NMR (300 MHz, $CDCl_3$) δ (ppm) 2.44 (s, 3H), 6.73 (d, J=8.3 Hz, 1H), 7.30 (d, J=7.9 Hz, 2H), 7.47 (d, J=8.1 Hz, 2H), 7.54 (dd, J=1.7, 8.3 Hz, 1H), 7.99 (d, J=1.7 Hz, 1H), 9.84 (s, 1H)

EIMS m/z 307(M+) C14H1179BrOS=307.

3-Bromo-4-[(4-methylphenyl)thio]benzaldehyde (0.2 g, 0.65 mmol) was dissolved in methanol (6.0 mL) and dichloromethane (6.0 mL). Sodium borohydride (0.025 g, 0.65 mmol) was added thereto, followed by stirring for 15 minutes and the conventional treatment was performed. The solvent was removed by using a vacuum dryer. The residue was dissolved in dichloromethane (7.0 mL). Tert-butyldimethylsilylchloride (0.12 g, 0.78 mmol) and imidazole (0.053 g, 0.65 mmol) were added thereto, followed by stirring for 2 hours and then the conventional treatment was performed. The product was purified by silica gel chromatography (hexane: ethyl acetate=16:1), to give 3-bromo-4-[(4-methylpheny)thio]benzyl(tert-butyldimethylsilyl)ether (0.27 g, 96.4%).

$^1$H-NMR (300 MHz, $CDCl_3$) (0.62 (s, 6H), 0.84 (s, 9H), 2.29 (s, 3H), 4.56 (s, 2H), 6.76 (d, J=8.3 Hz, 1H), 7.00 (dd, J=1.8, 8.3 Hz, 1H), 7.11 (d, J=8.4 Hz, 2H), 7.26 (d, J=1.8 Hz, 2H), 7.43 (d, J=1.7 Hz, 1H)

EIMS m/z 424 (M+H)+ C20H2779BrOSSi=423.

In an argon atmosphere, hexane (1.4 mL) and diethyl ether (10.4 mL) was cooled to −78° C. n-Butyl 1 ihlum (hexane solution) (2.17 mL, 3.47 mmol) and tetramethylethylenediamine (0.52 mL, 3.47 mmol) were added thereto, followed by stirring for 15 minutes. 3-Bromo-4-[4-methylphenyl)thio]benzyl tert-butyldimethylsilyl ether (0.37 mL, 0.87 mmol) was added thereto, further followed by stirring for 30 minutes. Then, dimethylformamide (0.3 mL, 3.47 mmol) dissolved in diethylether (4.3 mL) was added thereto by dropping, followed by stirring for 45 minutes. After heating the mixture up to room temperature, the conventional treatment was performed. The product was purified by thin-layer chromatography (hexane: ethyl acetate=16:1), to give 5-hydroxymethyl-2-[(4-methylphenyl)thio]benzaldehyde (0.58 g, 66.7%).

$^1$H-NMR (300 MHz, $CDCl_3$) ((ppm) 0.62 (s, 6H), 0.84 (s, 9H), 2.28 (s, 3H), 4.64 (s, 2H), 6.95 (d, J=8.1 Hz, 1H), 7.09 (d, J=7.9 Hz, 2H), 7.23 (d, J=8.3 Hz, 2H), 7.28 (dd, J=2.2, 8.2 Hz, 1H), 7.70 (d, J=1.8 Hz, 1H), 10.29 (9, 1H)

EIMS m/z 373$(M+H)^+$ $C_{21}H_{28}O2SSi$=372.

Compound 96 (0.067 g, 70.4%) was obtained by using 5-hydroxymethyl-2-[(4-methylphenyl)thio]benzaldehyde (0.1 g, 0.27 mmol) using the same method as Example 94.

$^1$H-NMR (300 MHz, DMSO-$d_6$) δ (ppm) 2.27 (s, 3H), 4.53 (d, J=5.5 Hz, 2H), 5.37 (t, J=5.5 Hz, 1H), 7.16 (d, J=3.5 Hz, 4H), 7.31 (s, 1H), 7.58 (s, 1H), 7.98 (s, 1H), 12.00 (br s, 1H)

EIMS m/z 356$(M-H)^-$ $C_{18}H_{15}NO_3S_2$=357.

Example 124

Preparation of Compound 97

In an argon atmosphere, 5-bromo-2-fluorobenzaldehyde (0.2 g, 1.0 mmol) was dissolved in toluene (2 mL). Tributyl (1-ethoxy, 1nyltin) (0.37 mL, 1.1 mmol) and bis (triphenylphosphine)palladiumchloride (0.007 g, 0.01 mmol) were added thereto, followed by heating at 100° C. for 10 hours. Then the conventional treatment was performed when the temperature of the residue fell to room temperature. The product was purified by thin-layer chromatography (hexane: ethyl acetate=8:1), to give 5-acetyl-2-fuluorobenzaldehyde (0.19 g, 58.3%).

$^1$H-NMR (300 MHz, $CDCl_3$) δ (ppm) 2.65 (s, 3H), 7.31 (d, J=9.3 Hz, 1H), 8.27 (m, 1H), 8.45 (dd, J=2.4, 6.6 Hz, 1H), 10.40 (s, 1H)

CIMS m/z 167$(M+H)^+$ $C_9H_7{}^{19}FO_2$=166.

5-Acetyl-2-[(4-methylphenyl)thio]benzaldehyde (0.043 g, 26.5%) was obtained by using 5-acetyl-2-fuluorobenzaldehyde (0.1 g, 0.6 mmol) using the same method as Example 114 (synthesis of 5-bromo-2-[(4-methylphenyl)thio]benzaldehyde).

$^1$H NMR (300 MHz, $CDCl_3$) δ (ppm) 2.43 (s, 3H), 2.60 (s, 3H), 6.93 (d, J=8.6 Hz, 1H), 7.29 (d, J=7.9 Hz, 2H), 7.44 (d, J=8.3 Hz, 2H), 7.86 (dd, J=8.5, 2.0 Hz, 1H), 8.38 (d, J=2.0 Hz, 1H), 10.34 (s, 1H)

FABMS m/z 271 $(M+H)^+$ $C_{16}H_{14}O_2S$=270.

Compound 97 (0.059 g,99.8%) was obtained by using 5-acetyl-2-[(4-methylphenyl)thio]benzaldehyde (0.043 g, 0.16 mmol) using the same method as Example 94.

$^1$H-NMR (300 MHz, DMSO-$d_6$) δ (ppm) 2.49 (s, 3H), 2.51 (s, 3H), 7.09 (d, J=8.3 Hz, 1H), 7.31 (d, J=8.3 Hz, 2H), 7.41 (d, J=6.8 Hz, 2H), 7.89 (d, J=8.6 Hz, 1H), 7.95 (s, 1H), 8.01 (s, 1H), 12.00 (br s, 1H)

EIMS m/z 370 $(M+H)^+$ $C_{19}H_{15}NO_3S_2$=369.

Example 125

Preparation of Compound 98

Compound 98 (0.040 g, 49.8%) was obtained by using Compound 97 (0.083 g, 0.21 mmol) using the same method as Example 96.

$^1$H-NMR (300 MHz, DMSO-$d_6$) δ (ppm) 2.29 (s, 3H), 2.50 (s, 3H), 7.30 (d, J=8.3 Hz, 2H), 7.47 (d, J=7.9 Hz, 2H), 7.78 (s, 1H), 7.88 (s, 1H), 8.04 (s, 1H), 8.16 (s, 1H), 8.17 (d, J=3.3 Hz, 1H), NH is not found EIMS m/z 386$(M+H)^+$ $C_{19}H_{15}NO_4S_2$=385.

Example 126

Preparation of Compound 98

2-[(4-Methylphenyl)thio]-6-(trifluoromethyl) benzaldehyde (0.44 g, 100%) was obtained by using 2-fluoro-6-(trifluoromethyl)benzaldehyde (0.19 g, 1.5 mmol) using the same method as Example 114 (synthesis of 5-bromo-2-[(4-methylphenyl)thio]benzaldehyde).

$^1$H-NMR (300 MHz, $CDCl_3$) δ (ppm) 2.42 (s, 3H), 7.08 (d, J=8.3 Hz, 1H), 7.27 (d, J=7.3 Hz, 2H), 7.33 (t, J=7.7 Hz, 1H), 7.43 (d, J=8.1 Hz, 2H), 7.50 (d, J=7.7 Hz, 1H), 10.53 (q, J=2.2 Hz, 1H)

EIMS m/z 296 $(M^+)$ $C_{15}H_{11}{}^{19}F_3OS$=296.

Compound 99 (0.11 g, 81.2%) was obtained by using 2-[(4-methylphenyl)thio]-6-(trifluoromethyl)benzaldehyde (0.1 g, 0.3 mmol) using the same method as Example 94 (synthesis of Compound 67).

$^1$H-NMR (300 MHz, DMSO-$d_6$) δ (ppm) 2.34 (s, 3H), 7.23 (d, J=7.7 Hz, 1H), 7.29 (d, J=7.9 Hz, 2H), 7.37 (d, J=8.3 Hz, 2H), 7.51 (t, J=7.7 Hz, 1H), 7.66 (d, J=7.7 Hz, 1H), 7.70 (s, 1H), 12.00 (br s, 1H)

EIMS m/z 394 $(M-H)^-$ $C_{18}H_{12}{}^{19}FNO_2S_2$=395.

Example 127

Preparation of Compound 100

2-[(4-Methylphenyl)thio]-5-(trifluoromethyl) benzaldehyde (0.45 g, 86.4%) was obtained by using 2-fluoro-5(trifluoromethyl)benzaldehyde (0.1 g, 0.5 mmol) using the same method as Example 114 (synthesis of 5-bromo-2-[(4-methylphenyl)thio]benzaldehyde).

$^1$H-NMR (300 MHz, $CDCl_3$) δ (ppm) 2.43 (s, 3H), 6.99 (d, J=8.6 Hz, 1H), 7.28 (d, J=11.0 Hz, 2H), 7.43 (d, J=8.1 Hz, 2H), 7.52 (d, J=8.4 Hz, 1H), 8.07 (s, 1H), 10.34 (s, 1H)

FABMS m/z 296 $(M^+)$ $C_{15}H_{11}{}^{19}F_3OS$=296

Compound 100 (0.068 g, 50.9%) was obtained by using 2-[(4-methylphenyl)thio]-5-(trifluoromethyl)benzaldehyde (0.1 g, 0.34 mmol) using the same method as Example 94.

$^1$H-NMR (300 MHz, DMSO-$d_6$) δ (ppm) 2.35 (s, 3H), 7.15 (d, J=8.8 Hz, 1H), 7.32 (d, J=7.7 Hz, 2H), 7.43 (d, J=7.7 Hz, 2H), 7.70 (s, 1H), 7.71 (d, J=7.0 Hz, 1H), 7.92 (s, 1H), 12.80 (br s, 1H)

EIMS m/z 394$(M-H)^-$ $C_{18}H_{12}{}^{19}F_3NO_2S_2$=395.

Example 128

Preparation of Compound 101

2-[(4-Methylphenyl)thio]-4-(trifluoromethyl) benzaldehyde (0.47 g, 89.5%) was obtained by using 2-fluoro-4(trifluoromethyl)benzaldehyde (0.1 g, 0.5 mmol) using the same method as Example 114 (synthesis of 5-bromo-2-[(4-methylphenyl)thio]benzaldehyde).

$^1$H-NMR (300 MHz, $CDCl_3$) δ (ppm) 2.41 (s, 3H), 7.23 (d, J=4.6 Hz, 2H), 7.24 (m, 1H), 7.38 (d, J=8.1 Hz, 2H), 7.50 (d, J=8.1 Hz, 1H), 7.95 (d, J=7.9 Hz, 1H), 10.41 (s, 1H)

FABMS m/z 296 $(M^+)$ $C_{15}H_{11}{}^{19}F_3OS$=296

Compound 101 (0.082 g, 60.9%) was obtained by using 2-[(4-methylphenyl)thio]-4-(trifluoromethyl)benzaldehyde (0.1 g, 0.34 mmol) using the same method as Example 94.

$^1$H-NMR (300 MHz, DMSO-$d_6$) δ (ppm) 2.33 (s, 3H), 7.28 (d, J=8.1 Hz, 2H), 7.35 (d, J=8.3 Hz, 2H), 7.38 (s, 1H), 7.71 (d, J=8.1 Hz, 1H), 7.77 (d, J=8.8 Hz, 1H), 7.96 (s, 1H), 12.78 (br s, 1H)

EIMS m/z 394 $(M-H)^-$ $C_{16}H_{12}{}^{19}F_3NO_2S_2$=395.

Example 129

Preparation of Compound 102

2-[(4-methylphenyl)thio]-3-(trifluoromethyl) benzaldehyde (0.44 g, 100%) was obtained by using 2-fluoro-3(trifluoromethyl)benzaldehyde (0.19 g, 1.5 mmol) using the same method as Example 114 (synthesis of 5-bromo-2-[(4-methylphenyl)thio]benzaldehyde).

$^1$H-NMR (300 MHz, $CDCl_3$) δ (ppm) 2.26 (s, 3H), 6.97 (d, J=2.2 Hz, 2H), 7.03 (d, J=8.1 Hz, 2H), 7.64 (t, J=7.9 Hz, 1H), 8.02 (d, J=7.9 Hz, 1H), 8.09 (d, J=7.7 Hz, 1H), 10.60 (d, J=0.7 Hz, 1H)

EIMS m/z 296 $(M^+)$ $C_{15}H_{11}{}^{19}F_3OS$=296.

Compound 102 (0.13 g, 97.5%) was obtained by using 2-[(4-methylphenyl)thio]-3-(trifluoromethyl)benzaldehyde (0.1 g, 0.3 mmol) using the same method as Example 94.

$^1$H-NMR (300 MHz, DMSO-$d_6$) δ (ppm) 2.19 (s, 3H), 6.89 (d, J=8.3 Hz, 2H), 7.05 (d, J=7.9 Hz, 2H), 7.80 (s, 1H), 7.81 (d, J=4.0 Hz, 1H), 7.87 (s, 1H), 8.00 (dd, J=2.8 6.6 Hz, 1H), 12.01 (br s, 1H)

EIMS m/z 394 $(M-H)^-$ $C_{18}H_{12}{}^{19}F_3NO_2S_2$=395.

Example 130

Preparation of Compound 103

Compound 103 (0.043 g, 41.7%) was obtained by using Compound 102 (0.1 g, 0.25 mmol) using the same method as Example 96.

$^1$H-NMR (300 MHz, DMSO-$d_6$) δ (ppm) 2.27 (s, 3H), 7.23 (d, J=8.3 Hz, 2H), 7.27 (d, J=8.8 Hz, 2H), 7.79 (d, J=7.7 Hz, 1H), 7.93 (t, J=7.7 Hz, 1H), 8.07 (d, J=7.7 Hz, 1H), 8.18 (s, 1H), 12.62 (br s, 1H)

EIMS m/z 412 $(M+H)^+$ $C_{18}H_{12}{}^{19}F_3NO_3S_2$=411.

Example 131

Preparation of Compound 104

By using 2-fluoro-5-methoxybenzaldehyde (0.25 g, 2.0 mmol), 2-[(4-methylphenyl)-thio]-5-methoxybenzaldehyde (0.05 g, 10.1%) was obtained through a reaction as described in Example 114 (synthesis of 5-bromo-2-[(4-methylphenyl) thio]-benzaldehyde), and a purification by thin layer chromatography (hexane: ethyl acetate=8:1), followed by another purification with thin layer chromatography (hexane: ethyl acetate=24: 1).

$^1$H-NMR (300 MHz, $CDCl_3$) δ (ppm) 2.32 (s, 3H), 3.86 (s, 3H), 7.07 (dd, J=3.1, 8.6 Hz, 2H), 7.13 (m, 4H), 7.32 (d, J=8.6 Hz, 1H), 7.44 (d, J=3.1 Hz, 1H), 10.51(s, 1H)

EIMS m/z 258$(M^+)$ $C_{15}H_{14}O_2S$=258.

Compound 104 (0.07 g, 97.1%)was obtained by using 2-[(4-methylphenyl)thio]-5-methoxybenzaldehyde (0.05 g, 0.2 mmol) using the same method as Example 94.

$^1$H-NMR (300 MHz, DMSO-$d_6$) δ (ppm) 2.24 (s, 3H), 3.84 (s, 3H), 7.02 (d, J=8.3 Hz, 2H), 7.09 (m, 2H), 7.12 (d, J=8.1 Hz, 2H), 7.52 (d, J=8.6 Hz, 1H), 8.04 (s, 1H), 12.01 (br s, 1H)

EIMS m/z 356 $(M-H)^-$ $C_{18}H_{15}NO_3S_2$=357.

Example 132

Preparation of Compound 105

2-[(4-Methylphenyl)thio]-4-methoxybenzaldehyde (0.078 g, 46.2%) was obtained by using 2-fluoro-4-methoxybenzaldehyde (0.1 g, 0.65 mmol) using the same method as Example 114 (synthesis of 5-bromo-2-[(4-methylphenyl)thio]benzaldehyde).

$^1$H-NMR (300 MHz, $CDCl_3$) δ (ppm) 2.39 (s, 3H), 3.70 (s, 3H), 6.45 (d, J=2.4 Hz, 1H), 6.76 (dd, J=2.4, 8.6 Hz, 1H), 7.22 (d, J=7.7 Hz, 2H), 7.39 (d, J=8.1 Hz, 2H) 7.80 (d, J=8.6 Hz, 1H), 10.20 (s, 1H)

FABMS m/z 259 $(M+H)^+$ $C_{15}H_{14}O_2S$=258

Compound 105 (0.091 g, 85.2%) was obtained by using 2-[(4-methylphenyl)thio]-4-methoxybenzaldehyde (0.078 g, 0.3 mmol) using the same method as Example 94 (synthesis of Compound 67).

$^1$H-NMR (300 MHz, DMSO-$d_6$) δ (ppm) 2.49 (s, 3H), 3.74 (s, 3H), 6.75 (d, J=2.7 Hz, 1H), 7.07 (dd, J=2.7, 8.6 Hz, 1H), 7.23 (d, J=8.3 Hz, 2H), 7.49 (d, J=8.8 Hz, 1H), 8.04 (s, 1H), 12.59 (br s, 1H)

EIMS m/z 358 $(M+H)^+$ $C_{16}H_{15}NO_3S_2$=357

Example 133

Preparation of Compound 106

5-Chloro-2-fluorobenzaldehyde (0.55 g, 77.6%) was obtained by using 4-chlorofluorobenzene (0.48 mL, 4.5 mmol) using the same method an Example 121 (synthesis of 2-fluoro-5-cyanobenzaldehyde).

$^1$H-NMR (300 MHz, $CDCl_3$) δ (ppm) 7.16 (t, J=9.4 Hz, 1H), 7.56 (m, 1H), 7.84 (dd, J=2.8, 5.9 Hz, 1H), 10.32 (s, 1H)

EIMS m/z 157(M−H) $C_7H_4{}^{35}Cl^{19}FNO$=158.

5-Chloro-2-[(4-methylphenyl)thio]benzaldehyde (0.21 g, 85.1%) was obtained by using 5-chloro-2-fluorobenzaldehyde (0.15 g, 0.95 mmol) using the same method as Example 114 (synthesis of 5-bromo-2-[(4-methylphenyl)thio]benzaldehyde).

$^1$H-NMR (300 MHz, $CDCl_3$) δ (ppm) 2.38 (s, 3H), 6.99 (d, J=8.6 Hz, 1H), 7.21 (d, J=7.9 Hz, 2H), 7.33 (m, 1H) 7.35 (d, J=8.3 Hz, 2H) 7.82 (d, J=2.4 Hz, 1H), 10.34 (s, 1H)

FABMS m/z 262$(M^+)$ $C_{14}H_{11}{}^{35}ClOS$=262.

Compound 106 (0.096 g,70. 1%) was obtained by using 5-chloro-2-[(4-methylphenyl)thio]benzaldehyde (0.1 g, 0.38 mmol) using the same method as Example 94.

$^1$H-NMR (300 MHz, DMSO-$d_6$) δ (ppm) 2.30 (s, 3H), 7.23 (d, J=8.6 Hz, 2H), 7.25 (m, 1H), 7.27 (d, J=8.4 Hz, 2H), 7.48 (s, 1H), 7.49 (d, J=7.0 Hz, 1H), 7.91 (s, 1H) 12.01 (br s, 1H)

EIMS m/z 362 $(M+H)^+$ $C_{17}H_{12}{}^{35}ClNO_2S_2$=361.

Example 134

Preparation of Compound 107

Compound 107 (0.094 g, 90.0%) was obtained by using Compound 106 (0.1 g, 0.28 mmol) using the same method as Example 96.

$^1$H-NMR (300 MHz, DMSO-$d_6$) δ (ppm) 2.30 (s, 3K), 7.31 (d, J=8.4 Hz, 2H), 7.43 (d, J=8.1 Hz, 2H), 7.49 (d, J=2.0 Hz, 1H), 7.79 (dd, J=2.0, 8.5 Hz, 1H), 7.88 (s, 1H), 8.02 (d, J=8.4 Hz, 1H), NH is not found EIMS m/z 378 $(M+H)^+$ $C_{17}H_{12}{}^{35}ClNO_3S_2$=377.

Example 135

Preparation of Compound 108

4-Chloro-2-[(4-methylphenyl)thio]benzaldehyde (0.32 g, 60.4%) was obtained by using 4-chloro-2- fluorobenzaldehyde (0.32 g, 2.0 mmol) using the same method as Example 114 (synthesis of 5-bromo-2-[(4-methylphenyl)thio]benzaldehyde).

$^1$H-NMR (300 MHz, $CDCl_3$) δ (ppm) 2.41 (s, 3H), 6.90 (d, J=1.8 Hz, 1H), 7.24 (m, 3H), 7.40 (d, J=8.1 Hz, 2H), 7.76 (d, J=8.3 Hz, 1H), 10.29 (s, 1H)

EIMS m/z 262 ($M^+$) $C_{14}H_{11}{}^{35}ClOS$=262

Compound 108 (0.052 g, 75.1%) was obtained by using 4-chloro-2-[(4-methylphenyl)thio]benzaldehyde (0.05 g, 0.2 mmol) using the same method as Example 94.

$^1$H-NMR (300 MHz, DMSO-$d_6$) δ (ppm) 2.33 (s, 3H), 7.11 (d, J=1.5 Hz, 1H), 7.28 (d, J=8.3 Hz, 2H), 7.35 (d,J=8.3 Hz, 2H), 7.50 (d, J=2.2 Hz, 1H), 7.51 (s, 1H),12.72 (br s, 1H)

EIMS m/z 326 ($M^+$) $C_{17}H_{12}NO_2S_2$=326.

Example 136

Preparation of Compound 109

3-Chloro-4-[(4-methylphenyl)thio]benzaldehyde (0.29 g, 87.9%) was obtained by using 3-chloro-4-fluorobenzaldehyde (0.2 g, 1.26 mmol) using the same method as Example 114 (synthesis of 5-bromo-2-[(4-methylphenyl)thio]benzaldehyde).

$^1$H-NMR (300 MHz, $CDCl_3$) δ (ppm) 2.44 (s, 3H), 6.77 (d, J=8.3 Hz, 1H), 7.30 (d, J=8.4 Hz, 2H), 7.46 (d, J=8.1 Hz, 2H), 7.50 (dd, J=1.8, 8.4 Hz, 1H), 7.82 (d, J=1.7 Hz, 1H), 9.85 (s, 1H)

FABMS m/z 262 ($M^+$) $C_{14}H_{11}{}^{35}ClOS$=262.

Compound 109 (0.13 g, 65.1%) was obtained by using 3-chloro-4-[(4-methylphenyl)-thio]benzaldehyde (0.15 g, 0.57 mmol) using the same method as Example 94.

$^1$H-NMR (300 MHz, DMSO-$d_6$) δ (ppm) 2.38 (s, 3H), 6.79 (d, J=8.4 Hz, 1H), 7.37 (d, J=7.9 Hz, 2H), 7.41 (dd, J=2.2, 8.7 Hz, 1H), 7.48 (d, J=8.1 Hz, 2H), 7.75 (d, J=1.8 Hz, 1H), NH is not found EIMS m/z 361($M^+$) $C_{17}H_{12}{}^{35}ClNO_2S_2$=361

Example 137

Preparation of Compound 110

2-Fluoro-5-nitrobenzaldehyde (0.055 g, 0.33 mmol) was dissolved in N,N-dimethyl-formamide (2.8 mL), and phenol (0.077 g, 0.82 mmol) and potassium carbonate (0.11 g, 0.82 mmol) were added thereto, followed by stirring at 25° C. for 1 hour. After a conventional treatment, the residue was purified by silica gel chromatography (eluted with chloroform), to obtain 5-nitro-2-phenoxybenzaldehyde (77 mg, 98%).

$^1$H NMR (300 MHz, $CDCl_3$) δ (ppm) 6.91 (d, J=9.4 Hz, 1H), 7.20–7.14 (m, 2H), 7.35 (dd, J=7.2 Hz, 7.2 Hz, 1H) 7.47–7.55 (m, 2H), 8.31 (dd, J=9.2, 2.8 Hz, 1H), 8.79 (d, J=3.0 Hz, 1H), 10.60 (s, 1H)

FABMS m/z 244 $(M+H)^+$ $C_{13}H_9NO_4$=243

5-Nitro-2-phenoxybenzaldehyde (77 mg, 0.32 mmol) was dissolved in toluene (3.9 mL), and 2,4-thiazolidinedione (0.15 g, 1.3 mmol), piperidine (0.013 mL, 0.13 mmol), acetic acid (0.0073 mL, 0.13 mmol) and molecular sieves 4A (0.39 g) were added thereto, followed by stirring at 110° C. for 3 hours. After the conventional post-reaction treatment, the residue was purified by thin layer chromatography (developed with chloroform/acetonitrile=10/1), to obtain Compound 110 (67 mg, 61%).

$^1$H NMR (300 MHz, DMSO-$d_6$) δ (ppm) 6.94 (d, J=9.2 Hz, 1H), 7.27 (d, J=7.7 Hz, 2H), 7.36 (d, J=7.1, 7.1 Hz, 1H), 7.50–7.58 (m, 2H), 7.99 (s, 1H), 8.28 (dd, J=2.7, 9.2 Hz, 1H), 8.38 (d, J=2.8 Hz, 1H), 12.81 (m, 1H)

FABMS m/z 341 $(M-H)^-$ $C_{16}H_{10}N_2O_5$=342.

Example 138

Preparation of Compound 111

2-Fluoro-5-nitrobenzaldehyde (0.13 g, 0.79 mmol) was dissolved in N,N-dimethylformamide (6.7 mL), and p-cresol (0.22 g, 2.0 mmol) and potassium carbonate (0.27 g, 2.0 mmol) were added thereto, followed by stirring at 25° C. for 1.5 hours. After a conventional treatment, the residue was purified by silica gel chromatography (eluted with chloroform), to obtain 5-nitro-2-(4methylphenoxy) benzaldehyde (0.20 g, 98%).

$^1$H NMR (300 MHz, $CDCl_3$) δ (ppm) 2.41 (s, 3H), 6.89 (d, J=9.4 Hz, 1H), 7.04 (d, J=8.5 Hz, 2H), 7.25–7.32 (m, 2H), 8.39 (dd, J=9.2, 3.0 Hz, 1H), 8.79 (d, J=2.9 Hz, 1H), 10.60 (s, 1H)

FABMS m/z 257 ($M^+$) $C_{14}H_{11}NO_4S$=257.

5-Nitro-2-(4-methylphenoxy)benzaldehyde (0.11 g, 0.41 mmol) was dissolved in toluene (5.3 mL), and 2,4-thiazolidinedione (0.19 g, 1.6 mmol), piperidine (0.016 mL, 0.16 mmol), acetic acid (0.0094 mL, 0.16 mmol) and molecular sieves 4A (0.53 g) were added thereto, followed by stirring at 11° C. for 2 hours. After the conventional post-reaction treatment, the residue was triturated with ethanol, to obtain Compound 111 (60 mg, 41%).

$^1$H NMR (300 MHz, DMSO-$d_6$) δ (ppm) 2.36 (s, 3H), 6.90 (d, J=9.2 Hz, 1H), 7.15 (d, J=8.2 Hz, 2H), 7.33 (d, J=8.6 Hz, 2H), 7.99 (s, 1H), 8.25 (dd, J=9.2, 1.8 Hz 1H), 8.36 (d, J=2.6 Hz, 1H), 12.80 (m, 1H)

FABMS m/z 355 $(M-H)^-$ $C_{17}H_{12}N_2O_5S$=356.

Example 139

Preparation of Compound 112

Commercially available 2-[4-(2,2-dimethylethyl) phenoxy]-5-nitrobenzaldehyde (0.12 g, 0.41 mmol) (MAYBRIDGE, Catalog Number: XAX00137) was dissolved in ethanol (4.9 mL), and 2,4-thiazolidinedione (0.19 g, 1.6 mmol) and piperidine (0.016 mL, 0.16 mmol) were added thereto, followed by stirring at 80° C. for 2 hours. After the conventional post-reaction treatment, the residue was purified by thin layer chromatography (developed with chloroform/acetonitrile=10/1), to obtain Compound 112 (49 mg, 30%).

$^1$H NMR (300 MHz, DMSO-$d_6$) δ (ppm) 1.31 (s, 9H), 6.92 (d, J=9.2 Hz, 1H), 7.18 (d, J=8.6 Hz, 2H), 7.53 (d, J=8.6 Hz, 2H), 7.98 (s, 1H), 8.27 (dd, J=9.2, 2.4 Hz, 1H), 8.35 (d, J=2.2 Hz, 1H), 12.78 (br s, 1H)

FABMS m/z 397 $(M-H)^-$ $C_{20}H_{18}N_2O_5S$=398.

Example 140

Preparation of Compound 113

Compound 113 (0.079 g, 71.1%) was obtained by using Compound 100 (0.11 g, 0.27 mmol) using the same method as Example 96.

$^1$H-NMR (300 MHz, DMSO-$d_6$) δ (ppm) 2.29 (s, 3H), 7.31 (d, J=8.3 Hz, 2H), 7.47 (d, J=8.1 Hz, 2H), 7.74 (s, 1H), 7.77 (s, 1H), 8.03 (d, J=7.9 Hz, 1H), 8.24 (d, J=7.9 Hz, 1H) NH is not found EIMS m/z 412 $(M+H)^+$ $C_{18}H_{12}{}^{19}F_3NO_3S_2$=411.

Example 141

Preparation of Compound 114

Compound 114 (0.046 g, 43.5%) was obtained by using Compound 94 (0.1 g, 0.28 mmol) using the same method as Example 96.

$^1$H-NMR (300 MHz, DMSO-$d_6$) δ (ppm) 2.29 (s, 3H), 7.29 (d, J=8.1 Hz, 2H), 7.47 (d, J=8.3 Hz, 2H), 7.83 (s, 1H), 7.86 (d, J=7.9 Hz, 1H), 8.01 (d, J=8.1 Hz, 1H), 8.15 (d, J=8.3 Hz, 1H), NH is not found EIMS m/z 369 $(M+H)^+$ $C_{16}H_{12}N_2O_3S_2$=368.

Example 142

Preparation of Compound 115

2-[(4-Trifluoromethylphenyl)thio]-5-nitrobenzaldehyde (0.13 g, 93%) was obtained from 4-trifluoromethylbenzenethiol (74 mg, 0.42 mmol), a 2.5 mol/L sodium hydroxide aqueous solution (0.71 mL, 1.8 mmol), tetrabutylammonium bromide (6.7 mg, 0.021 mmol) and a toluene (0.71 mL) solution of 2-fluoro-5-nitrobenzaldehyde (70 mg, 0.41 mmol) using the same method as Example 97.

$^1$H NMR (300 MHz, $CDCl_3$) δ (ppm) 7.04 (d, J=8.8 Hz, 1H), 7.70 (d, J=8.1 Hz, 2H), 7.77 (d, J=8.6 Hz, 2H), 8.18 (dd, J=8.8, 2.5 Hz, 1H), 8.71 (d, J=2.5 Hz, 1H), 10.31 (s, 1H)

FABMS m/z 327 $(M^-)$ $C_{14}H_8{}^{19}F_3NO_3S$=327.

Compound 115 (44 mg, 51%) was obtained from 2-[(4-trifluoromethylphenyl)thio]-5-nitrobenzaldehyde (0.12 g,0.35 mmol), toluene(5.8 mL), 2,4-thiazolidinedione (0.17 g, 1.4 mmol), piperidine (0.014 mL, 0.14 mmol), acetic acid (0.0080 mL, 0.14 mmol), and molecular sieves 4A (0.58 g) using the same method as Example 97.

$^1$H NMR (300 MHz, DMSO-$d_6$) δ (ppm) 7.52 (d, J=8.7 Hz, 1H), 7.65 (d, J=8.3 Hz, 2H), 7.81 (d, J=8.2 Hz, 2H), 7.88 (s, 1H), 8.24 (dd, J=8.6, 2.5 Hz, 1H), 8.29 (d, J=2.4 Hz, 1H), 12.82 (m, 1H)

FABMS m/z 425 $(M-H)^-$ $C_{17}H_9{}^{19}F_3N_2O_4S_2$=426.

Example 143

Preparation of Compound 116

Compound 74 (57 mg, 0.15 mmol) obtained in Example 101 was dissolved in dichloromethane (11 mL) and methanol (2.3 mL), and m-chloroperbenzoic acid (55 mg, 0.16 mmol) was added thereto, followed by stirring at 25° C. for 1.5 hours. After the conventional post-reaction treatment, the residue was purified by thin layer chromatography (developed with chloroform/methanol=15/1), to obtain Compound 116 (34 mg, 57%).

$^1$H NMR (300 MHz, DMSO-$d_6$) δ (ppm) 3.76 (s, 3H), 7.02–7.08 (m, 2H), 7.49–7.55 (m, 2H), 7.81 (s, 1H), 8.19 (d, J=2.0 Hz, 1H), 8.33 (d, J=8.6 Hz, 1H), 8.52 (dd, J=8.6, 2.2 Hz, 1H), 12.86 (m, 1H)

FABMS m/z 403 $(M-H)^-$ $C_{17}H_{12}N_2O_6S_2$=404.

Example 144

Preparation of Compound 117

Compound 117 (37 mg, 68%) was obtained from Compound 71 (52 mg, 0.13 mmol) obtained in Example 98, dichloromethane (10 mL), methanol (2.1 mL) and m-chloroperbenzoic acid (50 mg, 0.15 mmol) using the same method as Example 143.

$^1$H NMR (300 MHz, DMSO-$d_6$) δ (ppm) 7.55–7.66 (m, 3H), 7.80–7.85 (m, 1H), 8.08 (s, 1H), 8.15 (d, J=8.6 Hz, 1H), 8.27 (m, 1H), 8.45 (dd, J=8.6, 2.2 Hz, 1H), 12.88 (m, 1H)

FABMS m/z 407 $(M-H)^-$ $C_{16}H_9{}^{35}ClN_2O_5S_2$=408.

Example 145

Preparation of Compound 118

3-bromo-4-[(4-methylphenyl)thio]benzaldehyde (0.2 g, 0.65 mmol) was dissolved in acetone (3 mL), cooled to 0° C., and Jones reagent (0.082 mL) was added thereto, followed by stirring for 3.5 hours. Then, isopropyl alcohol (0.1 mL) was added thereto. After a conventional treatment, the residue was recrystallized and purified with hexane and ethyl acetate, to obtain 3-bromo-4-[(4-methylphenyl)thio] benzoic (0.18 g, 84.7%).

$^1$H-NMR (300 MHz, DMSO-$d_6$) δ (ppm) 2.39 (s, 3H), 6.70 (d, J=8.4 Hz, 1H), 7.37 (d, J=8.3 Hz, 2H), 7.49 (d, J=7.9 Hz, 2H), 7.76 (dd, J=1.1, 8.7 Hz, 1H), 8.07 (d, J=1.1 Hz, 1H), $CO_2H$ is not found FABMS m/z 322 $(M-H)^-$ $C_{14}H_{11}{}^{79}BrOS$=323

5-Carboxy-2-[(4-methylphenyl)thio]benzaldehyde (0.031 g, 36.7%) was obtained by using 3-bromo-4-[(4-methylphenyl)thio]benzoic acid (0.1 g, 0.31 mmol) using the same method as Example 115 (synthesis of 3-bromo-4-[(4-methylphenyl)thio]benzaldehyde).

$^1$H-NMR (300 MHz, DMSO-$d_6$) δ (ppm) 2.50 (s, 3H), 6.84 (d, J=8.4 Hz, 1H), 7.36 (d, J=8.1 Hz, 2H), 7.46 (d, J=8.1 Hz, 2H), 7.93 (dd, J=2.0, 8.4 Hz, 1H), 8.46 (d, J=2.0 Hz, 1H), 10.22 (s, 1H), $CO_2H$ is not found FABMS m/z 271 $(M-H)^-$ $C_{15}H_{12}O_3S$=272

Compound 118 (0.032 g, 25.3%) was obtained by using 5-carboxy-2-[(4-methylphenyl)thio]benzaldehyde (0.094 g, 0.34 mmol) using the same method as described in Example 94.

$^1$H-NMR (300 MHz, DMSO-$d_6$) δ (ppm) 2.34 (s, 3H), 6.96 (d, J=8.6 Hz, 1H), 7.29 (d, J=8.1 Hz, 2H), 7.33 (s, 1H), 7.37 (d, J=7.2 Hz, 2H), 7.64 (s, 1H), 7.69 (d, J=8.4 Hz, 1H), 8.20 (s, 1H), NH is not found FABMS m/z 370 $(M-H)^-$ $C_{18}H_{13}NO_4S_2$=371.

Example 146

Preparation of Compound 119

Compound 119 (0.120 g, 33.5%) was obtained by using commercially, available 5-nitro-2-(pyrid-2-ylthio) benzaldehyde (0.26 g, 1.0 mmol) (MAYBRIDGE, Catalog Number: XAX00153) using the same method an Example 94.

$^1$H-NMR (300 MHz, DMSO-$d_6$) δ (ppm) 7.28 (dd, J=4.8, 7.7 Hz, 1H), 7.40 (dd, J=0.9, 7.7 Hz, 1H), 7.78 (dd, J=1.3, 7.7 Hz, 1H), 7.86 (s, 1H), 7.87 (d, J=8.4 Hz, 1H), 8.28 (dd, J=2.4, 8.4 Hz, 1H), 8.32 (d, J=2.4 Hz, 1H), 8.42 (dd, J=0.9, 4.8 Hz, 1H), 12.78 (br s, 1H)

EIMS m/z=360 $(M+H)^+$ $C_{15}H_9N_3O_4S_2$=359.

Example 147

Preparation of Compound 120

Compound 120 (0.0044 g, 21.2%) was obtained by using Compound 119 (0.02 g, 0.056 mmol) obtained in Example 146 using the same method as Example 96.

$^1$H-NMR (300 MHz, DMSO-$d_6$) δ (ppm) 7.49 (m, 1H), 7.87 (s, 1H), 7.98 (d, J=7.9 Hz, 1H), 8.07 (m, 1H), 8.08 (d, J=8.5 Hz, 1H), 8.26 (dd, J=2.2, 8.5 Hz, 1H), 8.43 (d, J=2.2 Hz, 1H), 8.54 (d, J=4.8 Hz, 1H), NH is not found EIMS m/z=376 $(M+H)^+$ $C_{15}H_9N_3O_5S_2$=375.

Example 148

Preparation of Compound 121

N,N-diphenylbenzylamine (935 mg, 3.60 mmol) was suspended in acetic acid (20 mL), and hexamethylenetriamine (1.12 g, 7.96 mmol) was added thereto, followed by stirring at 90° C. for 12 hours. The reaction liquid was cooled to room temperature, a 6 mol/L sodium hydroxide aqueous solution and water were added thereto, and then the product was extracted with chloroform. The organic layer was washed with brine, and then dried over anhydrous sodium sulfate. The solvent was evaporated under reduced pressure, and the residue was purified by silica gel column chromatography (elution solvent: hexane/ethyl acetate=20/1→10/1), to obtain 4-(N-phenylbenzylamino)benzaldehyde (742 mg, 72%).

$^1$H NMR (270 MHz, $CDCl_3$) δ (ppm) 5.04 (s, 2H), 6.80 (d, J=8.6 Hz, 2H), 7.2–7.45 (m, 10H), 7.63 (d, J=8.6 Hz, 2H), 9.73 (s, 1H).

4-(N-phenylbenzylamino)benzaldehyde (109 mg, 0.378 mmol), 2,4-thiazolidinedione (59.9 mg, 0.511 mmol) and piperidine (0.045 mL, 0.46 mmol) were heated under reflux for 6 hours in ethanol (5 mL). The reaction liquid was cooled to room temperature, 1 mol/L HCl was added thereto, and then the product was extracted with chloroform. The organic layer was washed with brine, and then dried over anhydrous sodium sulfate. The solvent was evaporated under reduced pressure, and the residue was purified by preparative thin layer chromatography (chloroform/methanol=20/1), to obtain Compound 121 (123 mg, 84%).

$^1$H NMR (270 MHz, $CDCl_3$) δ (ppm) 5.08 (s, 2H), 6.88 (d, J=8.6 Hz, 2H), 7.15–7.45 (m, 12H), 7.61 (s, 2H), 12.38 (br s, 1H).

Example 149

Preparation of Compound 129

2-Fluoro-5-nitrobenzaldehyde(31 mg, 0.18 mmol) was dissolved in N,N-dimethylformamide (3.1 mL), and 4-mercaptobenzoic acid (85 mg, 0.55 mmol) and triethylamine (0.13 mL, 0.92 mmol) were added thereto, followed by stirring at 25° C. for 20 minutes. After the conventional post-reaction treatment, the product was purified by thin layer chromatography (developed with chloroform/methanol=10/1) to give 5-nitro-2-[(4-carboxylphenyl)thio]benzaldehyde (60 mg, 100%).

5-Nitro-2-[(4-carboxylphenyl)thio]benzaldehyde (60 mg, 0.20 mmol) was dissolved in ethanol (2.4 mL), and 2,4-thiazolidinedione (92 mg, 0.79 mmol), piperidine (0.027 mL, 0.28 mmol), acetic acid (0.0045 mL, 0.079 mmol) and molecular sieves 4A (0.30 g) were added thereto, followed by stirring at 80° C. for 2.5 hours. After the conventional post-reaction treatment, thin layer chromatography (developed with chloroform/methanol=5/1), to give Compound 129 (12 mg, 15%).

5-Nitro-2-[(4-carboxylphenyl)thio]benzaldehyde:

$^1$H NMR (300 MHz, $CDCl_3$) δ (ppm) 7.04 (d, J=8.8 Hz, 1H), 7.74 (d, J=8.0 Hz, 2H), 8.09 (d, J=8.2 Hz, 2H), 8.28 (dd, J=8.8, 2.5 Hz, 1H), 8.87 (d, J=2.5 Hz, 1H), 10.28 (s, 1H), 13.10 (m, 1H)

Compound 129:

$^1$H NMR (300 MHz, DMSO-$d_6$) δ (ppm) 7.46 (d, J=8.8 Hz, 1H), 7.55 (d, J=8.3 Hz, 2H), 7.87 (s, 1H), 7.98 (d, J=8.7 Hz, 2H), 8.21 (dd, J=8.7, 2.4 Hz, 1H), 8.30 (d, J=2.4 Hz, 1H), 12.57–13.31 (m, 2H)

FABMS m/z 401 $(M-H)^-$ $C_{17}H_{10}N_2O_6S_2$=402

Example 150

Preparation of Compound 130

5-Nitro-2-[(4-carboxylphenyl)thio]benzaldehyde (71 mg, 0.23 mmol) obtained in Example 149 was dissolved in N,N-dimethylformamide (7.1 mL), and a 2.0 mol/L dimethylamine methanol solution (0.23 mL, 0.47 mmol), 1-ethyl-3-(3-dimethylaminopropyl)carbodiimide hydrochloride (90 mg, 0.47 mmol), and 1-hydroxybenzotriazole hydrate (0.11 g, 0.94 mmol) were added thereto, followed by stirring at 25° C. for 30 minutes. After the conventional post-reaction treatment, the product was purified by silica gel chromatography (eluted by chloroform) to give N,N-dimethyl-4-[(2-formyl-4-nitrophenyl)thio]benzamido (59 mg, 75%).

N,N-Dimethyl-4-[(2-formyl-4-nitrophenyl)thio]benzamido (0.12 g, 0.36 mmol) was dissolved in toluene (6.0 mL), and 2,4-thiazolidinedione (0.17 g, 1.5 mmol), piperidine (0.014 mL, 0.15 mmol), acetic acid (0.0083 mL, 0.15 mmol) and molecular sieves 4A (0.60 g) were added thereto, followed by stirring at 110° C. for 4.5 hours. After the conventional post-reaction treatment, thin layer chromatography (developed with chloroform/acetonitrile 3/1), to give Compound 130 (48 mg, 31 %).

N,N-dimethyl-4-[(2-formyl-4-nitrophenyl)thio]benzamido:

$^1$H NMR (300 MHz, $CDCl_3$) δ (ppm) 3.02 (br s, 3H), 3.16 (br s, 3H), 7.02 (d, J=9.0 Hz, 1H), 7.53–7.64 (m, 4H), 8.13 (dd, J=8.8, 2.6 Hz, 1H), 8.69 (d, J=2.6 Hz, 1H), 10.31 (s, 1H)

FABMS m/z 331 $(M+H)^+$ $C_{16}H_{14}N_3O_4S$=330

Compound 130:

$^1$H NMR (300 MHz, DMSO-$d_6$) δ (ppm) 2.92 (br s, 3H), 2.99 (br s, 3H), 7.36 (d, J=8.8 Hz, 1H), 7.50 (d, J=8.2 Hz, 2H), 7.57 (d, J=8.0 Hz, 2H), 7.89 (s, 1H), 8.21 (dd, J=8.8, 2.2 Hz, 1H), 5.27 (d, J=2.2 Hz, 1H), 12.83 (m, 1H)

FABMS m/z 428 $(M-H)^-$ $C_{19}H_{15}N_3O_5S_2$=429

Example 151

Preparation of Compound 131

4-{4-[(2-Formyl-4-nitrophenyl)thio]benzoyl}morpholine (0.13 g, 78%) was obtained from 5-nitro-2-[(4-carboxylphenyl)thio]benzaldehyde (0.13 g, 0.42 mmol) obtained in Example 149, N,N-dimethylformamide (7.1 mL), morpholine (0.073 mL, 0.83 mmol), 1-ethyl-3-(3-dimethylaminopropyl)carbodiimide hydrochloride (0.16 g, 0.83 mmol), and 1-hydroxybenzotriazole monohydrate (0.11 g, 1.7 mmol), using the same method as Example 150.

Compound 131 (48 mg, 31%) was obtained from 4-{4-[(2-formyl-4-nitrophenyl)thio]benzoyl}morpholine (0.13 g, 0.34 mmol), toluene (6.3 mL), 2,4-thiazolidinedione (0.16 g, 1.3 mmol), piperidine (0.013 mL, 0.13 mmol), acetic acid (0.0077 mL, 0.13 mmol) and molecular sieves 4A (0.63 g).

4-{4-[(2-formyl-4-nitrophenyl)thio]benzoyl}morpholine:

$^1$H NMR (300 MHz, $CDCl_3$) δ (ppm) 3.39–3.93 (m, 8H), 7.04 (d, J=9.0 Hz, 1H), 7.56 (d, J=8.2 Hz, 2H), 7.62 (d, J=8.3 Hz, 2H), 8.13 (dd, J=8.8, 2.5 Hz, 1H), 8.69 (d, J=2.6 Hz, 1H), 10.30 (s, 1H)

FABMS m/z 373 $(M+H)^+$ $C_{18}H_{16}N_2O_5S$=372

Compound 131:

$^1$H NMR (300 MHz, DMSO-$d_6$) δ (ppm) 3.27–3.45 (m, 4H), 3.61 (br s, 4H), 7.39 (d, J=8.9 Hz, 1H), 7.51 (d, J=8.4

Hz, 2H), 7.57 (d, J=8.4 Hz, 2H), 7.89 (s, 1H), 8.21 (dd, J=8.8, 2.6 Hz, 1H), 8.27 (d, J=2.2 Hz, 1H), 12.83 (m, 1H)

FABMS m/z 470 $(M-H)^-$ $C_{21}H_{17}N_3O_6S_3$=471

Example 152

Preparation of Compound 132

A 2.5 mol/L sodium hydroxide aqueous solution (1.6 mL, 4.0 mmol) and tetrabutylammonium bromide (15 mg, 0.047 mmol) were added to 4-(methylthio)benzenethiol (0.15 mL, 0.93 mmol), followed by stirring at 25° C. for 10 minutes. A toluene solution (1.6 mL) of 2-fluoro-5-nitrobenzaldehyde (0.16 g, 0.93 mmol) was added to the reaction liquid, followed by stirring at 110° C. for 1.5 hours. After the conventional post-reaction treatment, the product was purified by silica gel chromatography (eluted by chloroform) to give 5-nitro-2-[(4-methylthio)phenyl]thiobenzaldehyde (0.25 g, 89%).

5-nitro-2-[4-(methylthio)phenyl]thiobenzaldehyde (0.23 g, 0.76 mmol) was dissolved in toluene (12 mL), and 2,4-thiazolidinedione (0.35 mg, 3.0 mmol), piperidine (0.030 mL, 0.30 mmol), acetic acid (0.017 mL, 0.30 mmol) and molecular sieves 4A (1.2 g) were added thereto, followed by stirring at 110° C. for 4 hours. After the conventional post-reaction treatment, the product was triturated by using ethanol to give Compound 132 (12 mg, 15%).

5-nitro-2-[4-(methylthio)phenyl]thiobenzaldehyde:

$^1$H NMR (300 MHz, $CDCl_3$) δ (ppm) 2.55 (s, 3H), 6.98 (d, J=9.0 Hz, 1H), 7.32–7.38 (m, 2H), 7.44–7.50 (m, 2H), 8.11 (dd, J=9.0, 2.5 Hz, 1H), 8.66 (d, J=2.4 Hz, 1H), 10.30 (s, 1H)

FABMS m/z 306 $(M+H)^+$ $C_{14}H_{11}NO_3S_2$=305

Compound 132:

$^1$H NMR (300 MHz, DMSO-$d_6$) δ (ppm) 2.52 (s, 3H), 7.09 (d, J=9.2 Hz, 1H), 7.41 (d, J=8.6 Hz, 2H), 7.52 (d, J=8.3 Hz, 2H), 7.38 (s, 1H), 8.16 (dd, J=8.8, 2.6 Hz, 1H), 8.23 (d, J=2.4 Hz, 1H), 12.83 (m, 1H)

FABMS m/z 403 $(M-H)^-$ $C_{17}H_{12}N_2O_4S_3$=464

Example 153

Preparation of Compound 133

Compound 133 (0.12 g, 100%) was obtained from Compound 75 (0.11 g, 0.27 mmol) obtained in Example 102, dichloromethane (21 mL), methanol (4.2 mL) and m-chloroperbenzoic acid (0.10 g, 0.30 mmol), using the same method as Example 134.

Compound 133:

$^1$H NMR (300 MHz, DMSO-$d_6$) δ (ppm) 2.46–2.55 (m, 3H), 3.93–4.04 (m, 2H), 8.73 (br d, J=7.7 Hz, 2H), 8.88 (br d, J=7.5 Hz, 2H), 9.27 (s, 1H), 9.58 (s, 1H), 9.72 (d, J=8.6 Hz, 1H), 9.91 (br d, J=8.3 Hz, 1H), 14.21 (m, 1H)

FABMS m/z 401 $(M-H)^-$ $C_{18}H_{14}N_2O_5S_2$=402

Example 154

Preparation of Compound 134

Compound 134 (90 mg, 76%) was obtained from Compound 70 (0.11 g, 0.29 mmol) obtained in Example 97, dichloromethane (23 mL), methanol (4.5 mL) and m-chloroperbenzoic acid (0.11 g, 0.32 mmol), using the same method as Example 134.

Compound 134:

$^1$H NMR (300 MHz, DMSO-$d_6$) δ (ppm) 7.49–7.62 (m, 3H), 7.66 (s, 1H), 7.99 (s, 1H), 8.21 (d, J=1.7 Hz, 1H), 8.30 (d, J=8.9 Hz, 1H), 8.49 (dd, J=8.4, 2.0 Hz, 1H), 12.89 (m, 1H)

FABMS m/z 407 $(M-H)^-$ $C_{16}H_9{}^{35}ClN_2O_5S_2$=408

Example 155

Preparation of Compound 135

Compound 135 (32 mg, 37%) was obtained from Compound 72 (83 mg, 0.19 mmol) obtained in Example 99, dichloromethane (17 mL), methanol (3.3 mL) and m-chloroperbenzoic acid (74 mg, 0.21 mmol), using the same method as Example 134.

Compound 135:

$^1$H NMR (300 MHz, DMSO-$d_6$) δ (ppm) 7.52 (dd, J=8.4, 1.8 Hz, 1H), 7.79 (d, J=8.4 Hz, 1H), 7.86 (d, J=2.1 Hz, 1H), 7.99 (s, 1H), 8.22 (d, J=2.0 Hz, 1H), 8.30 (d, J=8.6 Hz, 1H), 8.48 (dd, J=8.6, 2.0 Hz, 1H), 12.88 (m, 1H)

FABMS m/z 441 $(M-H)^-$ $C_{16}H_8{}^{35}Cl_2N_2O_5S_2$=442

Example 156

Preparation of Compound 136

Compound 80 (60 mg, 0.14 mmol) obtained in Example 107 was dissolved in N,N-dimethylformamide (3.0 mL), and m-chloroperbenzoic acid (0.11 g, 0.33 mmol) was added thereto, followed by stirring at 25° C. for 1 hour. After the conventional post-reaction treatment, thin layer chromatography (developed with chloroform/methanol=20/1), to give Compound 136 (20 mg, 33%).

Compound 136:

$^1$H NMR (300 MHz, DMSO-$d_6$) δ (ppm) 7.66 (d, J=8.6 Hz, 2H), 7.73 (d, J=8.4 Hz, 2H), 7.99 (s, 1H), 8.27–8.32 (m, 1H), 8.48 (d, J=8.2 Hz, 1H), 8.54 (d, J=1.8 Hz, 1H), 12.83 (m, 1H)

FABMS m/z 451 $(M-H)^-$ $C_{16}H_9{}^{79}BrN_2O_5S_2$=452.

Example 157

Preparation of Compound 137

A reaction similar to the synthesis of 5-bromo-2-[(4-methylphenyl)thio]benzaldehyde in Example 114 was performed using 4-fluoro-3-phenoxybenzaldehyde (0.20 g, 0.93 mmol), followed by the conventional treatment.

The solvent was removed from the obtained mixture of the starting material and the product by using a vacuum dryer, and, using the whole quantity, Compound 137 (0.11 g, 45%) was obtained in a manner similar to the synthesis of Compound 67.

Compound 137:

$^1$H-NMR(300 MHz, DMSO-$d_6$) δ (ppm) 2.50(s, 3H), 6.90(d, J=8.3 Hz, 1H), 7.06(d, J=9.0 Hz, 2H), 7.07(m, 1H), 7.21(t, J=7.3 Hz, 1H), 7.30(m, 1H), 7.32(d, J=8.1 Hz, 2H), 7.43 (d, J=8.1 Hz, 4H), 7.63(s, 1H), 12.55(br s, 1H)

EI-MS m/z 419($M^+$), $C_{23}H_{17}NO_3S_2$=419

Example 158

Preparation of Compound 138

A reaction similar to the synthesis of 5-bromo-2-[(4-methylphenyl)thio]benzaldehyde in Example 114 was performed using 4-fluoro-3-methoxybenzaldehyde (0.20 g, 1.3 mmol), followed by the conventional treatment.

The solvent was removed from the obtained mixture of the starting material and the product by using a vacuum dryer, and, using the whole quantity, Compound 138 (0.13 g, 44%) was obtained in a manner similar to the synthesis of Compound 67.

Compound 138:

$^1$H-NMR(300 MHz, DMSO-$d_6$) δ (ppm) 2.36(s, 3H), 3.90(s, 3H), 6.71(d, J=8.1 Hz, 1H), 7.06(d, J=8.1 Hz, 1H), 7.24(d, J=1.3 Hz, 1H), 7.31(d, J=8.3 Hz, 2H), 7.39(d, J=8.1 Hz, 2H), 7.74(s, 1H), 12.57(br s, 1H)

EI-MS m/z 357($M^-$), $C_{18}H_{15}NO_3S_2$=357

Example 159

Preparation of Compound 139

Compound 118 (0.33 g, 0.89 mmol) obtained in Example 145 was dissolved in dimethylformamide (15 mL), potassium carbonate (0.12 g, 0.89 mmol) and benzyl bromide (0.13 mL, 1.1 mmol) were added thereto, followed by stirring at room temperature for 10 hours. Then the conventional treatment was performed, and the product was purified with thin layer chromatography (hexane/ethyl acetate=8/1) to give Compound 139 (0.077 g, 50%).

Compound 139:

$^1$H-NMR(300 MHz, DMSO-$d_6$) δ (ppm) 2.33(s, 3H), 5.37(s, 2H), 7.11(d, J=8.4 Hz, 1H), 7.31(d, J=8.3 Hz, 2H), 7.38(d, J=8.3 Hz, 2H), 7.39(m, 1H), 7.41(d, J=8.3 Hz, 2H), 7.46(d, J=7.3 Hz, 2H), 7.91(dd, J=1.8, 8.4 Hz, 1H), 7.96(s, 1H), 8.08(d, J=1.5 Hz, 1H), 12.76(br s, 1H)

EI-MS m/z 461($M^-$), $C_{25}H_{19}NO_4S_2$=461

Example 160

Preparation of Compound 140

Compound 140 (0.067 g, 64.0%) was obtained by using Compound 95 (0.1 g, 0.28 mmol) using the same method as Example 96 (synthesis of Compound 69).

Compound 140:

$^1$H NMR (300 MHz, DMSO-$d_6$) δ (ppm) 2.34 (s, 3H), 7.40 (d, J=8.4 Hz, 2H), 7.63 (d, J=8.1 Hz, 2H), 7.80 (s, 1H), 8.09 (dd, J=1.7, 8.4 Hz, 1H), 8.19 (d, J=1.5 Hz, 1H), 8.22 (d, J=8.3 Hz, 1H), 12.80 (br s, 1H)

FABMS m/z 369 $(M+H)^+$ $C_{18}H_{12}N_2O_3S_2$=368

Example 161

Preparation of Compound 141

Compound 141 (0.094 g, 89.9%) was obtained by using Compound 109 (0.1 g, 0.28 mmol) using the same method as Example 96 (synthesis of Compound 69).

Compound 141:

$^1$H NMR (300 MHz, DMSO-$d_6$ δ (ppm) 2.49 (s, 3H), 7.36 (d, J=8.4 Hz, 2H), 7.62 (d, J=8.1 Hz, 2H), 7.76 (s, 1H), 7.79 (s, 1H), 7.82 (d, J=8.3 Hz, 1H), 8.10 (d, J=8.3 Hz, 1H), 12.77 (br s, 1H)

FABMS m/z 377 $(M-H)^-$ $C_{17}H_{12}{}^{35}ClNO_3S_2$=378

Example 162

Preparation of Compound 142

3-Bromo-4-[(4-methylphenyl)thio]benzaldehyde (0.1 g, 0.33 mmol) obtained in Example 123 was dissolved in methanol (5 mL), p-toluenesulfonic acid monohydrate (0.0006 g, 0.003 mmol) and orthoformic acid methyl (0.035 mL, 0.33 mmol) were added thereto, and the product was heated under reflux for 3 hours. After the conventional treatment, the solvent was removed by using a vacuum dryer, and 3-bromo-4-[(4-methylphenyl)thio]benzaldehydedimethylacetal was obtained in the form of the crude product.

Using the whole quantity of the crude product of 3-bromo-4-[(4-methylphenyl)thio]benzaldehydedimethylacetal, 3-formyl-4-[(4-methylphenyl)thio]benzaldehydedimethylacetal (0.09 g, yield 90.3%) was obtained in a manner similar to the synthesis of 5-[hydroxymethyl-2-[(4-methylphenyl)thio]benzaldehyde in Example 123.

Using 3-formyl-4-[(4-methylphenyl)thio]benzaldehydedimethylacetal (0.2 g, 0.67 mmol), Compound 142 (0.21 g, 76.3%) was obtained using the same method as Example 94 (synthesis of Compound 67).

3-Formyl-4-[(4-methylphenyl)thio]benzaldehydedimethylacetal:

$^1$H-NMR(300 MHz, $CDCl_3$) δ (ppm) 2.39 (s, 3H), 3.32 (s, 6H), 5.39 (s, 1H), 6.99 (d, J=8.3Hz, 1H), 7.22(d, J=7.9 Hz, 2H), 7.38(d, J=8.3 Hz, 2H), 7.43(dd, J=2.0, 8.3 Hz, 1H), 7.94(d, J=2.0 Hz, 1H), 10.35 (s, 1H)

FAB-MS m/z=302(M−), $C_{17}H_{18}O_3S$=302

Compound 142:

$^1$H NMR (300 MHz, DMSO-$d_6$) δ (ppm) 2.49 (s, 3H), 3.27 (s, 6H), 5.44 (s, 1H), 7.26 (d, J=2.6 Hz, 4H), 7.40 (d, J=8.4 Hz, 1H), 7.54 (s, 1H), 8.04 (s, 1H), 12.68 (br s, 1H)

FABMS m/z 401 $(M-H)^-$ $C_{20}H_{19}NO_4S_2$=402

Example 163

Preparation of Compound 143

Using Compound 88 (0.07 g, 0.17 mmol), Compound 143 (0.049 g, 69.4%) was obtained using the same method as Example 96 (synthesis of Compound 69).

Compound 143:

$^1$H NMR (300 MHz, DMSO-$d_6$) δ (ppm) 2.33 (s, 3H), 7.35 (d, J=8.1 Hz, 2H), 7.63 (d, J=8.3 Hz, 2H), 7.79 (s, 1H), 7.86 (d, J=8.4 Hz, 1H), 7.91 (s, 1H), 8.08 (d, J=8.3 Hz, 1H), 12.76 (br s, 1H)

FABMS m/z 422 $(M^+)$ $C_{17}H_{12}{}^{79}BrNO_3S_2$=422

Example 164

Preparation of Compound 144

Compound 142 (0.17 g, 0.43 mmol) was dissolved in dichloromethane (14 mL) and methanol (2.6 mL), and a 1 mol/L hydrogen chloride aqueous solution (0.5 mL) was added thereto. After heating under the reflux for 2 hours, the product was cooled to room temperature, and extracted with ethyl acetate. The solvent was evaporated under reduced pressure and the residue was recrystallized from ethyl acetate and hexane to obtain Compound 144 (0.15 g, 98.2%).

Compound 144:

$^1$H NMR (300 MHz, DMSO-$d_6$) δ (ppm) 2.49 (s, 3H), 7.12 (d, J=8.4 Hz, 1H), 7.34 (d, J=8.3 Hz, 2H), 7.45 (d, J=8.1 Hz, 2H), 7.83 (d, J=8.3 Hz, 1H), 7.95 (s, 1H), 7.97 (s, 1H), 9.97 (s, 1H), 12.78 (br s, 1H)

FABMS m/z 356 $(M+H)^+$ $C_{18}H_{13}NO_3S_2$=355

Example 165

Preparation of Compound 145

Compound 144 (0.05 g, 0.14 mmol) was dissolved in chloroform (4 mL), and [(tert-butoxycarbonyl)methylene]triphenylphosphine (0.13 g, 0.35 mmol) was added thereto. After heating under the reflux for 2 hours, the product was cooled to room temperature, and extracted with ethyl acetate. The solvent was evaporated under reduced pressure, and the residue was purified by preparative thin layer chromatography (development solvent: chloroform/acetonitrile=18/1). Then the product was recrystallized from ethyl acetate and hexane to give Compound 145 (0.038 g, 59.8%).

Compound 145:

$^1$H NMR (300 MHz, DMSO-$d_6$) δ (ppm) 1.48 (s, 9H), 2.33 (s, 3H), 6.49 (d, J=16.1 Hz, 1H), 7.08 (d, J=8.3 Hz, 1H), 7.27 (d, J=8.6 Hz, 2H), 7.35 (d, J=8.3 Hz, 2H), 7.56 (d, J=16.1 Hz, 1H), 7.69 (s, 1H), 7.72 (d, J=8.3 Hz, 1H), 7.95 (s, 1H), 12.70 (br s, 1H)

FABMS m/z 453 $(M-H)^-$ $C_{24}H_{23}NO_4S_2$=454

Example 166

Preparation of Compound 146

Compound 145 (0.02 g, 0.04 mmol) was dissolved in dichloromethane (4 mL), and trifluoroacetic acid (1 mL) was added thereto, followed by stirring at room temperature for 1 hour. Then the conventional treatment was performed, the solvent was evaporated under reduced pressure, and the residue was triturated with ethyl acetate to give Compound 146 (0.015 g, 87.5%).

Compound 146:

$^1$H NMR (300 MHz, DMSO-$d_6$) δ (ppm) 2.50 (s, 3H), 6.51 (d, J=16.0 Hz, 1H), 7.11 (d, J=8.1 Hz, 1H), 7.27 (d, J=8.4 Hz, 2H), 7.34 (d, J=8.1 Hz, 2H), 7.60 (d, J=16.0 Hz, 1H), 7.70 (s, 1H), 7.72 (d, J=8.4 Hz, 1H), 7.96 (s, 1H), 12.50 (br s, 1H), 12.71 (br s, 1H)

FABMS m/z 396 $(M-H)^-$ $C_{20}H_{15}NO_4S_2$=397

Example 167

Preparation of Compound 147

Using 4-fluoro-5-(trifluoromethyl)benzaldehyde (0.20 g, 1.0 mmol), 4-[(4-methylphenyl)thio]-3-(trifluoromethyl)benzaldehyde (0.30 g, 100%) was obtained in a manner similar to the synthesis of 5-bromo-2-[(4-methylphenyl)thio]benzaldehyde.

Compound 147 (0.13 g, 50.2%) was obtained by using 4-[(4-methylphenyl)thio]-3-(trifluoromethyl)benzaldehyde (0.2 g, 0.7 mmol) using the same method as Example 94 (synthesis of Compound 67).

4-[(4-methylphenyl)thio]-3-(trifluoromethyl)benzaldehyde:

$^1$H NMR (300 MHz, $CDCl_3$) δ (ppm) 2.43 (s, 3H), 7.01 (d, J=8.3 Hz, 1H), 7.29 (d, J=7.9 Hz, 2H), 7.46 (d, J=8.1 Hz, 2H), 7.73 (d, J=8.4 Hz, 1H), 8.11 (s, 1H), 9.93 (s, 1H)

FABMS m/z 296 $(M^+)$ $C_{15}H_{11}F_3OS$=296

Compound 147:

$^1$H NMR (300 MHz, DMSO-$d_6$) δ (ppm) 2.49 (s, 3H), 7.08 (d, J=8.3 Hz, 1H), 7.35 (d, J=8.1 Hz, 2H), 7.46 (d, J=8.1 Hz, 2H), 7.67 (d, J=8.4 Hz, 1H), 7.82 (s, 1H), 8.02 (s, 1H), 12.68 (br s, 1H)

FABMS m/z 395 $(M^+)$ $C_{18}H_{12}{}^{19}F_3NO_2S_2$=395

Example 168

Preparation of Compound 148

Compound 148 (0.047 g, 64.3%) was obtained by using Compound 147 (0.07 g, 0.18 mmol) using the same method as Example 96 (synthesis of Compound 69).

Compound 148:

$^1$H NMR (300 MHz, DMSO-$d_6$) δ (ppm) 2.49 (s, 3H), 7.37 (d, J=8.4 Hz, 2H), 7.53 (d, J=8.3 Hz, 2H), 7.93 (s, 1H), 8.10 (d, J=7.7 Hz, 1H), 8.11 (s, 1H), 8.35 (d, J=8.3 Hz, 1H), 12.80 (br s, 1H)

FABMS m/z 412 $(M+H)^+$ $C_{18}H_{12}{}^{19}F_3NO_3S_2$=411

Example 169

Preparation of Compound 149

A reaction similar to Example 81 was performed using 5-carboxy-2-[(4-methylphenyl)thio]benzaldehyde (0.10 g, 0.37 mmol) to obtain 5-(N,N-diethylaminocarbonyl)-2-[(4-methylphenyl)thio]benzaldehyde (0.046 g, 36.7%). Compound 149 (0.043 g, 76.1%) was obtained by using 5-(N,N-diethylaminocarbonyl)-2-[(4-methylphenyl)thio]benzaldehyde (0.046 g, 0.13 mmol) using the same method as Example 94 (synthesis of Compound 67).

5-(N,N-diethylaminocarbonyl)-2-[(4-methylphenyl)thio]benzaldehyde:

$^1$H NMR (300 MHz, $CDCl_3$) δ (ppm) 1.19 (m, 3H), 1.53 (m, 4H), 2.41 (s, 3H), 6.98 (d, J=8.3 Hz, 1H), 7.23 (d, J8.4 Hz, 2H), 7.36 (dd, J=2.0,8.3 Hz, 1H), 7.40 (d, J=8.3 Hz, 2H), 7.86 (d, J=2.0 Hz, 1H), 10.35 (s, 1H)

FABMS m/z 328 $(M+H)^+$ $C_{19}H_{21}NO_2S$=327

Compound 149:

$^1$H NMR (300 MHz, DMSO-$d_6$) δ (ppm) 1.1 (m, 6H), 2.50 (s, 3H), 3.38 (m, 4H), 7.16 (d, J=8.3 Hz, 1H), 7.27 (d, J=8.3 Hz, 2H), 7.34 (d, J=8.4 Hz, 2H), 7.37 (d, J=8.1 Hz, 1H), 7.39 (s, 1H), 7.97 (s, 1H), 12.03 (br s, 1H)

FABMS m/z 427 $(M)^+$ $C_{22}H_{22}N_2O_3S_2$=427

Example 170

Preparation of Compound 150

Compound 150 (0.024 g, 26.2%) was obtained by using Compound 149 (0.09 g, 0.21 mmol) using the same method as Example 96 (synthesis of Compound 69).

Compound 150:

$^1$H NMR (300 MHz, DMSO-$d_6$) δ (ppm) 1.1 (m, 6H), 2.29 (s, 3H), 2.49 (m, 4H), 7.31 (d, J=8.4 Hz, 2H), 7.40 (s, 1H), 7.46 (d, J=8.1 Hz, 2H), 7.63 (d, J=7.9 Hz, 1H), 7.84 (s, 1H), 8.05 (d, J=8.1 Hz, 1H), NH not found FABMS m/z 443 $(M)^+$ $C_{22}H_{22}N_2O_4S_2$=443

Example 171

Preparation of Compound 151

4-{3-Formyl-4-[(4-methylphenyl)thio]benzoyl}-morpholine (0.092g, 24.4%) was obtained by using 5-carboxy-2-[(4-methylphenyl)thio]benzaldehyde (0.3 g, 1.1 mmol) and using morpholine (0.19 mL, 2.2 mmol) instead of diethylamine with the same method as Example 81.

Compound 151 (0.066 g, 55.8%) was obtained by using 4-{3-formyl-4-[(4-methylphenyl)thio]benzoyl}-morpholine (0.092 g, 0.27 mmol) using the same method as Example 94 (synthesis of Compound 67).

4-{3-Formyl-4-[(4-methylphenyl)thio]benzoyl}-morpholine:

$^1$H NMR (300 MHz, $CDCl_3$) δ (ppm) 2.41 (s, 3H), 2.89 (s, 4H), 2.97 (s, 4H), 6.97 (d, J=8.3 Hz, 1H), 7.22 (m, 1H), 7.26 (d, J=7.9 Hz, 2H), 7.41 (d, J=8.1 Hz, 2H), 7.89 (d, J=1.8 Hz, 1H), 10.34 (s, 1H)

FABMS m/z 342 $(M+H)^+$ $C_{19}H_{19}NO_3S$=341

Compound 151:

$^1$H NMR (300 MHz, DMSO-$d_6$) δ (ppm) 2.30 (s, 3H), 3.40 (s, 4H), 3.60 (s, 4H), 7.13 (d, J=8.3 Hz, 1H), 7.27 (d, J=8.4 Hz, 2H), 7.35 (d, J=7.7 Hz, 2H), 7.39 (d, J=8.3 Hz, 1H), 7.92 (s, 1H), 8.29 (d, J=3.9 Hz, 1H), 12.02 (br s, 1H)

FABMS m/z 441 $(M)^+$ $C_{22}H_{20}N_2O_4S_2$=441

Example 172

Preparation of Compound 152

3-Acetyl-4-fluorobenzaldehyde (0.38 g, 47.0%) was obtained by using 5-bromo-4-fluorobenzaldehyde (1.0 g, 4.9 mmol) in a manner similar to the synthesis of 5-acetyl-2-fluorobenzaldehyde in Example 124.

3-Acetyl-4-[(3,4-dichlorophenyl)thio]benzaldehyde (0.10 g, 13.7%) was obtained by using 3-acetyl-4-fluorobenzaldehyde (0.38 g, 2.3 mmol) and using 3,4-dichlorothiophenol instead of 4-methylthiophenol in a manner similar to the synthesis of 5-bromo-2-[(4-methylphenyl) thio]benzaldehyde in Example 114.

Compound 152 (0.044 g, 32.5%) was obtained by using 3-acetyl-4-[(3,4-dichlorophenyl)thio]benzaldehyde (0.1 g, 0.32 mmol) using the same method as Example 94 (synthesis of Compound 67).

3-acetyl-4-fluorobenzaldehyde:

$^1$H NMR (300 MHz, $CDCl_3$) δ (ppm) 2.64 (s, 3H), 7.25 (dd, J=8.4, 10.4 Hz, 1H), 8.01 (m, 1H), 8.35 (dd, J=2.4, 7.1 Hz, 1H), 9.95 (s, 1H)

CIMS m/z 167 $(M+H)^+$ $C_9H_7FO_2$=166

3-Acetyl-4-[(3,4-dichlorophenyl)thio]benzaldehyde:

$^1$H NMR (300 MHz, $CDCl_3$) δ (ppm) 2.72 (s, 3H), 6.95 (d, J=2.0 Hz, 1H), 7.37 (dd, J=2.0, 8.1 Hz, 1H), 7.53 (d, J=2.0 Hz, 1H), 7.62 (d, J=2.0 Hz, 1H), 7.72 (dd, J=1.8, 8.3 Hz, 1H) 8.35 (d, J=1.8 Hz, 1H), 9.95 (s, 1H)

FABMS m/z 325 $(M^+)$ $C_{15}H_{10}Cl_2O_2S$=325

Compound 152:

$^1$H NMR (300 MHz, DMSO-$d_6$) δ (ppm) 2.69 (s, 3H), 6.96 (d, J=8.4 Hz, 1H), 7.53 (dd, J=2.0, 8.3 Hz, 1H) 7.66 (dd, J=1.8, 8.5 Hz, 1H), 7.74 (s, 1H), 7.78 (d, J=8.3 Hz, 1H), 7.86 (d, J=2.0 Hz, 1H), 8.32 (d, J=1.8 Hz, 1H), NH not found FABMS m/z 424 $(M^+)$ $C_{18}H_{11}Cl_2NO_3S_2$=424

Example 173

Preparation of Compound 153

Compound 153 (0.094 g, 89.9%) was obtained by using Compound 152 (0.03 g, 0.071 mmol) using the same method as Example 96 (synthesis of Compound 69).

Compound 153:

$^1$H NMR (300 MHz, DMSO-$d_6$) δ (ppm) 2.50 (s, 3H), 7.65 (dd, J=2.0, 8.3 Hz, 1H), 7.74 (d, J=8.6 Hz, 1H), 7.93 (d, J=1.7 Hz, 1H), 7.96 (s, 1H), 8.11 (dd, J=1.8, 8.3 Hz, 1H), 8.43 (s, 1H), 8.46 (d, J=8.8 Hz, 1H), 12.77 (br s, 1H)

FABMS m/z 440 $(M^+)$ $C_{18}H_{11}Cl_2NO_4S_2$=440

Example 174

Preparation of Compound 154

2-[(2,3-Dichlorophenyl)thio]-5-nitrobenzaldehyde (0.57 g, 97.9%) was obtained by using 5-nitro-2-fluorobenzaldehyde (0.30g, 1.77 mmol) and using 2,3-dichlorothiophenol instead of p-toluenethiol in a manner similar to the synthesis of 5-bromo-2-[(4-methylphenyl) thio]benzaldehyde in Example 114.

Compound 154 (0.088 g, 22.5%) was obtained by using 2-[(2,3-dichlorophenyl)thio]-5-nitrobenzaldehyde (0.3 g, 0.91 mmol) using the same method as Example 96 (synthesis of Compound 69).

2-[(2,3-Dichlorophenyl)thio]-5-nitrobenzaldehyde:

$^1$H NMR (300 MHz, $CDCl_3$) δ (ppm) 6.91 (d, J=8.8 Hz, 1H), 7.34 (d, J=8.1 Hz, 1H), 7.58 (dd, J=1.5, 7.7 Hz, 1H), 7.66 (dd, J=1.7, 8.1 Hz, 1H), 8.19 (dd, J=2.6, 8.9 Hz, 1H), 8.72 (d, J=2.6 Hz, 1H), 10.31 (s, 1H)

FABMS m/z 328 $(M^+)$ $C_{13}H_7Cl_2NO_3S$=328

Compound 153:

$^1$H NMR (300 MHz, DMSO-$d_6$) δ (ppm) 7.25 (d, J=8.6 Hz, 1H), 7.55 (d, J=2.0 Hz, 1H), 7.57 (s, 1H), 7.81 (s, 1H), 7.92 (d, J=2.0 Hz, 1H), 8.16 (dd, J=2.4, 8.7 Hz, 1H), 8.30 (d, J=2.4 Hz, 1H), NH not found FABMS m/z 425 $(M-H)^-$ $C_{16}H_8{}^{35}Cl_2N_2O_4S_2$=426

Example 175

Preparation of Compound 155

2-[(2,4-Dichlorophenyl)thio]-5-nitrobenzaldehyde (0.53 g, 91.7%) was obtained by using 5-nitro-2-fluorobenzaldehyde (0.30 g, 1.77 mmol) and using 2,4-dichlorothiophenol instead of p-toluenethiol in a manner similar to the synthesis of 5-bromo-2-[(4-methylphenyl) thio]benzaldehyde in Example 114.

Compound 155 (0.13 g, 32.4%) was obtained by using 2-[(2,4-dichlorophenyl)thio]-5-nitrobenzaldehyde (0.3 g, 0.91 mmol) using the same method as Example 96 (synthesis of Compound 69).

2-[(2,4-Dichlorophenyl)thio]-5-nitrobenzaldehyde:

$^1$H NMR (300 MHz, $CDCl_3$) δ (ppm) 6.86 (d, J=8.8 Hz, 1H), 7.40 (dd, J=2.2, 8.3 Hz, 1H), 7.61 (s, 1H), 7.64 (t, J=2.6 Hz, 1H), 8.17 (dd, J=2.6, 8.8 Hz, 1H), 8.71 (d, J=2.6 Hz, 1H), 10.30 (s, 1H)

FABMS m/z 328 $(M+H)^+$ $C_{13}R_7{}^{35}Cl_2NO_3S$=327

Compound 155:

$^1$H NMR (300 MHz, DMSO-$d_6$)_ppm) 7.38 (d, J=8.8 Hz, 1H), 7.41 (s, 1H), 7.43 (d, J=1.3 Hz, 1H), 7.75 (dd, J=3.9, 5.7 Hz, 1H), 7.80 (s, 1H), 8.20 (dd, J=2.4, 8.8 Hz, 1H), 8.32 (d, J=2.4 Hz, 1H), NH not found FABMS m/z 425 $(M-H)^-$ $C_{16}H^{35}Cl_2N_2O_4S_2$=426

Example 176

Preparation of Compound 156

Compound 156 (0.016 g, 43.1%) was obtained by using Compound 154 (0.037 g, 0.085 mmol) using the same method as Example 96 (synthesis of Compound 69).

Compound 156:

$^1$H NMR (300 MHz, DMSO-$d_6$) δ (ppm) 7.74 (dd, J=2.0, 8.4 Hz, 1H), 7.77 (s, 1H), 7.79 (s, 1H), 7.82 (t, J=2.2 Hz, 1H), 8.00 (d, J=8.6 Hz, 1H), 8.30 (dd, J=2.2, 8.7 Hz, 1H), 8.42 (d, J=2.2 Hz, 1H), NH not found FABMS m/z 441 $(M-H)^-$ $C_{16}H_8{}^{35}Cl_2N_2O_5S_2$=442

Example 177

Preparation of Compound 157

Compound 157 (0.030g, 44.1%) was obtained by using Compound 155 (0.066 g, 0.15 mmol) using the same method as Example 96 (synthesis of Compound 69).

Compound 157:

$^1$H NMR (300 MHz, DMSO-$d_6$) δ (ppm) 7.67 (t, J=7.7 Hz, 1H), 7.85 (d, J=0.9 Hz, 1H), 7.88 (s, 1H), 8.10 (d, J=8.8 Hz, 1H), 8.14 (s, 1H), 8.28 (d, J=2.2 Hz, 1H), 8.42 (d, J=2.4 Hz, 1H), NH not found FABMS m/z 441 $(M-H)^-$ $C_{16}H_8{}^{35}Cl_2N_2O_5S_2$=442

Example 178

Preparation of Compound 158

Compound 158 (0.0085 g, 26.4%) was obtained by using Compound 154 (0.03 g, 0.070 mmol) using the same method as Example 96 (synthesis of Compound 69).

Compound 158:

$^1$H NMR (300 MHz, DMSO-$d_6$) δ (ppm) 7.19 (d, J=8.8 Hz, 1H), 7.55 (d, J=1.7 Hz, 1H), 7.55 (s, 1H), 7.70 (s, 1H), 7.92 (s, 1H), 8.11 (dd, J=2.6, 8.8 Hz, 1H), 8.36 (d, J=2.4 Hz, 1H), NH not found Example 179

Preparation of Compound 159

Compound 159 (0.013 g, 38.9%) was obtained by using Compound 155 (0.03 g, 0.070 mmol) using the same method as Example 96 (synthesis of Compound 69).

Compound 159:

$^1$H NMR (300 MHz, DMSO-$d_6$) δ (ppm) 7.35 (d, J=8.8 Hz, 1H), 7.40 (s, 1H), 7.42 (d, J=4.4 Hz, 1H), 7.75 (dd, J=2.4,6.7 Hz, 1H), 7.76 (s, 1H), 8.18 (dd, J=2.6, 8.8 Hz, 1H), 8.35 (d, J=2.6 Hz, 1H), NH not found Example 180

Preparation of Compound 160

2-Fluoro-5-nitrobenzaldehyde (0.16 g, 0.95 mmol) was dissolved in N,N-dimethylformamide (8.1 mL), and 4-mercaptophenol (0.11 g, 0.86 mmol) and triethylamine (0.27 mL, 1.9 mmol) were added thereto, followed by stirring at 25° C. for 1 hour. After the conventional treatment, the product was purified by silica gel column chromatography (eluted by n-hexane/acetone=4/1–1/1) to give 5-nitro-2-[(4-hydroxyphenyl)thio]benzaldehyde (0.18 g, 70%).

5-Nitro-2-[(4-hydroxyphenyl)thio]benzaldehyde (0.17 g, 0.61 mmol) was dissolved in toluene (8.4 mL), and 2,4-thiazolidinedione (0.29 mg, 2.4 mmol), piperidine (0.024 mL, 0.24 mmol), acetic acid (0.014 mL, 0.24 mmol) and molecular sieves 4A (0.84 g) were added thereto, followed by stirring at 110° C. for 2 hours. After the conventional post-reaction treatment, thin layer chromatography (developed with chloroform/methanol=10/1) to give Compound 160 (34 mg, 15%).

5-Nitro-2-[(4-hydroxyphenyl)thio]benzaldehyde:

$^1$H NMR (300 MHz, $CDCl_3$) δ (ppm) 6.97 (d, J=9.0 Hz, 1H), 7.03 (d, J=8.6 Hz, 2H), 7.40 (d, J=8.8 Hz, 2H), 8.06 (m, 1H), 8.61 (br s, 1H), 8.63 (d, J=2.3 Hz, 1H), 10.29 (s, 1H)

Compound 160:

$^1$H NMR (300 MHz, DMSO-$d_6$) δ (ppm) 6.94 (d, J=8.8 Hz, 3H), 7.45 (d, J=8.6 Hz, 2H), 7.87 (s, 1H), 8.13 (dd, J=2.4, 8.8 Hz, 1H), 8.20 (d, J=2.2 Hz, 1H), 10.20 (s, 1H), 12.86 (br s, 1H)

FABMS m/z 373 $(M-H)^-$ $C_{16}H_{10}N_2O_5S_2$=374

Example 181

Preparation of Compound 161

2-[(3,4-Dimethylphenyl)thio]-5-nitrobenzaldehyde (0.16 g, 45%) was obtained from 3,4-dimethylbenzenethiol (0.16 mL, 1.2 mmol), a 2.5 mol/L sodium hydroxide aqueous solution (2.1 mL, 5.2 mmol), tetrabutylammonium bromide (0.020 mg, 0.61 mmol) and a toluene solution (2.1 mL) of 2-fluoro-5-nitrobenzaldehyde (0.21 g, 1.2 mmol) using the same method as Example 97.

Compound 161 (0.13 g, 64%) was obtained from 2-[(3,4-dimethylphenyl)thio]-5-nitrobenzaldehyde (0.16 g, 0.54 mmol), toluene (7.8 mL), 2,4-thiazolidinedione (0.26 mg, 2.2 mmol), piperidine (0.022 mL, 0.22 mmol), acetic acid (0.012 mL, 0.22 mmol) and molecular sieves 4A (0.78 g).

2-[(3,4-Dimethylphenyl)thio]-5-nitrobenzaldehyde:

$^1$H NMR (300 MHz, $CDCl_3$) δ (ppm) 2.31 (s, 3H), 2.36 (s, 3H), 6.97 (d, J=9.0 Hz, 1H), 7.24–7.36 (m, 3H), 8.09 (dd, J=9.0, 2.5 Hz, 1H), 8.67 (d, J=2.6 Hz, 1H), 10.31 (s, 1H)

FABMS m/z 287 $(M)^+$$C_{15}H_{13}NO_3S$=287

Compound 169:

$^1$H NMR (300 MHz, DMSO-$d_6$) δ (ppm) 2.25 (s, 3H), 2.28 (s, 3H), 7.06 (d, J=9.0 Hz, 1H), 7.33 (s, 2H), 7.40 (s, 1H), 7.88 (s, 1H), 8.15 (m, 1H), 8.21 (m, 1H), 12.86 (br s, 1H)

FABMS m/z 385 $(M-H)^-$ $C_{18}H_{14}N_2O_4S_2$=386

Example 182

Preparation of Compound 162

Compound 162 (0.60 mg, 0.9%) was obtained from Compound 72 (0.061 g, 0.14 mmol) obtained in Example 56, dichloromethane (6.1 mL), methanol (1.2 mL) and m-chloroperbenzoic acid (0.75 g, 2.1 mmol) using the same method as Example 134.

Compound 162:

$^1$H NMR (300 MHz, DMSO-$d_6$) δ (ppm) 7.96 (d, J=8.4 Hz, 1H), 8.02 (dd, J=8.7, 2.2 Hz, 1H), 8.17 (s, 1H), 8.28 (s, 1H), 8.32 (d, J=2.2 Hz, 1H), 8.44 (d, J=1.3 Hz, 2H)

Example 183

Preparation of Compound 163

Compound 163 (0.034 g, 32%) was obtained from Compound 81 (0.10 g, 0.26 mmol) obtained in Example 108, N,N-dimethylformamide (5.1 mL) and m-chloroperbenzoic acid (0.14 g, 0.82 mmol) using the same method as Example 156.

Compound 163:

$^1$H NMR (300 MHz, DMSO-$d_6$) δ (ppm) 7.58 (d, J=8.4 Hz, 2H), 7.74 (d, J=8.4 Hz, 2H), 8.00 (s, 1H), 8.30 (dd, J=8.2, 1.4 Hz, 1H), 8.48 (d, J=8.2 Hz, 1H), 8.53 (d, J=1.4 Hz, 1H), 12.83 (br s, 1H)

FABMS m/z 407 $(M-H)^-$ $C_{16}H_9{}^{35}ClN_2O_5S_2$=408

Example 184

Preparation of Compound 164

A 2.5 mol/L sodium hydroxide aqueous solution (2.0 mL, 4.9 mmol), and tetrabutylammonium bromide (0.019 g, 0.58 mmol) were added to 4-ethylbenzenethiol (0.20 g, 1.2 mmol), followed by stirring at 25° C. for 5 minutes. A toluene solution (2.0 mL) of 4-fluoro-3-nitrobenzaldehyde (0.20 g, 1.2 mmol) was added to the reaction liquid, followed by stirring at 25° C. for 12 hours. After the conventional post-reaction treatment, the product was purified by silica gel column chromatography (eluted by chloroform) to give 4-[(4-ethylphenyl)thio]-3-nitrobenzaldehyde (0.25 g, 75%).

4-[(4-Ethylphenyl)thio]-3-nitrobenzaldehyde (0.25 g, 0.86 mmol) was dissolved in ethanol (9.9 mL), and 2,4-thiazolidinedione (0.40 g, 3.4 mmol) and piperidine (0.034 mL, 0.34 mmol) were added thereto, followed by stirring at 80° C. for 7 hours. The precipitated crystals were collected by filtration to give Compound 164 (0.061 g, 19%).

4- [(4-ethylphenyl)thio]-3-nitrobenzaldehyde:

$^1$H NMR (300 MHz, $CDCl_3$) δ (ppm) 1.31 (t, J=7.7 Hz, 3H), 2.76 (q, J=7.5 Hz, 2H), 7.01 (d, J=8.4 Hz, 1H), 7.37 (d, J=8.2 Hz, 2H), 7.50 (d, J=8.2 Hz, 2H), 7.81 (dd, J=8.4, 1.8 Hz, 1H), 8.69 (d, J=1.6 Hz, 1H), 9.97 (s, 1H)

FABMS m/z 287 $(M)^+C_{15}H_{13}NO_3S$=287

Compound 164:

$^1$H NMR (300 MHz, DMSO-$d_6$) δ (ppm) 1.24(t, J=7.5 Hz, 3H), 2.70 (q, J=7.3 Hz, 2H), 6.92 (d, J=8.6 Hz, 1H), 7.08 (br s, 1H), 7.43 (d, J=8.1 Hz, 2H), 7.56 (d, J=8.0 Hz, 2H), 7.58 (s, 1H), 7.72 (dd, J=8.6, 2.0 Hz, 1H), 8.44 (d, J=1.8 Hz, 1H)

FABMS m/z 385 $(M-H)^-$ $C_{18}H_{14}N_2O_4S_2$=386

Example 185

Preparation of Compound 165 and Compound 166

Compound 165 (0.014 g, 26%) and Compound 166 (0.016 g, 26%) were obtained from Compound 164 (0.052 g, 0.14 mmol) obtained in Example 184, N,N-dimethylformamide (2.6 mL) and m-chloroperbenzoic acid (0.44 g, 1.3 mmol) using the same method as Example 156.

Compound 165:

$^1$H NMR (300 MHz, DMSO-$d_6$) δ (ppm) 1.13 (t, J=7.5 Hz, 3H), 2.61 (q, J=7.5 Hz, 2H), 7.34 (d, J=8.3 Hz, 2H), 7.51–7.56 (m, 2H), 7.95 (s, 1H), 8.30 (dd, J=8.4, 1.6 Hz, 1H), 8.48–8.52 (m, 2H), 12.87 (m, 1H)

FABMS m/z 401 $(M-H)^-$ $C_{18}H_{14}N_2O_5S_2$=402

Compound 166:

$^1$H NMR (300 MHz, DMSO-$d_6$) δ (ppm) 1.19 (t, J=7.7 Hz, 3H), 2.71 (q, J=8.4 Hz, 2H), 7.51–7.60 (m, 2H), 7.80 (s, 1H), 7.86–7.95 (m, 2H), 8.03 (dd, J=8.8, 1.5 Hz, 1H), 8.21 (d, J=1.1 Hz, 1H), 8.45 (d, J=8.2 Hz, 1H), 12.90 (m, 1H)

FABMS m/z 417 $(M-H)^-$ $C_{18}H_{14}N_2O_6S_2$=418

Example 186

Preparation of Compound 167

4-[(3,4-Dichlorophenyl)thio]-3-nitrobenzaldehyde (0.29 g, 84%) was obtained from 3,4-dichlorobenzenethiol (0.13 mL, 1.0 mmol), a 2.5 mol/L sodium hydroxide aqueous solution (1.8 mL, 4.4 mmol), tetrabutylammonium bromide (0.017 g, 0.52 mmol) and a toluene solution (1.8 mL) of 4-fluoro-3-nitrobenzaldehyde (0.18 g, 1.0 mmol) using the same method as Example 184.

Compound 167 (0.077 g, 15%) was obtained from 4-[(3, 4-dichlorophenyl)thio]-3-nitrobenzaldehyde (0.40 g, 1.2 mmol), ethanol (16 mL), 2,4-thiazolidinedione (0.57 g, 4.9 mmol) and piperidine (0.048 mL, 0.49 mmol).

4-[(3,4-dichlorophenyl)thio]-3-nitrobenzaldehyde:

$^1$H NMR (300 MHz, $CDCl_3$) δ (ppm) 7.03 (d, J=8.4 Hz, 1H), 7.44 (dd, J=8.3, 2.0 Hz, 1H), 7.63 (d, J=8.3 Hz, 1H), 7.72 (d, J=2.0 Hz, 1H), 7.88 (dd, J=8.4, 1.8 Hz, 1H), 8.73 (d, J=1.8 Hz, 1H), 10.00 (s, 1H)

FABMS m/z 328 $(M+H)^+C_{13}H_7{}^{35}Cl_2NO_3S$=327

Compound 167:

$^1$H NMR (300 MHz, DMSO-$d_6$) δ (ppm) 7.11 (d, J=8.6 Hz, 1H), 7.65 (dd, J=8.3, 2.2 Hz, 1H), 7.77 (dd, J=2.0, 8.6 Hz, 1H), 7.85 (d, J=8.2 Hz, 1H), 7.87 (s, 1H), 8.02 (d, J=2.0 Hz, 1H), 8.52 (d, J=2.0 Hz, 1H), 12.74 (br s, 1H)

FABMS m/z 425 $(M-H)^-$ $C_{16}H_8{}^{35}Cl_2N_2O_4S_2$=426

Example 187

Preparation of Compound 168

Compound 168 (0.017 g, 54%) was obtained from Compound 167 (0.031 g, 0.073 mmol) obtained in Example 186, N,N-dimethylformamide (1.6 mL) and m-chloroperbenzoic acid (0.035 g, 0.10 mmol) using the same method as Example 156.

$^1$H NMR (300 MHz, DMSO-$d_6$) δ (ppm) 7.69 (m, 1H), 7.78 (d, J=8.5 Hz, 1H), 8.00 (s, 2H), 8.28 (d, J=8.1 Hz, 1H), 8.48 (d, J=8.9 Hz, 1H), 8.53 (s, 1H), 12.84 (br s, 1H)

FABMS m/z 441 $(M-H)^-$ $C_{16}H_8{}^{35}Cl_2N_2O_5S_2$=44

Example 188

Preparation of Compound 169 and Compound 170

Compound 169 (0.080 g, 75%) and Compound 170 (2.5 mg, 2.3%) were obtained from Compound 161 (0.10 g, 0.27 mmol) obtained in Example 181, N,N-dimethylformamide (5.2 mL) and m-chloroperbenzoic acid (0.46 g, 4.0 mmol) using the same method as Example 156.

Compound 169: FABMS m/z 401 $(M-H)^-$ $C_{18}H_{14}N_2O_5S_2$=402

Compound 170: FABMS m/z 417 $(M-H)^-$ $C_{18}H_{14}N_2O_6S_2$=418

Example 189

Preparation of N-(4-Chlorophenyl)-4-(2,4-dioxo-thiazolidin-5-ylidenemethyl)-benzenesulfonamide

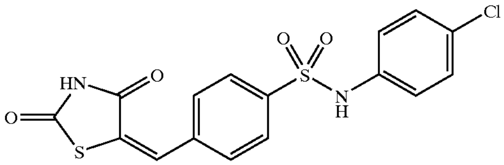

Step A: General Procedure 1.

General Procedure 1 with benzaldehyde was followed to obtain 5-benzylidene-thiazolidine-2,4-dione.

NMR (DMSO-$d_6$): 7.75 (s, 1H), 7.6–7.4 (m, 5H)

MS (ESI) 205. Found 204 (M–H).

Step B. Preparation of 4-(2,4-Dioxo-thiazolidin-5-ylidenemethyl)-benzenesulfonyl chloride.

To a flask charged with chlorosulfonic acid (10 eq.) cooled in an ice bath was added 5-benzylidene-thiazolidine-2,4-dione. The solution was stirred at 0° C. for one hour, warmed to room temperature and stirred overnight. The reaction was then poured carefully onto ice and the resulting precipitate was filtered and air dried to give pure product.

NMR (DMSO-$d_6$): 7.72 (s, 1H), 7.66 (d, 2H), 7.51 (d, 2H)

MS (ESI) 303. Found 302 (M–H).

Step C. Sulfonylation Reaction

The sulfonyl chloride and 4-chloro-phenylamine were stirred together in pyridine heated at 60° C. for 12 h. The solution was diluted with EtOAc and washed with 10% aq. NaHSO4 followed by sat aq. NaCl. The organic phase was separated, dried over $Na_2SO_4$ and concentrated under reduced pressure to give pure compound.

MS (ESI) 394. Found 393 (M–H).

Example 190

Preparation of 4-(2,4-Dioxo-thiazolidin-5-ylidenemethyl)-N-p-tolyl-benzenesulfonamide

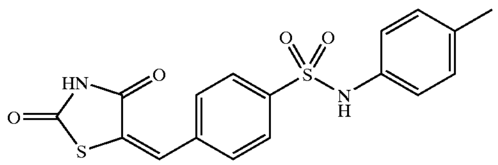

4-(2,4-Dioxo-thiazolidin-5-ylidenemethyl)-N-p-tolyl-benzenesulfonamide was prepared by the method of Example 189 from p-toluidine.

MS (ESI) 374. Found 373 (M−H).

Example 191

Preparation of 4-(2,4-Dioxo-thiazolidin-5-ylidenemethyl)-N-(4-methoxy-phenyl) benzenesulfonamide

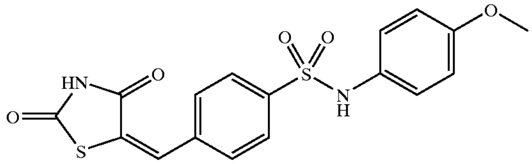

4-(2,4-Dioxo-thiazolidin-5-ylidenemethyl)-N-(4-methoxy-phenyl)-benzenesulfonamide was prepared by the method of Example 189 from p-anisidine.

MS (ESI) 390. Found 389 (M−H).

Example 192

Preparation of 4-(2,4-Dioxo-thiazolidin-5-ylidenemethyl)-N-(4-trifluoromethyl-phenyl)-benzenesulfonamide

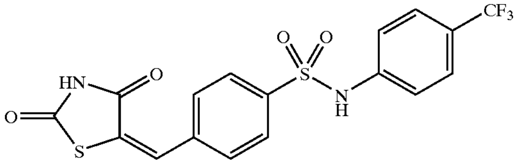

4-(2,4-Dioxo-thiazolidin-5-ylidenemethyl)-N-(4-trifluoromethyl-phenyl)-benzenesulfonamide was prepared by the method of Example 189 from 4-(trifluoromethyl) aniline.

MS (ESI) 428. Found 427 (M−H).

Example 193

Preparation of 4,5-Dichloro-N-[3-(2,4-dioxo-thiazolidin-5-ylidenemethyl)-phenyl]-phthalamic acid

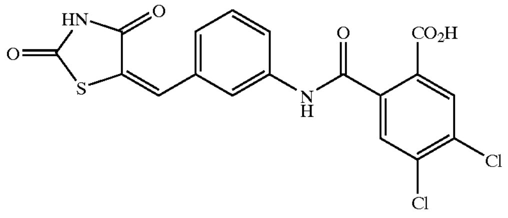

Step A: Coupling 2,4-thiazolidinedione (TZD) to Aldehyde Under Acidic Conditions 3-Nitro benzaldehyde, TZD (1.25 eq.), NaOAc (2 eq.), and acetic anhydride (1 eq.) were dissolved in acetic acid and heated to reflux for 12 hours. The reaction was allowed to cool and a precipitate was collected, washed and air dried to give pure product. The filtrate was poured into water and the resulting precipitate was filtered to afford an additional yield of product.

MS (ESI) 250. Found 249 (M−H).

Step B: Reduction of the Nitro Group 5-(3-Nitro-benzylidene)-thiazolidine-2,4-dione was dissolved in a large volume of acetic acid. A small amount of methanol was added as needed to completely dissolve the starting material. The solution was warmed gently and iron powder (5 eq.) was added. After 4 hours the mixture was filtered to remove iron then diluted with an equal volume of water and extracted with EtOAc. The organic phase was concentrated under vacuum to give a brown solid. The residue was dissolved in methanol and impurities were remove by filtration. The filtrate was concentrated and the resulting residue was triturated with hexane and collected by filtration to give product.

MS (ESI) 220. Found 219 (M−H).

Step C: Condensation with Anhydride 5-(3-Amino-benzylidene)-thiazolidine-2,4-dione was dissolved in THF and treated with a solution of 4,5-dichlorophthalic anhydride and a catalytic amount of DMAP. The solution was stirred for 8 hours, then filtered and concentrated under vacuum. The residue was dissolved in EtOAc and washed with water. The organic layer was concentrated to an oil and triturated with hexane to give the product as a solid which was collected by filtration.

MS (ESI) 436. Found 435 (M−H).

Example 194

Preparation of 3,6-Dichloro-N-[3-(2,4-dioxo-thiazolidin-5-ylidenemethyl)-phenyl]-phthalamic acid

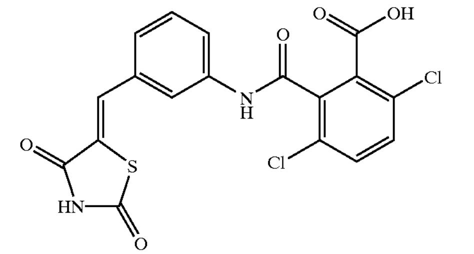

3,6-Dichloro-N-[3-(2,4-dioxo-thiazolidin-5-ylidenemethyl)-phenyl]-phthalamic acid was prepared by the method of Example 193 from 3,6-dichlorophthalic anhydride.

MS (ESI) 436. Found 435 (M–H).

Example 195

Preparation of 4-tert-Butyl-N-[3-(2,4-dioxo-thiazolidin-5-ylidenemethyl)-phenyl]-phthalamic acid

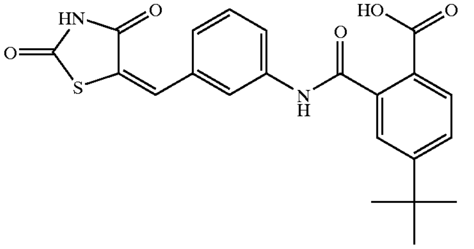

4-tert-Butyl-N-[3-(2,4-dioxo-thiazolidin-5-ylidenemethyl)-phenyl]-phthalamic acid was prepared by the method of Example 193 from 4-tert-butylphthalic anhydride and isolated as a 64:36 mixture of regioisomers.

MS (ESI) 425. Found 423 (M–2H).

Example 196

Preparation of N-[3-(2,4-Dioxo-thiazolidin-5-ylidenemethyl)-phenyl]-3-hydroxy-phthalamic acid

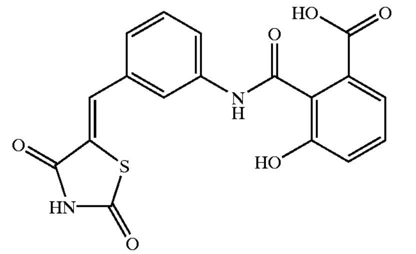

N-[3-(2,4-Dioxo-thiazolidin-5-ylidenemethyl)-phenyl]-3-hydroxy-phthalamic acid was prepared by the method of Example 193 from 3-hydroxyphthalic anhydride to give a 80:20 mixture of regioisomers.

MS (ESI) 384. Found 383 (M–H).

Example 197

Preparation of 3-[3-(2,4-Dioxo-thiazolidin-5-ylidenemethyl)-phenylcarbamoyl]-pyrazine-2-carboxylic acid

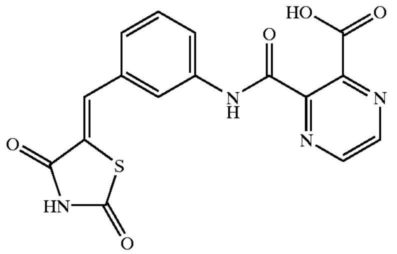

3-[3-(2,4-Dioxo-thiazolidin-5-ylidenemethyl)-phenylcarbamoyl]-pyrazine-2-carboxylic acid was prepared by the method of Example 193 from 2,3-pyrazinedicarboxylic anhydride MS (ESI) 370. Found 369 (M–H).

Example 198

Preparation of 3-[3-(2,4-Dioxo-thiazolidin-5-ylidenemethyl)-phenylcarbamoyl]-isonicotinic acid

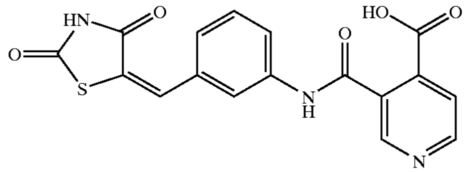

3-[3-(2,4-Dioxo-thiazolidin-5-ylidenemethyl)-phenylcarbamoyl]-isonicotinic acid was prepared by the method of Example 193 from pyridine-3,4-dicarboxylic anhydride as a 70:30 mixture of isomers.

MS (ESI) 369. Found 368 (M–H).

Example 199

Preparation of 3-[3-(2,4-Dioxo-thiazolidin-5-ylidenemethyl)-phenylcarbamoyl]-pyridine-2-carboxylic acid

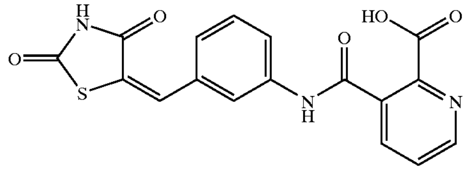

3-[3-(2,4-Dioxo-thiazolidin-5-ylidenemethyl)-phenylcarbamoyl]-pyridine-2-carboxylic acid was prepared by the method of Example 193 from 2,3-pyridinedicarboxylic anhydride and isolated as a mixture of isomers.

MS (ESI) 369. Found 368 (M–H).

Example 200

Preparation of 4-(4-Chloro-benzenesulfonylamino)-N-[3-(2,4-dioxo-thiazolidin-5-ylidenemethyl)-phenyl]-benzamide

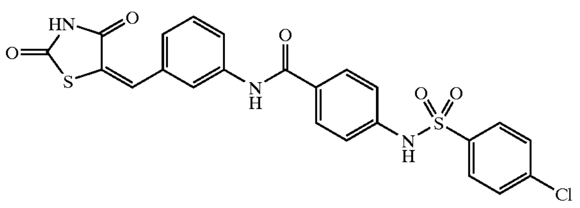

Step A: Condensation with Acid Chloride 5-(3-Amino-benzylidene)-thiazolidine-2,4-dione prepared in was dissolved in pyridine and treated with 4-nitrobenzoyl chloride and a catalytic amount of DMAP. The reaction was stirred for 20 minutes then a precipitate was collected by filtration. The solid was washed repeatedly with water, saturated aq. $NaHCO_3$, and 10% aq HCl solution. The resulting solid was air dried.

MS (ESI) 369. Found 368 (M−H).

Step B: Reduction of the Nitro Group

4-Nitro-N-[3-(2,4-dioxo-thiazolidin-5-ylidenemethyl)-phenyl]-benzamide was suspended in isopropanol. A small amount of ammonium chloride dissolved in water was added and the mixture was heated to 70° C. for several hours. Iron powder was added and stirring continued for four hours. The solids were removed by filtration and the filtrate concentrated under vacuum. The residue was dissolved in EtOAc and washed with water. The organic layer was concentrated to an oil and the product precipitated with the addition of hexanes.

MS (ESI) 339. Found 338 (M−H).

Step C: Condensation with Sulfonyl Chlorides

4-Amino-N-[3-(2,4-dioxo-thiazolidin-5-ylidenemethyl)-phenyl]-benzamide was dissolved in pyridine and treated with 4-chloro-benzenesulfonyl chloride in pyridine at 60° C. for 12 h. The solution-was cooled and diluted with EtOAc then washed with 10% aq. NaHSO4 followed by saturated aq. NaCl. The organic phase was separated, dried over $Na_2SO_4$ and concentrated under reduced pressure to give an oil. Trituration with hexane gave pure product.

MS (ESI) 513. Found 512 (M−H).

Example 201

Preparation of N-[3-(2,4-dioxo-thiazolidin-5-ylidenemethyl)-phenyl]-4-(toluene-4-sulfonylamino)-benzamide

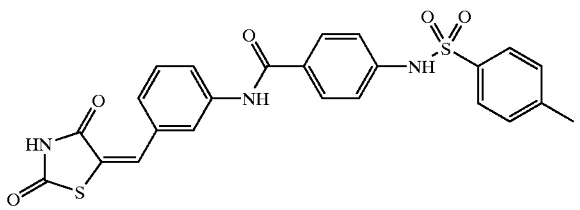

N-[3-(2,4-Dioxo-thiazolidin-5-ylidenemethyl)-phenyl]-4-(toluene-4-sulfonylamino)-benzamide was prepared by the method of Example 200 from p-toluenesulfonyl chloride.

MS (ESI) 493. Found 492 (M−H).

Example 202

Preparation of N-[3-(2,4-Dioxo-thiazolidin-5-ylidenemethyl)-phenyl]-4-(4-methoxy-benzenesulfonylamino)-benzamide

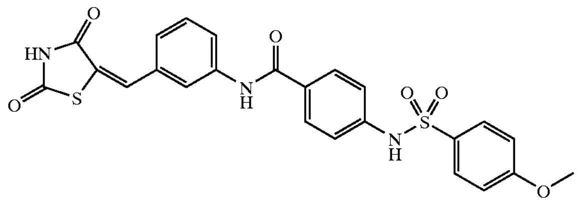

N-[3-(2,4-Dioxo-thiazolidin-5-ylidenemethyl)-phenyl]-4-(4-methoxy-benzenesulfonylamino)-benzamide was prepared by the method of Example 200 from 4-methoxybenzenesulfonyl chloride.

MS (ESI) 509. Found 508 (M−H).

Example 203

Preparation of N-[3-(2,4-Dioxo-thiazolidin-5-ylidenemethyl)-phenyl]-4-(4-trifluoromethoxy-benzenesulfonylamino)-benzamide

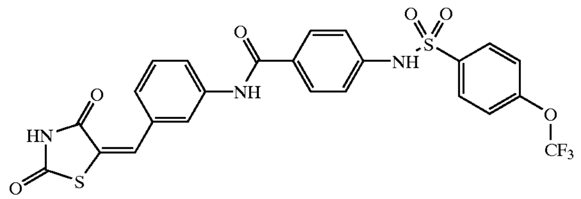

N-[3-(2,4-Dioxo-thiazolidin-5-ylidenemethyl)-phenyl]-4-(4-trifluoromethoxy-benzenesulfonylamino)-benzamide was prepared by the method of Example 200 from 4-(trifluoromethoxy)benzenesulphonyl chloride MS (ESI) 563. Found 562 (M−H).

Example 204

Preparation of 4-Benzenesulfonylamino-N-[3-(2,4-dioxo-thiazolidin-5-ylidenemethyl)-phenyl]-benzamide

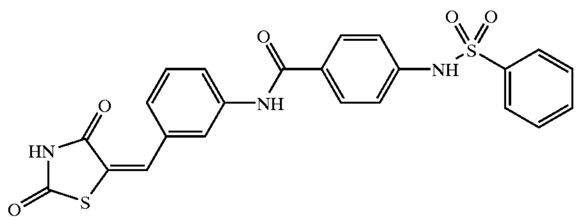

4-Benzenesulfonylamino-N-[3-(2,4-dioxo-thiazolidin-5-ylidenemethyl)-phenyl]-benzamide was prepared by the method of Example 200 from benzenesulfonyl chloride MS (ESI) 479. Found 478 (M−H).

Example 205

Preparation of N-(4-Chloro-phenyl)-4-[4-(2,4-dioxo-thiazolidin-5-ylidenemethyl)-phenoxy]-benzenesulfonamide

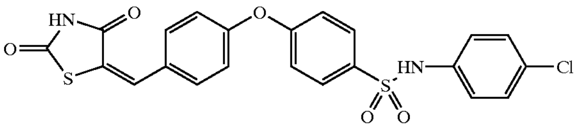

Step A: Preparation of 4-Phenoxy-benzaldehyde

A suspension of potassium carbonate (1 eq.), 4-flurobenzaldehyde, and phenol (1.2 eq.) was heated to 150° C. and stirred for two days. The reaction was allowed to cool to room temperature and poured into saturated aq. sodium bicarbonate and ice. The solution was extracted with ether. The combined organic layers were washed with water and dried with $Na_2SO_4$. Concentration under vacuum gave pure product as an orange oil.

Step B: Condensation with TZD to give 5-(4-Phenoxy-benzylidene)-thiazolidine-2,4-dione A solution of 4-Phenoxy-benzaldehyde, TZD (1.5 eq.) and piperidine (2 eq.) in EtOH was heated at 70° C. and stirred overnight. The reaction was cooled to room temperature and poured into 10% aq. HCl. The resulting precipitate was filtered, washed with water and allowed to air dry.

MS (ESI) 297. Found 296 (M−H).

Step C: Chlorosulfonylation to give 4-[4-(2,4-Dioxo-thiazolidin-5-ylidenemethyl)-phenoxy]-benzenesulfonyl chloride 5-(4-Phenoxy-benzylidene)-thiazolidine-2,4-dione was dissolved in chlorosulfonic acid and stirred at 0° C. for 30 minutes. The solution was then poured onto ice and the precipitate was collected by filtration and air dried to give crude product.

MS (ESI) 395. Found 394 (M−H).

Step D: Condensation with 4-chloroaniline to give the Sulfonamide

A solution of 4-[4-(2,4-dioxo-thiazolidin-5-ylidenemethyl)-phenoxy]-benzenesulfonyl chloride and 4-chloroaniline (1.1 eq.) was stirred in pyridine with gentle warming. Pyridine was then removed under vacuum and the residue dissolved in EtOAc. The organic phase was washed with 10% aq HCl solution, aq. sodium bicarbonate and aq. sodium chloride solution then concentrated under vacuum. The resulting residue was triturated with hexane to give pure product.

MS (ESI) 486. Found 485 (M−H).

Example 206

Preparation of 4-[4-(2,4-dioxo-thiazolidin-5-ylidenemethyl)-phenoxy]-N-p-tolyl-benzenesulfonamide

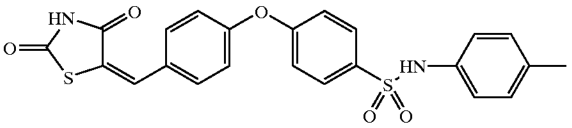

4-[4-(2,4-Dioxo-thiazolidin-5-ylidenemethyl)-phenoxy]-N-p-tolyl-benzenesulfonamide was prepared by the method of Example 205 from p-toluidine.

MS (ESI) 466. Found 465 (M−H).

Example 207

Preparation of 4-[4-(2,4-dioxo-thiazolidin-5-ylidenemethyl)-phenoxy]-N-(4-trifluoromethoxy-phenyl)-benzenesulfonamide

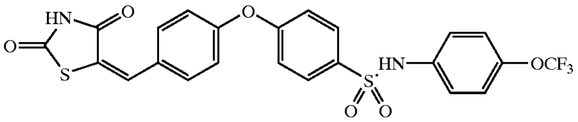

4-[4-(2,4-Dioxo-thiazolidin-5-ylidenemethyl)-phenoxy]-N-(4-trifluoromethoxy-phenyl)-benzenesulfonamide was prepared by the method of Example 205 from 4-(trifluoromethoxy)aniline.

MS (ESI) 536. Found 535 (M−H).

Example 208

Preparation of 4-[4-(2,4-dioxo-thiazolidin-5-ylidenemethyl)-phenoxy]-N-(4-methoxy-phenyl)-benzenesulfonamide

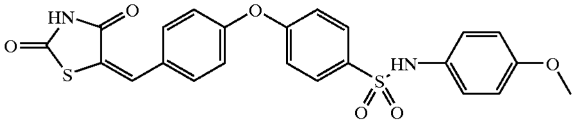

4-[4-(2,4-dioxo-thiazolidin-5-ylidenemethyl)-phenoxy]-N-(4-methoxy-phenyl)-benzenesulfonamide was prepared by the method of Example 205 from p-anisidine.

MS (ESI) 482. Found 481 (M−H).

Example 209

Preparation of 4-[4-(2,4-dioxo-thiazolidin-5-ylidenemethyl)-phenoxy]-N-phenyl-benzenesulfonamide

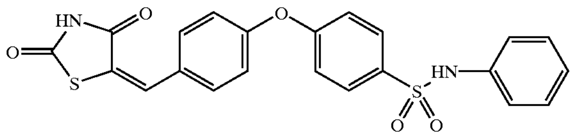

4-[4-(2,4-dioxo-thiazolidin-5-ylidenemethyl)-phenoxy]-N-phenyl-benzenesulfonamide was prepared by the method of Example 205 from aniline.

MS (ESI) 452. Found 451 (M−H).

Example 210

Preparation of 4-[4-(2,4-dioxo-thiazolidin-5-ylidenemethyl)-phenoxy]-N-(3,4,5-trimethoxy-phenyl)-benzenesulfonamide

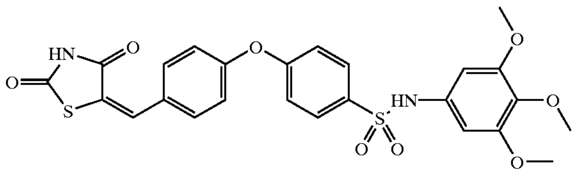

4-[4-(2,4-Dioxo-thiazolidin-5-ylidenemethyl)-phenoxy]-N-(3,4,5-trimethoxy-phenyl)-benzenesulfonamide was prepared by the method of Example 205 from 3,4,5-trimethoxyaniline.

MS (ESI) 542. Found 541 (M−H).

Example 211

Preparation of 4-[4-(2,4-Dioxo-thiazolidin-5-ylidenemethyl)-phenoxy]-N-(4-morpholin-4-yl-phenyl)-benzenesulfonamide

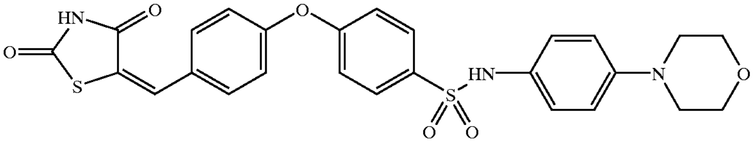

4-[4-(2,4-Dioxo-thiazolidin-5-ylidenemethyl)-phenoxy]-N-(4-morpholin-4-yl-phenyl)-benzenesulfonamide was prepared by the method of Example 205 from 4-morpholinoaniline.

MS (ESI) 537. Found 536 (M−H).

Example 212

Preparation of 4-[4-(2,4-Dioxo-thiazolidin-5-ylidenemethyl)-phenoxy]-N-(4-isopropyl-phenyl)-benzenesulfonamide

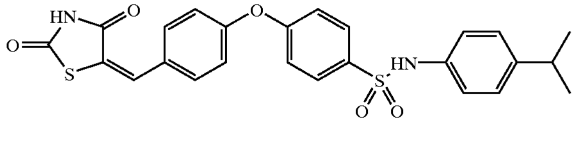

4-[4-(2,4-Dioxo-thiazolidin-5-ylidenemethyl)-phenoxy]-N-(4-isopropyl-phenyl)-benzenesulfonamide was prepared by the method of Example 205 from 4-isopropylaniline.

MS (ESI) 494. Found 493 (M−H).

Example 213

Preparation of N-(2-Chloro-phenyl)-4-[4-(2,4-dioxo-thiazolidin-5-ylidenemethyl)-phenoxy]-benzenesulfonamide

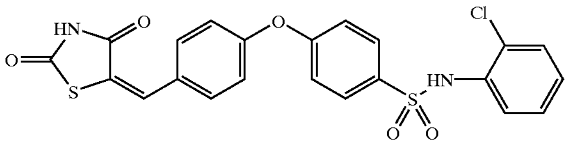

N-(2-Chloro-phenyl)-4-[4-(2,4-dioxo-thiazolidin-5-ylidenemethyl)-phenoxy]-benzenesulfonamide was prepared by the method of Example 205 from 2-chloroaniline.

MS (ESI) 486. Found 485 (M−H).

Example 214

Preparation of N-(3-Chloro-phenyl)-4-[4-(2,4-dioxo-thiazolidin-5-ylidenemethyl)-phenoxy]-benzenesulfonamide

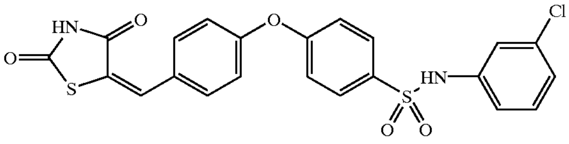

N-(3-Chloro-phenyl)-4-[4-(2,4-dioxo-thiazolidin-5-ylidenemethyl)-phenoxy]-benzenesulfonamide was prepared by the method of Example 205 from 3-chloroaniline.

MS (ESI) 486. Found 485 (M−H).

Example 215

Preparation of 4-[4-(2,4-Dioxo-thiazolidin-5-ylidenemethyl)-phenoxy]-N-(4-hydroxy-phenyl)-benzenesulfonamide

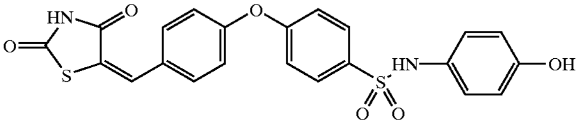

4-[4-(2,4-Dioxo-thiazolidin-5-ylidenemethyl)-phenoxy]-N-(4-hydroxy-phenyl)-benzenesulfonamide was prepared by the method of Example 205 from 4-aminophenol.

MS (ESI) 468. Found 467 (M−H).

Example 216

Preparation of 4-[4-(2,4-Dioxo-thiazolidin-5-ylidenemethyl)-phenoxy]-N-(2-hydroxy-phenyl)-benzenesulfonamide

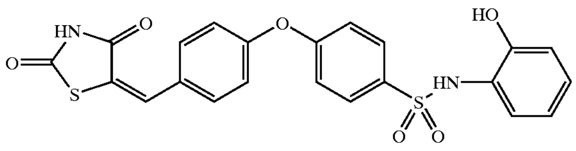

4-[4-(2,4-Dioxo-thiazolidin-5-ylidenemethyl)-phenoxy]-N-(2-hydroxy-phenyl)-benzenesulfonamide was prepared by the method of Example 205 from 2-aminophenol.

MS (ESI) 468. Found 467 (M–H).

Example 217

Preparation of N-(2-tert-Butyl-phenyl)-4-[4-(2,4-dioxo-thiazolidin-5-ylidenemethyl)-phenoxy]-benzenesulfonamide

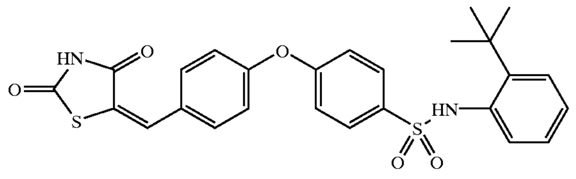

N-(2-tert-Butyl-phenyl)-4-[4-(2,4-dioxo-thiazolidin-5-ylidenemethyl)-phenoxy]-benzenesulfonamide was prepared by the method of Example 205 from 2-tert-butylaniline.

MS (ESI) 508. Found 507 (M–H).

Example 218

Preparation of 4-[4-(2,4-Dioxo-thiazolidin-5-ylidenemethyl)-phenoxy]-N-isopropyl-N-phenyl-benzenesulfonamide

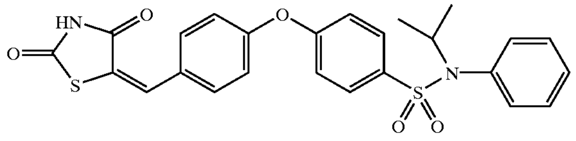

4-[4-(2,4-Dioxo-thiazolidin-5-ylidenemethyl)-phenoxy]-N-isopropyl-N-phenyl-benzenesulfonamide was prepared by the method of Example 205 from N-isopropylaniline.

MS (ESI) 494. Found 493 (M–H).

Example 219

Preparation of 4- [4-(2,4-Dioxo-thiazolidin-5-ylidenemethyl)-phenoxy]-N-(3-hydroxy-phenyl)-benzenesulfonamide

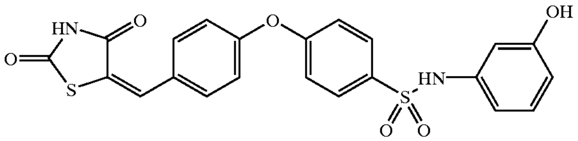

4-[4-(2,4-Dioxo-thiazolidin-5-ylidenemethyl)-phenoxy]-N-(3-hydroxy-phenyl)-benzenesulfonamide was prepared by the method of Example 205 from 3-aminophenol.

MS (ESI) 468. Found 467 (M–H).

Example 220

Preparation of 5-[2-(3,4-Dichloro-benzylsulfanyl)-pyrimidin-4-ylmethyl]-2-thioxo-thiazolidin-4-one

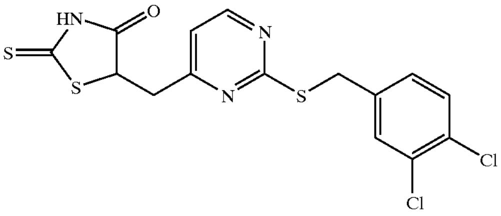

Step A: Alkylation of a Pyrimidine Thiol with a Benzyl Halide

To a suspension of the sodium salt of 4-Dimethoxymethyl-pyrimidine-2-thiol in DMF with potassium carbonate (2 eq.) was added alpha, 3,4-trichlorotoluene (1 eq.). the suspension was stirred for 2 days. The reaction mixture was diluted with water and extracted with EtOAc. The organic layer was washed with water, aq. sodium chloride, dried over $MgSO_4$ and concentrated in vacuum.

Step B: Deprotection of the Acetal

A suspension of 2-(3,4-Dichloro-benzylsulfanyl)-4-dimethoxymethyl-pyrimidine in concentrated HCl was refluxed for 5 minutes. The reaction was cooled and poured into water. Saturated aqueous sodium bicarbonate was added and the neutralized solution was extracted with EtOAc. The organic phase was dried over $Na_2SO_4$ and concentrated under vacuum to give the product.

Step C: Condensation with Rhodanine

A solution of rhodanine (1 eq.), ethylenediamine diacetate (1 eq.) and 2-(3,4-Dichloro-benzylsulfanyl)-pyrimidine-4-carbaldehyde in methanol was stirred reflux for 1 hour. The resulting precipitate was collected by filtration and washed with methanol, water, aq. sodium bisulfate and aq. sodium bicarbonate. The solid was air dried.

Step D: Reduction of the Double Bond

A suspension of 5-[2-(3,4-dichloro-benzylsulfanyl)-pyrimidin-4-ylmethylene]-2-thioxo-thiazolidin-4-one in toluene was heated to 80° C. in the presence of 2,6-dimethyl-1,4-dihydro-3,5-pyridine carboxylate (1.1 eq.) and activated silica gel. The suspension was filtered and rinsed with EtOAc. The filtrate was evaporated in vacuum and the resulting residue was redissolved in EtOAc and washed with 1N aq. HCl solution. The organic layer was dried over $Na_2SO_4$ and concentrated under vacuum to give the crude product. Flash chromatography afforded pure product.

MS (ESI) 415. Found 414 (M−H).

Example 221

5-[3-Amino-2-(2,4-dichloro-benzoyl)-thieno[2,3-b]pyridin-6-ylmethylene]-thiazolidine-2,4-dione

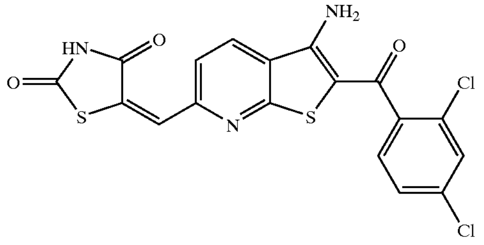

Step A: Alkylation and Cyclization of 6-dimethoxymethyl-2-mercapto-nicotinonitrile A mixture of 6-dimethoxymethyl-2-mercapto-nicotinonitrile and potassium carbonate (1.52 eq.) was treated with 2,4-dibromoacetopheneone (3.1 eq.) and stirred overnight. The alkylated and cyclized product was isolated as a solid precipitate.

Step B: Deprotection of the Acetal

A solution of (3-amino-6-dimethoxymethyl-thieno[2,3-b]pyridin-2-yl)-(2,4-dichloro-phenyl)-methanone in a mixture of TFA and $H_2O$ was stirred at room temperature until TLC indicated the reaction was complete. The reaction was neutralized with cold aq. $NaHCO_3$ and extracted with EtOAc. The organic layer was washed with aq. sodium chloride, then partially concentrated under vacuum and stored at 0° C. overnight. The resulting precipitate was collected to give the product as a pure yellow powder.

Step C: Condensation with TZD

The aldehyde was heated with TZD and piperidine in ethanol at 90° C. for 3 days. The reaction was allowed to cool, then poured into 10% aq. HCl solution. Pure product was isolted by filtration as a yellow solid.

MS (ESI) 449. Found 448 (M−H).

Example 222

Preparation of 2-Chloro-3-(2,4-dioxothiazolidin-5-ylidene-methyl)quinoline

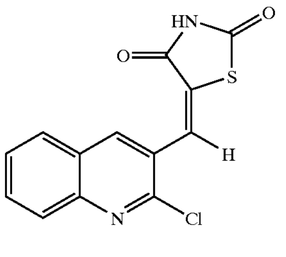

Step A: Coupling 2,4-thiazolidinedione (TZD) to Aldehyde Under Basic Conditions

2-Chloro-3-quinolinecarboxaldehyde, TZD (1.5 eq.), piperidine (1.5 eq) were dissolved in ethanol and heated to reflux for 5 hours. The reaction mixture was allowed to cool to RT and poured into ethanol, 1N HCl was added and a yellow precipitate was collected, washed several times with ether, air dried for 24 hrs at RT to give pure product (Yield-45%).

$^1H$ NMR (DMSO-$d_6$) δ: 12.8 (br.s, 1H, NH), 8.5 (s, 1H), 8.2 (d, 1H), 8.0–7.8 (m, 3H), 7.7 (t, 1H).

MS (ESI) 290. Found 289 (M−H). HPLC: 92% pure.

Example 223

Preparation of 2-Phenylthio-3-(2,4-dioxothiazolidin-5-ylidene-methyl)quinoline

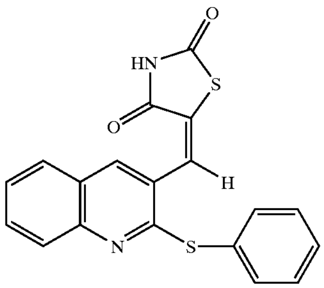

Step A: 2-Chloro-3-(2,4-dioxothiazolidin-5-ylidene-methyl)quinoline and thiophenol (1.2 eq) were mixed with ethoxyethanol and heated to reflux under $N_2$ for 2 hours. The reaction mixture was allowed to cool to RT, ether was added and bright-yellow precipitate was filtered off, washed several times with ether, air dried for 24 hrs at RT to give pure product (Yield-36%).

$^1H$ NMR (DMSO-$d_6$) δ (br.s, 1H, NH), 8.3 (s, 1H), 8.1(d, 1H), 7.7 (t, 1H), 7.6–7.5 (m, 4H), 7.4–7.4 (m,3H).

MS (ESI) 364. Found 363 (M−H). HPLC: 88% pure.

Example 224

Preparation of 2-(4-Chlorophenylthio)-3-(2,4-dioxothiazolidin-5-ylidene-methyl)quinoline.

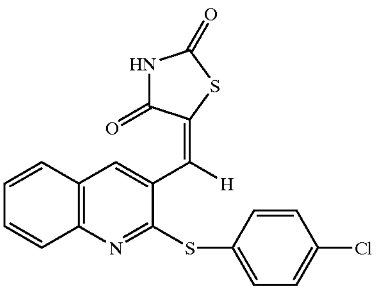

The title compound was prepared by the method of Example 223. Yield-69%.

$^1H$ NMR (DMSO-$d_6$) δ 12.8 (br,s, 1H, NH), 8.3 (s, 1H), 8.00 (d, 2H), 7.9 (s, 1H), 7.7 (t, 1H), 7.6–7.4 (m, 6H).

MS(ESI) 398. Found 397 (M−H); 399 (M+H). HPLC: 92% pure.

Example 225

Preparation of 2-(3,4-Dichlorophenylthio)-3-(2,4-dioxothiazolidin-5-ylidene-methyl)quinoline

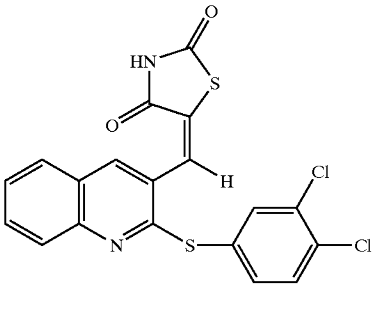

The title compound was prepared by the method of Example 223, using ethanol as a solvent. Yield-72%.

$^{1}$H NMR (DMSO-$d_6$) δ 12.8 (br.s, 1H, NH), 8.34 (s, 1H), 8.05 (d, 1H, J=8), 7.87 (d, 1H, J=1.6), 7.83 (s, 1H), 7.71–7.53 (m, 6H).

MS(ESI) 433. Found 431;432; 433 (M−H). 433; 435; 436 (M+H), HPLC: 96% pure.

Example 226

Preparation of 2-(4-Fluorophenylthio)-3-(2,4-dioxothiazolidin-5-ylidene-methyl)quinoline.

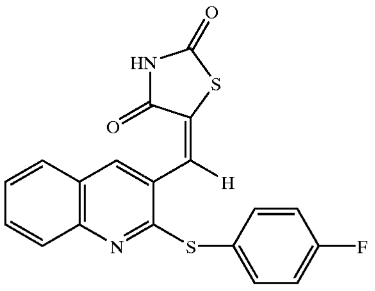

The title compound was prepared by the method of Example 223. Yield-23%.

$^{1}$H NMR (DMSO-$d_6$) δ 12.6 (br.s 1H, NH), 8.3 (s, 1H), 8.00 (d, 1H), 7.9 (s, 1H), 7.7–7.4 (m, 5H), 7.3 (t, 2H).

MS(ESI) 382. Found 381 (M−H). HPLC: 100% pure.

Example 227

Preparation of 2-(4-Methylphenylthio)-3-(2,4-dioxothiazolidin-5-ylidene-methyl)quinoline The title compound was prepared by the method of Example 223. Yield-24%.

$^{1}$H NMR (DMSO-$d_6$) δ 12.8 (br.s, 1H, NH), 8.3 (s, 1H), 8.00 (d, 1H), 7.9 (s, 1H), 7.7 (t, 1H), 7.6–7.5 (m, 2H), 7.4 (d, 2H), 7.3 (d, 2H), 2.1 (s, 3H).

MS (ESI) 378. Found 377 (M−H). HPLC: 86% pure.

Example 228

Preparation of 2-(4-Methoxyphenylthio)-3-(2,4-dioxothiazolidin-5-ylidene-methyl)quinoline

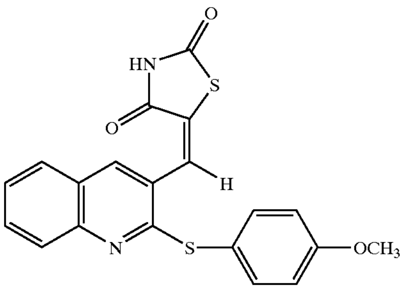

The title compound was prepared by the method of Example 223. Yield-35%.

$^{1}$H NMR (DMSO-$d_6$) δ 12.8 (br.s, 1H, NH), 8.2 (s, 1H), 8.0 (d, 1H), 7.9 (s, 1H), 7.8–7.4 (m, 5H), 7.0 (d, 2H), 3.8 (s, 3H).

MS (ESI) 394. Found 393 (M−H). HPLC: 98% pure.

Example 229

Preparation of 2-[4-Trifluoromethylphenylthio]-3-(2,4-dioxothiazolidin-5-ylidene-methyl)quinoline

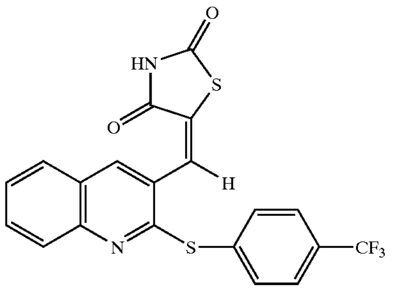

The title compound was prepared by the method of Example 223. Yield-55%

$^{1}$H NMR (DMSO-$d_6$) δ 12.8 (br.s. 1H, NH), 8.3 (s, 1H), 8.1 (d, 1H), 7.9 (s, 1H), 7.8–7.6 (m, 5H), 7.5 (t, 2H).

MS (ESI) 432. Found 431 (M−H). HPLC: 100% pure.

Example 230

Preparation of 2-(4-Chlorophenylsulfinyl)-3-(2,4-dioxothiazolidin-5-ylidene-methyl)quinoline

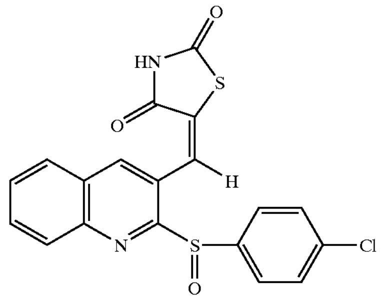

Step A

The compound prepared in Example 224 was dissolved in $CH_2Cl_2/CH_3OH$ (5:1), and to this solution was added 3-chloroperoxybenzoic acid (2 eq. of 77% max. purity). The mixture was stirring at RT for 4 hrs before TLC analysis showed the disappearance of the starting compound. The reaction mixture was stirring for an additionally 2 hrs. At the end of the reaction, white crystalline product precipitated. The product was collected by filteration, washed several times with ether, and air dried for 48 hrs to provide the final product with a yield of 30%.

$^1H$ NMR (DMSO-$d_6$) δ 12.8 (br. s, 1H, NH), 8.5 (s, 1H), 8.4 (s, 1H), 8.2 (d, 1H), 8.1 (d, 1H), 7.9 (t, 1H), 7.7 (t, 1H), 7.6–7.4 (m, 4H).

MS (ESI) 414. Found 413 (M–H); 415 (M+H). HPLC: 100% purity.

Reference Example 1

Preparation of Compound 122

Compound 5 (23 mg, 0.056 mmol) obtained in Example 5 was dissolved in dimethyl sulfoxide (2.0 mL) and a 0.04 mol/L buffer solution (pH 7.2) (4.1 mL), and 2-mercaptoethanol (0.012 mL, 0.17.mmol) was added thereto, followed by stirring at 25° C. for 40 minutes. After the conventional post-reaction treatment, the residue was purified by thin layer chromatography (developed with chloroform/methanol=10/1), to obtain a coarse purified product. The product was further purified with preparative HPLC [ODS column; eluted with an acetonitrile/disodium hydrogenphosphate-potassium dihydrogen phosphate buffer solution (0.04 mol/L; pH 7.2)=30/70], to obtain Compound 122 (5.7 mg, 31%).

$^1H$ NMR (300 MHz, DMSO-$d_6$) δ (ppm) 3.26–3.39 (m, 2H), 3.65–3.73 (m, 2H), 5.12 (m, 1H), 7.73 (d, J=8.6 Hz, 1H), 7.82 (s, 1H), 8.16–8.24 (m, 2H), 12.80 (m, 1H)

FABMS m/z 325 $(M-H)^-$ $C_{12}H_{10}N_2O_5S_2$=326

Reference Example 2

Preparation of Compound 123

2-Fluoro-5-nitrobenzaldehyde (48 mg, 0.28 mmol) was dissolved in N,N-dimethylformamide (2.4 mL), and di-n-propylamine (0.15 mL, 1.1 mmol) and potassium carbonate (0.16 g, 1.1 mmol) were added thereto, followed by stirring at 25° C. for 1 hour. After the conventional post-reaction treatment, the residue was purified by silica gel chromatography(eluted with chloroform), to obtain 2-(N,N-di-n-propylamino)-5-nitrobenzaldehyde (49 mg, 69%).

$^1H$ NMR (300 MHz, $CDCl_3$) δ (ppm) 0.89 (t, J=7.6 Hz, 6H), 1.66 (tq, J=7.6, 7.6 Hz, 4H), 3.38 (m, 4H), 7.03 (d, J=9.1 Hz, 1H), 8.21 (dd, J=9.1, 2.7 Hz, 1H), 8.60 (d, J=3.0 Hz, 1H), 10.01 (s, 1H)

FABMS m/z 251 $(M+H)^+$$C_{13}H_{18}O_3N_2$=250

2-(N,N-di-n-propylamino)-5-nitrobenzaldehyde (46 mg, 0.18 mmol) was dissolved in ethanol (1.8 mL), and 2,4-thiazolidinediione (86 mg, 0.74 mmol) and piperidine, (0.0073 mL, 0.073 mmol) were added thereto, followed by stirring at 80° C. for 1 hour. After the conventional post-reaction treatment, the residue was purified by thin layer column chromatography (developed with chloroform/acetonitrile=10/1), to obtain Compound 123 (53 mg,82%).

$^1H$ NMR (300 MHz, DMSO-$d_6$) δ (ppm) 0.81 (t, J=7.3 Hz, 6H), 1.48–1.61 (m, 4H), 3.21 (t, J=7.2 Hz, 4H), 7.24 (d, J=9.4 Hz, 1H), 7.62 (s, 1H), 8.13 (m, 1H), 8.20 (m, 1H), 12.63 (br s, 1H)

FABMS m/z 348 $(M-H)^-$ $C_{16}H_{19}O_4N_3S$=349

Reference Example 3

Preparation of Compound 124

2-Fluoro-5-nitrobenzaldehyde (0.11 g, 0.63.mmol) was dissolved in ethanol (4.2 mL), and 2,4-thiazolidinedione (0.29 mg, 2.5 mmol) and piperidine (0.025 mL, 0.25 mmol) were added thereto, followed by stirring at 80° C. for 6.5 hours. After the conventional post-reaction treatment, the residue was purified by thin layer column chromatography (eluted with chloroform/acetonitrile=10/1), to obtain Compound 124 (24 mg, 12%).

$^1H$ NMR (300 MHz, DMSO-$d_6$) δ (ppm) 1.57–1.72 (m, 6H), 3.08–3.14 (m, 4H), 7.26 (d, J=8.6 Hz, 1H), 7.65 (s, 1H), 8.20 (m, 1H), 8.21 (s, 1H), 12.66 (m, 1H)

FABMS m/z 332 $(M-H)^-$ $C_{15}H_{15}N_3O_4S$ =333

Reference Example 4

Preparation of Compound 125

Commercially available 2-morpholino-5-nitrobenzaldehyde (0.11 g, 0.44 mmol) (MAYBRIDGE, Catalog Number: RHO1290) was dissolved in ethanol (4.2 mL), and 2,4-thiazolidinedione (0.21 g, 1.8 mmol) and piperidine (0.018 mL, 0.18 mmol) were added thereto, followed by stirring at 80° C. for 6 hours. The reaction liquid was cooled to 25° C., and the precipitated crystals were collected by filtration to give Compound 125 (0.12 g, 82%).

$^1H$ NMR (300 MHz, DMSO-$d_6$) δ (ppm) 3.10–3.16 (m, 4H), 3.73–3.80 (m, 4H), 7.30 (m, 1H), 7.67 (br s, 1H), 8.221–8.28 (m, 2H), 12.65 (m, 1H)

FABMS m/z 334 $(M-H)^-$ $C_{14}H_{13}N_3O_5S$=335

Reference Example 5

Preparation of Compound 126

Compound 126 (85 mg, 73%) was obtained from 4-hydroxy-2-methoxybenzaldehyde (71 mg, 0.47 mmol), ethanol (2.8 mL), 2,4-thiazolidinedione (0.22 g, 1.9 mmol) and piperidine (0.019 mL, 0.19 mmol) using the same method as Reference Example 4.

$^1H$ NMR (300 MHz, DMSO-$d_6$) δ (ppm) 3.82 (s, 3H), 6.51 (s, 1H), 6.53 (dd, J=11.7, 2.2 Hz, 1H), 7.25 (d, J=8.5 Hz, 1H), 7.93 (s, 1H), 10.39 (s, 1H), 12.38 (br s, 1H)

FABMS m/z 250 $(M-H)^-$ $C_{11}H_9NO_4S$=251

Reference Example 6

Preparation of Compound 127

Compound 127 (53 mg, 47%) was obtained from 2-trifluoromethoxybenzaldehyde (73 mg. 0.38 mmol), ethanol (2.9 mL), 2,4-thiazolidinedione (0.18 g, 1.5 mmol) and piperidine (0.015 mL, 0.15 mmol) using the same method as Reference Example 3.

$^1$H NMR (300 MHz, DMSO-$d_6$) δ (ppm) 7.53–7.68 (m, 4H), 7.80 (s, 1H)

FABMS m/z 288 $(M-H)^-$ $C_{11}H_6{}^{19}NO_3S$=289

Reference Example 7

Preparation of Compound 128

Compound 128 (34 mg, 20%) was obtained from 10-[(4-chlorophenyl)thio]anthracene-9-carboxaldehyde (0.13 g, 0.38 mmol), ethanol (5.4 mL), 2,4-thiazolidiedione (0.18 g, 1.5 mmol) and piperidine (0.015 mL, 0.15 mmol) using the same method as Reference Example 4.

$^1$H NMR (300 MHz, DMSO-$d_6$) δ (ppm) 6.92 (d, J=8.6 Hz, 2H), 7.25 (d, J=8.4 Hz, 2H), 7.64–7.77 (m, 4H), 8.18 (d, J=7.9 Hz, 2H), 8.65 (s, 1H), 8.78 (d, J=8.1 Hz, 2H), 12.68 (m, 1H)

FABMS m/z 446 $(M-H)^-$ $C_{24}H_{14}{}^{35}ClNO_2S^2$=447

Reference Example 8

Preparation of Compound 171

A 2.5 mol/L sodium hydroxide aqueous solution (2.1 mL, 5.2 mmol) and tetrabutylammonium bromide (0.020 g, 0.061 mmol) were added to 2-naphthalenethiol (0.20 g, 1.2 mmol), followed by stirring at 25° C. for 15 minutes. A toluene (2.1 mL) solution of 2-fluoro-5-nitrobenzaldehyde (0.21 g, 1.2 mmol) was added to the reaction liquid, followed by stirring at 110° C. for 3.5 hours. The conventional post-reaction treatment was performed to give 2-[(2-formyl-4-nitrophenyl)thio]naphthalene. 2-[(2-Formyl-4-nitrophenyl)thio]naphthalene (0.30 g, 0.98 mmol) was dissolved in toluene (15 mL), and 2,4-thiazolidinedione (0.46 g, 3.9 mmol), piperidine (0.039 mL, 0.39 mmol), acetic acid (0.022 mL, 0.039 mmol) and molecular sieves 4A (1.5 g) were added thereto, followed by stirring at 110° C. for 2.5 hours. After the conventional post-reaction treatment, the product was triturated with ethanol to give Compound 171 (0.13 g, yield 33%).

2-[(2-formyl-4-nitrophenyl)thio]naphthalene:

$^1$H NMR (300 MHz, $CDCl_3$) δ (ppm) 6.99 (d, J=8.8 Hz, 1H), 7.52 (dd, J=8.4, 1.7 Hz, 1H), 7.56–7.68 (m, 2H), 7.85–7.98 (m, 3H), 8.05 (dd, J=2.4, 8.8 Hz, 1H), 8.15 (s, 1H), 8.68 (d, J=2.4 Hz, 1H), 10.33 (s, 1H)

FABMS m/z 310$(M+H)^+$$C_{17}H_{11}NO_3S$=309

Compound 171:

$^1$H NMR (300 MHz, DMSO-$d_6$) δ (ppm) 7.19 (d, J=8.8 Hz, 1H), 7.57 (br d, J=8.5 Hz, 1H), 7.59–7.68 (m, 2H), 7.95 (s, 1H), 7.97–8.04 (m, 2H), 8.08 (d, J=8.8 Hz, 1H), 8.13 (dd, J=8.4, 1.8 Hz, 1H), 8.28 (br s, 2H), 12.82 (m, 1H)

FABMS m/z 407 $(M-H)^+$$C_{20}H_{12}N_2O_4S_2$=464

Example 231

Preparation of Affinity Purified Extract

Extracts used for screening telomerase inhibitors were routinely prepared from 293 cells over-expressing the protein catalytic subunit of telomerase (hTERT). These cells were found to have 2–5 fold more telomerase activity than parental 293 cells. 200 ml of packed cells (harvested from about 100 liters of culture) were resuspended in an equal volume of hypotonic buffer (10 mM Hepes pH 7.9, 1 mM $MgCl_2$, 1 mM DTT, 20 mM KCl, 1 mM PMSF) and lysed using a dounce homogenizer. The glycerol concentration was adjusted to 10% and NaCl was slowly added to give a final concentration of 0.3 M. The lysed cells were stirred for 30 min and then pelleted at 100,000×g for 1 hr. Solid ammonium sulfate was added to the S100 supernatant to reach 42% saturation. The material was centrifuged; the pellet was resuspended in one fifth of the original volume and dialyzed against Buffer ‘A’ containing 50 mM NaCl. After dialysis the extract was centrifuged for 30 min at 25,000×g. Prior to affinity chromatography, Triton X-100 (0.5 %), KCl (0.3 M) and tRNA (50 μg/ml) were added. Affinity oligo (5'biotinTEG-biotinTEG-biotinTEG-GTA GAC CTG TFA CCA guu agg guu ag 3' (SEQ ID NO:2); lower case represents 2' O-methyl ribonucleotides and upper case represents deoxynucleotides) was added to the extract (1 nmol per 10 ml of extract). After an incubation of 10 min at 30° C., Neutravidin beads (Pierce; 250 μl of a 50% suspension) were added and the mixture was rotated overnight at 4° C. The beads were pelleted and washed three times with Buffer ‘B’ containing 0.3 M KCl, twice with Buffer ‘B’ containing 0.6 M KCl, and twice more with Buffer B containing 0.3 M KCl. Telomerase was eluted in Buffer ‘B’ containing 0.3 M KCl, 0.15% Triton X-100 and a 2.5 molar excess of displacement oligo (5'-CTA ACC CTA ACT GGT AAC AGG TCT AC-3' at 0.5 ml per 125 μl of packed Neutravidin beads) (SEQ ID NO:3) for 30 min. at room temperature. A second elution was performed and pooled with the first. Purified extracts typically had specific activities of 10 fmol nucleotides incorporated/min/μl extract, or 200 nucleotides/min/mg total protein.

| Buffer ‘A’ | Buffer ‘B’ |
|---|---|
| 20 mM Hepes pH 7.9 | 20 mM Hepes pH 7.9 |
| 1 mM MgCl2 | 1 mM EDTA |
| 1 mM DTT | 1 mM DTT |
| 1 mM EGTA | 10% glycerol |
| 10% glycerol | 0.5 Triton |

Example 232

Telomerase Specific Activity Determination

Three separate 100 μl telomerase assays are set up with the following buffer solutions: 50 mM Tris acetate, pH 8.2, 1 mM DTT, 1 mM EGTA, 1 mM $MgCl_2$, 100 mM K acetate, 500 μM dATP, 500 μM TTP, 10 μM $^{32}$P-dGTP (25 Ci/mmol), and a00 nM $d(TTAGGG)_3$. To the individual reactions 2.5, 5 or 10 μl of affinity-purified telomerase (see Example 231) is added and the reactions are incubated at 37° C. At 45 and 90 minutes, 40 μl aliquots are removed from each reaction and added to 160 μl of Stop Buffer (100 mM NaCl, 10 mM Na pyrophosphate, 0.2% SDS, 2 mM EDTA, 100 μg/ml tRNA). 10 μl trichloroacetic acid (TCA) (100%) is added and the sample is incubated on ice for 30 minutes. The sample is pelleted in a microcentrifuge (12000×g force) for 15 minutes. The pellet is washed with 1 ml 95% ethanol and pelleted again in the microcentrifuge (12000×g force) for 5 minutes. The pellet is resuspended in 50 μl $dH_2O$ and transferred to a 12×75 glass test tube containing 2.5 ml of ice cold solution of 5% TCA and 10 mM Na pyrophosphate. The sample is incubated on ice for 30 minutes. The sample is filtered through a 2.5 cm wet ($dH_2O$) GFC membrane (S&S) on a vacuum filtration manifold. The filter is washed three times under vacuum with 5 ml ice cold 1% TCA, and once with 5 ml 95% ethanol. The filter is dried and counted in a scintillation counter using scintillation fluid. The fmol of nucleotide incorporated is determined from the specific activity of radioactive tracer. The activity of extract is calculated based on the dNTP incorporated and is expressed as fmol dNTP/min/μl extract.

Example 233

Telomerase Activity Assay

Bio-Tel FlashPlate Assay

An assay is provided for the detection and/or measurement of telomerase activity by measuring the addition of TTAGGG telomeric repeats to a biotinylated telomerase substrate primer; a reaction catalyzed by telomerase. The biotinylated products are captured in streptavidin-coated microtiter plates. An oligonucleotide probe complementary to 3.5 telomere repeats labeled with [$^{33}P$] is used for measuring telomerase products, as described below. Unbound probe is removed by washing and the amount of probe annealing to the captured telomerase products is determined by scintillation counting.

Method:

1. Compounds are stored as concentrated stocks and dissolved in 100 % dimethylsulfoxide (DMSO).

2. For testing, the compounds are diluted to a 15×working stock in 50% DMSO and 2 μl is dispensed into two wells of a 96-well microtiter dish (assayed in duplicate).

3. Telomerase extract is diluted to a specific activity of 0.04–0.09 fmol dNTP incorporated/min./μl in Telomerase Dilution Buffer and 18 μl added to each sample well to preincubate with compound for 30 minutes at room temperature.

4. The telomerase reaction is initiated by addition of 10 μl Master Mix to the wells containing telomerase extract and compound. The plates are sealed and incubated at 37° C. for 90 min.

5. The reaction is stopped by the addition of 10 μl HCS.

6. 25 μl of the reaction mixture is transferred to a 96-well streptavidin-coated FlashPlate (NEN) and incubated for 2 hours at room temperature with mild agitation.

7. The wells are washed three times with 180 μl2×SSC without any incubation.

8. The counts of probe annealed to biotinylated telomerase products are detected on a scintillation counter.

Buffers:

Telomerase Dilution Buffer 50 mM Tris-acetate, pH 8.2

1 mM DTT 1 mM EGTA 1 mM $MgCl_2$ 830 nM BSA

Master Mix (MM)

50 mM Tris-acetate, pH 8.2

1 mM DTT 1 mM EGTA 1 mM $MgCl_2$ 150 mM K acetate

10 μM dATP

20 μM dGTP

120 μM dTTP 100 nM biotinylated primer (5'-biotin-AATCCGTCGAGCAGAGTT-3') (SEQ ID NO:4)

5.4 nM labeled probe [5'-CCCTAACCCTAACCC-TAACCC-($^{33}P$) $A_{1-50}$-3'] (SEQ ID NO:5); specific activity approximately $10^9$ cpm/μg or higher Hybridization Capture Solution (HCS)

12×SSC (1×=150 mM NaCl/30 mM $Na_3$Citrate)

40 mM EDTA 40 mM Tris-HCl, pH 7.0

Using the foregoing assay, the compounds of Examples 1–29 were shown to have telomerase $IC_{50}$ values below 100 μM.

Example 234

Anti-tumor Activity

Ex vivo Studies a. Reduction of Telomere Length in Tumor Cells

Colonies of the tumor cell lines, such as the ovarian tumor cell lines OVCAR-5 and SK-OV-3, and normal human cells used as a control (e.g., normal human BJ cells) are prepared using standard methods and materials. In one test, the colonies are prepared by seeding 15-centimeter dishes with about $10^6$ cells in each dish. The dishes are incubated to allow the cell colonies to grow to about 80% confluence, at which time each of the colonies are divided into two groups. One group is exposed to a subacute dose of a compound of the invention at a predetermined concentration (e.g., between about 5 μM and about 20 μM) for a period of about 4–8 hours after plating following the split; the other group is exposed to a control (e.g., DMSO).

Each group is then allowed to continue to divide, and the groups are split evenly again (near confluence). The same number of cells are seeded for continued growth. The compound or control is added every fourth day to the samples at the same concentration delivered initially. Remaining cells are analyzed for telomere length. As the untested cell cultures near confluence, the samples are split again as just described. This sequence of cell doubling and splitting is continued for about 20 to 25 doublings. Thus, a determination of telomere length as a function of cell doublings is obtained.

Telomere length is determined by digesting the DNA of the cells using restriction enzymes specific for sequences other than the repetitive $T_2$ $AG_3$ sequence of human telomeres (TRF analysis). The digested DNA is separated by size using standard techniques of gel electrophoresis to determine the lengths of the telomeric repeats, which appear, after probing with a telomere DNA probe, on the gel as a smear of high-molecular weight DNA (approximately 2 Kb-15 Kb).

The results of the telomere length analysis are expected to indicate that the compounds of the invention have no affect on the rate of decrease in telomere length for control cells as a function of progressive cell doublings. With respect to the tumor cell lines, however, measurable decreases in telomere length are expected to be determined for tumor cells exposed to the compounds of the invention. Tumor cells exposed to the control are expected to maintain steady telomere lengths. Thus, the compounds of the invention are expected to cause resumption of the normal loss of telomere length as a function of cell division in tumor cells.

In another experiment, HEK-293 cells are incubated with a compound of the invention and a control at concentrations between about 1 μM and about 20 μM using the protocol just described. Cells are expected to enter crisis (i.e., the cessation of cell function) within several weeks following administration of the test compound of the invention. In addition, TRF analysis of the cells using standard methodology is expected to show that the test compounds of the invention are effective in reducing telomere length. In addition to the HEK-293 cells described above, this assay can be performed with any telomerase-positive cell line, such as HeLa cells.

b. Specificity

Compounds of the invention are screened for activity ($IC_{50}$) against telomerase and several enzymes having nucleic acid binding or modifying activities related to telomerase using standard techniques. The enzymes being screened include Telomerase, DNA Polymerase I, HeLa RNA Polymerase II, T3 RNA Polymerase, MMLV Reverse Transcriptase, Topoisomerase I, Topoisomerase II, Terminal Transferase and Single-Stranded DNA Binding Protein (SSB). The specificity of a compound of the invention for telomerase is determined by comparing the $IC_{50}$ of the compound with respect to telomerase with the $IC_{50}$ values of the compound for each of the enzymes being screened. The compound is determined to have high specificity for telomerase if the $IC_{50}$ for telomerase of the compound is lower than the $IC_{50}$ vaules for each of the enzymes being screened.

Alternatively, telomerase inhibitory activity of the compounds was measured in accordance with a known method (U.S. Pat. No. 5,760,062). That is, a dimethyl sulfoxide (DMSO) solution of each agent was mixed with partially purified telomerase from a nuclear extract of HEK293 cells and incubated in the presence of an oligodeoxynucleotide to be used as the substrate and deoxynucleotide triphosphate. The obtained reacted product (DNA having a telomere sequence) was adsorbed on a membrane, and hybridization was carried out using a labeled oligonucleotide probe having a sequence complementary to the telomere sequence. The inhibition ratio was calculated based on the ratio of the signal of label on the membrane in the presence of the agent to the signal of label in the absence of the agent (control). Also, concentration of each agent which inhibits 50% of the enzyme activity based on the control was used as $IC_{50}$. Results of the measurement of inhibition activity of selected compounds are shown in Table 7.

TABLE 7

In vitro telomerase inhibition activity

| Compound | $IC_{50}$ (μM) |
|---|---|
| 1 | 21 |
| 4 | 30 |
| 5 | 23 |
| 9 | 8.3 |
| 12 | 5.8 |
| 13 | 5.9 |
| 14 | 4.0 |
| 16 | 26 |
| 17 | 10 |
| 18 | 11 |
| 19 | 70 |
| 20 | 9.0 |
| 21 | 4.3 |
| 23 | 14 |
| 24 | 5.3 |
| 25 | 4.2 |
| 26 | 4.2 |
| 31 | 15 |

TABLE 7-continued

In vitro telomerase inhibition activity

| Compound | $IC_{50}$ (μM) |
|---|---|
| 32 | 21 |
| 33 | 5.5 |
| 35 | 3.9 |
| 36 | 5.1 |
| 37 | 6.0 |
| 43 | 2.6 |
| 44 | 1.9 |
| 47 | 4.1 |
| 48 | 1.6 |
| 49 | 4.4 |
| 53 | 0.77 |
| 54 | 7.4 |
| 55 | 5.3 |
| 56 | 7.9 |
| 57 | 54 |
| 58 | (56%) |
| 59 | 2.1 |
| 60 | 4.5 |
| 61 | 0.33 |
| 62 | 7.8 |
| 63 | 6.5 |
| 64 | 9.7 |
| 65 | 6.2 |
| 66 | 3.7 |
| 67 | 1.0 |
| 68 | 2.7 |
| 69 | 0.48 |
| 70 | 4.8 |
| 71 | 2.7 |
| 72 | 4.3 |
| 73 | 7.0 |
| 74 | 3.7 |
| 76 | 3.9 |
| 78 | 5.5 |
| 79 | 3.5 |
| 80 | 5.5 |
| 82 | (51%) |
| 83 | (58%) |
| 84 | 3.9 |
| 86 | 8.0 |
| 87 | 6.9 |
| 89 | (56%) |
| 90 | 3.7 |
| 91 | (61%) |
| 92 | 5.6 |
| 93 | (55%) |
| 94 | 7.8 |
| 96 | (62%) |
| 97 | 5.6 |
| 99 | 6.9 |
| 100 | 4.4 |
| 101 | (62%) |
| 104 | (61%) |
| 106 | 4.5 |
| 108 | 6.2 |
| 110 | (53%) |
| 113 | (68%) |
| 115 | 2.7 |
| 120 | 9.3 |
| 121 | 4.0 |
| 122 | 7.7 |
| 123 | 6.9 |
| 124 | (54%) |
| 125 | 1.6 |
| 126 | 1.3 |
| 127 | 5.7 |
| 128 | 2.6 |
| 129 | 8.1 |
| 132 | 2.6 |
| 133 | 9.1 |
| 134 | (59%) |
| 135 | 4.5 |
| 137 | 5.5 |
| 138 | 4.3 |
| 139 | 4.4 |

TABLE 7-continued

| In vitro telomerase inhibition activity | |
|---|---|
| Compound | $IC_{50}$ ($\mu$M) |
| 141 | (64%) |
| 143 | (62%) |
| 153 | (53%) |
| 171 | 7.2 |
| Troglitazone | 16 |
| Pioglitazone | 83 |

In parenthesis, residual activity of in vitro telomerase activity is shown in the presence of the compound at a concentration of 10 $\mu$m.

c. Cytotoxicity is performed using HeLa cells. The cell lines used in the assay are exposed to a compound of the invention for 72 hours at concentrations ranging from about 1 $\mu$M to about 1,000 $\mu$M. During this period, the optical density (OD) of the samples is determined for light at 540 nanometers (nm). No significant cytotoxic effects are expected to be observed at concentrations less than about 5 $\mu$M. It will be appreciated that other tumor cells lines such as the ovarian tumor cell lines OVCAR-5 and SK-OV-3 can be used to determine cytoxicity in addition to control cell lines such as normal human BJ cells. Other assays for cytotoxicity such as the MTT assay (see Berridge et al., 1996, Biochemica 4:14–19) and the alamarBlue™ assay (U.S. Pat. No. 5,501,959) can be used as well.

Some compounds may induce G2 arrest at concentrations above about 5 $\mu$M (i.e., at 10 $\mu$M–20 $\mu$M or higher). Preferably, to observe any telomerase inhibiting effects the compounds should be administered at a concentration below the level of cytotoxicity. Nevertheless, since the effectiveness of many cancer chemotherapeutics derives from their cytotoxic effects, it is within the scope of the present invention that the compounds of the present invention be administered at any dose for which chemotherapeutic effects are observed.

In vivo Studies

A human tumor xenograft model in which OVCAR-5 tumor cells are grafted into nude mice can be constructed using standard techniques and materials. The mice are divided into two groups. One group is treated intraperitoneally with a compound of the invention. The other group is treated with a control comprising a mixture of either DMSO or ethanol and emulphor (oil) and phosphate buffer solution (PBS). The average tumor mass for mice in each group is determined periodically following the xenograft using standard methods and materials.

In the group treated with a compound of the invention, the average tumor mass is expected to increase following the initial treatment for a period of time, after which time the tumor mass is expected to stabilize and then begin to decline. Tumor masses in the control group are expected to increase throughout the study. Thus, the compounds of the invention are expected to lessen dramatically the rate of tumor growth and ultimately induce reduction in tumor size and elimination of the tumor.

In another experiment, each agent was allowed to contact with human renal carcinoma cell line ACHN for 3 days, and then a cell extract was prepared by a known method (U.S. Pat. No. 5,629,154) to measure the enzyme activity. That is, a cell extract was prepared using a buffer solution containing 0.5% CHAPS. Using the extract, TRAP (Telomeric Repeat Amplification Protocol) assay was carried out in vitro ($TRAP_{EZE}$™ ELISA Telomerase Detection Kit, manufactured by Intergen). The ratio (%) of the enzyme activity in the extract from agent-treated cells to the enzyme activity in the extract from agent-untreated cells was calculated. The results are shown in Table 8.

TABLE 8

| In vivo telomerase inhibition activity | | |
|---|---|---|
| Compound | Concentration ($\mu$M) | Residual Enzyme Activity (%) |
| 1 | 30 | 11 |
| 3 | 100 | 0 |
| 4 | 10 | 16 |
| 5 | 10 | 16 |
| 11 | 100 | 50 |
| 12 | 100 | 26 |
| 14 | 100 | 47 |
| 16 | 100 | 0 |
| 21 | 30 | 35 |
| 22 | 100 | 33 |
| 37 | 30 | 39 |
| 38 | 30 | 36 |
| 54 | 30 | 50 |
| 56 | 30 | 26 |
| 57 | 30 | 24 |
| 66 | 30 | 0 |
| 68 | 10 | 18 |
| 69 | 10 | 16 |
| 78 | 10 | 25 |
| 82 | 3 | 23 |
| 83 | 10 | 32 |
| 86 | 10 | 44 |
| 89 | 30 | 2 |
| 92 | 30 | 41 |
| 97 | 30 | 41 |
| 113 | 30 | 37 |
| 120 | 10 | 40 |
| 133 | 10 | 11 |
| 134 | 10 | 4 |
| 135 | 3 | 14 |
| 141 | 30 | 26 |
| 143 | 30 | 36 |

Thus, the present invention provides novel compounds, compositions and methods for inhibition telomerase activity and treating disease states in which telomerase activity has deleterious effects, especially cancer. The compounds of the invention provide a highly selective and effective treatment for malignant cells that require telomerase activity to remain immortal; yet, without affecting non-malignant cells.

While the preferred embodiment of the invention has been illustrated and described, it will be appreciated that various changes can be made therein without departing from the spirit and scope of the invention.

We claim:

1. A method of inhibiting a telomerase enzyme comprising contacting the telomerase enzyme with a compound having a 2,4-dioxothiazolidine skeleton or a 4-oxo-2-thioxothiazolidine skeleton wherein the compound has telomerase inhibitory activity.

2. The method of claim 1, wherein the compound has a 2,4-dioxothiazolidine skeleton.

3. The method of claim 1, wherein the compound has a 4-oxo-2-thioxothiazolidine skeleton.

4. A method of inhibiting a telomerase enzyme comprising contacting the telomerase enzyme with a compound of formula (I):

(I)

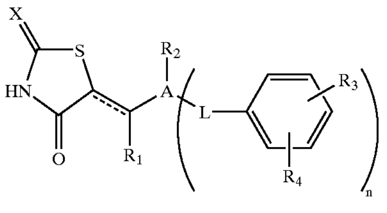

wherein

X is O or S;

 is a single or double bond;

A is aryl or heteroaryl;

$R_1$ is hydrogen or lower alkyl;

$R_2$, $R_3$ and $R_4$ are independently selected from the group consisting of hydrogen, halo, alkyl, aryl, hydroxyl, alkoxyl, aryloxyl, aralkoxyl, cyano, nitro, alkylcarbamido, arylcarbamido, dialkylcarbamido, diarylcarbamido, alkylarylcarbamido, alkylthiocarbamido, arylthiocarbamido, dialkylthiocarbamido, diarylthiocarbamido, alkylarylthiocarbamidb, amino, alkylamino, arylamino, dialkylamino, diarylamino, arylalkylamino, aminocarbonyl, alkylaminocarbonyl, arylaminocarbonyl, dialkylaminocarbonyl, diarylaminocarbonyl, arylalkylamino-carbonyl, alkylcarbonyloxy, arylcarbonyloxy, carboxyl, alkoxycarbonyl, aryloxycarbonyl, sulfo, alkylsulfonylamido, arylsulfonylarnido, alkylsulfonyl, arylsulfonyl, alkylsulfinyl, arylsulfinyl and heteroaryl;

L is a direct bond or a linking group having from 1 to 3 atoms independently selected from unsubstituted or substituted carbon, N, O or S; and n is 1 or 2;

or a pharmaceutically acceptable salt thereof.

5. The method of claim 4 wherein X is O.

6. The method of claim 4, wherein  is a single bond.

7. The method of claim 4 wherein  is a double bond.

8. The method of claim 4 wherein $R_1$ is H.

9. The method of claim 4 wherein A is aryl.

10. The method of claim 9 wherein the aryl is selected from the group consisting of phenyl, biphenyl, napthyl and anthryl.

11. The method of claim 10 wherein the compound is of the formula (II):

(II)

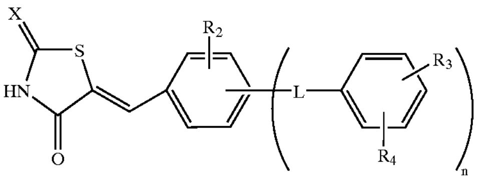

wherein X, $R_2$, $R_3$, $R_4$, L, and n are as defined above; or a pharmaceutically acceptable salt thereof.

12. The method of claim 11 wherein X is O, $R_1$ is H, A is anthryl, and L is S, $R_3$ is 4-halogen, $R_4$ is hydrogen, and n is 1.

13. The method of claim 4 wherein A is heteroaryl.

14. The method of claim 13 wherein the heteroaryl is selected from the group consisting of pyridine, quinoline, isoquinoline, thiophene, furan, imidazole, benzimidazole, and pyrazole.

15. The method of claim 13 wherein the compound is of the formula (III).

(III)

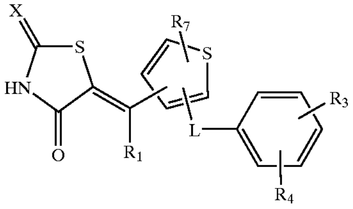

wherein X, $R_1$, $R_2$, $R_3$, $R_4$, and L are as defined above; or a pharmaceutically acceptable salt thereof.

16. The method of claim 4 wherein $R_3$ and $R_4$ are halo.

17. The method of claim 4 wherein n is 1 and $R_2$ is not hydrogen.

18. The method of claim 4 wherein the compound is selected from the group consisting of 5-(2-(3,4-dichlorophenyl)benzylidene)thiazolidine-2,4-dione, 5-(3-(3,4-dichlorophenyl)benzylidene)thiazolidine-2,4-dione, 5-(4-(3,4-dichlorobenzyloxy)benzylidene)thiazolidine-2,4-dione, 5-(2-(3,4-dichlorobenzyloxy)benzylidene)thiazolidine-2,4-dione, 5-(4-(3,4-dichlorobenzamido)benzylidene)thiazolidine-2,4-dione, 5-(4-(N-3,4-dichlorophenyureido)benzylidene)thiazolidine-2,4-dione, 5-(2-(N-3,4-dichlorophenyureido)benzylidene)thiazolidine-2,4-dione, 5-(2-(N-3,4-dichlorophenylcarbamido)benzylidene)thiazolidine-2,4-dione, 5-(3-(N-3,4-dichlorophenylcarbamido)benzylidene)thiazolidine-2,4-dione, 5-(4-(N-3,4-dichlorophenylcarbamido)benzylidene)thiazolidine-2,4-dione, 5-(4-(N-3,4-dichlorophenylcarbamoyloxy)benzylidene)thiazolidine-2,4-dione, 5-(4-(3,4-dichlorophenoxycarbonyl)benzylidene)thiazolidine-2,4-dione, 5-(2-(3,4-dichlorophenoxycarbonyl)benzylidene)thiazolidine-2,4-dione, 5-(2-(3,4-dichlorophenylacetoxy)benzylidene)thiazolidine-2,4-dione, 5-(3-(3,4-dichlorophenylacetoxy)benzylidene)thiazolidine-2,4-dione, 5-(4-(3,4-dichlorophenylacetoxy)benzylidene)thiazolidine-2,4-dione, 5-(2-(3,4-dichlorobenzoyloxy)benzylidene)thiazolidine-2,4-dione, 5-(3-(3,4-dichlorobenezoyloxy)benzylidene)thiazolidine-2,4-dione, 5-(4-(3,4-dichlorobenzoyloxy)benzylidene)thiazolidine-2,4-dione, 5-(3,4-bis-(3,4-dichlorobenzyloxy)benzylidine)thiazolidine-2,4-dione, 5-(2-(3,4-dichlorophenoxy)benzylidine)thiazolidine-2,4-dione, 5-(4-(3,4-dichlorophenoxy)benzylidine)thiazolidine-2,4-dione, 5-(2,5-bis-(3,4-dichlorobenzyloxy)benzylidine)thiazolidine-2,4-dione, 5-(2,4-bis-(3,4-dichlorobenzyloxy)benzylidine)thiazolidine-2,4-dione, 5-(2-(3,4-dichlorobenzylthio)-3H-pyrimidin4-on-6-ylmethylidene)rhodanine, 5-(2-(3,4-dichlorobenzylthio)pyrimidin-4-ylmethylidene)rhodanine, 5-(2-(3,4-dichlorobenzylthio)pyrimidin-4-ylmethylidene)rhodanine, 5-(3-cyano-2-(3,4-dichlorobenzylthio)pyridin-6-ylmethylidene)thiazolidine-2,4-dione and 5-(3-(3,4-dichlorobenzyloxy)benzylidene)thiazolidine-2,4-dione and the pharmaceutically acceptable salts thereof.

19. A method of inhibiting a telomerase enzyme comprising contacting the telomerase enzyme with a compound of formula (IV):

(IV)

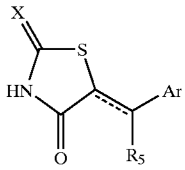

wherein

X is O or S;

 is a single or double bond;

$R_5$ is H or lower alkyl; and

Ar is a substituted or unsubstituted aryl, heteroaryl, aralkyl, heteroarylalkyl, arylalkenyl, heteroarylalkenyl, arylalkynyl or heteroarylalkynyl;

or a pharmaceutically acceptable salt thereof.

20. The method of claim 19 wherein z, is a double bond.

21. A method of inhibiting a telomerase enzyme comprising contacting the telomerase enzyme with a compound of formula (V):

(V)

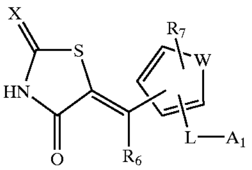

wherein

X is S or O;

W is CH═CH, S, or —N═C—;

$R_6$ is H or lower alkyl;

$R_7$ is OH, halogen, mercapto, nitro, cyano, lower alkylthio, lower alkyl, lower alkoxy, lower alkanoyloxy, $NR_{11}R_{12}$ (wherein $R_{11}$ and $R_{12}$ are independently selected from the group consisting of hydrogen, lower alkyl, lower alkanoyl, aryl, heteroaryl, heteroarylalkyl, or $R_{11}$ and $R_{12}$ form a substituted or unsubstituted heterocyclic ring), $CO_2R_{13}$ (wherein $R_{13}$ is selected from the group consisting of hydrogen, lower alkyl, aralkyl, and heteroarylalkyl), $CONR_{11}R_{12}$, substituted or unsubstituted aryl, substituted or unsubstituted heteroaryl, aryloxy, heteroaryloxy, aralkyloxy, heteroarylalkyloxy, lower alkanoyl, aroyl, lower alkenyl, arylthio, or lower alkynyl; and when W represents S, $R_7$ may also be H;

L is O, S, SO, $SO_2$, $OCH_2$, $SCH_2$, $SOCH_2$, $SO_2CH_2$, or $N(R_{10})(CH_2)_m$ (wherein $R_{10}$ is substituted or unsubstituted aryl, heteroaryl, aralkyl, or heteroarylalkyl, and m is 0 or 1), $(CH_2)N(R_{10})(CH_2)_m$, or $CR_{13}R_{14}$ (wherein $R_{13}$ and $R_{14}$ are independently selected from the group consisting of hydrogen, hydroxy, aryl, and heteroaryl); and $A_1$ is cycloalkyl or formula (A1):

(A1)

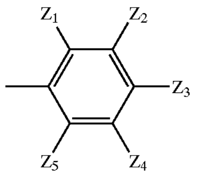

wherein $Z_1$ to $Z_5$ are independently selected from the group consisting of hydrogen, lower alkyl, lower alkenyl, lower alkanoyloxy, mercapto, alkylthio, $NR_{11}R_{12}$, nitro, cyano, $CO_2R_{13}$, $CONR_{11}R_{12}$, aryl, heteroaryl, aryloxy, heteroaryloxy, aralkyloxy, heteroarylalkyloxy, halogen, and lower alkanoyl provided that when W is CH═CH, A may also by pyridyl;

or a pharmaceutically acceptable salt thereof.

22. The method of claim 21 wherein W is S.

23. The method of claim 21 wherein W is CH═CH.

24. The method of claim 21 wherein L is $OCH_2$.

25. The method of claim 21 wherein L is $N(R_{10})(CH_2)$.

26. The method of claim 21 wherein L is S.

27. The method of claim 21 wherein L is SO.

28. The method of claim 21 wherein L is $SO_2$.

29. The method of claim 23 wherein L is SO.

30. The method of claim 23 wherein L is $SO_2$.

31. The method of claim 21 wherein $R_7$ is nitro.

32. The method of claim 21 wherein $A_1$ is 4-methylphenyl.

33. The method of claim 23 wherein $A_1$ is 4-methylphenyl.

* * * * *

SEQUENCE LISTING

<160> NUMBER OF SEQ ID NOS: 5

<210> SEQ ID NO 1
<211> LENGTH: 6
<212> TYPE: DNA
<213> ORGANISM: Artificial Sequence
<220> FEATURE:
<223> OTHER INFORMATION: oligonucleotide

<400> SEQUENCE: 1 ttaggg 6

<210> SEQ ID NO 2
<211> LENGTH: 26
<212> TYPE: DNA
<213> ORGANISM: Artificial Sequence
<220> FEATURE:
<223> OTHER INFORMATION: oligonucleotide

<400> SEQUENCE: 2
gtagacctgt taccaguuag gguuag 26

<210> SEQ ID NO 3
<211> LENGTH: 26
<212> TYPE: DNA
<213> ORGANISM: Artificial Sequence
<220> FEATURE:
<223> OTHER INFORMATION: oligonucleotide

<400> SEQUENCE: 3
ctaaccctaa ctggtaacag gtctac 26

<210> SEQ ID NO 4
<211> LENGTH: 18
<212> TYPE: DNA
<213> ORGANISM: Artificial Sequence
<220> FEATURE:
<223> OTHER INFORMATION: oligonucleotide

<400> SEQUENCE: 4
aatccgtcga gcagagtt 18

<210> SEQ ID NO 5
<211> LENGTH: 22
<212> TYPE: DNA
<213> ORGANISM: Artificial Sequence
<220> FEATURE:
<223> OTHER INFORMATION: oligonucleotide

<400> SEQUENCE: 5
ccctaaccct aaccctaacc ca 22